US011505575B2

(12) United States Patent
Ricardo et al.

(10) Patent No.: US 11,505,575 B2
(45) Date of Patent: Nov. 22, 2022

(54) CYCLIC POLYPEPTIDES FOR PCSK9 INHIBITION

(71) Applicants: Merck Sharp & Dohme LLC, Rahway, NJ (US); Ra Pharmaceuticals, Inc., Cambridge, MA (US)

(72) Inventors: Alonso Ricardo, Cambridge, MA (US); Thomas Joseph Tucker, North Wales, PA (US); Nicolas Cedric Boyer, Somerville, MA (US); Ketki Ashok Dhamnaskar, Cambridge, MA (US); Zhong Ma, Lexington, MA (US); Angela Dawn Kerekes, Plainfield, MA (US); Chengwei Wu, Ambler, PA (US); Sookhee Nicole Ha, Warren, NJ (US); Hyewon Youm, Berkeley Heights, NJ (US); Elisabetta Bianchi, Rome (IT); Danila Branca, Pomezia (IT); Raffaele Ingenito, Pomezia (IT); Willy Costantini, Pomezia (IT); Aurash Shahripour, Gaithersburg, MD (US); Yusheng Xiong, Plainsboro, NJ (US)

(73) Assignees: Merck Sharp & Dohme LLC, Rahway, NJ (US); Ra Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 17/253,783

(22) PCT Filed: Jun. 20, 2019

(86) PCT No.: PCT/US2019/038247
§ 371 (c)(1),
(2) Date: Dec. 18, 2020

(87) PCT Pub. No.: WO2020/009805
PCT Pub. Date: Jan. 9, 2020

(65) Prior Publication Data
US 2021/0163538 A1 Jun. 3, 2021

Related U.S. Application Data

(60) Provisional application No. 62/688,050, filed on Jun. 21, 2018.

(51) Int. Cl.
*C07K 7/64* (2006.01)
*A61K 38/00* (2006.01)

(52) U.S. Cl.
CPC .............. *C07K 7/64* (2013.01); *A61K 38/00* (2013.01)

(58) Field of Classification Search
None
See application file for complete search history.

(56) References Cited

U.S. PATENT DOCUMENTS

| 4,393,046 A | 7/1983 | Baylis et al. |
|---|---|---|
| 2010/0041102 A1 | 2/2010 | Sitlani et al. |
| 2012/0219558 A1 | 8/2012 | Nl et al. |
| 2013/0158021 A1 | 6/2013 | Dong et al. |
| 2013/0281366 A1 | 10/2013 | Pingali et al. |
| 2017/0081383 A1* | 3/2017 | Gruber .................. C07K 14/68 |
| 2017/0189470 A1* | 7/2017 | Wang .................. A61K 9/0051 |
| 2018/0023071 A1 | 1/2018 | Basak |

FOREIGN PATENT DOCUMENTS

| WO | WO 2010/144038 A1 | 12/2010 |
|---|---|---|
| WO | WO 2012/040259 A2 | 3/2012 |
| WO | WO 2017/181061 A1 | 10/2017 |
| WO | WO 2017/220701 A1 | 12/2017 |
| WO | WO 2018/053517 A1 | 3/2018 |
| WO | WO 2019/246349 A1 | 12/2019 |
| WO | WO 2019/246352 A1 | 12/2019 |
| WO | WO 2019/246386 A1 | 12/2019 |
| WO | WO 2019/246387 A1 | 12/2019 |
| WO | WO 2019/246405 A1 | 12/2019 |
| WO | WO 2020/009805 A3 | 1/2020 |

OTHER PUBLICATIONS

Chaudhary et al., "PCSK9 inhibitors: A new era of lipid lowering therapy", World Journal of Cardiology, Feb. 26, 2017, vol. 9, No. 2, pp. 76-91.

Elbitar et al., "Proprotein convertase subtilisin/kexin 9 (PCSK9) inhibitors and the future of dyslipidemia therapy: an updated patent review (2011-2015)", Expert Opinion on Therapeutic Patents, 2016, 26(12): 1377-1392.

He et al. "Lowering serum lipids via PcSK9-targeting drugs: current advances and future perspectives", ACTA Pharmacologica Sinica, Jan. 23, 2017, vol. 38, pp. 301-311.

International Search Report and Written Opinion in related PCT Application No. PCT/US2020/048342, dated Nov. 18, 2020, 11 pages.

International Search Report and Written Opinion in related PCT Application No. PCT/US2019/038220, Dated Nov. 5, 2019, 11 pages.

(Continued)

*Primary Examiner* — Sergio Coffa

(74) *Attorney, Agent, or Firm* — Lathrop GPM LLP; Brian Trinque

(57) ABSTRACT

Provided herein are cyclic polypeptide compounds that can, e.g., bind specifically to human proprotein convertase subtilisin/kexin type 9 (PCSK9) and optionally also inhibit interaction between human PCSK9 and human low density lipoprotein receptor (LDLR), and pharmaceutical compositions comprising one or more of these compounds. Also provided are methods of reducing LDL cholesterol level in a subject in need thereof that include administering to the subject one or more of the cyclic polypeptide compounds or a pharmaceutical composition provided herein.

23 Claims, No Drawings

(56) References Cited

OTHER PUBLICATIONS

International Search Report and Written Opinion in related PCT Application No. PCT/US2019/038155, dated Nov. 15, 2019, 6 pages.
International Search Report and Written Opinion in related PCT Application No. PCT/US2019/038221, dated Nov. 18, 2019, 12 pages.
International Search Report and Written Opinion in related PCT Application No. PCT/US2019/038247, dated Apr. 20, 2020, 13 pages.
International Search Report and Written Opinion in related PCT Application No. PCT/US2019/038250, dated Sep. 17, 2019, 7 pages.
International Search Report and Written Opinion in related PCT Application No. PCT/US2019/038158, dated Dec. 26, 2019, 7 pages.
Umemura et al., Characterization of the biosynthetic gene cluster for the ribosomally synthesized cyclic peptide ustiloxin B in *Aspergillus flavus*, Fungal Genetics and Biology, 2014, vol. 68, pp. 23-30.
Zhang et al., "Identification of a Small Peptide That Inhibits PCSK9 Protein Binding to the Low Density Lipoprotein Receptor", The Journal of Biological Chemistry, Jan. 10, 2014, vol. 289, No. 2, pp. 942-955.
International Search Report and Written Opinion in related PCT Application No. PCT/US2020/066046, dated Mar. 2, 2021, 3 pages.

\* cited by examiner

CYCLIC POLYPEPTIDES FOR PCSK9 INHIBITION

CROSS REFERENCE TO RELATED APPLICATIONS

This application is a 35 U.S.C. 0 371 filing of International Patent Application No. PCT/US2019/038247, filed Jun. 20, 2019, which claims priority to U.S. Ser. No. 62/688,050, filed Jun. 21, 2018, which is incorporated herein by reference in its entirety.

BACKGROUND

Hypercholesterolemia is characterized by the presence of high levels of low-density lipoprotein (LDL) cholesterol in the blood, which can lead to the development of atherosclerosis and associated ischemic cardiovascular disease (e.g., myocardial infarction and stroke) (Lambert et al., J. Lipid Res. 53:2515-2524, 2012). More than 34 million American adults have hypercholesterolemia (NIH Genetics Home Reference Website, 2014). Proprotein convertase subtilisin/kexin type 9 (PCSK9) has been proposed as a target for treatment of hypercholesterolemia.

PCSK9 is a proprotein convertase belonging to the proteinase K subfamily of the secretory subtilase family. PCSK9 binds to the epidermal growth factor-like-repeat A (EGF-A) domain of the low-density lipoprotein receptor (LDLR) and directs LDLR to lysosomes, where it is degraded. Inhibition of PCSK9 leads to increased LDLRs at the cell surface, resulting in increased removal of LDL from the extracellular fluid. Therefore, the inhibition of PCSK9 results in lower LDL cholesterol concentrations in the blood.

There remains a need in the art for compounds that inhibit the binding of PCSK9 to LDLR, and treat or prevent hypercholesterolemia. Administration of these compounds can lead to significantly improved prognosis, diminished progression of hypercholesterolemia, and a decrease in diseases related to hypercholesterolemia.

SUMMARY

Provided herein are cyclic polypeptides useful for the inhibition of PCSK9 in a subject in need thereof. In particular, provided herein are cyclic polypeptide compounds having the structure of Formula (I):

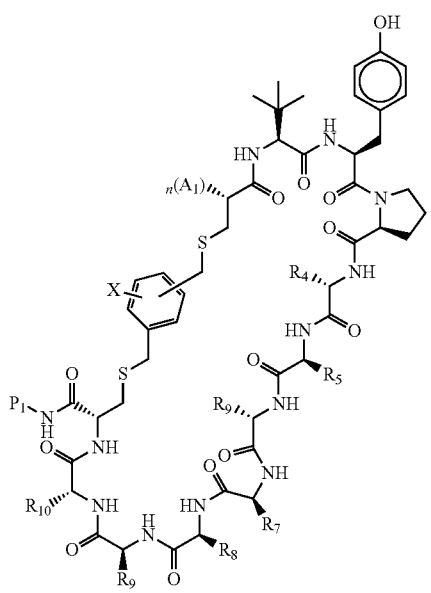

(I)

or a pharmaceutically acceptable salt thereof.

Also provided herein are cyclic polypeptide compounds having the structure of Formula (II):

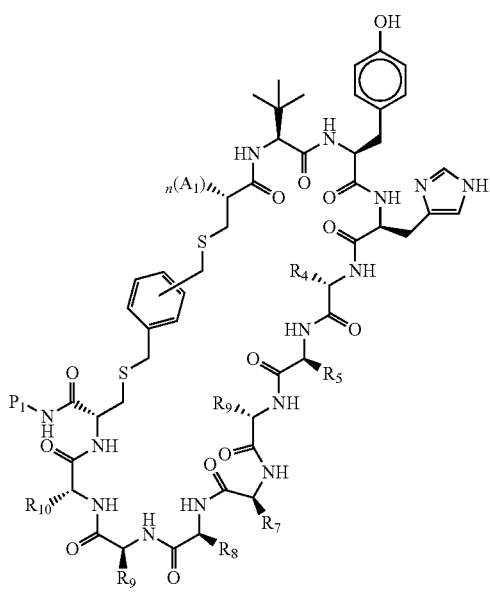

(II)

or a pharmaceutically acceptable salt thereof.

Also provided herein are bicyclic polypeptide compounds having the structure of Formula (III):

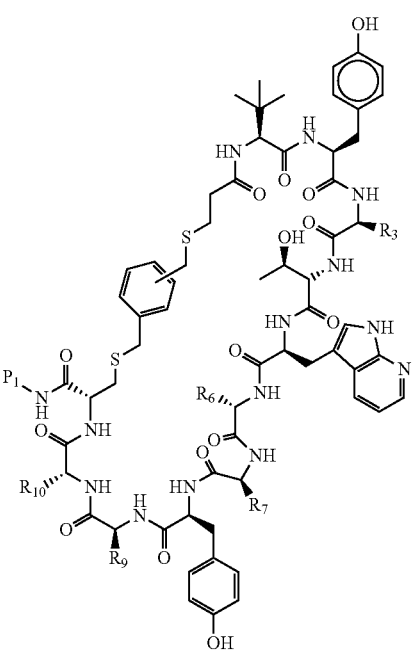

(III)

or a pharmaceutically acceptable salt thereof;

provided either $R_3$ and $R_7$, or $R_6$ and $R_{10}$ are covalently bound by a linking moiety selected from the group consisting of

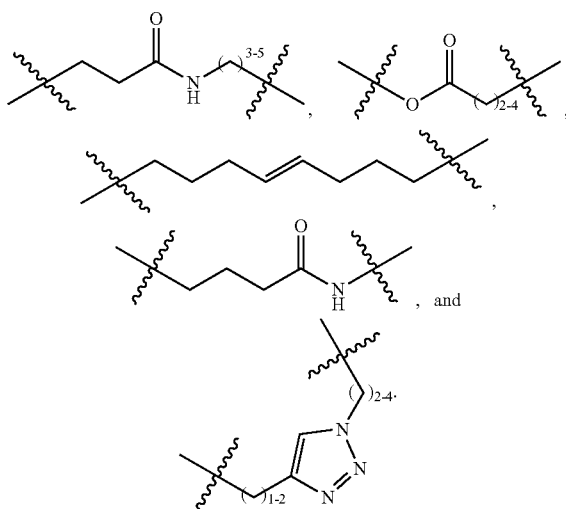

Also provided herein is a cyclic polypeptide compound selected from compounds 001, 002, 003, 004, 005, 006, 007, 008, 09, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 50, 51, 52, and 53.

Also provided herein is a bicyclic polypeptide compound selected from compounds 045, 049, 102, 103, 104, 105, 116, and 117.

In an embodiment, provided herein is a pharmaceutical composition comprising one of the compounds of Formula (I), Formula (II), Formula (III), or compounds 001-105, together with a pharmaceutically acceptable carrier.

Also provided herein is a method of reducing low density lipoprotein (LDL) cholesterol level in a subject in need thereof comprising administering to the subject a therapeutically effective amount of one or more of cyclic polypeptide compounds of Formula (I), Formula (II), Formula (III), or compounds 001-105, or a pharmaceutical composition comprising one or more of cyclic polypeptide compounds of Formula (I), Formula (II), Formula (III), or compounds 001-105.

In addition, provided herein is a method of treating hypercholesterolemia in a subject in need thereof comprising administering to the subject a therapeutically effective amount of one or more cyclic polypeptide compounds of Formula (I), Formula (II), Formula (III), or compounds 001-105, or a pharmaceutical composition comprising one or more of cyclic polypeptide compounds of Formula (I), Formula (II), Formula (III), or compounds 001-105.

Additionally, provided herein is a method of treating a disease that shows comorbidity with hypercholesterolemia in a subject in need thereof comprising administering to the subject a therapeutically effective amount of one or more cyclic polypeptide compounds of Formula (I), Formula (II), Formula (III), or compounds 001-105, or a pharmaceutical composition comprising one or more of cyclic polypeptide compounds of Formula (I), Formula (II), Formula (III), or compounds 001-105. For example, the disease that shows comorbidity can be one or more of nephrotic syndrome, kidney failure, coronary artery disease, atherosclerosis, stroke, peripheral vascular disease, diabetes, and high blood pressure.

Also provided herein is a method of inhibiting PCSK9 activity comprising administering to a subject in need thereof a therapeutically effective amount of one or more cyclic polypeptide compounds of Formula (I), Formula (II), Formula (III), or compounds 001-105, or a pharmaceutical composition comprising one or more of cyclic polypeptide compounds of Formula (I), Formula (II), Formula (III), or compounds 001-105.

In addition, provided herein is a method of inhibiting the interaction between PCSK9 and the EGF-A domain of LDLR in a subject in need thereof comprising administering a therapeutically effective amount of one or more cyclic polypeptide compounds of Formula (I), Formula (II), Formula (III), or compounds 001-105, or a pharmaceutical composition comprising one or more of cyclic polypeptide compounds of Formula (I), Formula (II), Formula (III), or compounds 001-105.

Also provided herein is a method of inhibiting PCSK9 activity in a cell comprising contacting the cell with one or more cyclic polypeptide compounds of Formula (I), Formula (II), Formula (III), or compounds 001-105, or a pharmaceutical composition comprising one or more of cyclic polypeptide compounds of Formula (I), Formula (II), Formula (III), or compounds 001-105.

DETAILED DESCRIPTION OF THE DISCLOSURE

Provided herein are cyclic polypeptide compounds, and pharmaceutical compositions comprising such compounds, that are useful for the inhibition of PCSK9. For example, the compounds are useful in inhibiting the interaction between human PCSK9 and the EGF-A domain of human LDLR in subject. These compounds and pharmaceutical compositions are also useful for the treatment of hypercholesterolemia, as well as diseases that show comorbidity with hypercholesterolemia.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "cyclic polypeptide compounds" means polypeptide chains in which the amino termini and carboxyl termini; amino termini and side chain; carboxyl termini and side chain; or side chain and side chain, are linked with a covalent bond that generates the ring.

As used herein, the term "disease that has comorbidity with hypercholesterolemia" means a disease in which elevated cholesterol levels (e.g., elevated LDL cholesterol levels) (e.g., as compared to a reference level) are associated with an elevated risk of developing the disease and/or an elevated risk of poor prognosis of the disease (e.g., increased risk of severe disease, increased risk of death, and/or an increased risk of cardiovascular event (such as stroke, myocardial infarction, or heart disease)) (e.g., as compared to a subject not having an elevated LDL cholesterol level, e.g., as compared to a reference level).

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has hypercholesterolemia, or related diseases, a symptom of hypercholesterolemia, or related diseases, or the potential to develop hypercholesterolemia, or related diseases, with the purpose to cure, heal, alleviate, relieve, alter, remedy, ameliorate, improve or affect the hypercholesterolemia, or related diseases, the symptoms of hypercholesterolemia, or related diseases, or the potential to develop hypercholesterolemia, or related diseases. Such treatments may be specifically tailored or modified, based on knowledge obtained from the field of pharmacogenomics. As used herein, to "treat" includes systemic amelioration of the symptoms associated with the pathology and/or a delay in onset of symptoms. Clinical and sub-clinical evidence of "treatment" will vary with the pathology, the individual and the treatment.

As used herein, the term "prevent" or "preventing" comprises the prevention of at least one symptom associated with or caused by the state, disease or disorder being prevented. As used herein, the term "prevent" or "prevention" also means no disorder or disease development if none had occurred, or no further disorder or disease development if there had already been development of the disorder or disease. Also considered is the ability of one to prevent some or all of the symptoms associated with the disorder or disease.

As used herein, "inhibit" means to decrease an activity, such as the activity of PCSK9 or the activity of a molecule that binds PCSK9.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case can be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

A "pharmaceutically acceptable salt" is intended to mean a salt of a free acid or base of the compounds provided herein that is non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", J. Med. Chem., 2007, 50:6665-72, S. M. Berge, et al., "Pharmaceutical Salts", J Pharm Sci., 1977, 66:1-19, and Handbook of Pharmaceutical Salts, Properties, Selection, and Use, Stahl and Wermuth, Eds., Wiley-VCH and VHCA, Zurich, 2002.

Examples of pharmaceutically acceptable salts are those that are pharmacologically effective and suitable for contact with the tissues of patients without undue toxicity, irritation, or allergic response. The compounds provided herein may possess a sufficiently acidic group, a sufficiently basic group, or both types of functional groups, and accordingly react with a number of inorganic or organic bases, and inorganic and organic acids, to form a pharmaceutically acceptable salt.
As used herein, unnatural amino acids used in this invention have the following amino acid code and structure:
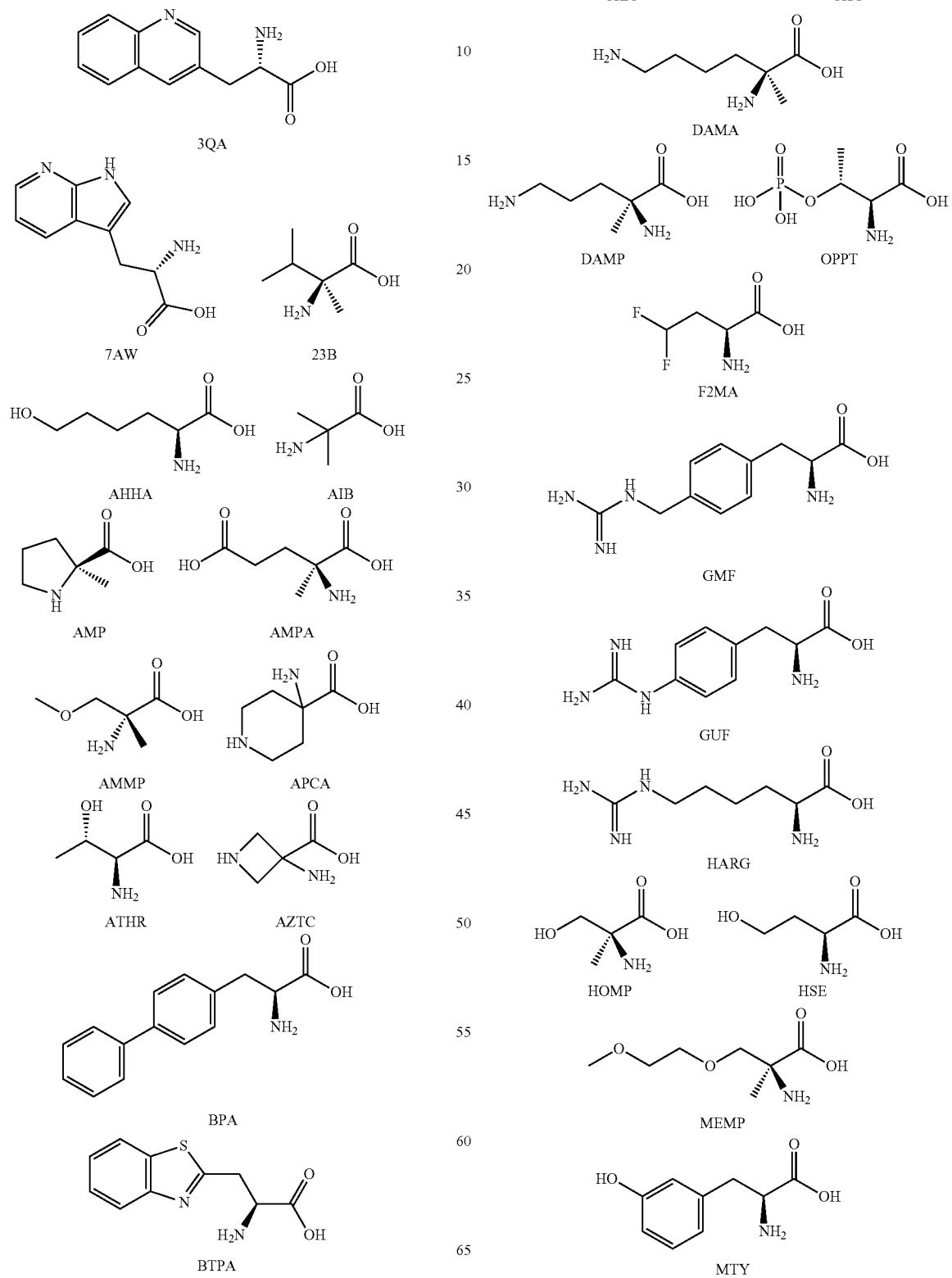

[Structures shown: NA3, NVA, OMT, OPPS, PPPP, UPPA]

Compounds

Provided herein are cyclic polypeptide compounds (also referred herein as "compounds of the invention") that are useful for inhibiting PCSK9 activity. In one aspect, the compounds of the invention are useful for inhibiting the interaction between PCSK9 and EGF-A domain of LDLR in a subject. Additionally, the compounds of the invention are useful for reducing low density lipoprotein (LDL) cholesterol level in a subject. The subject whose LDL cholesterol is being lowered can suffer from a diagnosis of elevated LDL levels. The subject can also have hypercholesterolemia.

In another aspect, the compounds of the invention are useful for treating or preventing hypercholesterolemia. In addition, the compounds of the invention are useful for treating or preventing diseases that show comorbidity with hypercholesterolemia.

In another aspect, provided herein are cyclic peptides having the structure of Formula (I):

[Structure of Formula (I) shown]

or a pharmaceutically acceptable salt thereof;
wherein:
$A_1$ is an acyl or sulfonyl protected NVA, or is an acyl protected amine;
$R_4$ is selected from the group consisting of the amino acid side chains of THR, OMT, and ATHR;
$R_5$ is 7AW;
$R_6$ is selected from the group consisting of the amino acid side chains of DAMA, DAMP, HOMP, APCA, AMMP, MEMP, AMPA, AZTC, GLU, and AIB;
$R_7$ is selected from the group consisting of the amino acid side chains of GLU and ALA;
$R_3$ is selected from the group consisting of the amino acid side chains of TYR and PPPP;
$R_9$ is 23B;
$R_{10}$ is selected from the group consisting of the amino acid side chains of THR, OPPT, OPPS, SER, and LYS;
$P_1$ is H, methyl, an acetyl group, or

[Structure shown]

X is H or F;
n is 0 or 1;
p is 2, 3, or 4;
wherein each amino acid residue is optionally an N-methylated amino acid; and
wherein each amino acid residue can be in the R or S configuration.

In an embodiment, the compound of Formula (I), or a pharmaceutically acceptable salt thereof, is selected from the following compounds of Table 1 below:

TABLE 1
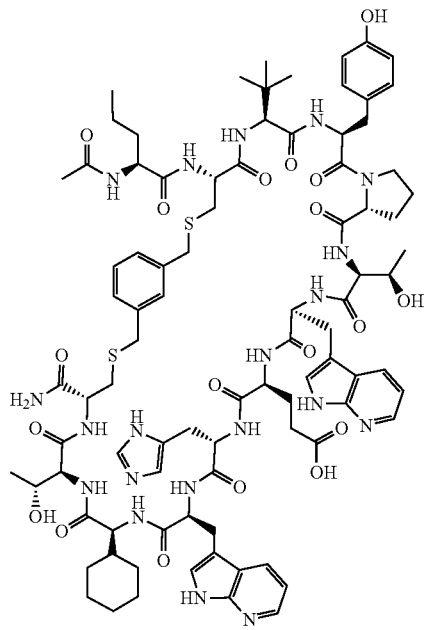 [SMILES: CCC[C@H](NC(C)=O)C(=O)N[C@H]1CSCc2cccc(c2)CSC[C@@H](C(N)=O)NC(=O)[C@H]([C@@H](C)O)NC(=O)[C@H](C2CCCCC2)NC(=O)[C@H](Cc2c[nH]c3ncccc23)NC(=O)[C@H](Cc2cnc[nH]2)NC(=O)[C@H](CCC(=O)O)NC(=O)[C@H](Cc2c[nH]c3ncccc23)NC(=O)[C@H]([C@@H](C)O)NC(=O)[C@H]2CCCN2C(=O)[C@H](Cc2ccc(O)cc2)NC(=O)[C@H](C(C)(C)C)NC1=O]
001
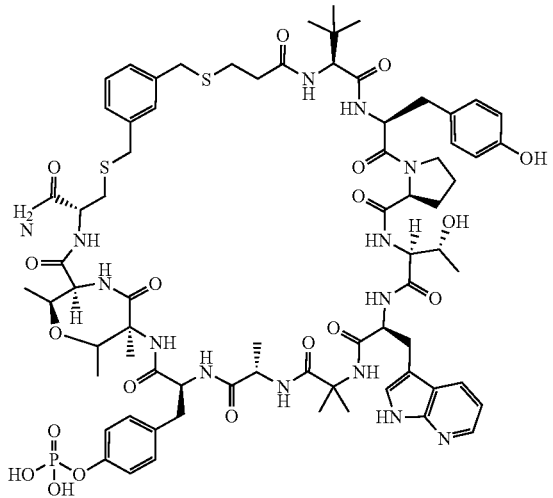 [SMILES: CC1O[C@@H](C)[C@@H]2NC(=O)[C@@]1(C)NC(=O)[C@H](Cc1ccc(OP(=O)(O)O)cc1)NC(=O)[C@H](C)NC(=O)C(C)(C)NC(=O)[C@H](Cc1c[nH]c3ncccc13)NC(=O)[C@H]([C@@H](C)O)NC(=O)[C@@H]1CCCN1C(=O)[C@H](Cc1ccc(O)cc1)NC(=O)[C@H](C(C)(C)C)NC(=O)CCSCc1cccc(c1)CSC[C@@H](C(N)=O)NC2=O]
014
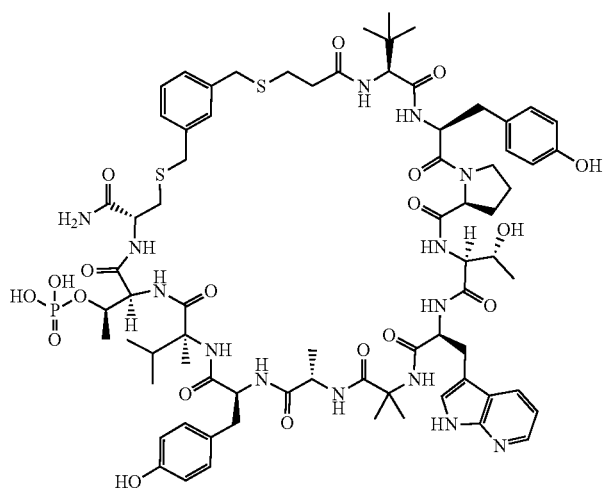 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)OP(=O)(O)O)NC1=O]
015

TABLE 1-continued
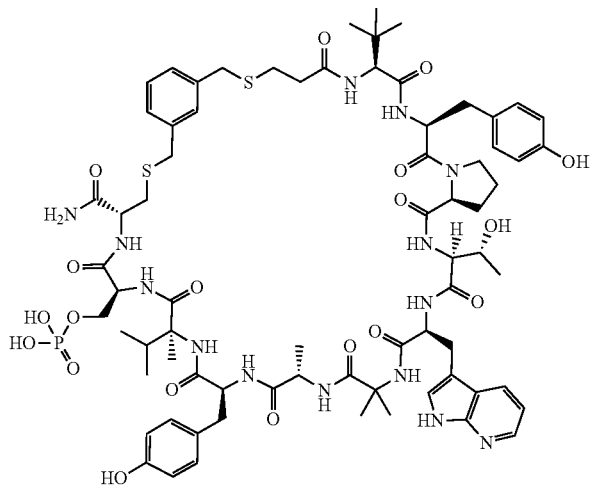 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H](COP(=O)(O)O)NC1=O]
016
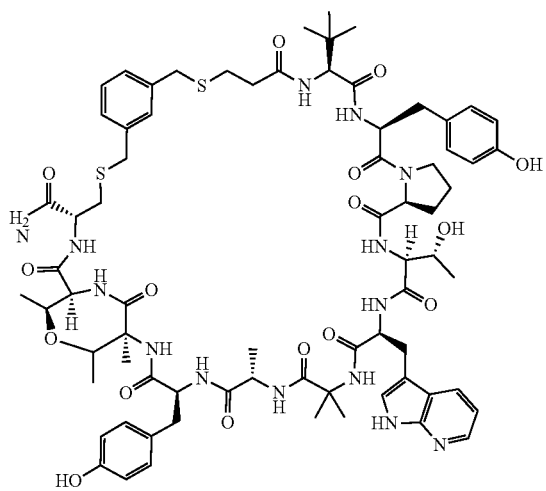 [SMILES: CC1O[C@@H](C)[C@@H]2NC(=O)[C@@]1(C)NC(=O)[C@H](Cc1ccc(O)cc1)NC(=O)[C@H](C)NC(=O)C(C)(C)NC(=O)[C@H](Cc1c[nH]c3ncccc13)NC(=O)[C@H]([C@@H](C)O)NC(=O)[C@@H]1CCCN1C(=O)[C@H](Cc1ccc(O)cc1)NC(=O)[C@H](C(C)(C)C)NC(=O)CCSCc1cccc(c1)CSC[C@@H](C(N)=O)NC2=O]
017
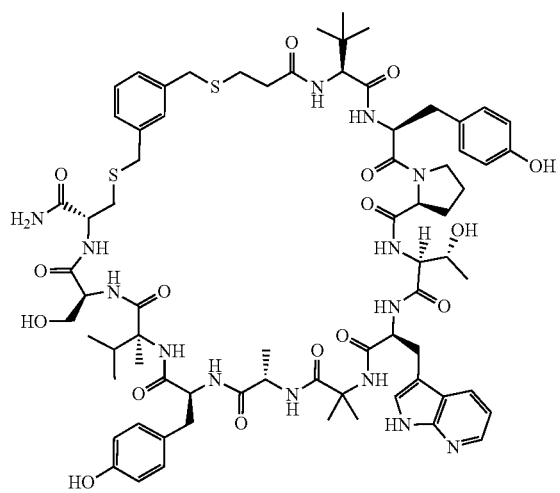 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CO)NC1=O]
018

TABLE 1-continued
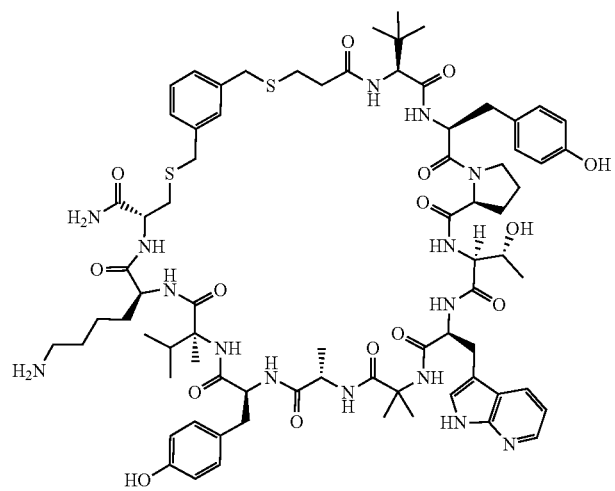 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CCCCN)NC1=O]
019
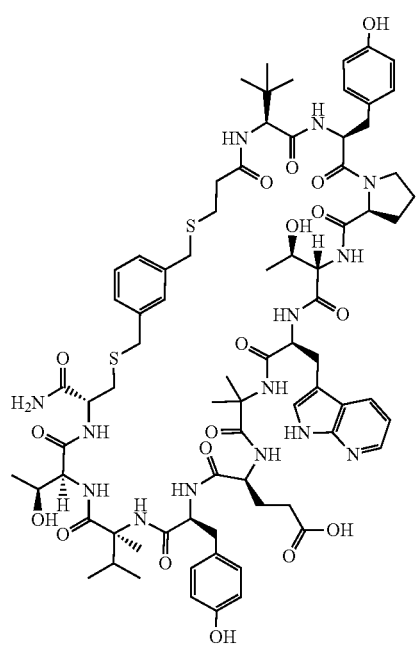 [SMILES: CC(C)[C@]1(C)NC(=O)[C@H](Cc2ccc(O)cc2)NC(=O)[C@H](CCC(=O)O)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@H](C)O)NC1=O]
020

TABLE 1-continued
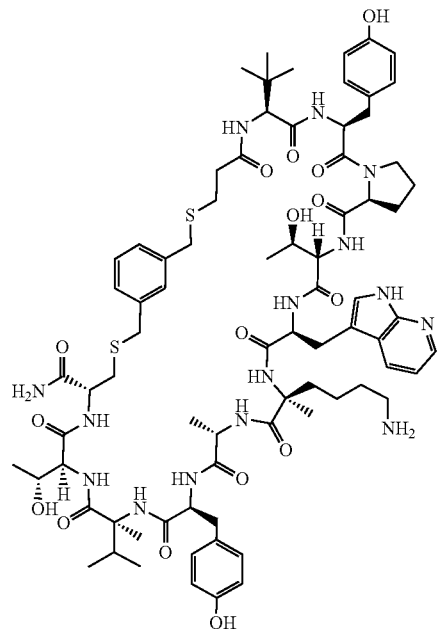 [SMILES: CC(C)[C@]1(C)NC(=O)[C@H](Cc2ccc(O)cc2)NC(=O)[C@H](C)NC(=O)[C@](C)(CCCCN)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]
023
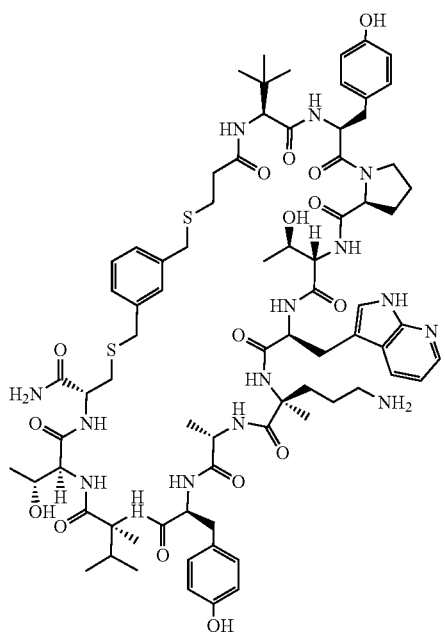
024

TABLE 1-continued
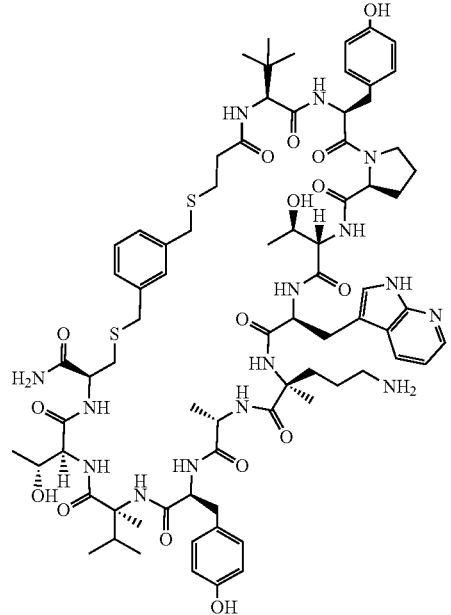 [SMILES: CC(C)[C@]1(C)NC(=O)[C@H](Cc2ccc(O)cc2)NC(=O)[C@H](C)NC(=O)[C@](C)(CCCN)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@H](C(N)=O)NC(=O)[C@H]([C@@H](C)O)NC1=O]
025
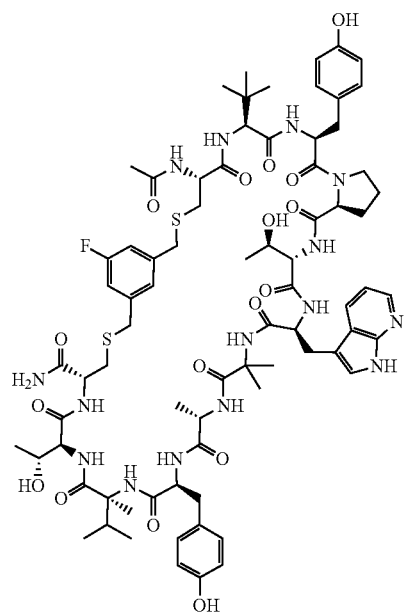 [SMILES: CC(=O)N[C@H]1CSCc2cc(F)cc(c2)CSC[C@@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]
026

TABLE 1-continued
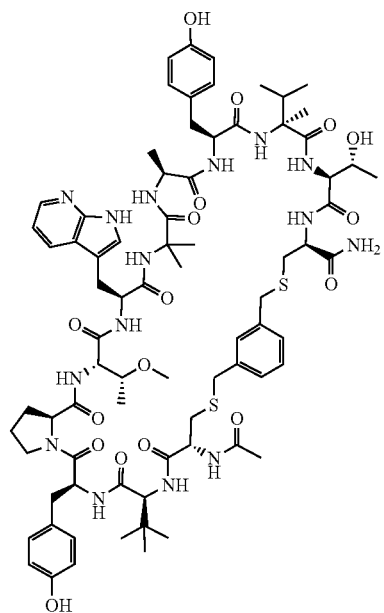 [SMILES: CO[C@H](C)[C@@H]1NC(=O)[C@@H]2CCCN2C(=O)[C@H](Cc2ccc(O)cc2)NC(=O)[C@H](C(C)(C)C)NC(=O)[C@@H](NC(C)=O)CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC1=O]
027
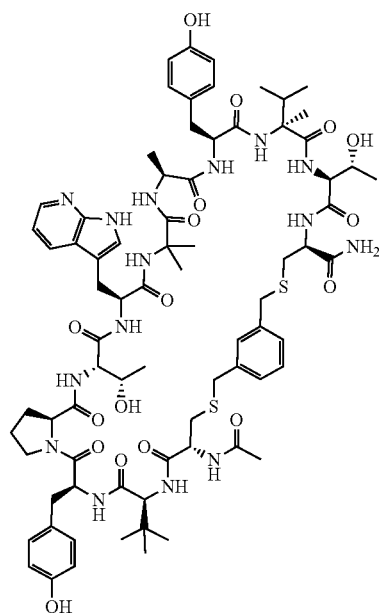 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@H](C)O)NC(=O)[C@@H]2CCCN2C(=O)[C@H](Cc2ccc(O)cc2)NC(=O)[C@H](C(C)(C)C)NC1=O]
028

TABLE 1-continued
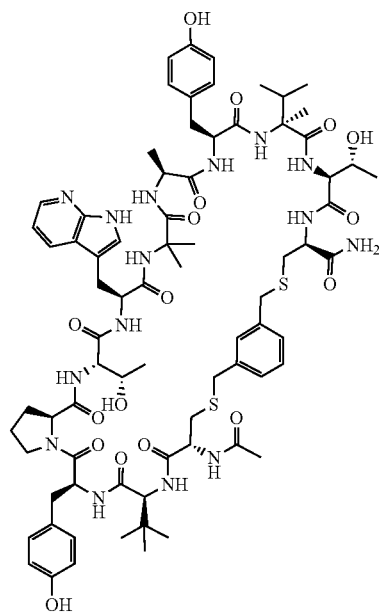 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@H](C)O)NC(=O)[C@@H]2CCCN2C(=O)[C@H](Cc2ccc(O)cc2)NC(=O)[C@H](C(C)(C)C)NC1=O]
029
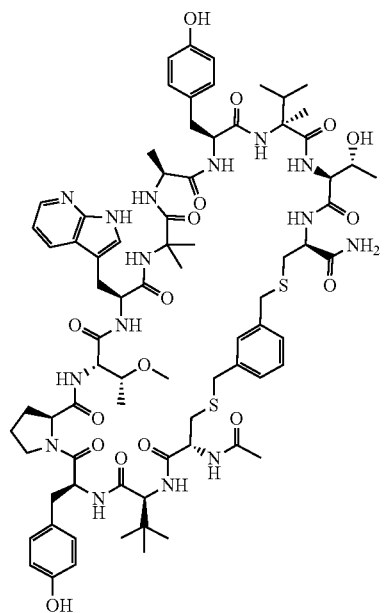 [SMILES: CO[C@H](C)[C@@H]1NC(=O)[C@@H]2CCCN2C(=O)[C@H](Cc2ccc(O)cc2)NC(=O)[C@H](C(C)(C)C)NC(=O)[C@@H](NC(C)=O)CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC1=O]
030

TABLE 1-continued
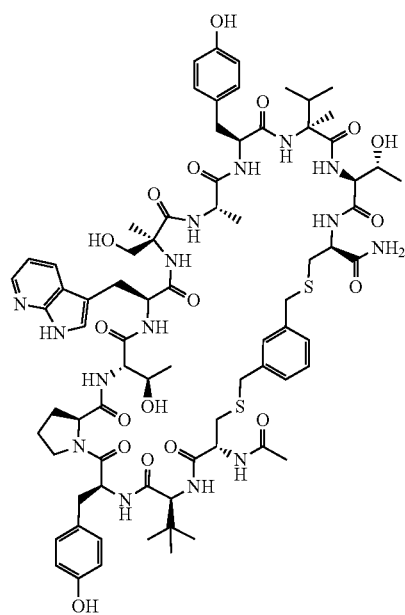 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)[C@](C)(CO)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]
031
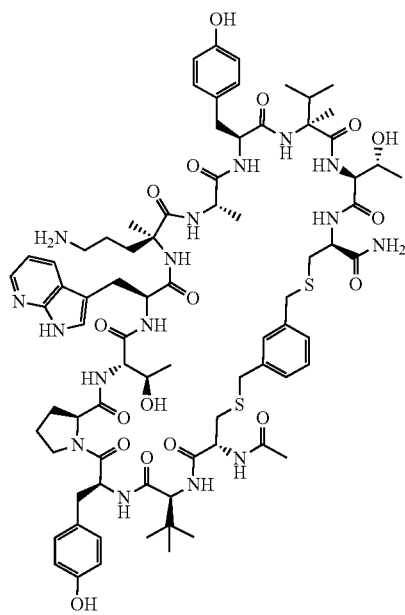 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)[C@](C)(CCCN)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]
033

TABLE 1-continued
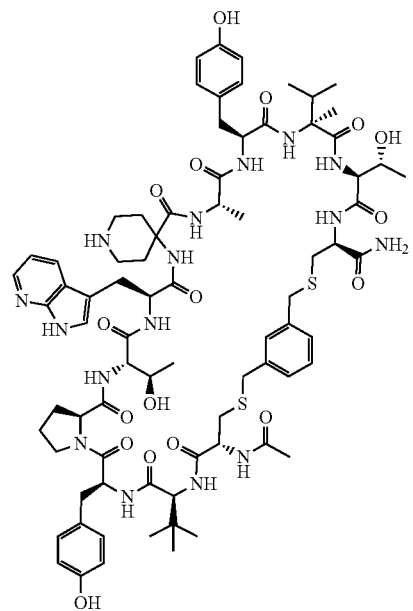 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C2(CCNCC2)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]
034
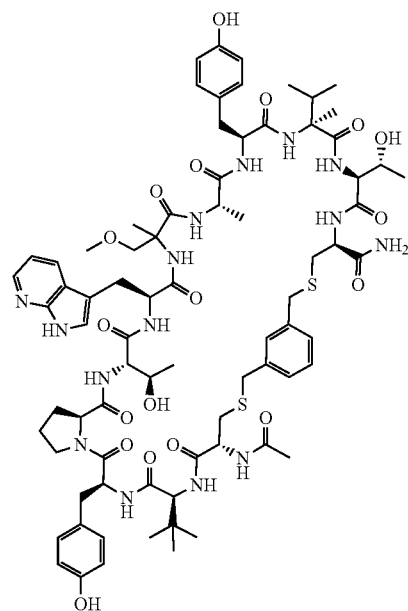 [SMILES: COCC1(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)[C@@H](NC(C)=O)CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC1=O]
035

TABLE 1-continued
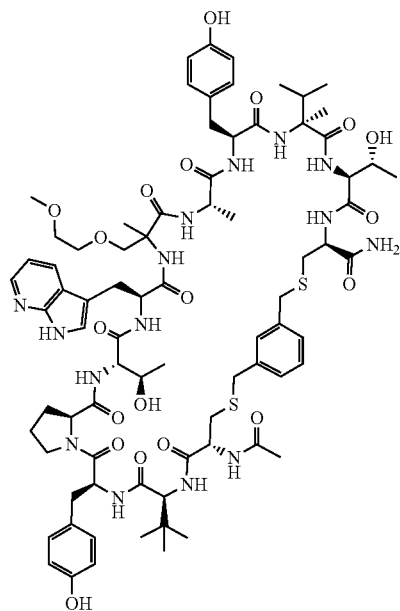 [SMILES: COCCOCC1(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)[C@@H](NC(C)=O)CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC1=O]
036
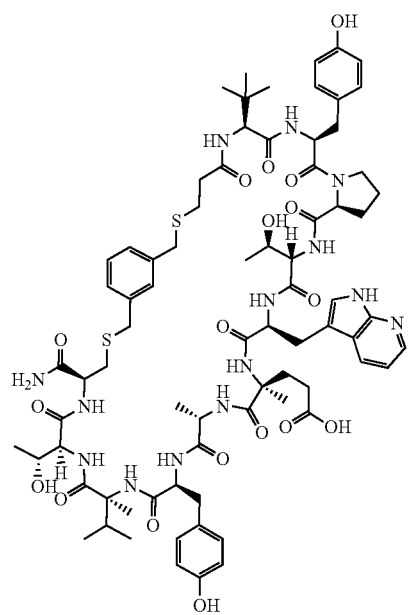 [SMILES: CC(C)[C@]1(C)NC(=O)[C@H](Cc2ccc(O)cc2)NC(=O)[C@H](C)NC(=O)[C@](C)(CCC(=O)O)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@H](C(N)=O)NC(=O)[C@H]([C@@H](C)O)NC1=O]
037

TABLE 1-continued
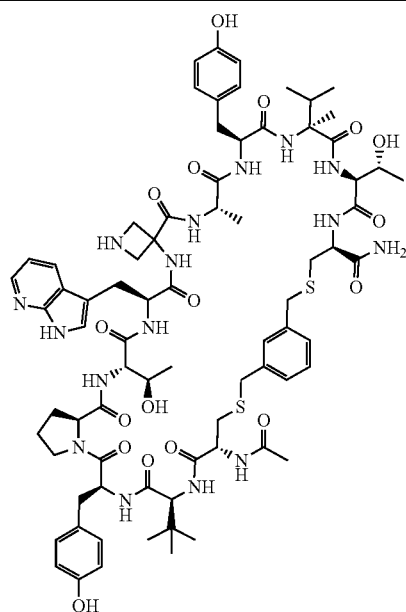
038
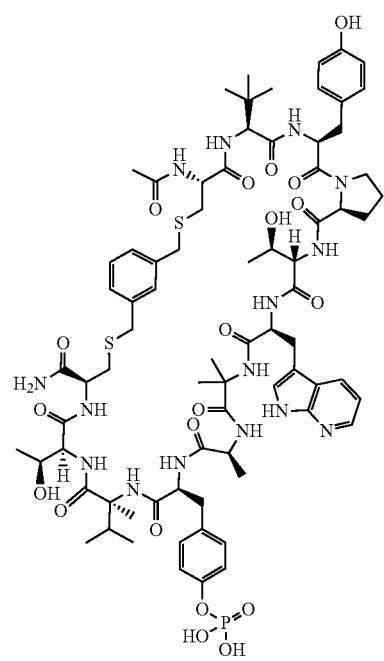 [SMILES: CC(=O)N[C@H]1CSCc2cccc(c2)CSC[C@H](C(N)=O)NC(=O)[C@H]([C@H](C)O)NC(=O)[C@](C)(C(C)C)NC(=O)[C@H](Cc2ccc(OP(=O)(O)O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]
039

In another aspect, provided herein are cyclic peptides having the structure of Formula (II):

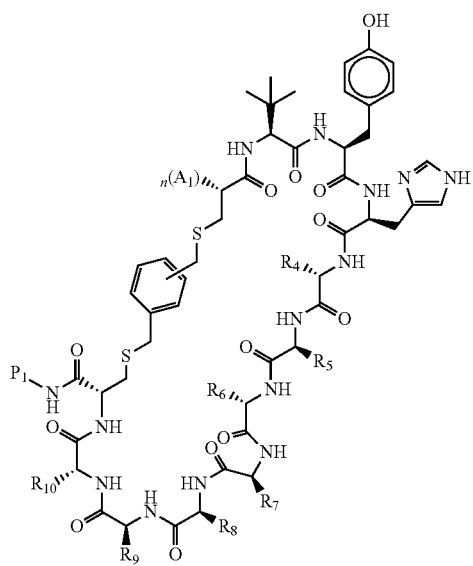

(II)

or a pharmaceutically acceptable salt thereof;
wherein:
$A_1$ is an acyl or sulfonyl protected amino acid selected from the group consisting of NVA, UPPA, GUF, GMF, and HARG, or is an acyl protected amine;

$R_4$ is THR;
$R_5$ is selected from the group consisting of the amino acid side chains of 7AW, BPA, 3QA, GUF, NA3, and BTPA;
$R_6$ is selected from the group consisting of the amino acid side chains of NVA, LEU, CHA, GLU, ALA, HSE, LYS, and AHHA;
$R_7$ is selected from the group consisting of the amino acid side chains of GLU and NVA;
$R_3$ is selected from the group consisting of the amino acid side chains of TYR and MTY;
$R_9$ is selected from the group consisting of the amino acid side chains of CHG, NVA, TYR, HSE, AMP, and 23B;
$R_{10}$ is selected from the group consisting of the amino acid side chains of THR, F2MA, and HSE;
$P_1$ is H, methyl, an acetyl group, or

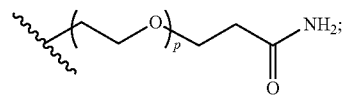

n is 0 or 1
p is 2, 3, 4, 5, or 6;
wherein each amino acid residue is optionally an N-methylated amino acid; and
wherein each amino acid residue can be in the R or S configuration.

In an embodiment, the compound of Formula (II), or a pharmaceutically acceptable salt thereof, is selected from the following compounds of Table 2 below:

TABLE 2

043

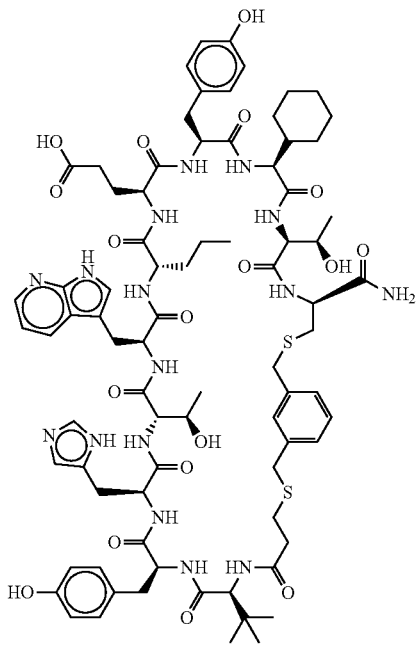

TABLE 2-continued
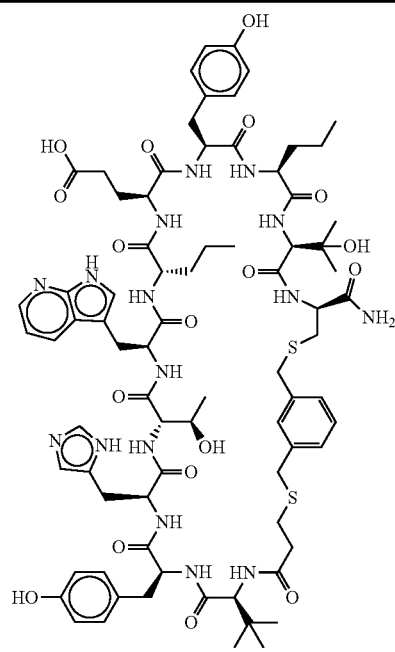
044
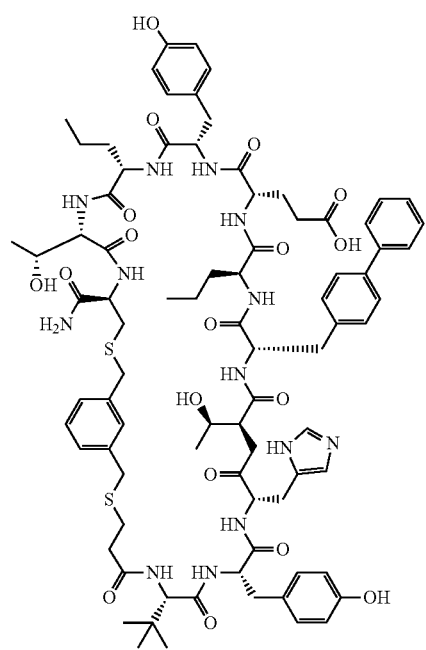 [SMILES: CCC[C@@H]1NC(=O)[C@H](Cc2ccc(-c3ccccc3)cc2)NC(=O)[C@H]([C@@H](C)O)CC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
051

TABLE 2-continued
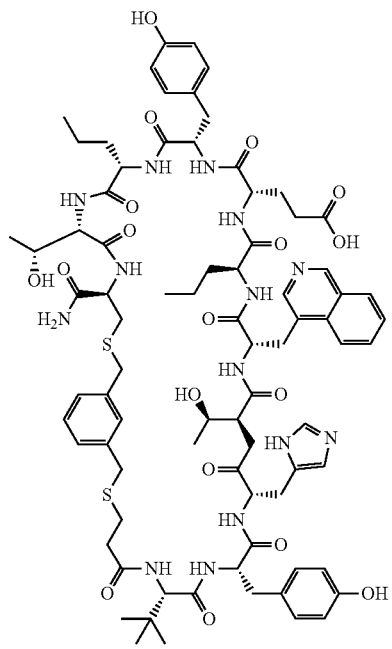 [SMILES: CCC[C@@H]1NC(=O)[C@H](Cc2cncc3ccccc23)NC(=O)[C@H]([C@@H](C)O)CC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
052
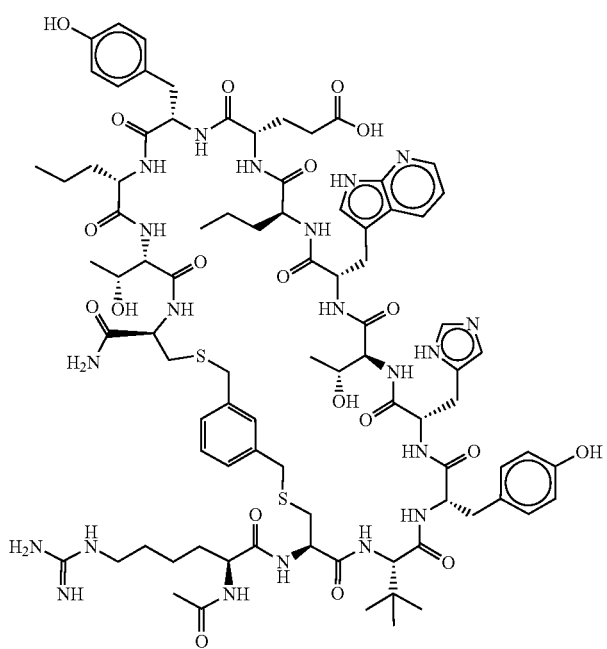
054

TABLE 2-continued
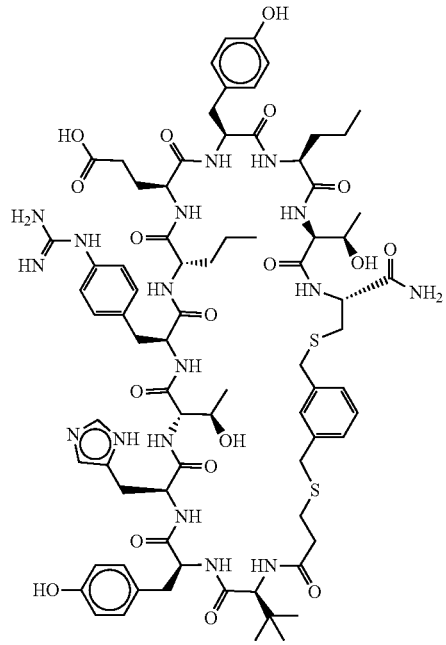
055
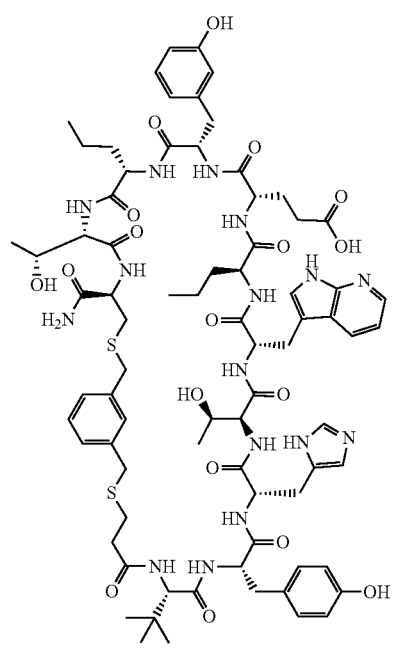 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2cccc(O)c2)NC(=O)[C@H](CCC(=O)O)NC1=O]
070

TABLE 2-continued
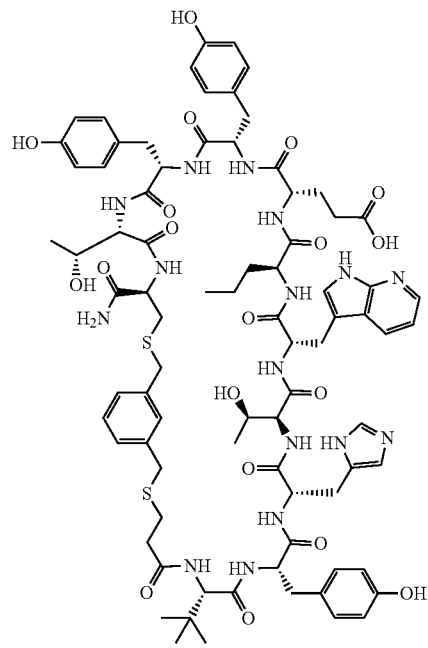 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](Cc2ccc(O)cc2)NC(=O)[C@H](Cc2ccc(O)cc2)NC(=O)[C@H](CCC(=O)O)NC1=O]
071
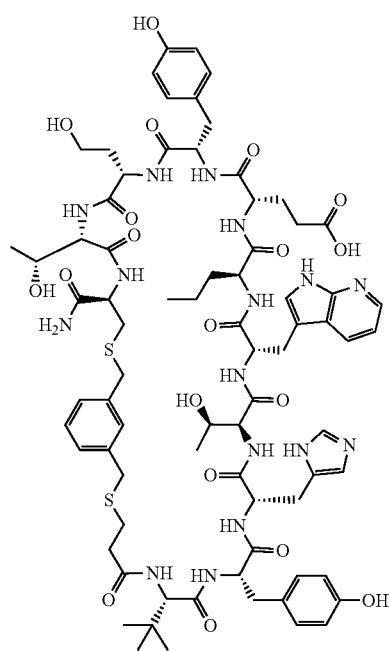 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCO)NC(=O)[C@H](Cc2ccc(O)cc2)NC(=O)[C@H](CCC(=O)O)NC1=O]
072

TABLE 2-continued
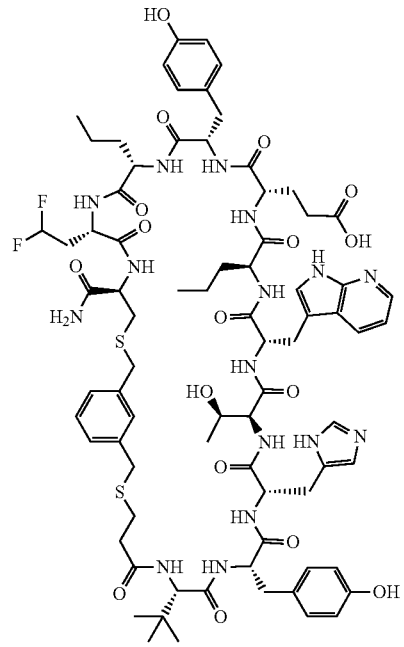 [SMILES: CCC[C@@H]1NC(=O)[C@H](Cc2ccc(O)cc2)NC(=O)[C@H](CCC(=O)O)NC(=O)[C@H](CCC)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CC(F)F)NC1=O]
073
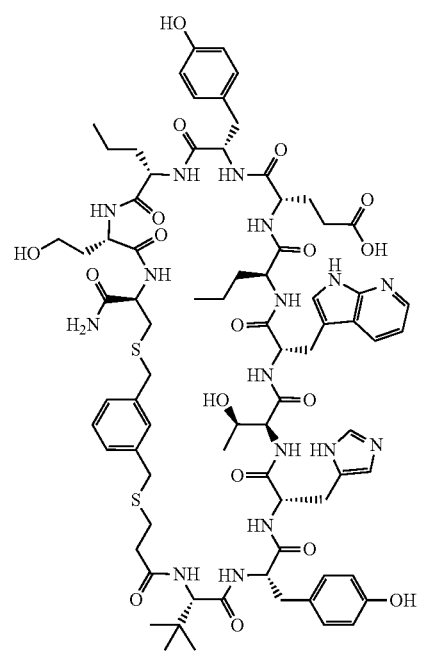 [SMILES: CCC[C@@H]1NC(=O)[C@H](Cc2ccc(O)cc2)NC(=O)[C@H](CCC(=O)O)NC(=O)[C@H](CCC)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CCO)NC1=O]
074

TABLE 2-continued
075
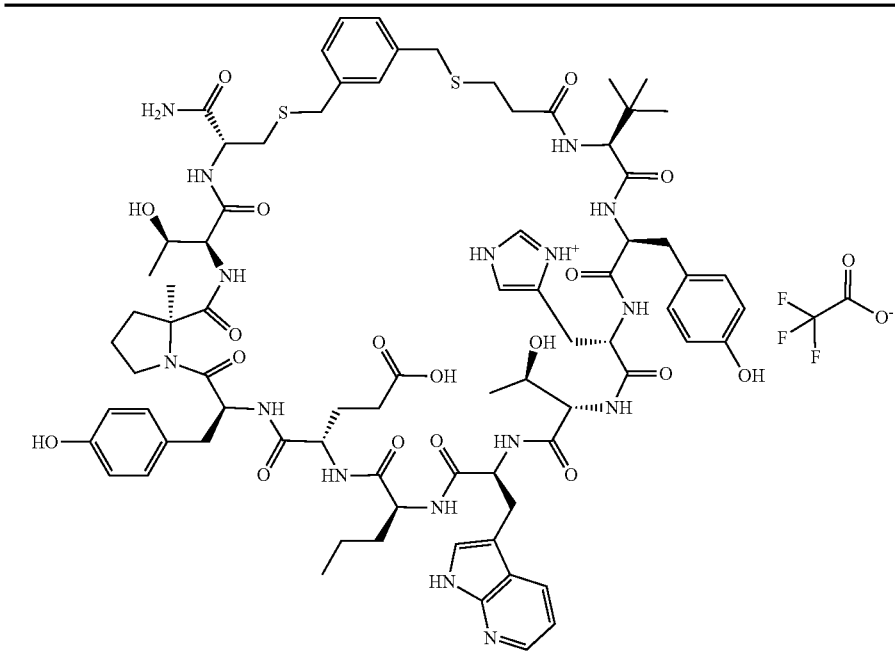
078
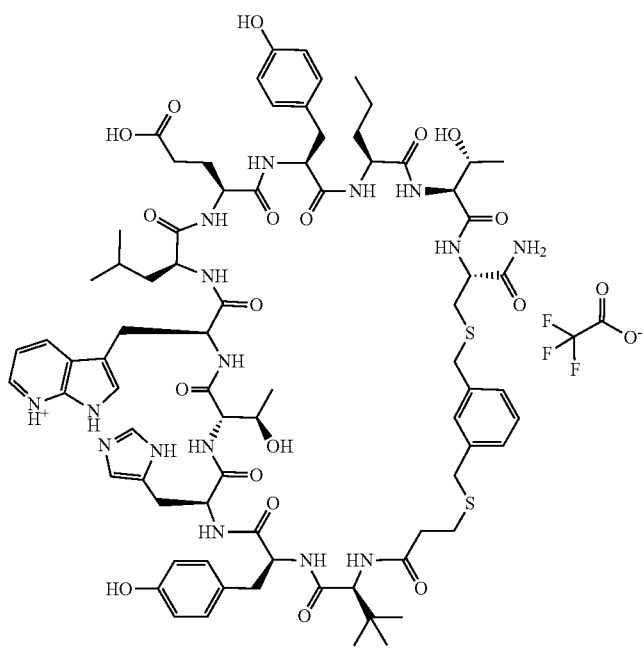 [SMILES: CCC[C@@H]1NC(=O)[C@H](Cc2ccc(O)cc2)NC(=O)[C@H](CCC(=O)O)NC(=O)[C@H](CC(C)C)NC(=O)[C@H](Cc2c[nH]c3[nH+]cccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O ; O=C([O-])C(F)(F)F]

TABLE 2-continued
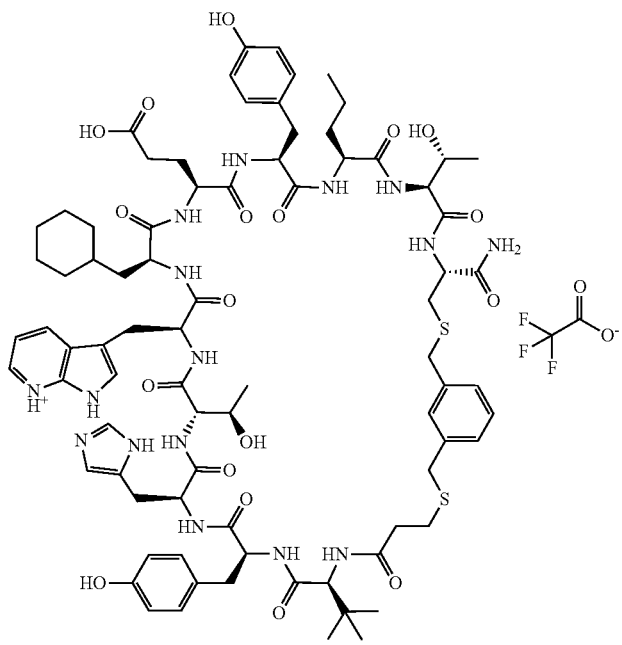 [SMILES: CCC[C@@H]1NC(=O)[C@H](Cc2ccc(O)cc2)NC(=O)[C@H](CCC(=O)O)NC(=O)[C@H](CC2CCCCC2)NC(=O)[C@H](Cc2c[nH]c3[nH+]cccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O ; O=C([O-])C(F)(F)F]
079
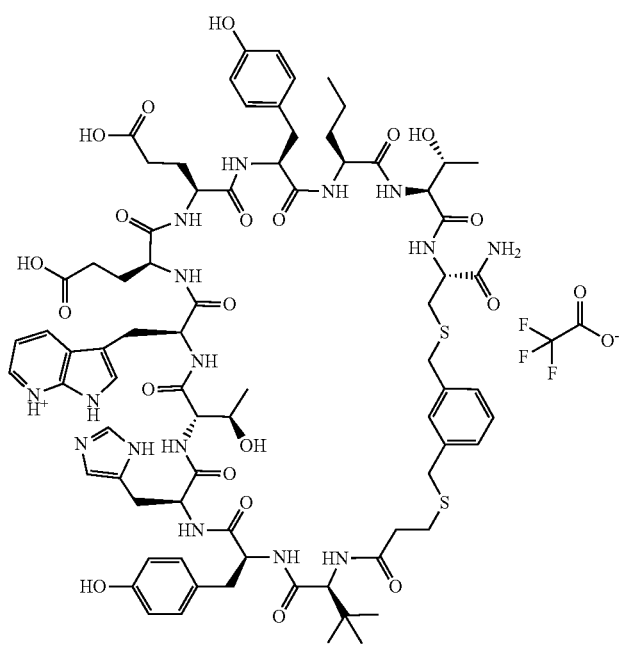 [SMILES: CCC[C@@H]1NC(=O)[C@H](Cc2ccc(O)cc2)NC(=O)[C@H](CCC(=O)O)NC(=O)[C@H](CCC(=O)O)NC(=O)[C@H](Cc2c[nH]c3[nH+]cccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O ; O=C([O-])C(F)(F)F]
080

TABLE 2-continued
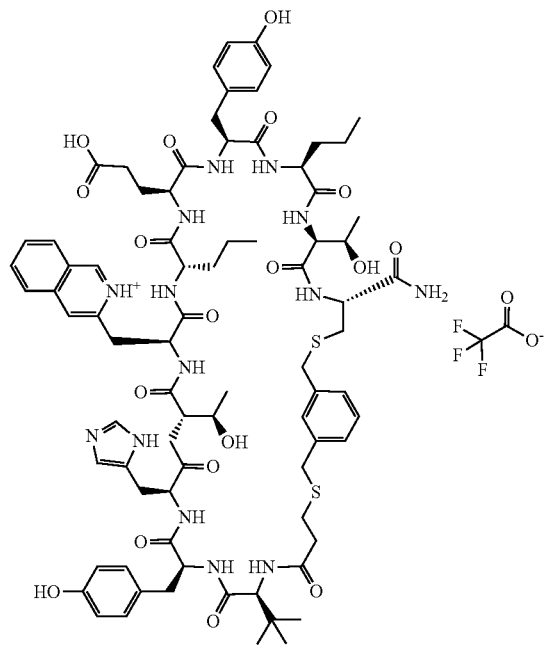 [SMILES: CCC[C@@H]1NC(=O)[C@H](Cc2cc3ccccc3c[nH+]2)NC(=O)[C@H]([C@@H](C)O)CC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O ; O=C([O-])C(F)(F)F]
081
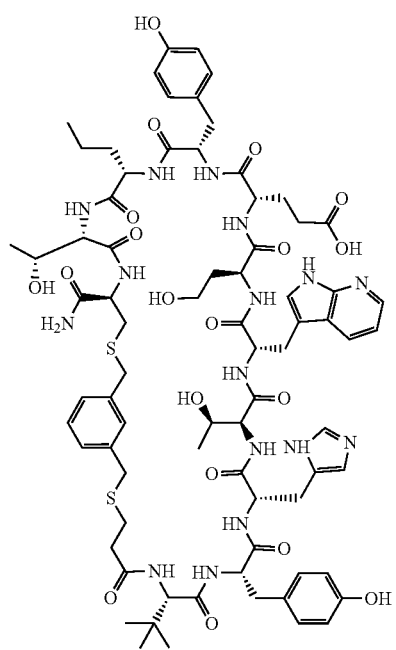 [SMILES: CCC[C@@H]1NC(=O)[C@H](Cc2ccc(O)cc2)NC(=O)[C@H](CCC(=O)O)NC(=O)[C@H](CCO)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]
083

TABLE 2-continued
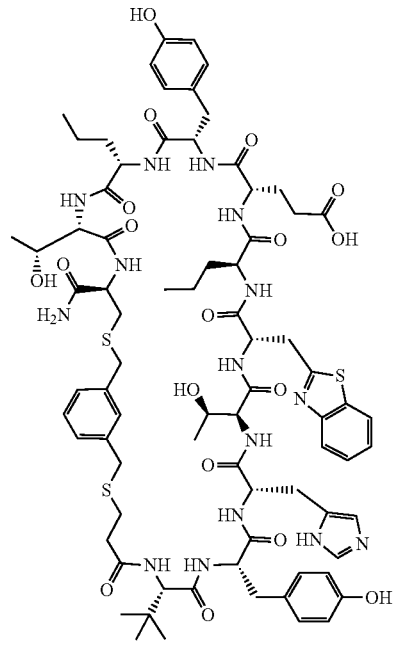 [SMILES: CCC[C@@H]1NC(=O)[C@H](Cc2nc3ccccc3s2)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
084
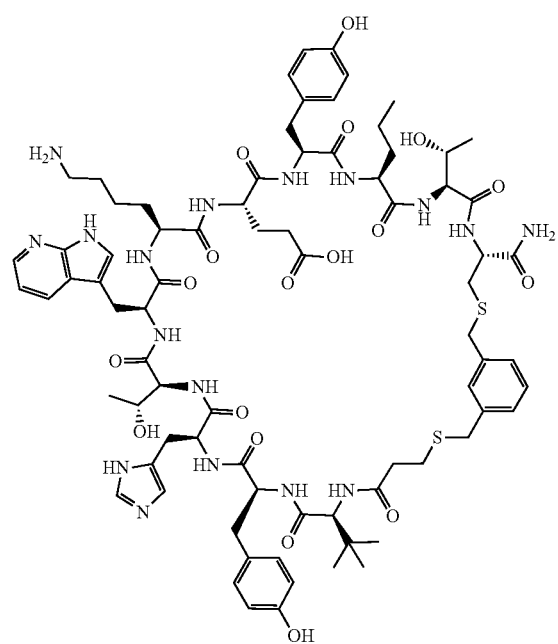 [SMILES: CCC[C@@H]1NC(=O)[C@H](Cc2ccc(O)cc2)NC(=O)[C@H](CCC(=O)O)NC(=O)[C@H](CCCCN)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]
085

TABLE 2-continued
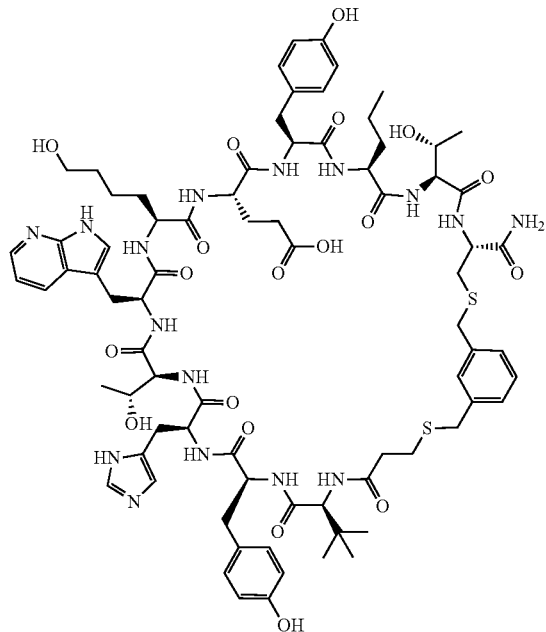 [SMILES: CCC[C@@H]1NC(=O)[C@H](Cc2ccc(O)cc2)NC(=O)[C@H](CCC(=O)O)NC(=O)[C@H](CCCCO)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]
088
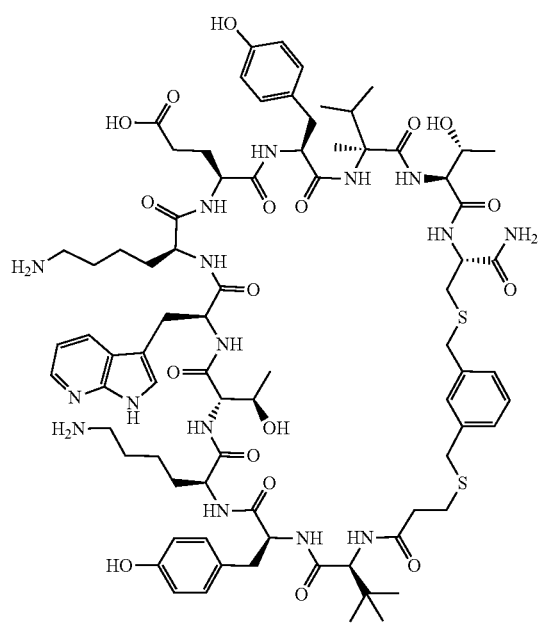 [SMILES: CC(C)[C@]1(C)NC(=O)[C@H](Cc2ccc(O)cc2)NC(=O)[C@H](CCC(=O)O)NC(=O)[C@H](CCCCN)NC(=O)[C@H](Cc2c[nH]c3ncccc23)NC(=O)[C@H]([C@@H](C)O)NC(=O)[C@H](CCCCN)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]
089

TABLE 2-continued
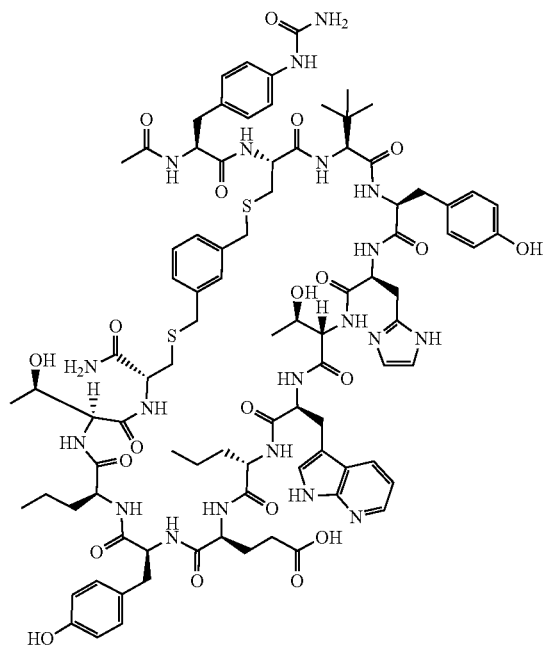 [SMILES: CCC[C@@H]1NC(=O)[C@H](Cc2c[nH]c3ncccc23)NC(=O)[C@H]([C@@H](C)O)NC(=O)[C@H](Cc2ncc[nH]2)NC(=O)[C@H](Cc2ccc(O)cc2)NC(=O)[C@H](C(C)(C)C)NC(=O)[C@@H](NC(=O)[C@H](Cc2ccc(NC(N)=O)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
096
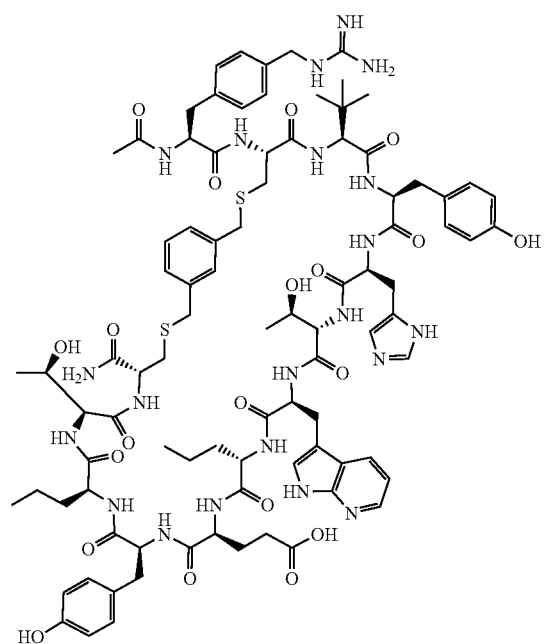 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)[C@@H](NC(=O)[C@H](Cc2ccc(CNC(=N)N)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
098

TABLE 2-continued

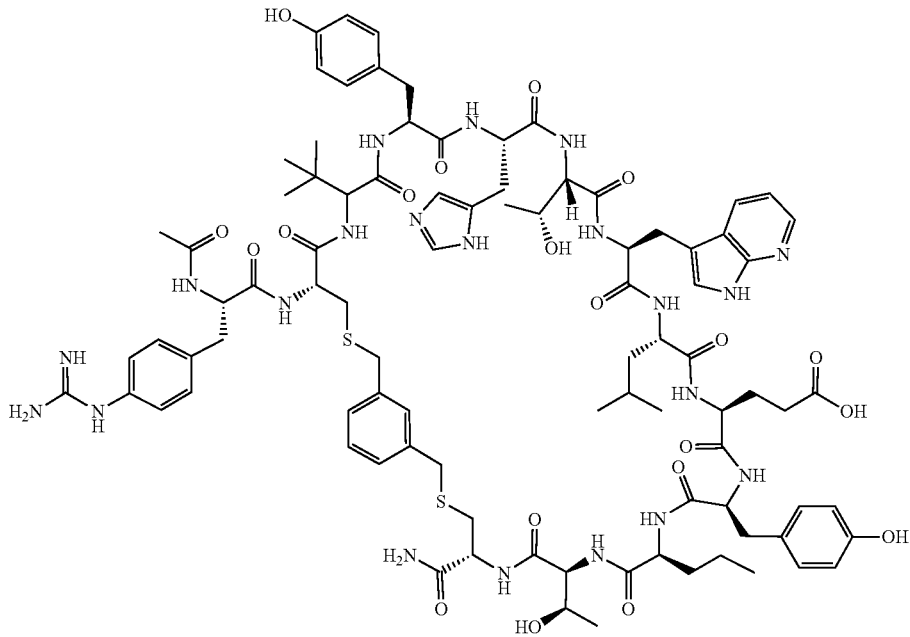 [SMILES: CCC[C@@H]1NC(=O)[C@H](Cc2ccc(O)cc2)NC(=O)[C@H](CCC(=O)O)NC(=O)[C@H](CC(C)C)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)C(C(C)(C)C)NC(=O)[C@@H](NC(=O)[C@H](Cc2ccc(NC(=N)N)cc2)NC(C)=O)CSCc2cccc(c2)CSC[C@@H](C(N)=O)NC(=O)[C@H]([C@@H](C)O)NC1=O]

099

In another aspect, provided herein are cyclic peptides having the structure of Formula (III):

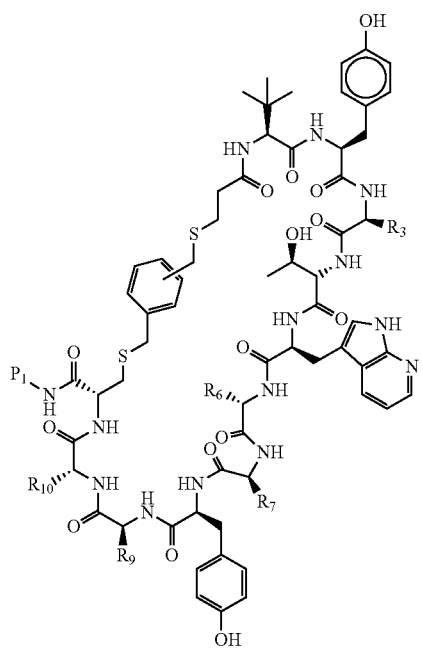

(III)

or a pharmaceutically acceptable salt thereof;
wherein:
R₃ is selected from the group consisting of the amino acid side chains of PRO and HIS;
R₆ is selected from the group consisting of the amino acid side chains of NVA and AIB;
R₇ is selected from the group consisting of the amino acid side chains of ALA and GLU or is covalently bound to R₃ by a linking moiety;
R₉ is selected from the group consisting of the amino acid side chains of NVA, AIB, 23B, and CHG;
R₁₀ is the amino acid side chain of THR;
wherein each amino acid residue is optionally an N-methylated amino acid;
wherein each amino acid residue can be in the R or S configuration; and
provided either R₃ and R₇, or R₆ and R₁₀ are covalently bound by a linking moiety selected from the group consisting of

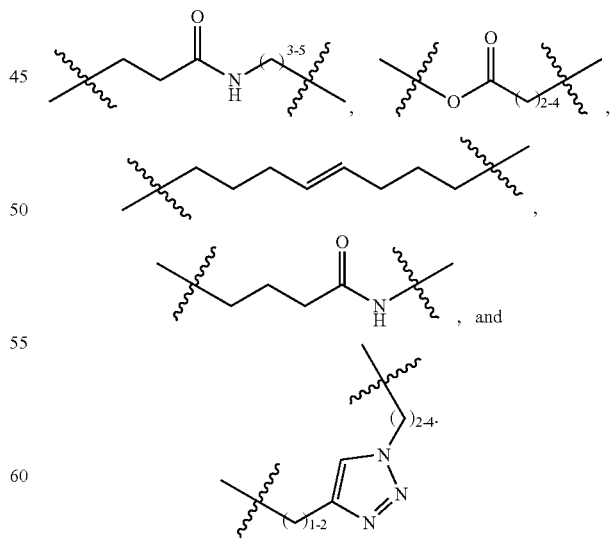

In an embodiment of Formula (III), R₃ and R₇, or R₆ and R₁₀ are covalently bound by a linking moiety selected from the group consisting of

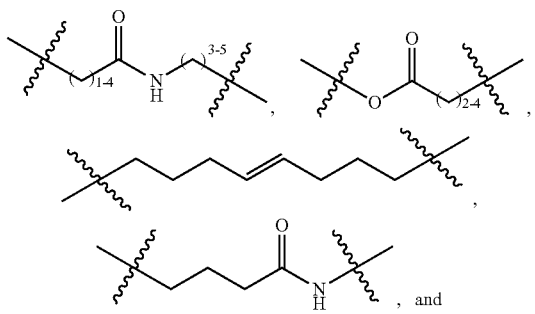
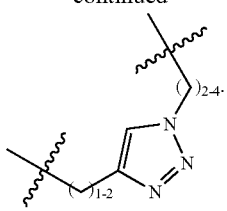
In an embodiment, the compound of Formula (III), or a pharmaceutically acceptable salt thereof, is selected from the following compounds of Table 3 below:
TABLE 3
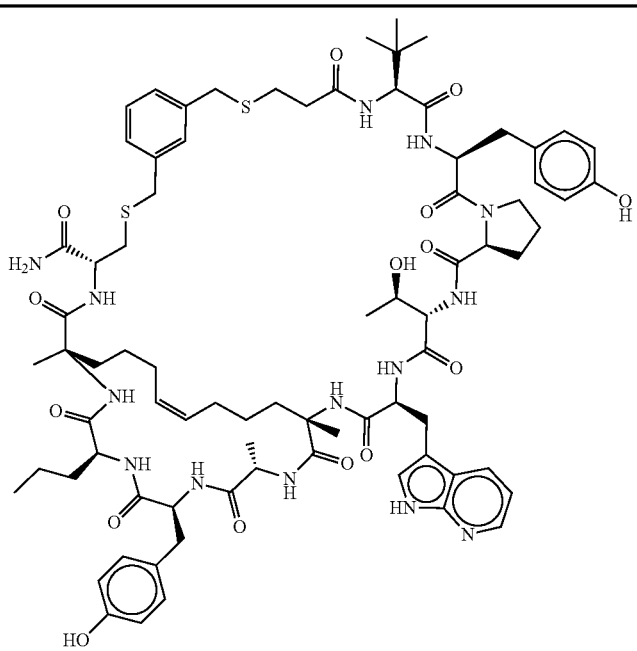
101
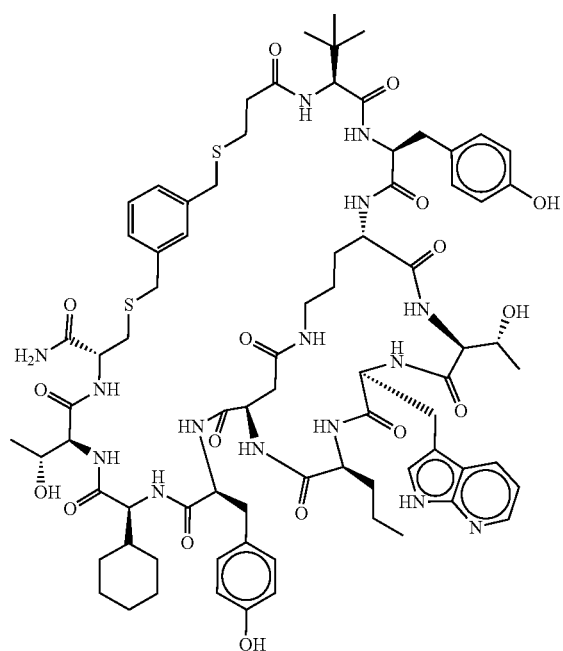
106

TABLE 3-continued
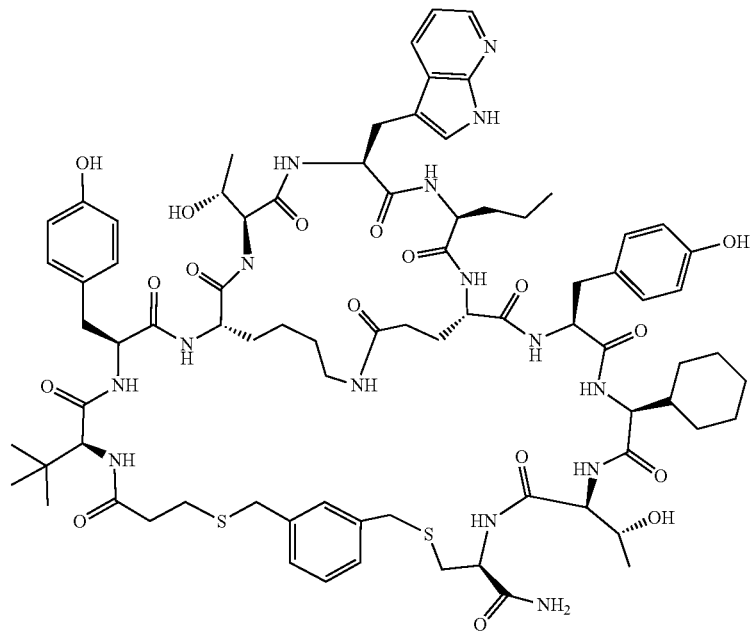
107
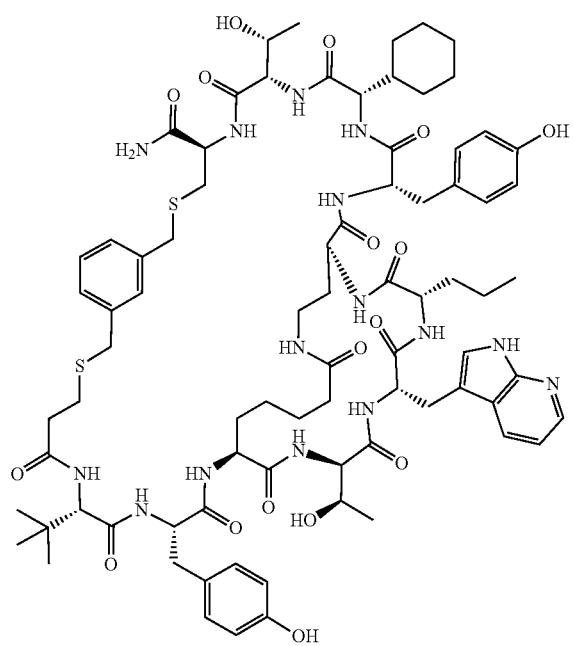 [SMILES: CCC[C@@H]1NC(=O)[C@H](Cc2c[nH]c3ncccc23)NC(=O)[C@@H]([C@@H](C)O)NC(=O)[C@@H]2CCCCC(=O)NCC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@H](C(N)=O)CSCc1cccc(c1)CSCCC(=O)N[C@@H](C(C)(C)C)C(=O)N[C@@H](Cc1ccc(O)cc1)C(=O)N2]
108

TABLE 3-continued
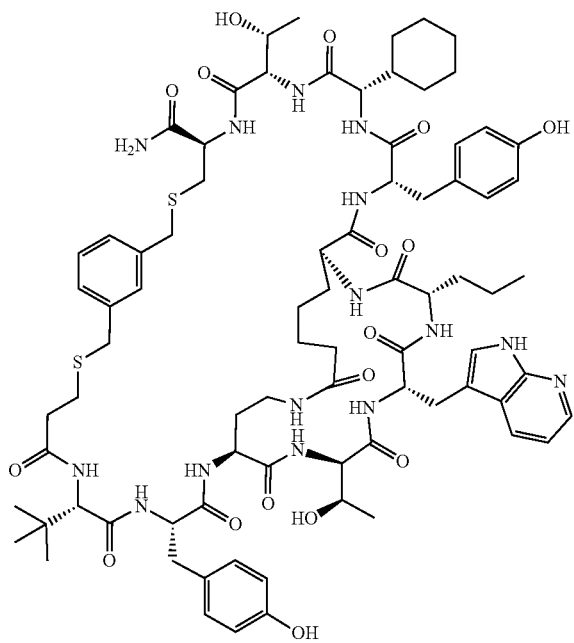 [SMILES: CCC[C@@H]1NC(=O)[C@H](Cc2c[nH]c3ncccc23)NC(=O)[C@@H]([C@@H](C)O)NC(=O)[C@@H]2CCNC(=O)CCCC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@H](C(N)=O)CSCc1cccc(c1)CSCCC(=O)N[C@@H](C(C)(C)C)C(=O)N[C@@H](Cc1ccc(O)cc1)C(=O)N2]
109
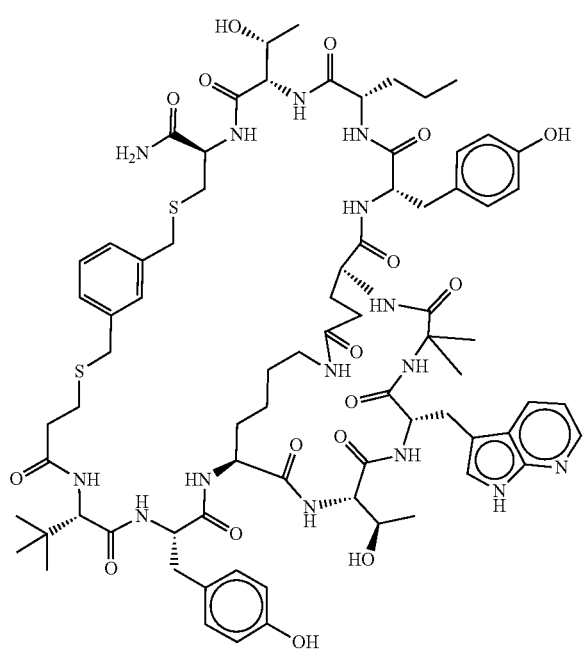
110

TABLE 3-continued
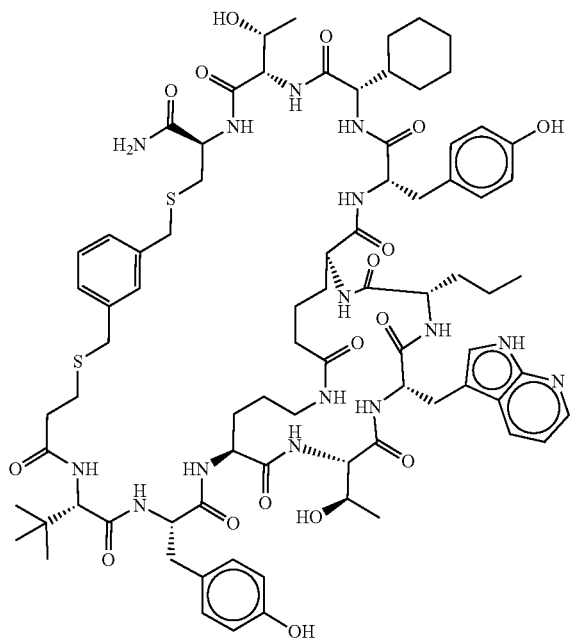
111
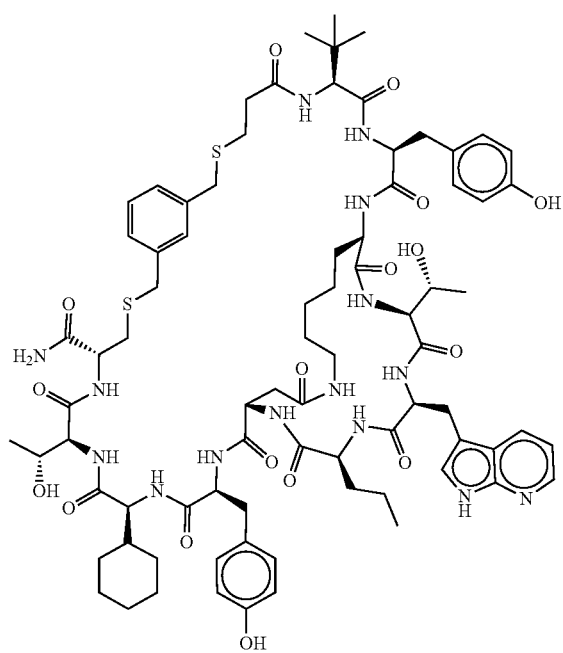
112

TABLE 3-continued
114
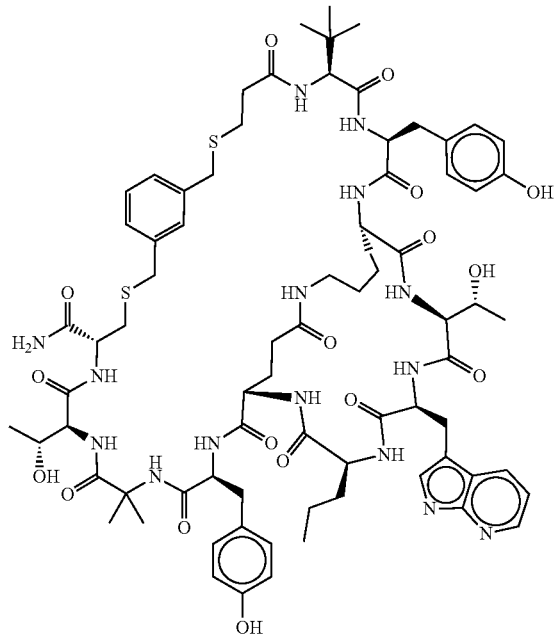
115
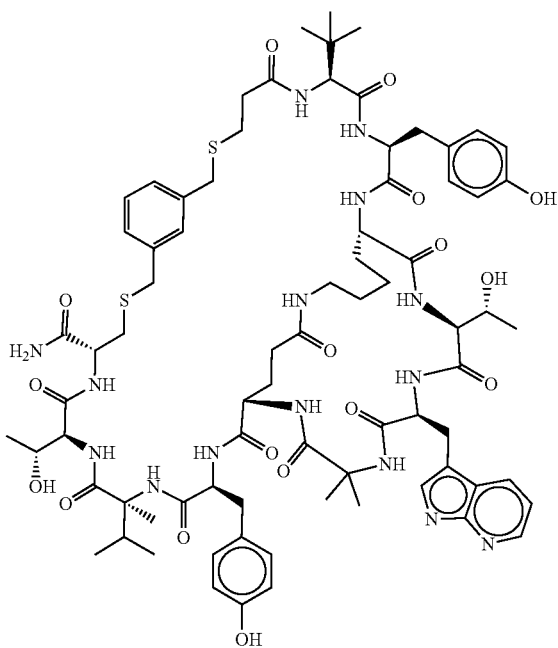

TABLE 3-continued
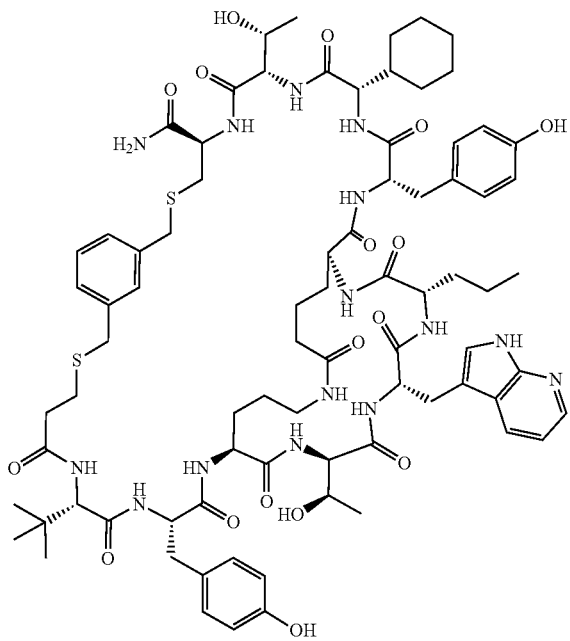 [SMILES: CCC[C@@H]1NC(=O)[C@H](Cc2c[nH]c3ncccc23)NC(=O)[C@@H]([C@@H](C)O)NC(=O)[C@@H]2CCCNC(=O)CCC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@H](C(N)=O)CSCc1cccc(c1)CSCCC(=O)N[C@@H](C(C)(C)C)C(=O)N[C@@H](Cc1ccc(O)cc1)C(=O)N2]
118
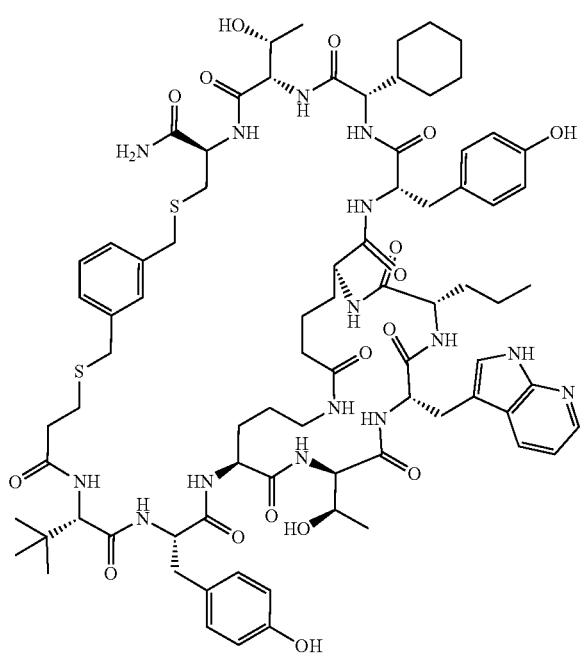 [SMILES: CCC[C@@H]1NC(=O)[C@H](Cc2c[nH]c3ncccc23)NC(=O)[C@@H]([C@@H](C)O)NC(=O)[C@@H]2CCCNC(=O)CCC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@H](C(N)=O)CSCc1cccc(c1)CSCCC(=O)N[C@@H](C(C)(C)C)C(=O)N[C@@H](Cc1ccc(O)cc1)C(=O)N2]
119

TABLE 3-continued
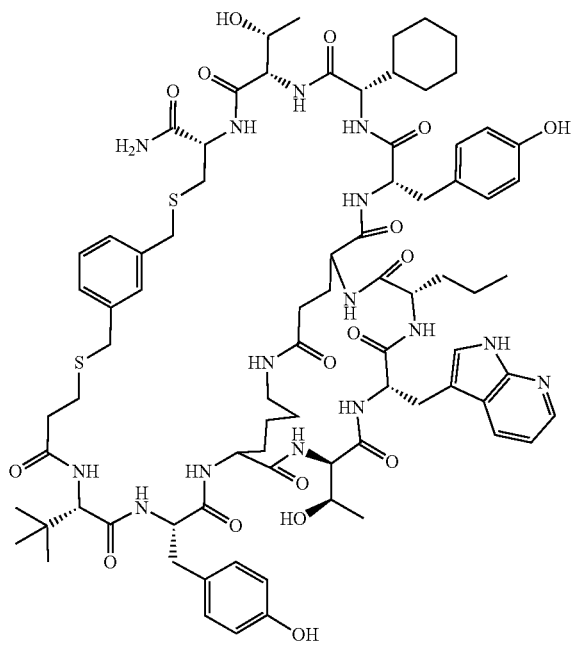 [SMILES: CCC[C@@H]1NC(=O)[C@H](Cc2c[nH]c3ncccc23)NC(=O)[C@@H]([C@@H](C)O)NC(=O)C2CCCCNC(=O)CCC(NC1=O)C(=O)N[C@@H](Cc1ccc(O)cc1)C(=O)N[C@@H](C1CCCCC1)C(=O)N[C@@H]([C@@H](C)O)C(=O)N[C@@H](C(N)=O)CSCc1cccc(c1)CSCCC(=O)N[C@@H](C(C)(C)C)C(=O)N[C@@H](Cc1ccc(O)cc1)C(=O)N2]
120
In another aspect, the compounds of the invention are selected from the following compounds of Table 4, or a pharmaceutically acceptable salt thereof, below:
TABLE 4
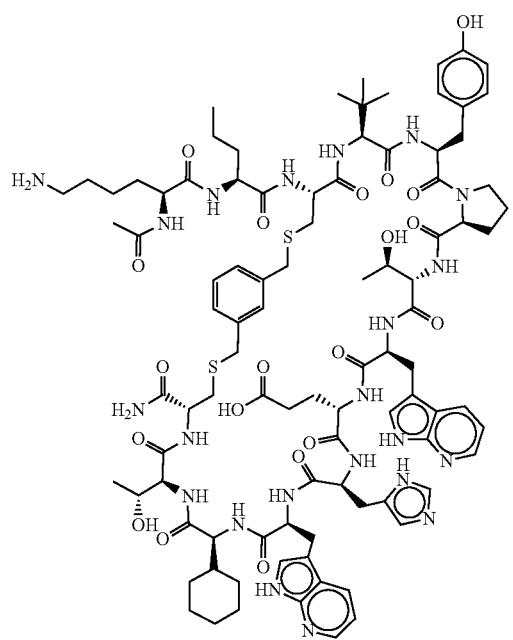
002

TABLE 4-continued
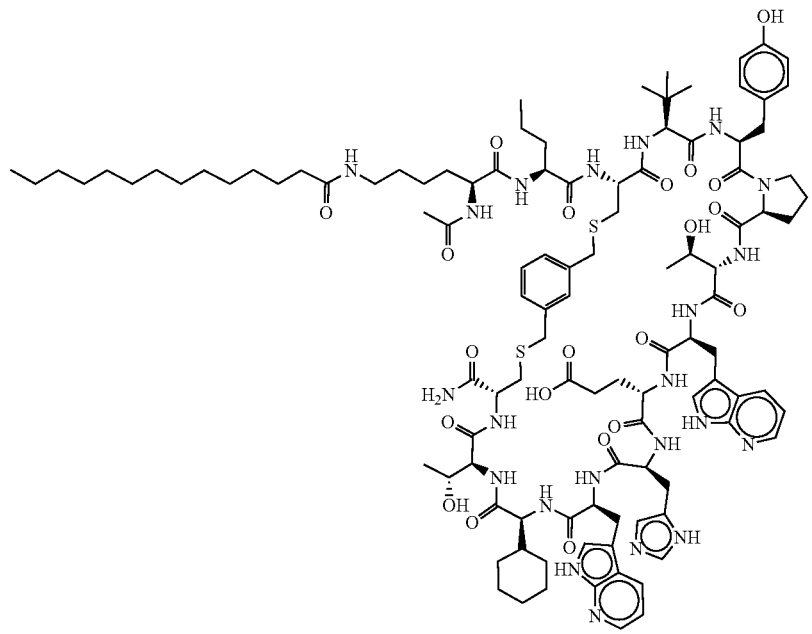
003
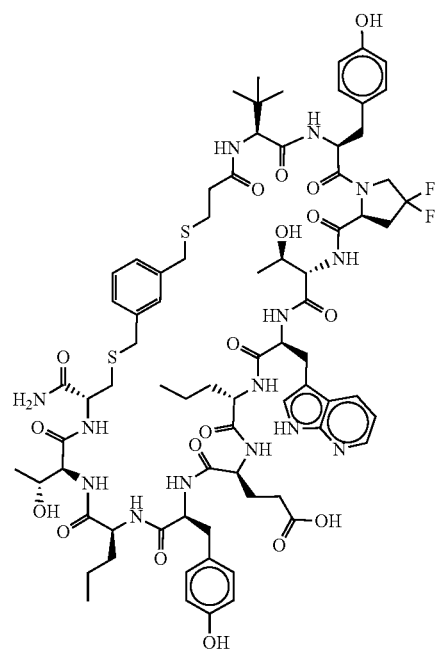
004

TABLE 4-continued
005
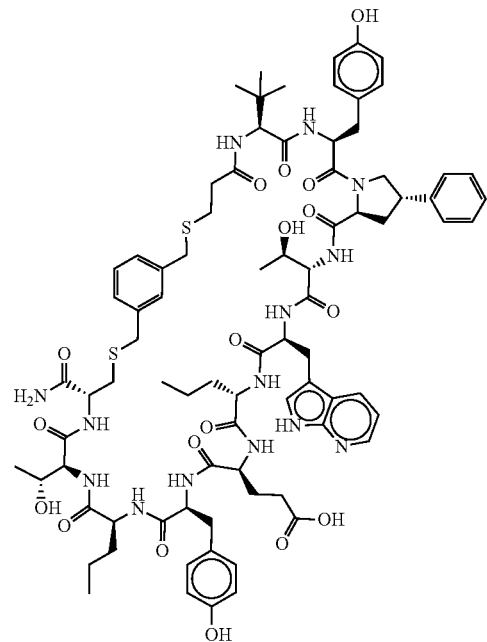
006
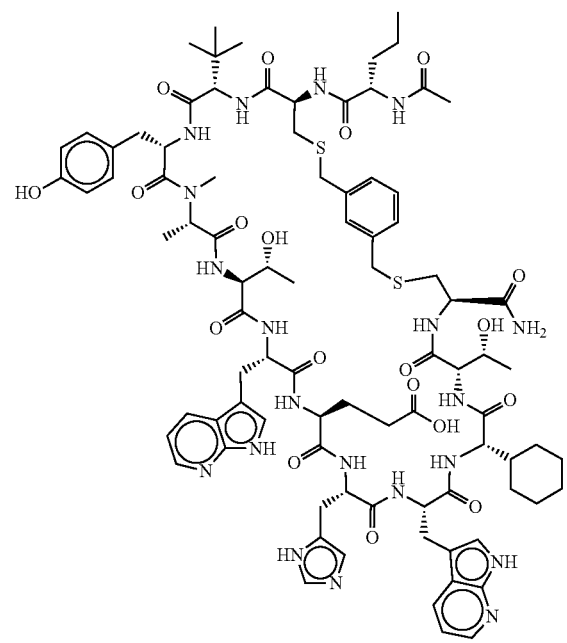

TABLE 4-continued
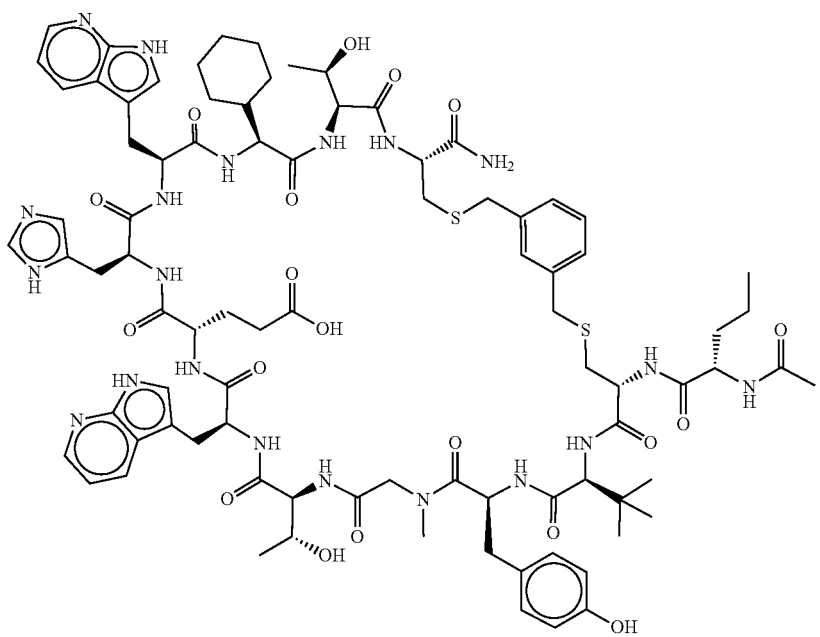
007
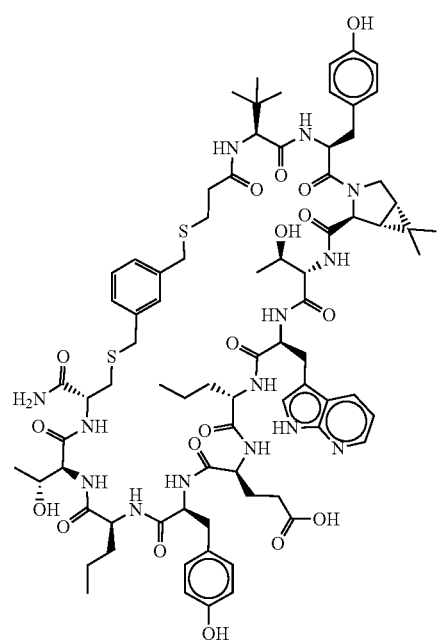
008

TABLE 4-continued
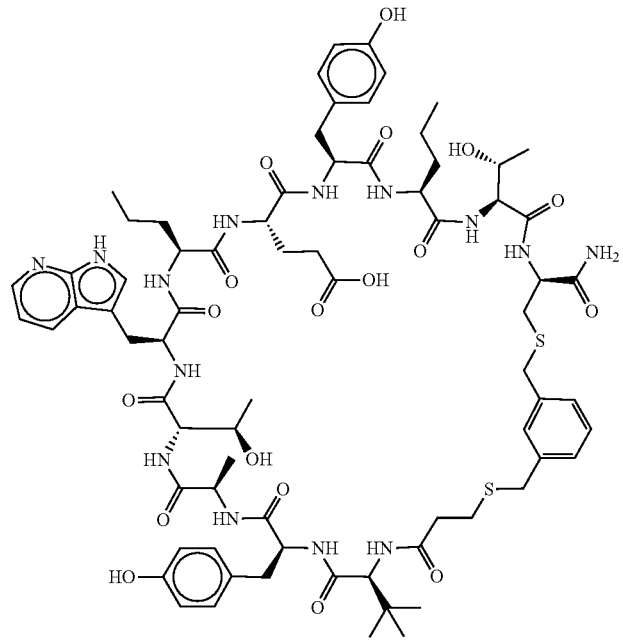
009
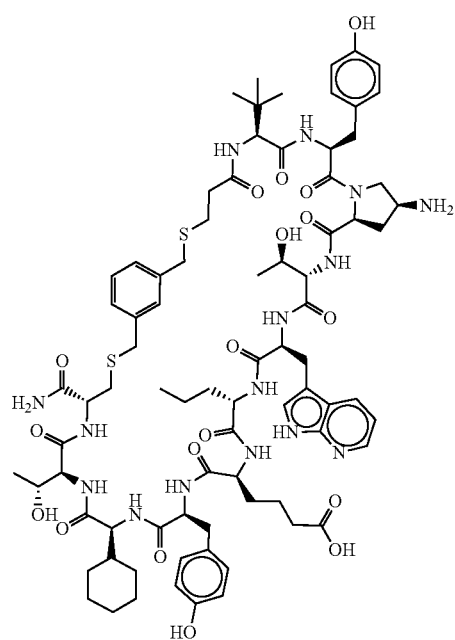
010

TABLE 4-continued
011
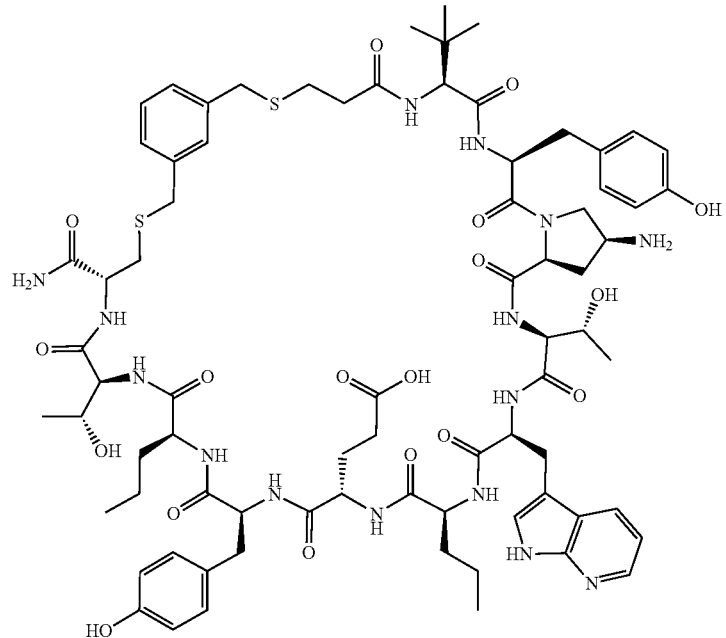 [SMILES: CCC[C@@H]1NC(=O)[C@H](Cc2c[nH]c3ncccc23)NC(=O)[C@H]([C@@H](C)O)NC(=O)[C@@H]2C[C@H](N)CN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
012
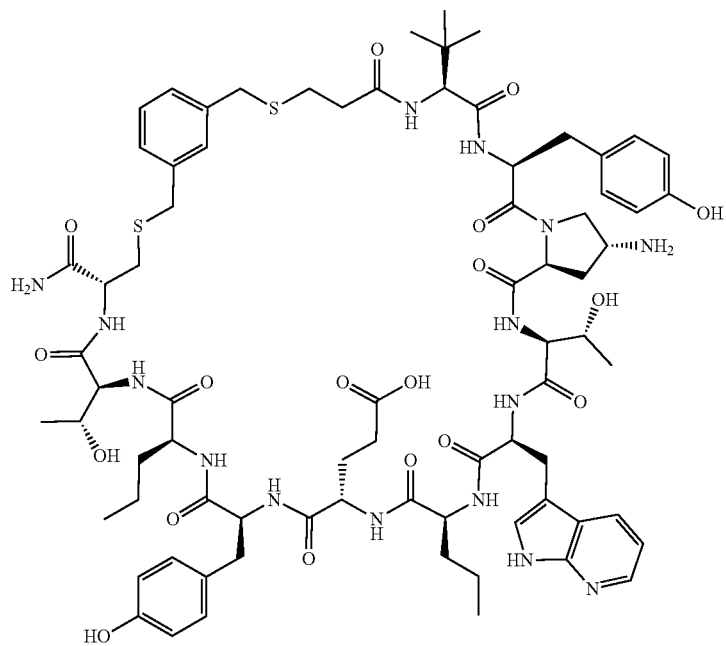 [SMILES: CCC[C@@H]1NC(=O)[C@H](Cc2c[nH]c3ncccc23)NC(=O)[C@H]([C@@H](C)O)NC(=O)[C@@H]2C[C@@H](N)CN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]

TABLE 4-continued
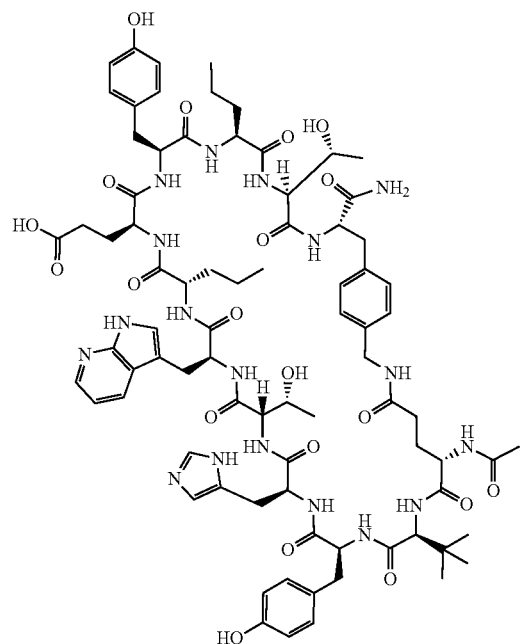 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)[C@@H](NC(C)=O)CCC(=O)NCc2ccc(cc2)C[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
013
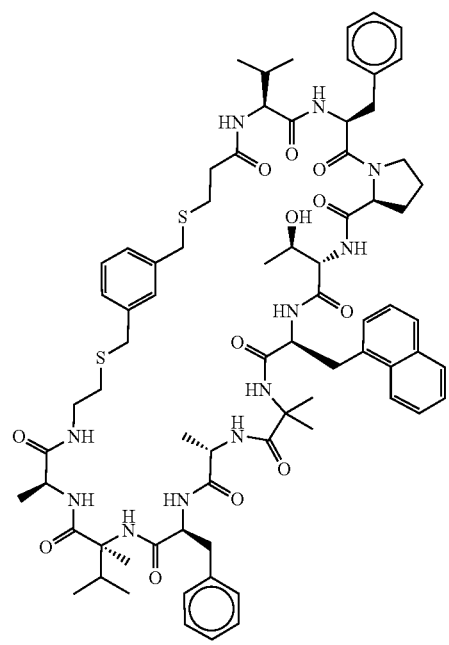
021

TABLE 4-continued
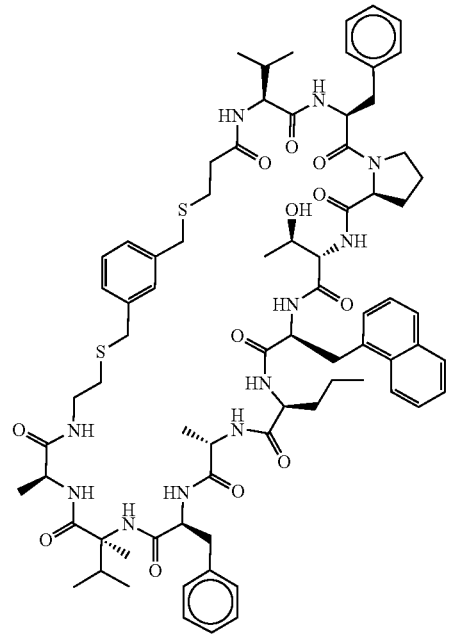
022
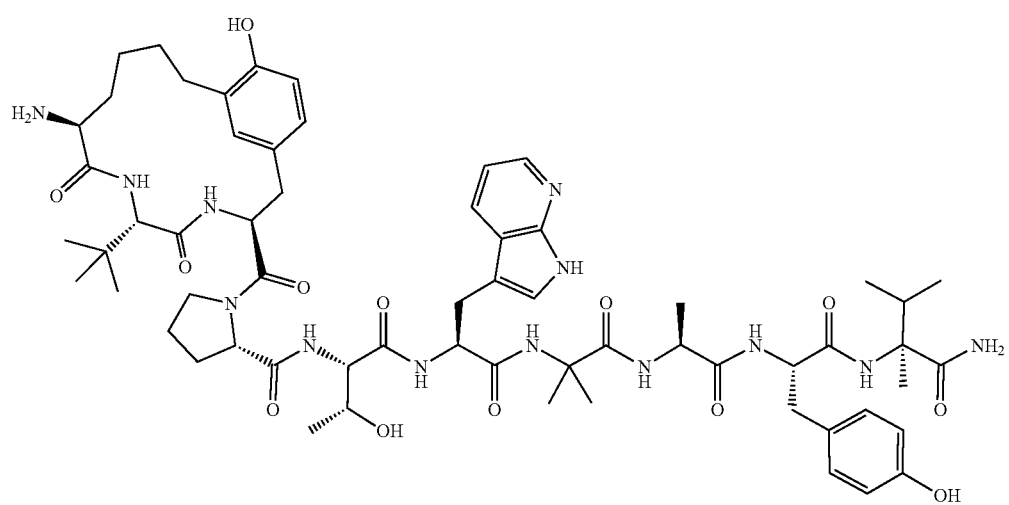 [SMILES: CC(C)[C@](C)(NC(=O)[C@H](Cc1ccc(O)cc1)NC(=O)[C@H](C)NC(=O)C(C)(C)NC(=O)[C@H](Cc1c[nH]c2ncccc12)NC(=O)[C@@H](NC(=O)[C@@H]1CCCN1C(=O)[C@@H]1Cc2ccc(O)c(c2)CCCC[C@H](N)C(=O)N[C@@H](C(C)(C)C)C(=O)N1)[C@@H](C)O)C(N)=O]
032

TABLE 4-continued
040
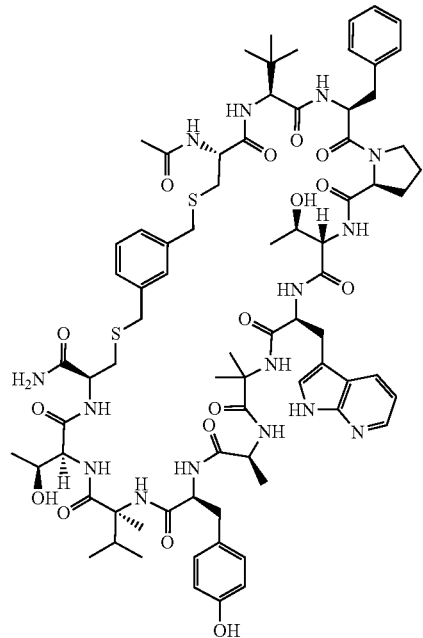 [SMILES: CC(=O)N[C@H]1CSCc2cccc(c2)CSC[C@H](C(N)=O)NC(=O)[C@H]([C@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccccc2)NC(=O)[C@H](C(C)(C)C)NC1=O]
041
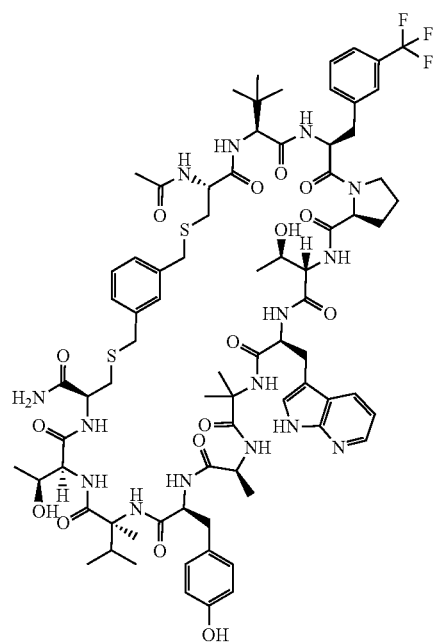 [SMILES: CC(=O)N[C@H]1CSCc2cccc(c2)CSC[C@H](C(N)=O)NC(=O)[C@H]([C@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2cccc(C(F)(F)F)c2)NC(=O)[C@H](C(C)(C)C)NC1=O]

TABLE 4-continued
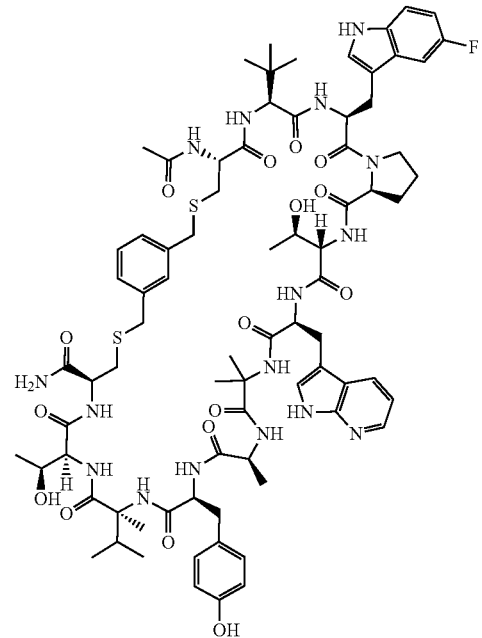 [SMILES: CC(=O)N[C@H]1CSCc2cccc(c2)CSC[C@H](C(N)=O)NC(=O)[C@H]([C@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2c[nH]c3ccc(F)cc23)NC(=O)[C@H](C(C)(C)C)NC1=O]
042
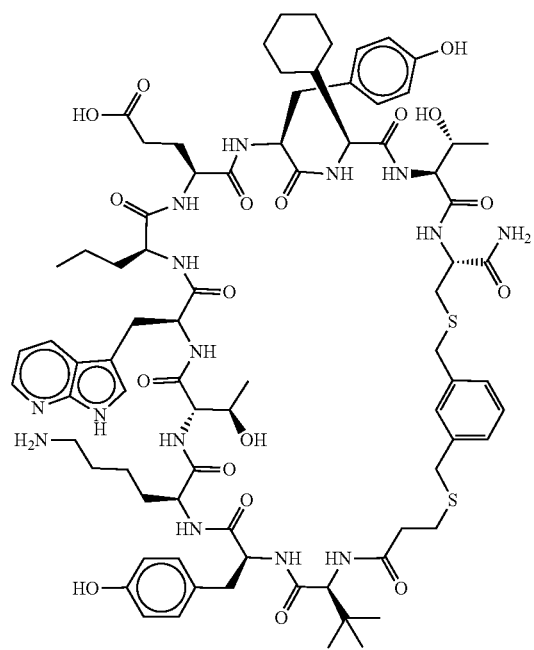
046

TABLE 4-continued
047
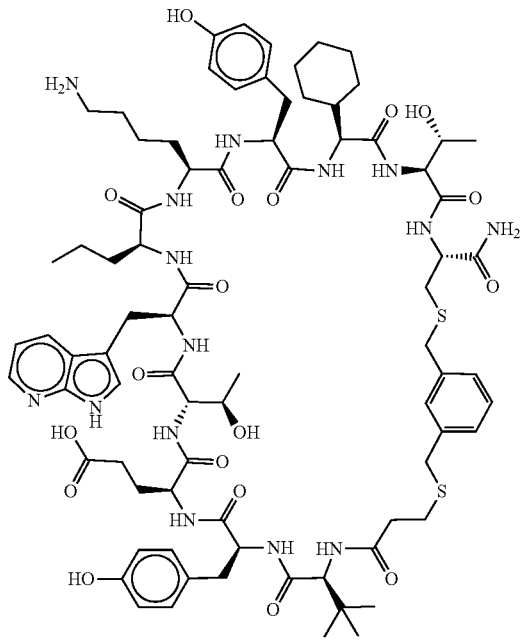
048
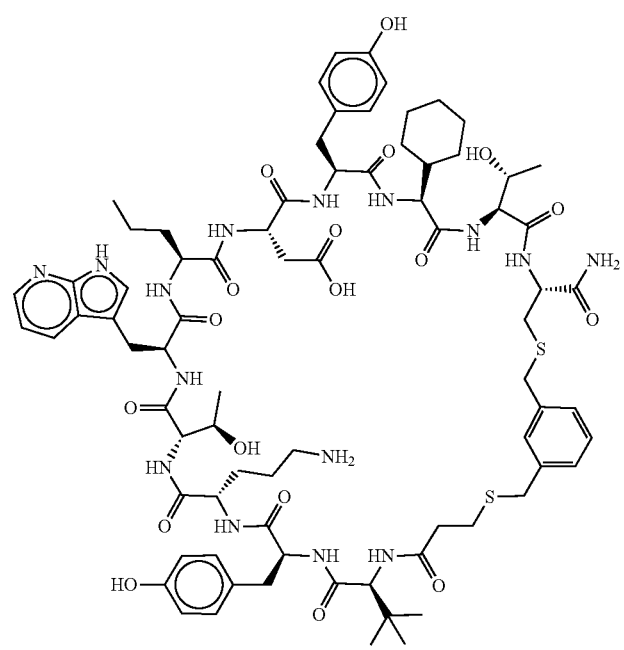

TABLE 4-continued
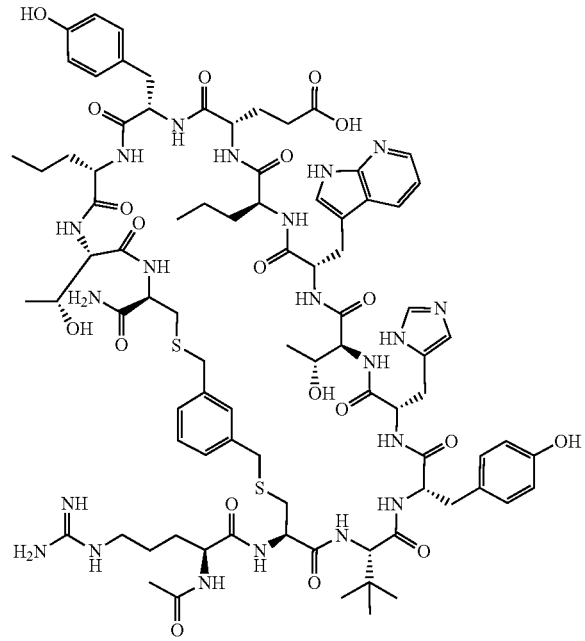 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)[C@@H](NC(=O)[C@H](CCCNC(=N)N)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
050
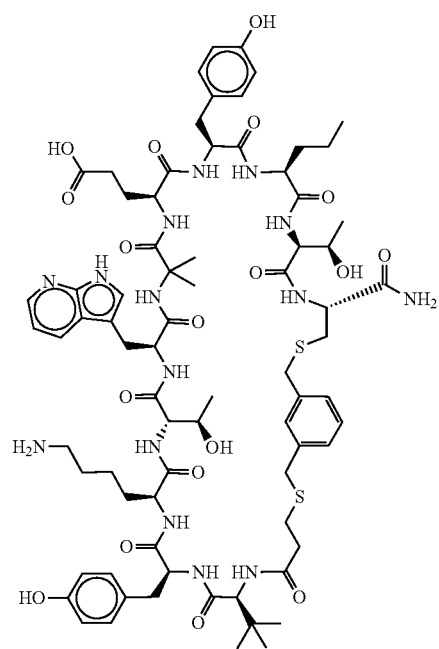
053

TABLE 4-continued
056
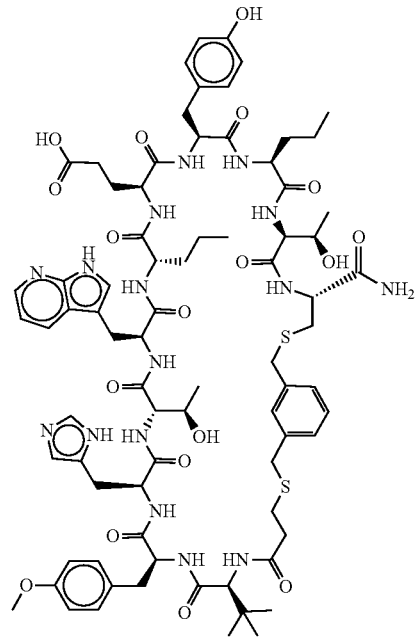
057
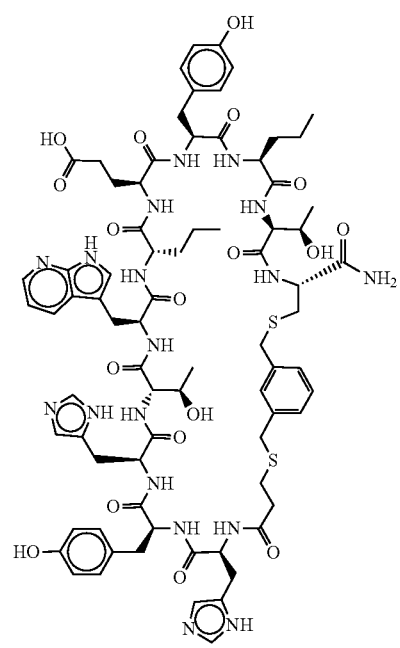

TABLE 4-continued
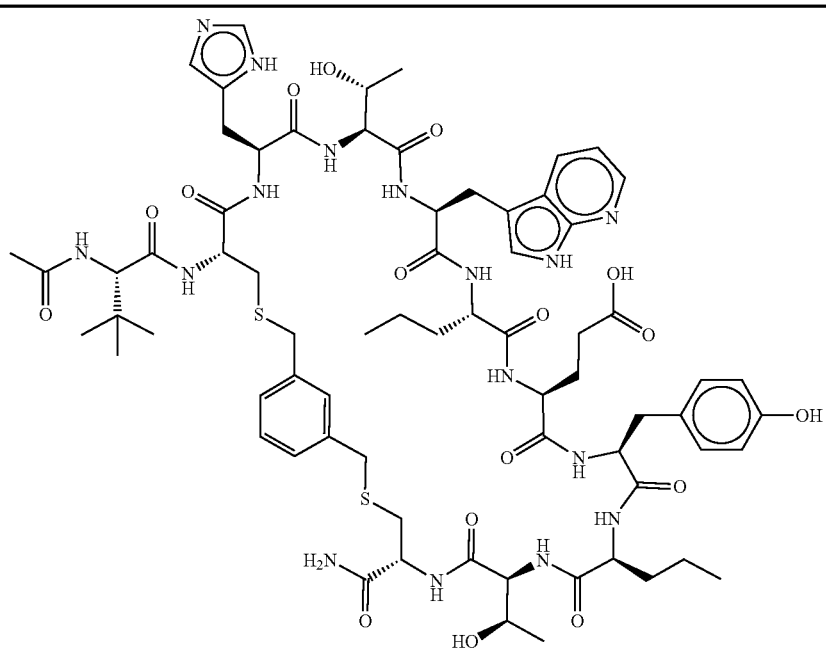
058
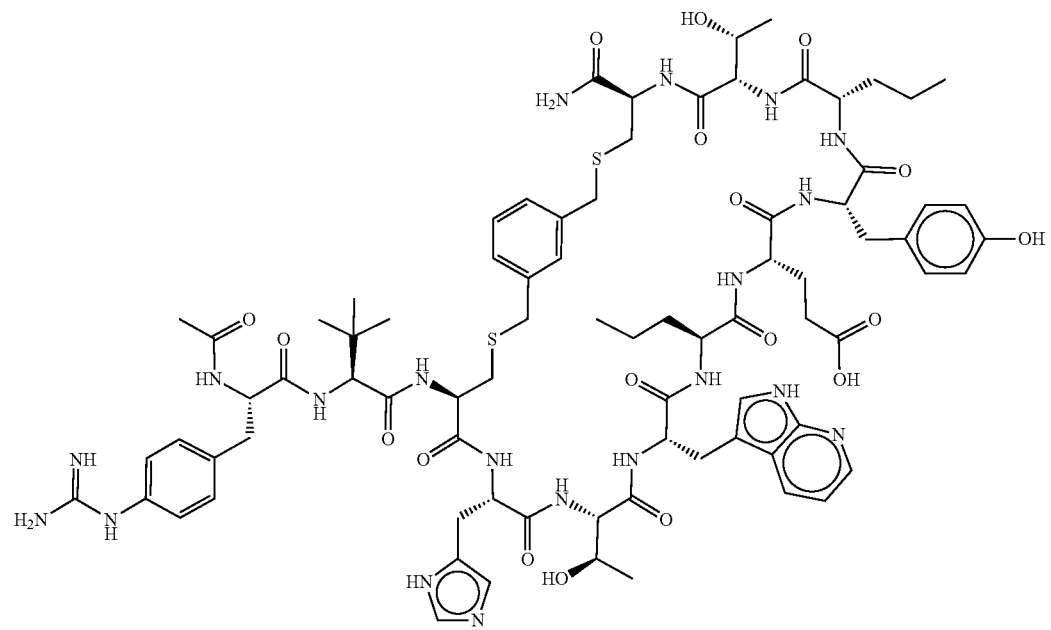
059

TABLE 4-continued
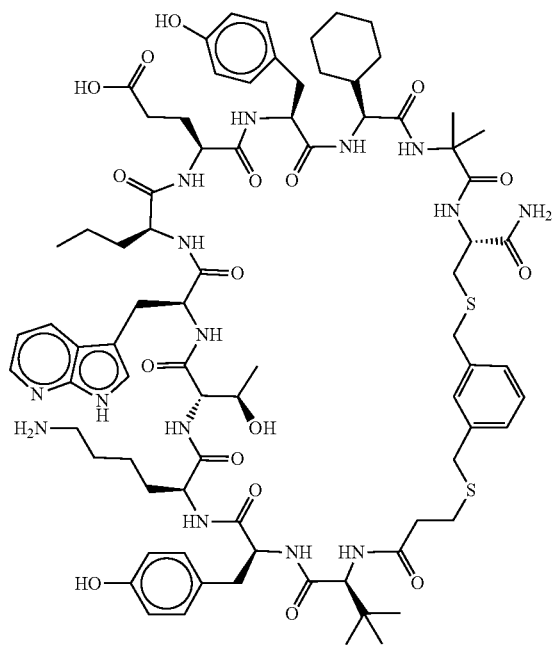
060
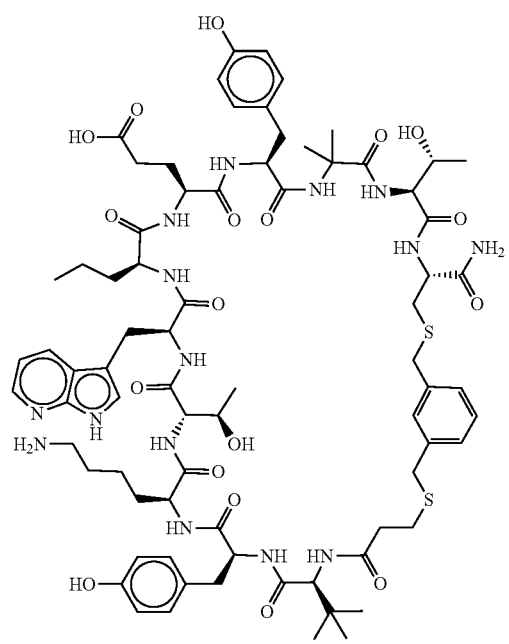
061

TABLE 4-continued
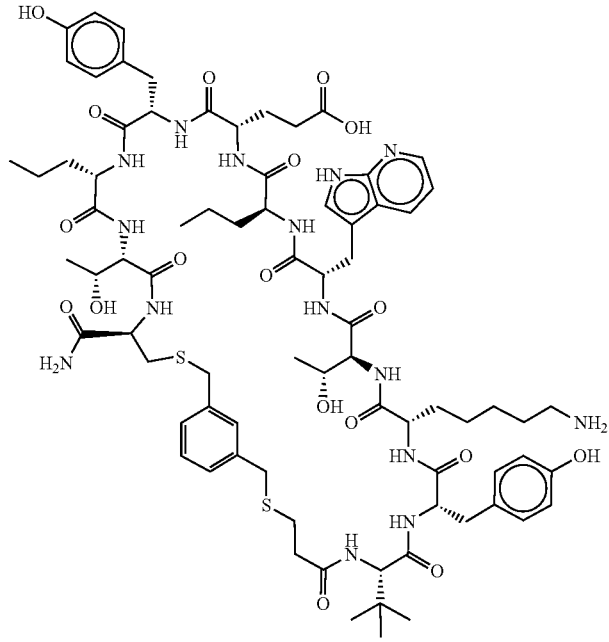
062
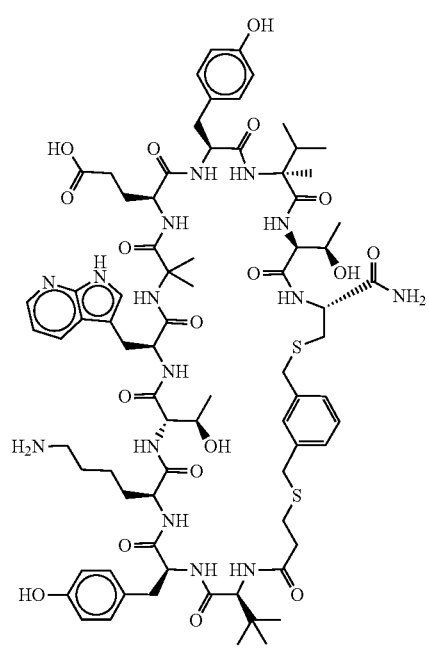
063

TABLE 4-continued
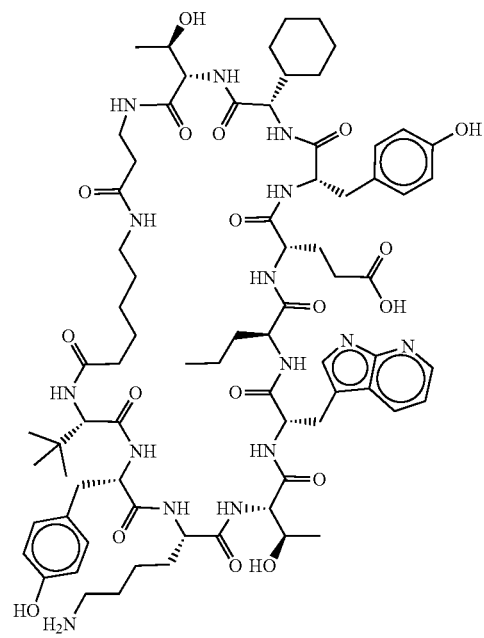
064
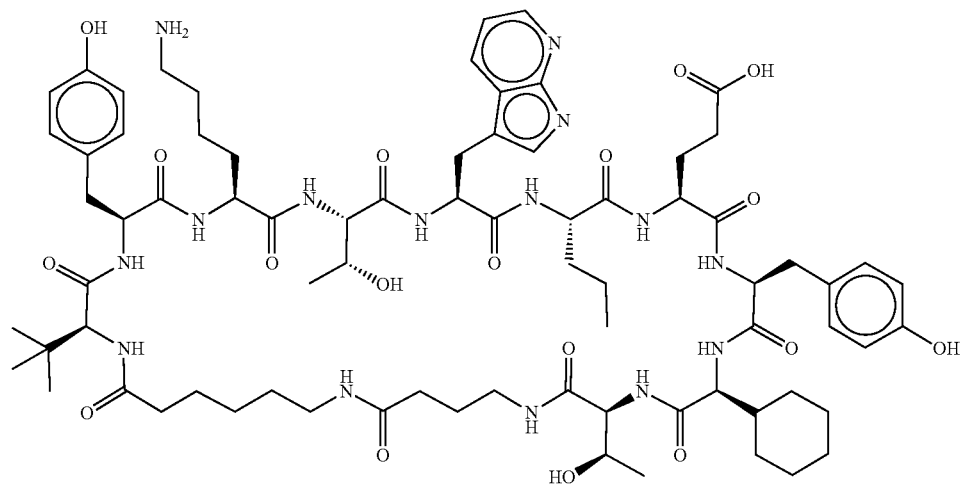
065

TABLE 4-continued
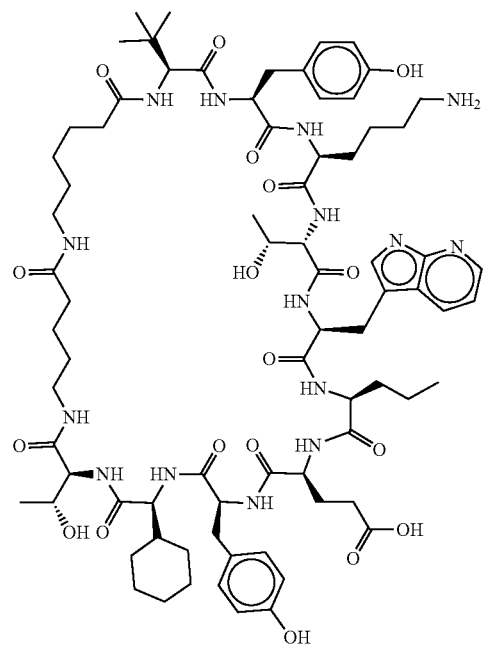
066
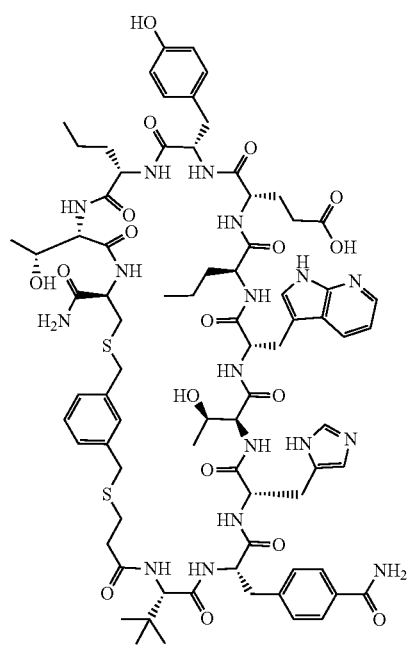 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(C(N)=O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
067

TABLE 4-continued
068
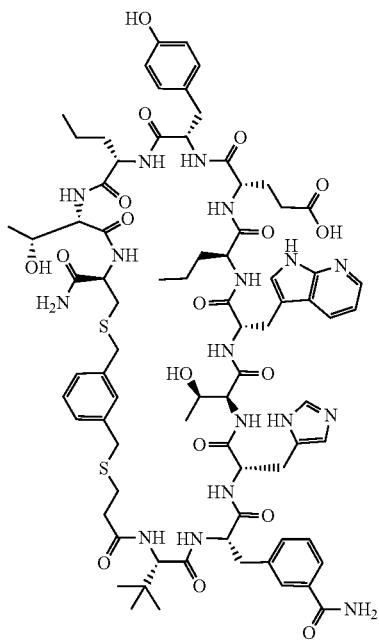 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2cccc(C(N)=O)c2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
069
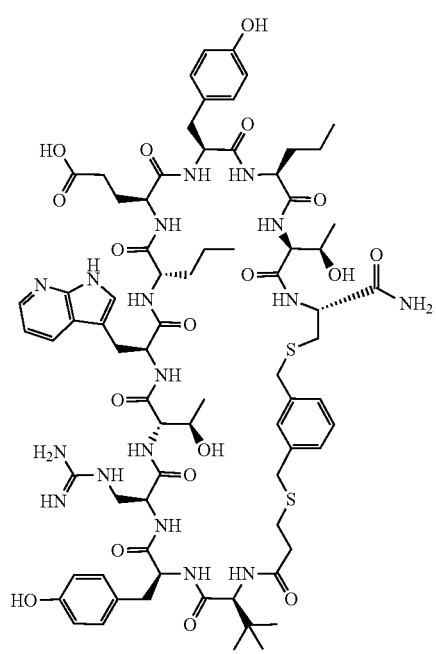 [SMILES: CCC[C@@H]1NC(=O)[C@H](Cc2c[nH]c3ncccc23)NC(=O)[C@H]([C@@H](C)O)NC(=O)[C@H](CNC(=N)N)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]

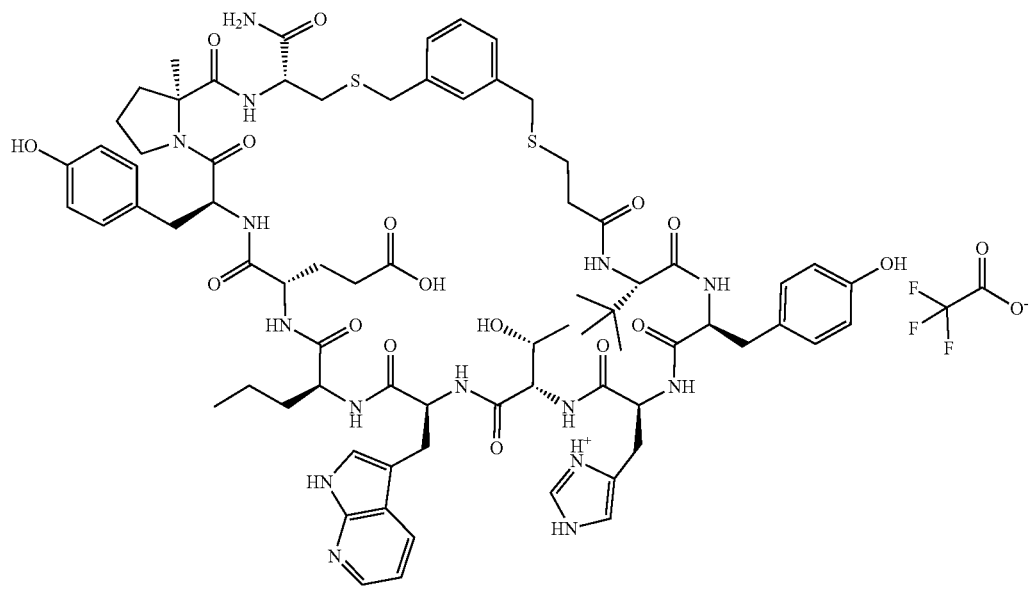
076
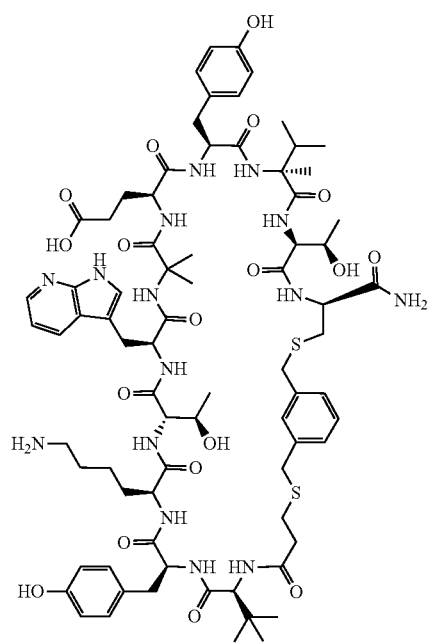 [SMILES: CC(C)[C@]1(C)NC(=O)[C@H](Cc2ccc(O)cc2)NC(=O)[C@H](CCC(=O)O)NC(=O)C(C)(C)NC(=O)[C@H](Cc2c[nH]c3ncccc23)NC(=O)[C@H]([C@@H](C)O)NC(=O)[C@H](CCCCN)NC(=O)[C@H](Cc2ccc(O)cc2)NC(=O)[C@H](C(C)(C)C)NC(=O)CCSCc2cccc(c2)CSC[C@H](C(N)=O)NC(=O)[C@H]([C@@H](C)O)NC1=O]
077

TABLE 4-continued
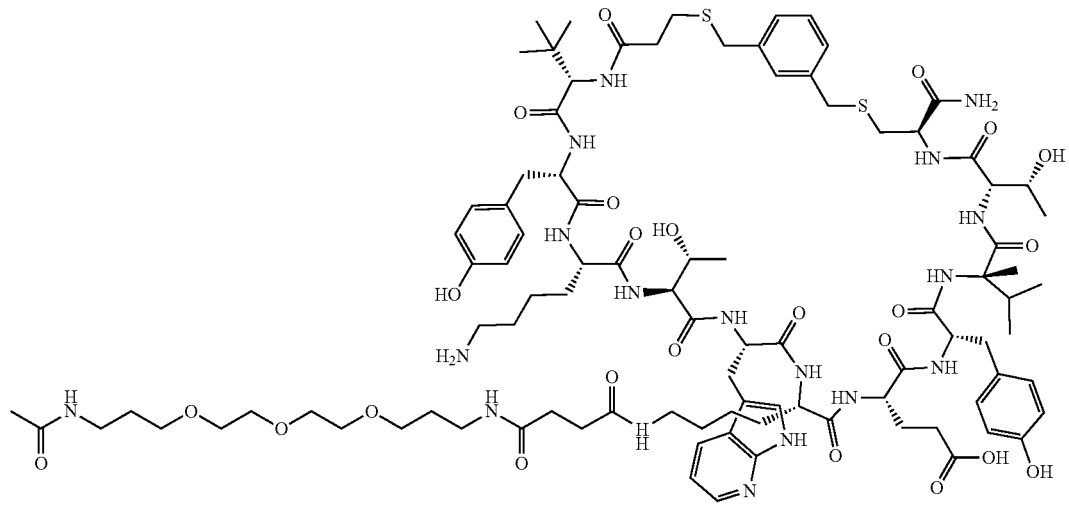
082
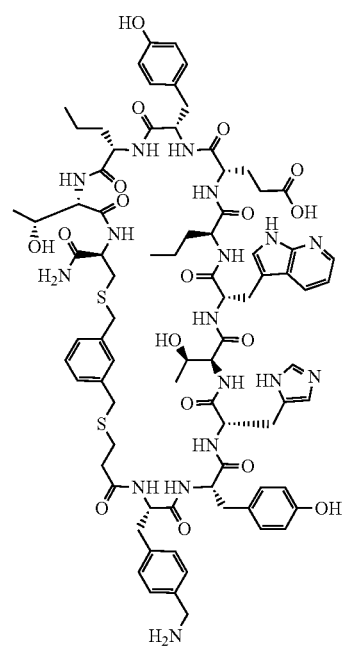 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](Cc2ccc(CN)cc2)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
086

TABLE 4-continued
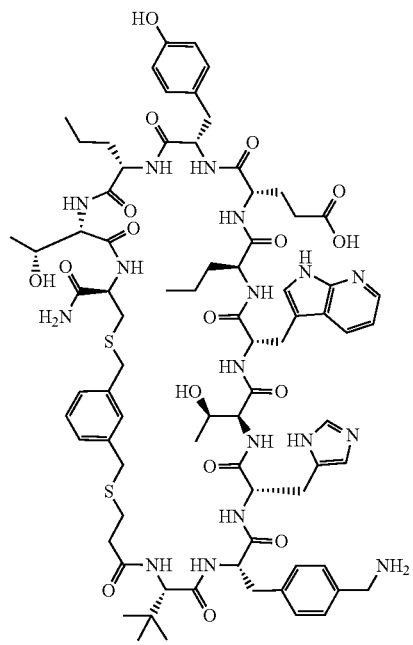 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(CN)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
087
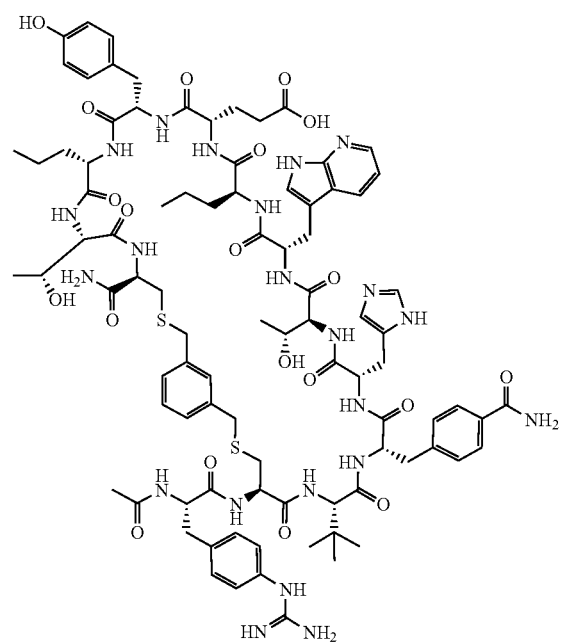 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(C(N)=O)cc2)NC(=O)[C@H](C(C)(C)C)NC(=O)[C@@H](NC(=O)[C@H](Cc2ccc(NC(=N)N)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
090

TABLE 4-continued
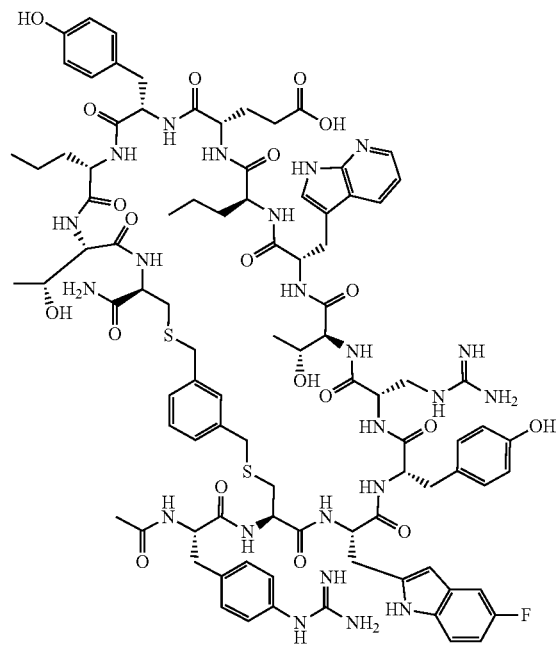 [SMILES: CCC[C@@H]1NC(=O)[C@H](Cc2c[nH]c3ncccc23)NC(=O)[C@H]([C@@H](C)O)NC(=O)[C@H](CNC(=N)N)NC(=O)[C@H](Cc2ccc(O)cc2)NC(=O)[C@H](Cc2cc3cc(F)ccc3[nH]2)NC(=O)[C@@H](NC(=O)[C@H](Cc2ccc(NC(=N)N)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
091
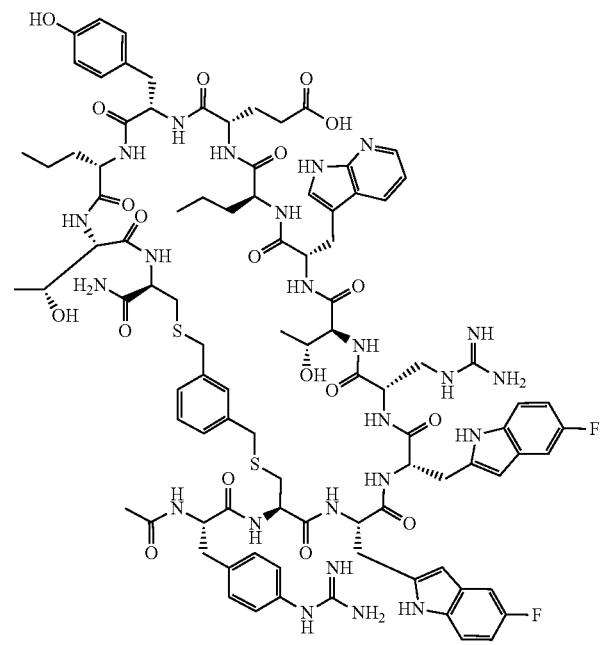 [SMILES: CCC[C@@H]1NC(=O)[C@H](Cc2c[nH]c3ncccc23)NC(=O)[C@H]([C@@H](C)O)NC(=O)[C@H](CNC(=N)N)NC(=O)[C@H](Cc2cc3cc(F)ccc3[nH]2)NC(=O)[C@H](Cc2cc3cc(F)ccc3[nH]2)NC(=O)[C@@H](NC(=O)[C@H](Cc2ccc(NC(=N)N)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
092

TABLE 4-continued
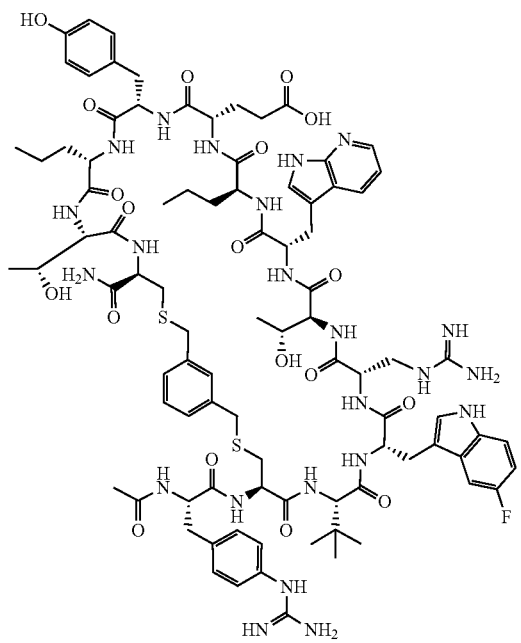 [SMILES: CCC[C@@H]1NC(=O)[C@H](Cc2c[nH]c3ncccc23)NC(=O)[C@H]([C@@H](C)O)NC(=O)[C@H](CNC(=N)N)NC(=O)[C@H](Cc2c[nH]c3ccc(F)cc23)NC(=O)[C@H](C(C)(C)C)NC(=O)[C@@H](NC(=O)[C@H](Cc2ccc(NC(=N)N)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
093
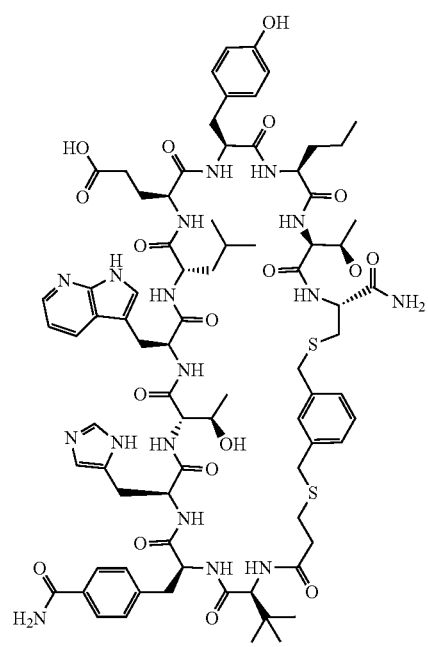
094

TABLE 4-continued
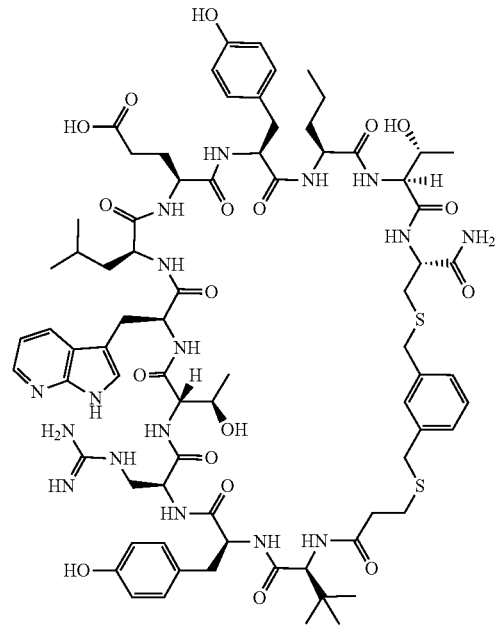 [SMILES: CCC[C@@H]1NC(=O)[C@H](Cc2ccc(O)cc2)NC(=O)[C@H](CCC(=O)O)NC(=O)[C@H](CC(C)C)NC(=O)[C@H](Cc2c[nH]c3ncccc23)NC(=O)[C@H]([C@@H](C)O)NC(=O)[C@H](CNC(=N)N)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]
095
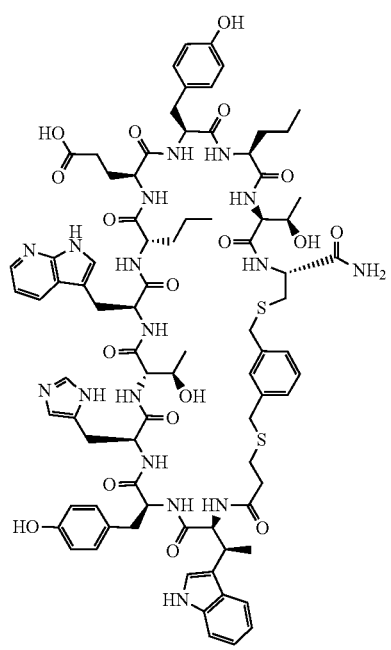 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H]([C@@H](C)c2c[nH]c3ccccc23)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
097

TABLE 4-continued
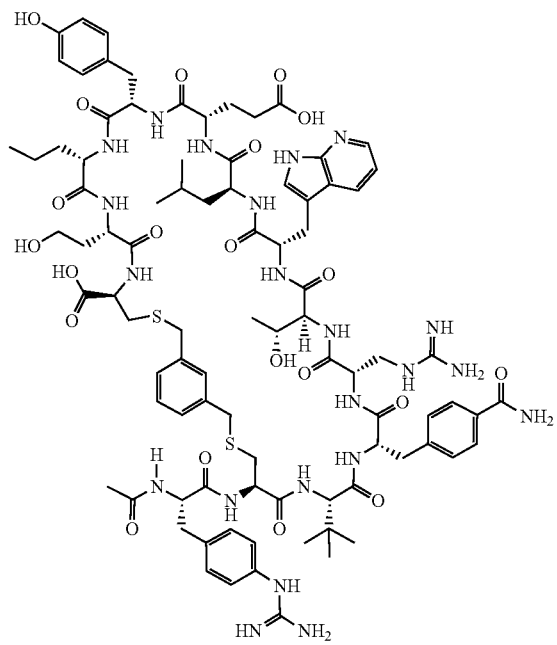 [SMILES: CCC[C@@H]1NC(=O)[C@H](Cc2ccc(O)cc2)NC(=O)[C@H](CCC(=O)O)NC(=O)[C@H](CC(C)C)NC(=O)[C@H](Cc2c[nH]c3ncccc23)NC(=O)[C@H]([C@@H](C)O)NC(=O)[C@H](CNC(=N)N)NC(=O)[C@H](Cc2ccc(C(N)=O)cc2)NC(=O)[C@H](C(C)(C)C)NC(=O)[C@@H](NC(=O)[C@H](Cc2ccc(NC(=N)N)cc2)NC(C)=O)CSCc2cccc(c2)CSC[C@@H](C(=O)O)NC(=O)[C@H](CCO)NC1=O]
100
In another aspect, the compounds of the invention are selected from the following compounds of Table 5, or a pharmaceutically acceptable salt thereof, below:
TABLE 5
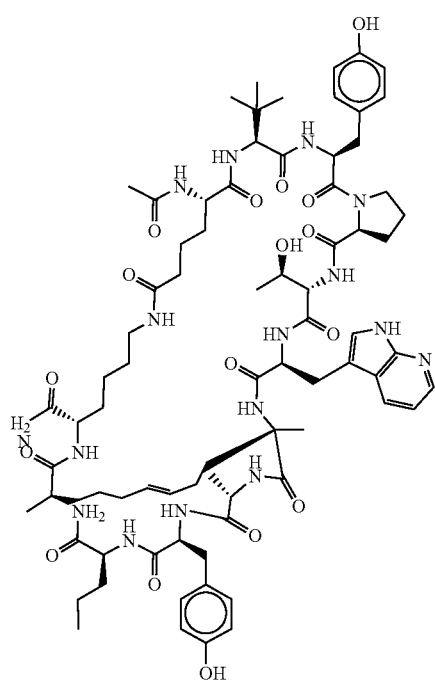
103

TABLE 5-continued
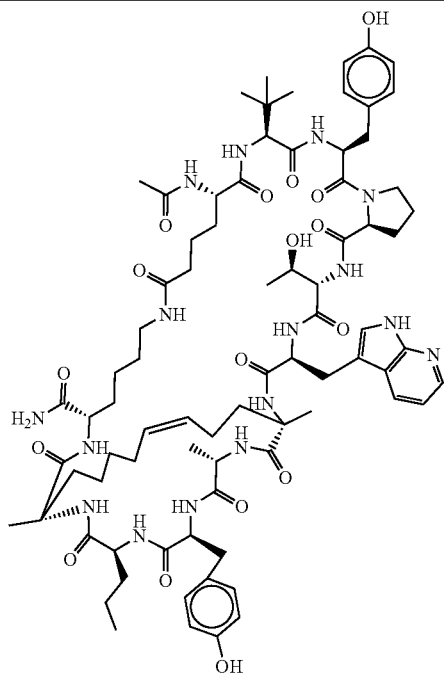
104
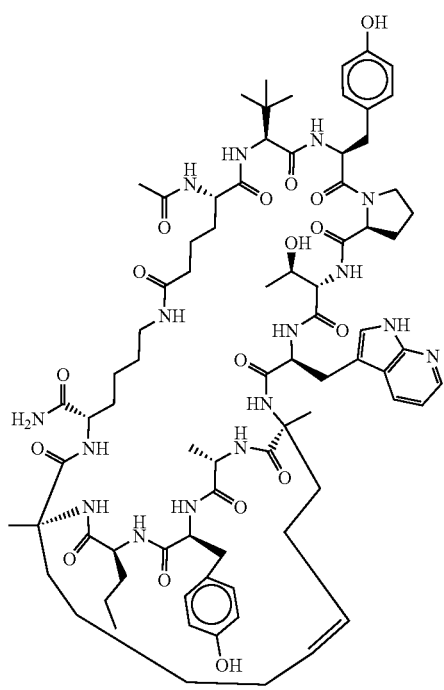
105

TABLE 5-continued
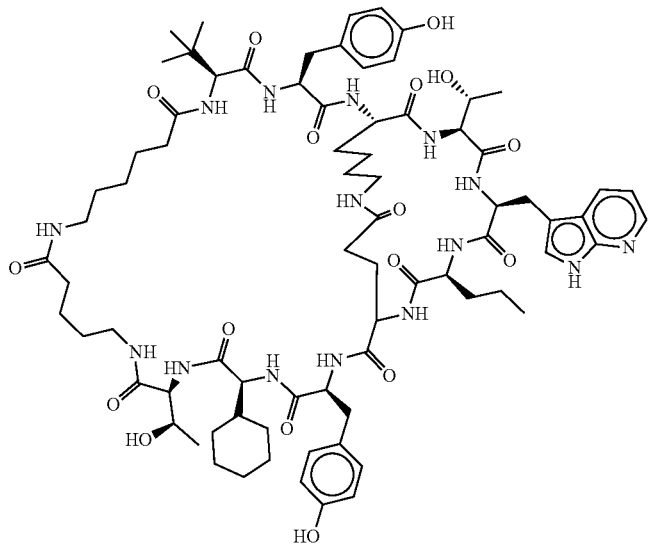
116
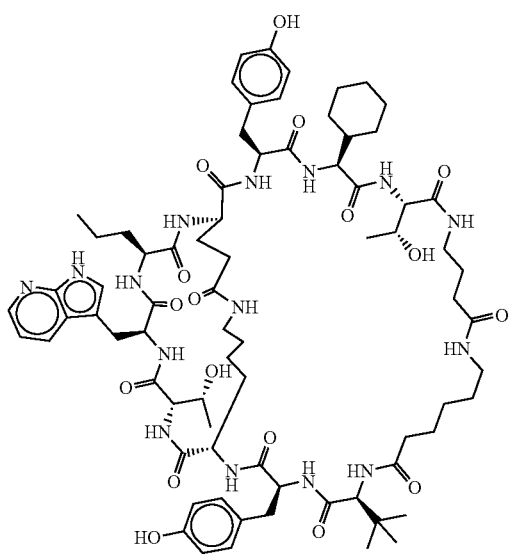
117

TABLE 5-continued
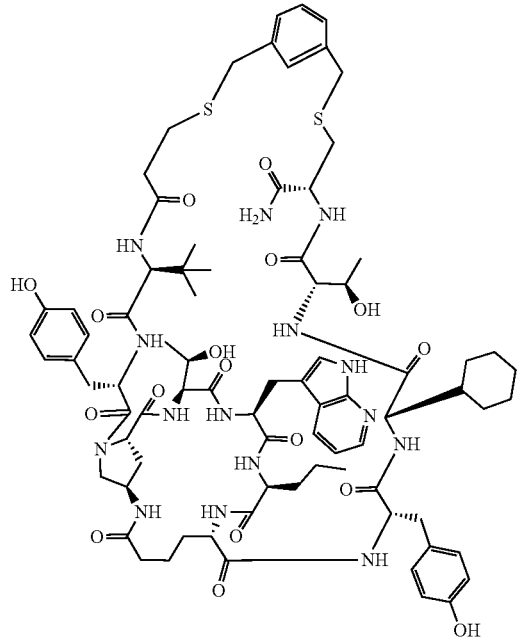 [SMILES: CCC[C@@H]1NC(=O)[C@H](Cc2c[nH]c3ncccc23)NC(=O)[C@H]([C@@H](C)O)NC(=O)[C@@H]2C[C@@H]3CN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](C2CCCCC2)NC(=O)[C@H](Cc2ccc(O)cc2)NC(=O)[C@H](CCCC(=O)N3)NC1=O]
102
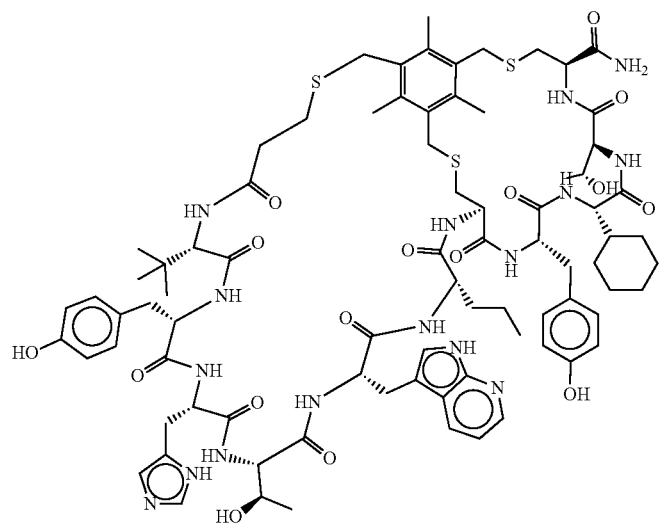
045

TABLE 5-continued

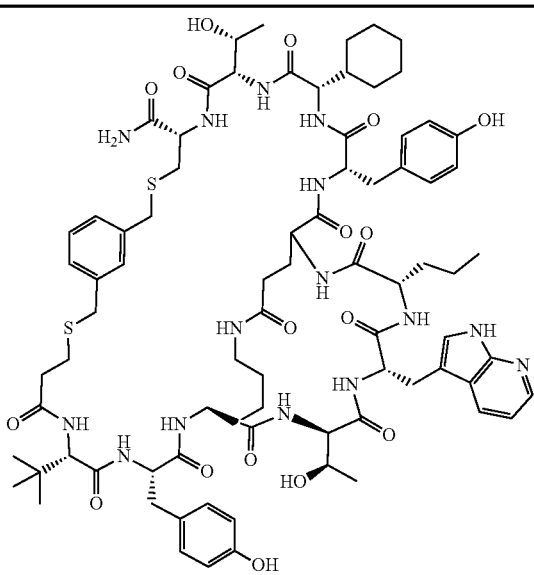

049

The compounds of Formulae (I), (II), and (III), as well as compounds 001-105, are referred to herein as "compounds of the invention."

It is to be understood that the compounds described herein encompass racemic, optically-active, regioisomeric and stereoisomeric forms, or combinations thereof that possess the therapeutically useful properties described herein.

The preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the compound of the invention described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

In embodiments, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. Isotopically-labeled compounds are useful in drug or substrate tissue distribution studies. In another embodiment, substitution with heavier isotopes such as deuterium affords greater metabolic stability (for example, increased in vivo half-life or reduced dosage requirements).

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

Without being bound to any particular mechanism of action, the cyclic polypeptide compounds provided herein can inhibit interaction between PCSK9 (e.g., human PCSK9) and LDLR (e.g., human LDLR) at an $IC_{50}$ of less than 50 µM, less than 45 µM, less than 40 µM, less than 35 µM, less than 30 µM, less than 25 µM, less than 20 µM, less than 15 µM, less than 10 µM, less than 9 µM, less than 8 µM, less than 7 µM, less than 6 µM, less than 5 µM, less than 4 µM, less than 3 µM, less than 2 µM, less than 1 µM, less than 900 nM, less than 800 nM, less than 700 nM, less than 600 nM, or less than 500 nM (e.g., as determined using the assay described in the Examples). In any of these examples, the $IC_{50}$ could be as low as 10 nM, 25 nM, 50 nM, or 100 nM (e.g., as determined using the assay described in the Examples). Additional methods for determining the $IC_{50}$ of any of the compounds for inhibiting the interaction between PCSK9 (e.g., human PCSK9) and LDLR (e.g., human LDLR) are known in the art.

Pharmaceutical Compositions

Also provided are pharmaceutical compositions comprising at least one (e.g., one, two, three, or four) of the cyclic polypeptide compounds provided herein. Two or more (e.g., two, three, or four) of any of the cyclic polypeptide compounds can be present in a pharmaceutical composition in any combination. The pharmaceutical compositions may be formulated in any manner known in the art.

Pharmaceutical compositions for use in accordance with a method disclosed herein thus may be formulated in conventional manner using one or more pharmaceutically acceptable carriers including excipients and auxiliaries that facilitate processing of the compound into preparations that can be used pharmaceutically. Proper formulation is dependent upon the route of administration chosen.

In an embodiment, the administration of the pharmaceutical composition is selected from the group consisting of oral, intravenous, intramuscular, intraperitoneal, subcutaneous, transdermal, and intravitreal.

In an embodiment, the pharmaceutical composition comprises at least one of compounds of Formula (I), Formula (II), Formula (III), or compounds 001-105 and a pharmaceutically acceptable carrier.

A pharmaceutical composition as disclosed herein comprises at least one compound of the invention. Such a pharmaceutical composition may be manufactured in a manner that is itself known, e.g., by means of conventional mixing, dissolving, granulating, levigating, emulsifying, encapsulating, entrapping or lyophilizing processes.

For intravenous, intramuscular, intraperitoneal, subcutaneous, transdermal, and intravitreal administration, the agents disclosed herein may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compound can be formulated readily by combining the compound with pharmaceutically acceptable carriers well known in the art. Such carriers enable the compounds of the invention to be formulated as a tablet, pills, capsule, liquid, gel, syrup, slurry or suspension, for oral ingestion by a subject to be treated.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients. For example, a pharmaceutical composition of a compound of the invention can be encapsulated by a pharmaceutical grade capsule in a dry powdered form.

Compound formulations include controlled duodenal release formulations, time release formulations, osmotic-controlled release delivery systems, microemulsions, microspheres, liposomes, nanoparticles, patches, pumps, drug depots, and the like. Specifically included herein are solid oral dosage forms, such as powders, softgels, gelcaps, capsules, pills, and tablets.

In one embodiment, the peptide is formulated as a sterile aqueous solution. In one embodiment, the peptide is formulated in a non-lipid formulation. In another embodiment, the peptide is formulated in a cationic or non-cationic lipid formulation. In either embodiment, the sterile aqueous solution may contain additional active or inactive components. Inactive components ("excipients") can include, but are not limited to, physiologically compatible salts, sugars, bulking agents, surfactants, or buffers.

Methods of Treatment

Provided herein is a method of reducing low density lipoprotein (LDL) cholesterol level in a subject in need thereof comprising administering to the subject a therapeutically effective amount of a cyclic polypeptide compound, or a pharmaceutical composition comprising a cyclic polypeptide compound.

In an embodiment, the subject has hypercholesterolemia. Some subjects of the embodiment can be diagnosed as having a disease that shows comorbidity with hypercholesterolemia, such as nephrotic syndrome, kidney failure, coronary artery disease, atherosclerosis, stroke, peripheral vascular disease, diabetes, and high blood pressure.

In a further embodiment, the compound inhibits the interaction between human PCSK9 and epidermal growth factor-like repeat A (EGF-A) domain of human low density lipoprotein (LDLR) in a subject.

In another embodiment, the compound inhibits the interaction between human PCSK9 and epidermal growth factor-like repeat A (EGF-A) domain of human low density lipoprotein (LDLR) in a cell.

Also provided herein is a method of treating hypercholesterolemia in a subject in need thereof comprising administering to the subject a therapeutically effective amount of a compound of the invention.

Hypercholesterolemia is a disease characterized by the presence of elevated levels of cholesterol (total cholesterol and/or LDL levels) in a sample obtained from a subject (e.g., as compared to a reference level that is a preselected threshold level). In some examples of hypercholesterolemia, the subject can also have a decreased level of high density lipoprotein (HDL) cholesterol as compared to a reference level, e.g., a preselected threshold level. Hypercholesterolemia is typically diagnosed by a medical professional by determining a cholesterol level(s) in a subject. In a general patient population, a preselected threshold level of total cholesterol (LDL plus HDL) can be, e.g., 180 mg/dL, 185 mg/dL, 190 mg/dL, 195 mg/dL, 200 mg/dL, 205 mg/dL, 210 mg/dL, 215 mg/dL, 220 mg/dL, 225 mg/dL, 230 mg/dL, 235 mg/dL, 240 mg/dL, 245 mg/dL, 250 mg/dL, 255 mg/dL, or 260 mg/dL. In a general patient population, a preselected threshold level of LDL cholesterol can be, e.g., 125 mg/dL, 130 mg/dL, 135 mg/dL, 140 mg/dL, 145 mg/dL, 150 mg/dL, 155 mg/dL, 160 mg/dL, 165 mg/dL, 170 mg/dL, 175 mg/dL, 180 mg/dL, 185 mg/dL, 190 mg/dL, 195 mg/dL, 200 mg/dL, 205 mg/mL, 210 mg/dL, 215 mg/dL, 220 mg/dL, 225 mg/dL, or 230 mg/dL. In a general patient population, a preselected threshold level of HDL cholesterol can be, e.g., 60 mg/dL, 58 mg/dL, 56 mg/dL, 54 mg/dL, 52 mg/dL, 50 mg/dL, 48 mg/dL, 46 mg/dL, 44 mg/dL, 42 mg/dL, 40 mg/dL, 38 mg/dL, 36 mg/dL, 34 mg/dL, 32 mg/dL, 30 mg/dL, 28 mg/dL, 26 mg/dL, or 24 mg/dL.

For subjects having a high risk of coronary disease (e.g., a subject having greater than a 20% risk of myocardial infarction in 10 years, or a subject having coronary artery disease, diabetes, peripheral artery disease, carotid artery disease, or aortic aneurysm), the preselected threshold level of LDL cholesterol can be, e.g., 60 mg/dL, 65 mg/dL, 70 mg/dL, 75 mg/dL, 80 mg/dL, 85 mg/dL, 90 mg/dL, 95 mg/dL, or 100 mg/dL. For subjects having a moderately high risk of coronary disease (e.g., a subject having a 10% to 20% risk of myocardial infarction in 10 years and two or more risk factors of coronary disease), the preselected threshold level of LDL can be, e.g., 90 mg/dL, 95 mg/dL, 100 mg/dL, 105 mg/dL, 110 mg/dL, 115 mg/dL, 120 mg/dL, 125 mg/dL, 130 mg/dL, 135 mg/dL, 140 mg/dL, 145 mg/dL, or 150 mg/dL. For subjects having a moderate risk of coronary disease (e.g., a subject having a less than 10% risk of having a myocardial infarction in 10 years and having greater than one risk factor of coronary artery disease), the preselected threshold level of LDL cholesterol can be, e.g., 115 mg/dL, 120 mg/dL, 125 mg/L, 130 mg/dL, 135 mg/dL, 140 mg/L, 145 mg/dL, or 150 mg/dL. Risk factors of coronary disease include, but are not limited to, family history, smoking behavior, high blood pressure, diabetes, obesity, physical inactivity, and high stress.

In any of the methods, the subject can be a subject having, diagnosed, or identified as having hypercholesterolemia, that is, for example, caused by diet and/or a genetic mutation (e.g., familial hypercholesterolemia) (e.g., any of the genetic mutations described herein or known in the art to result in an increased LDL cholesterol level).

In some of examples of any of the methods, the subject can be a subject having, diagnosed, or identified as having a disease showing comorbidity with hypercholesterolemia.

Non-limiting examples of diseases showing comorbidity with hypercholesterolemia include hypertension, heart disease, arthritis, diabetes, coronary artery disease, stroke, breast cancer, and myocardial infarction.

Accordingly, provided herein is a method of treating a disease that shows comorbidity with hypercholesterolemia such as nephrotic syndrome, kidney failure, coronary artery disease, atherosclerosis, stroke, peripheral vascular disease, diabetes, and high blood pressure, in a subject in need thereof comprising administering to the subject a therapeutically effective amount of a compound of the invention.

Methods for diagnosing hypertension, heart disease, arthritis, diabetes, coronary artery disease, stroke, breast cancer, and myocardial infarction are well known in the art. For example, hypertension can be diagnosed in a subject by measuring the subject's blood pressure at one or more time points. Heart disease can be diagnosed in a subject, e.g., using blood tests, chest X-rays, electrocardiogram, echocardiography, an exercise stress test, radionuclide ventriculography, multiple-gated acquisition scanning, or cardiac catheterization. Diabetes (type I or type II) can be diagnosed, e.g., by measuring blood glucose level(s) in a subject (e.g., fasting blood glucose levels) and/or detecting ketones in urine from the subject. Arthritis can be diagnosed in a subject, e.g., by physical examination for pain, stiffness, swelling, redness, and decreased range of motion in one or more joints, laboratory tests, X-rays, computerized tomography, magnetic resonance imaging, ultrasound, or arthroscopy. Coronary artery disease can be diagnosed in a subject, e.g., by electrocardiogram, echocardiogram, stress test, cardiac catheterization, angiogram, heart scan (e.g., using computerized tomography), or magnetic resonance angiography. Stroke can be diagnosed, e.g., by examination, blood tests, computerized tomography, magnetic resonance imaging, carotid ultrasound, cerebral angiogram, or echocardiogram. Breast cancer can be diagnosed, e.g., by breast examination, mammogram, breast ultrasound, biopsy, or magnetic resonance imaging. Myocardial infarction is diagnosed, e.g., by electrocardiogram, blood tests, chest X-ray, echocardiogram, coronary catheterization, exercise stress test, cardiac computerized tomography, or magnetic resonance imaging.

Provided are methods of treating a disease showing comorbidity with hypercholesterolemia, where the methods include administering to a subject in need thereof (e.g., a subject having hypercholesterolemia) a cyclic polypeptide compound or a pharmaceutical composition provided herein. The administration reduces the risk as compared to the risk of developing such a disease in a subject having similar cholesterol levels but administered a different treatment or administered no treatment. Also provided are methods of delaying the onset or delaying the worsening of a disease showing comorbidity with hypercholesterolemia, where the methods include administering to a subject in need thereof (e.g., a subject having hypercholesterolemia and optionally, one or more risk factors of developing a disease showing comorbidity with hypercholesterolemia, or a subject having, diagnosed as having, or identified as having a disease showing comorbidity with hypercholesterolemia) a compound or a pharmaceutical composition provided herein (e.g., as compared to a subject having the same disease showing co-morbidity with hypercholesterolemia but administered a different treatment or administered no treatment).

Also provided are methods of reducing LDL cholesterol level in a subject in need thereof that include administering to the subject a therapeutically effective amount of any of the compounds or pharmaceutical compositions described herein (the reducing being as compared to, for example, a level in a control subject or a baseline level in the subject prior to treatment with any of the compounds or any of the pharmaceutical compositions provided herein). Successful reduction in a LDL cholesterol level in a subject can be determined by a health professional (e.g., a nurse, a physician, or a physician's assistant). For example, successful treatment can result in at least a 2%, at least a 3%, at least a 4%, at least a 5%, at least a 6%, at least a 7%, at least a 8%, at least a 9%, at least a 10%, at least a 11%, at least a 12%, at least a 13%, at least a 14%, at least a 15%, at least a 16%, at least a 17%, at least a 18%, at least a 19%, at least a 20%, at least a 21%, at least a 22%, at least a 23%, at least a 24%, at least a 25%, at least a 26%, at least a 27%, at least a 28%, at least a 29%, or at least a 30% reduction in a subject's LDL cholesterol level (e.g., as compared to a control subject or as compared to a LDL cholesterol level in the subject prior to the administration of any of the compounds or any of the pharmaceutical compositions provided herein). In any of these examples, the reduction in a subject's LDL level can be as high as 40%, 45%, 50%, 55%, 60%, or 65% (e.g., as compared to a control subject or as compared to a LDL cholesterol level in the subject prior to the administration of any of the compounds or any of the pharmaceutical compositions provided herein). In addition, the methods can further provide for a reduction in the total cholesterol level of a subject, e.g., a reduction of at least 2%, at least 3%, at least 4%, at least 5%, at least 6%, at least 7%, at least 8%, at least 9%, at least 10%, at least 11%, at least 12%, at least 13%, at least 14%, or at least 15% (e.g., as compared to a control subject or compared to a total cholesterol level in the subject prior to the administration of any of the compounds or any of the pharmaceutical compositions provided herein). In any of these examples, the reduction in a subject's total cholesterol level can be as high as 40%, 45%, 50%, 55%, 60%, or 65% (e.g., as compared to a control subject or compared to a total cholesterol level in the subject prior to the administration of any of the compounds or any of the pharmaceutical compositions provided herein).

Methods for determining levels of LDL cholesterol and total cholesterol are well known in the art. Non-limiting examples of kits for determining the levels of LDL cholesterol and total cholesterol are commercially available from Abcam (Cambridge, Mass.), Sigma Aldrich (St. Louis, Mo.), Cell Biolabs, Inc. (San Diego, Calif.), Genway Biotech (San Diego, Calif.), Biolabo (Lawrenceville, Ga.), BioAssay Systems (Hayward, Calif.), Medibena (Vienna, Austria), and Abnova (Taipei, Taiwan).

The subject in these methods can, e.g., be a subject having, diagnosed as having, or identified as having hypercholesterolemia (e.g., familial hypercholesterolemia) or a subject identified or previously identified as having an increased risk of developing hypercholesterolemia. In some examples, the subject in these methods can be, e.g., a subject having, diagnosed as having, or identified as having a disease showing comorbidity with hypercholesterolemia (e.g., any of the examples of diseases showing comorbidity with hypercholesterolemia described herein or known in the art). Also provided are methods of reducing the risk of developing a disease showing comorbidity with hypercholesterolemia (e.g., as compared to the risk in a control patient or patient population that has not received treatment with any of the compounds or has not received any of the pharmaceutical compositions provided herein) that include administering to a subject in need thereof a compound or a pharmaceutical composition provided herein. The subject in these methods can be a subject having, diagnosed as having, or identified as having hypercholesterolemia or identified or previously identified as having an increased risk of developing hypercholesterolemia. In some examples, the subject can be identified or previously identified as having an increased risk of developing a disease showing comorbidity with hypercholesterolemia (e.g., a subject having one or more risk factors for developing a disease showing comorbidity with hypercholesterolemia or having one or more risk factors for developing hypercholesterolemia).

In some examples, the subject may already be receiving or have received a treatment for hypercholesterolemia (e.g., a statin, niacin, bile-acid resins, fibrates, and cholesterol adsorption inhibitors). In some examples, the prior treatment for hypercholesterolemia resulted in no significant reduction in LDL cholesterol level in the subject in need thereof (e.g., any of the subjects descried herein), and/or insufficient reduction in the LDL cholesterol level in the subject (e.g., any of the subjects described herein) (i.e., not sufficient to reduce LDL cholesterol level to below a reference level that is a preselected threshold level).

In some embodiments, the subject is administered a dose of between 1 mg to 400 mg of any of the compounds or any of the pharmaceutical compositions (e.g., between 1 mg and 300 mg, between 1 mg and 250 mg, between 1 mg and 200 mg, between 1 mg and 150 mg, between 1 mg and 100 mg, between 1 mg and 80 mg, between 1 mg and 70 mg, between 1 mg and 60 mg, between 1 mg and 50 mg, between 1 mg and 40 mg, between 1 mg and 30 mg, between 1 mg and 20 mg, between 1 mg and 10 mg, between 20 mg and 120 mg, between 30 mg and 90 mg, or between 40 mg and 80 mg). In some examples, the subject is administered a dose of the compound or pharmaceutical composition described herein of about 0.1 mg/kg to about 4.0 mg/kg (e.g., between about 0.1 mg/kg and about 3.5 mg/kg, between about 0.1 mg/kg and about 3.0 mg/kg, between about 0.1 mg/kg and about 2.5 mg/kg, between about 0.1 mg/kg and about 2.0 mg/kg, between about 0.1 mg/kg and about 1.5 mg/kg, between about 0.5 mg/kg and about 1.5 mg/kg, or between about 0.7 mg/kg and about 1.3 mg/kg).

Also provided are methods of inhibiting the interaction between PCSK9 (e.g., any of the exemplary mammalian PCSK9 described herein, such as human PCSK9) and LDLR (e.g., any of the exemplary mammalian LDLR described herein, such as human LDLR) that include contacting PCSK9 and LDLR with any of the compounds or pharmaceutical compositions provided herein (e.g., the inhibition being compared to, for example, a level of interaction between PCSK9 and LDLR in the absence of the compounds or pharmaceutical composition). In some examples, the contacting takes place in vitro (e.g., in a cell culture). In other examples, the contacting takes place in vivo (e.g., in any of the exemplary subjects described herein or any of the animal models described herein). In any of these methods, LDLR can be present in the plasma membrane of a mammalian cell (e.g., a hepatocyte, an epithelial cell, or an endothelial cell), and oriented in the plasma membrane such that LDLR can interact with PCSK9 present in an extracellular medium (e.g., culture medium).

Non-limiting methods for detecting the interaction (or amount of interaction) between PCSK9 and LDLR are described herein. For example, LDLR can be attached to a solid substrate (e.g., a plate, film, or a bead) (e.g., in such a way that allows LDLR to interact with PCSK9) and contacted with PCSK9 in the presence or absence of any of the compounds or pharmaceutical compositions described herein, and the amount of PCSK9 bound to the LDLR in the presence of the compound or pharmaceutical composition can be compared to the amount bound in a control assay that does not include the compound or pharmaceutical composition. Detecting the amount of PCSK9 bound to LDLR in the presence or absence of the compound or pharmaceutical composition can be performed by immunoprecipitation and immunoblotting, surface plasmon resonance, or time-resolved fluorescence energy transfer (TR-FRET).

As is known in the art, an inhibition of the interaction between PCSK9 and LDLR can be measured as an increase in the $K_D$ value and/or a decrease in $K_A$ value for the interaction between PCSK9 (e.g., human PCSK9) and LDLR (e.g., human LDLR) (e.g., the EGF-A domain of LDLR) in the presence of any of the compounds or pharmaceutical compositions provided herein (e.g., as compared to levels of interaction in the absence of the compound or pharmaceutical composition).

The interaction between PCSK9 and LDLR can be indirectly detected when the interaction between PCSK9 and LDLR occurs in vitro. For example, interaction between PCSK9 and LDLR, where the LDLR is expressed in the plasma membrane of a hepatocyte, can be indirectly detected by determining the amount of LDLR remaining in the hepatocyte it has been contacted with PCSK9 in the presence or absence of any the compounds or pharmaceutical compositions provided herein (where a higher level of LDLR in the hepatocyte after incubation in the presence of the compound or pharmaceutical composition as compared to the level of LDLR in the hepatocyte after incubation in the absence of the compound or pharmaceutical composition indicates that the interaction between LDLR and PCSK9 has been inhibited).

The amount of inhibition of the interaction between LDLR and PCSK9 in vivo can also be indirectly determined by measuring the level of LDL cholesterol in a subject administered the compound or pharmaceutical composition as compared to a control level of LDL (e.g., a level of LDL cholesterol in the same subject prior to treatment with the compound or pharmaceutical composition). In such an assay, a decreased level of LDL cholesterol in the subject after treatment, as compared to the level of LDL cholesterol in the subject before treatment, indicates that the compound or pharmaceutical composition administered to the subject inhibited the interaction between PCSK9 and LDLR in the subject.

In an embodiment of these methods, the administration is selected from the group consisting of oral, intravenous, intramuscular, intraperitoneal, subcutaneous, transdermal, and intravitreal.

In an embodiment of these methods, provided herein is a method of treating hypercholesterolemia in a subject in need thereof comprising administering to the subject at least one of compounds of Formula (I), Formula (II), Formula (III), or compounds 001-105 or a pharmaceutically composition comprising at least one of compounds of Formula (I), Formula (II), Formula (III), or compounds 001-105.

It is to be understood that the methods described in this disclosure are not limited to particular methods and experimental conditions disclosed herein, as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting. As used herein, unless otherwise stated, the singular forms "a," "an," and "the" include plural reference. Thus, for example, a reference to "a protein" includes a plurality of protein molecules.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

The invention is now described with reference to the following Examples. These Examples are provided for the purpose of illustration only, and the invention is not limited to these Examples, but rather encompasses all variations that are evident as a result of the teachings provided herein.

Compounds of the invention can be prepared according to the following examples.

Example 1: Synthesis of Cyclic Polypeptide Compounds

Procedure A
Step 1: Peptide Synthesis

The peptides were synthesized using Fmoc-protected amino acids on a solid-phase Rink Amide MBHA (NovaBiochem, ~0.5 meq/g, 100-200 mesh) or AM (NovaBiochem, ~0.73 meq/g, 100-200 mesh) or 2-aminoethanethiol-2-chlorotrityl resin (AnaSpec, ~0.9 meq/g, 200-400 mesh) with a CEM Liberty Blue automated microwave peptide synthesizer. Peptides were typically synthesized on a 0.1 mmol scale. Typical reaction conditions were as follows: Deprotection Conditions: 20% piperidine (v/v) in DMF (2×2 min at 75° C.); Residue Coupling Conditions: 5 eq (relative to resin) of activated amino acid (2.5 mL of a 0.2 M amino acid stock solution in DMF) was delivered to the resin, followed by 5 eq of DIC activator (1 mL of a 0.5 M solution in DMF), and 5 eq of Oxyma Pure (0.5 mL of a 1 M solution in DMF) and allowed to react for 5 min at 75° C. The resultant product was used directly in the next step.

Step 2: Deprotection and Cyclization

The peptide from Step 1 was not cleaved from the resin. The resin-bound peptide was transferred to a 15 mL polypropylene centrifuge tube. To deprotect the alloc/allyl protecting groups, the resin was treated with a solution of tetrakis(triphenylphosphine) palladium (0) (55 mg, 0.05 mmol) and phenylsilane (125 µL, 1.0 mmol) in dry DCM (degassed by bubbling N2 gas for 5 min). The reaction vessel was rocked at room temperature for 2 h (released the pressure every 15 min). The solution was drained and the resin washed with DCM (3×5 mL). The deprotection step was repeated, after which the resin was washed with DCM (5×5 mL), DMF (5×5 mL), 1 M diethyldithiocarbamic acid sodium salt in DMF (2×5 mL), DMF (5×5 mL), and DCM (2×5 mL).

A solution of PyAOP (105 mg, 0.2 mmol; (7-Azabenzotriazol-1-yloxy)tripyrrolidino-phosphonium hexafluorophosphate), HOAt (14 mg, 0.1 mmol; 1-Hydroxy-7-azabenzotriazole) and DIPEA (90 µL, 0.5 mmol) in DMF (5 mL) was then added to the resin and the mixture shaken for 3 h at room temperature. The solution was drained and the resin washed with DMF (3×5 mL) and DCM (3×5 mL). The cyclization step was repeated for 12 h, after which the resin was washed with DMF (5×5 mL) and DCM (5×5 mL) and dried. The resultant product was used directly in the next step.

Step 3: Cleavage from Solid-Support

The resin from Step 2 was transferred to either a 50 mL polypropylene centrifuge tube or a 10 mL fritted syringe. The peptides were cleaved from their solid support using trifluoroacetic acid/triisopropylsilane/DL-dithiothreitol/water (92.5/2.5/2.5 (w/v)/2.5) mixture. For 0.1 mmol scale of resin, ~10 mL cleavage solution was used. The suspended resin was rocked in cleavage solution for 3 hours at room temperature. The filtrate was collected in 50 mL polypropylene centrifuge tubes and precipitated with chilled diethyl ether (~50 mL per ~5 mL cleavage filtrate). The precipitated crude peptide was collected by centrifugation. The white pellet was then subsequently suspended in chilled diethyl ether and collected by centrifugation two additional times. The resulting solid was air-dried to afford the crude peptide.

Step 4: Cyclization

For a 0.1 mmol scale: The linear peptide was synthesized, cleaved from solid support, and isolated according to Step 3. The solid crude peptide was dissolved with stirring in 30 mL of a degassed water:acetonitrile (1:1) solution in a 50 mL polypropylene centrifuge tube. Additional acetonitrile was added as needed to ensure complete dissolution of the peptide. To this stirred solution, aqueous ammonium bicarbonate (200 mM, degassed) was added dropwise to bring the pH to ~8. Alkylating reagent 1,3-bis(bromomethyl)benzene (0.1 mmol/1 eq) in acetonitrile (1 mL) was added dropwise to the reaction over ~2 min. After complete addition, the reaction was tested to ensure the pH was maintained at ~8. If the pH was below ~8, additional aqueous ammonium bicarbonate (200 mM, degassed) was added dropwise to the reaction until the pH was ~8. The centrifuge tube was capped and the resulting reaction mixture was stirred at room temperature for 1 h. The reaction was then acidified to pH~1 with trifluoroacetic acid and lyophilized to afford the crude peptide as a powder. The desired product was purified by C18 reverse phase chromatography.

Procedure A1

Step 1: Peptide Synthesis

The peptides were synthesized using Fmoc-protected amino acids on a solid-phase Rink Amide MBHA (NovaBiochem, ~0.5 meq/g, 100-200 mesh) or AM (NovaBiochem, ~0.73 meq/g, 100-200 mesh) or 2-aminoethanethiol-2-chlorotrityl resin (AnaSpec, ~0.9 meq/g, 200-400 mesh) with a CEM Liberty Blue automated microwave peptide synthesizer. Peptides were typically synthesized on a 0.1 mmol scale. Typical reaction conditions were as follows: Deprotection Conditions: 20% piperidine (v/v) in DMF (2×2 min at 75° C.); Residue Coupling Conditions: 5 eq (relative to resin) of activated amino acid (2.5 mL of a 0.2 M amino acid stock solution in DMF) was delivered to the resin, followed by 5 eq of DIC activator (1 mL of a 0.5 M solution in DMF), and 5 eq of Oxyma Pure (0.5 mL of a 1 M solution in DMF) and allowed to react for 5 min at 75° C. The resultant product was used directly in the next step.

Step 2: Deprotection and Cyclization

The peptide from Step 1 was not cleaved from the resin. The resin-bound peptide was transferred to a 15 mL polypropylene centrifuge tube. To deprotect the alloc/allyl protecting groups, the resin was treated with a solution of tetrakis(triphenylphosphine) palladium (0) (55 mg, 0.05 mmol) and phenylsilane (125 µL, 1.0 mmol) in dry DCM (degassed by bubbling N2 gas for 5 min). The reaction vessel was rocked at room temperature for 2 h (released the pressure every 15 min). The solution was drained and the resin washed with DCM (3×5 mL). The deprotection step was repeated, after which the resin was washed with DCM (5×5 mL), DMF (5×5 mL), 1 M diethyldithiocarbamic acid sodium salt in DMF (2×5 mL), DMF (5×5 mL), and DCM (2×5 mL).

A solution of PyAOP (105 mg, 0.2 mmol; (7-Azabenzotriazol-1-yloxy)tripyrrolidino-phosphonium hexafluorophosphate), HOAt (14 mg, 0.1 mmol; 1-Hydroxy-7-azabenzotriazole) and DIPEA (90 µL, 0.5 mmol) in DMF (5 mL) was then added to the resin and the mixture shaken for 3 h at room temperature. The solution was drained and the resin washed with DMF (3×5 mL) and DCM (3×5 mL). The cyclization step was repeated for 12 h, after which the resin was washed with DMF (5×5 mL) and DCM (5×5 mL) and dried. The resultant product was used directly in the next step.

Step 3: Cleavage from Solid-Support

The resin from Step 2 was transferred to either a 50 mL polypropylene centrifuge tube or a 10 mL fritted syringe. The peptides were cleaved from their solid support using trifluoroacetic acid/triisopropylsilane/DL-dithiothreitol/water (92.5/2.5/2.5 (w/v)/2.5) mixture. For 0.1 mmol scale of resin, ~10 mL cleavage solution was used. The suspended resin was rocked in cleavage solution for 3 hours at room temperature. The filtrate was collected in 50 mL polypropylene centrifuge tubes and precipitated with chilled diethyl ether (~50 mL per ~5 mL cleavage filtrate). The precipitated crude peptide was collected by centrifugation. The white pellet was then subsequently suspended in chilled diethyl ether and collected by centrifugation two additional times. The resulting solid was air-dried to afford the crude peptide.

Step 4: Cyclization

To a 250 mL round-bottomed flask fitted with a stir bar, was added PyAOP (210 mg, 0.4 mmol; (7-Azabenzotriazol-1-yloxy)tripyrro-lidinophosphonium hexafluorophosphate), HOAt (14 mg, 0.1 mmol; 1-Hydroxy-7-azabenzotriazole) and DIPEA (90 µL, 0.5 mmol) in DMF (80 mL). The precipitated solid crude peptide from Step 3 was dissolved in DMF (25 mL) and added dropwise to the activator solution using a syringe pump (addition over 1.5 h). The resulting yellow solution was stirred overnight at room temperature. After completion of the cyclization (monitored by LCMS), the reaction mixture was acidified by addition of TFA (100 µL). DMF solvent was evaporated under high vacuum and the resulting crude residue was purified by C18 reverse-phase HPLC.

Procedure B

Step 1: Peptide Synthesis

The peptides were synthesized using Fmoc-protected amino acids on a solid-phase Rink Amide MBHA (NovaBiochem, ~0.5 meq/g, 100-200 mesh) or AM (NovaBiochem, ~0.73 meq/g, 100-200 mesh) or 2-aminoethanethiol-2-chlorotrityl resin (AnaSpec, ~0.9 meq/g, 200-400 mesh) with a CEM Liberty Blue automated microwave peptide synthesizer. Peptides were typically synthesized on a 0.1 mmol scale. Typical reaction conditions were as follows: Deprotection Conditions: 20% piperidine (v/v) in DMF (2×2 min at 75° C.); Residue Coupling Conditions: 5 eq (relative to resin) of activated amino acid (2.5 mL of a 0.2 M amino acid stock solution in DMF) was delivered to the resin, followed by 5 eq of DIC activator (1 mL of a 0.5 M solution in DMF), and 5 eq of Oxyma Pure (0.5 mL of a 1 M solution in DMF) and allowed to react for 5 min at 75° C. The resultant product was used directly in the next step.

Step 2: Olefin Metathesis

For a 0.1 mmol scale: The linear peptide was synthesized on solid-support according to Step 1. The peptide was not cleaved from resin. A solution of Benzylidene-bis(tricyclohexylphosphine)-dichlororuthenium (Grubb's generation I catalyst) was prepared by dissolving 16 mg (0.2 equiv) (based on peptide resin of 0.1 mmol) in anhydrous 1,2-dichloroethane (5 mL). The solution was degassed by bubbling nitrogen through the solution for 10 minutes. The degassed solution was then added to the resin-bound peptide in a 10 mL fritted syringe. The reaction was allowed to proceed at 45° C. for two hours and then the catalyst was filtered off. The resin was then re-subjected to the metathesis conditions by adding an additional 5 mL of freshly-prepared catalyst solution (16 mg Grubb's generation I catalyst in 5 mL of degassed anhydrous 1,2-dichloroethane). The reaction was allowed to proceed for 2 hours at 45° C. The resin-bound peptide was then washed with dichloromethane (5×10 mL). The reaction can be monitored for completion by removing a few beads, cleaving the peptide (95% TFA/2.5% H20/2.5% triisopropylsilane) and analyzing by LCMS.

Step 3: Cleavage from Solid-Support

The resin from Step 2 was transferred to either a 50 mL polypropylene centrifuge tube or a 10 mL fritted syringe. The peptides were cleaved from their solid support using trifluoroacetic acid/triisopropylsilane/DL-dithiothreitol/water (92.5/2.5/2.5 (w/v)/2.5) mixture. For 0.1 mmol scale of resin, ~10 mL cleavage solution was used. The suspended resin was rocked in cleavage solution for 3 hours at room temperature. The filtrate was collected in 50 mL polypropylene centrifuge tubes and precipitated with chilled diethyl ether (~50 mL per ~5 mL cleavage filtrate). The precipitated crude peptide was collected by centrifugation. The white pellet was then subsequently suspended in chilled diethyl ether and collected by centrifugation two additional times. The resulting solid was air-dried to afford the crude peptide.

Step 4: Cyclization

To a 250 mL round-bottomed flask fitted with a stir bar, was added PyAOP (210 mg, 0.4 mmol; (7-Azabenzotriazol-1-yloxy)tripyrro-lidinophosphonium hexafluorophosphate), HOAt (14 mg, 0.1 mmol; 1-Hydroxy-7-azabenzotriazole) and DIPEA (90 μL, 0.5 mmol) in DMF (80 mL). The precipitated solid crude peptide from Step 3 was dissolved in DMF (25 mL) and added dropwise to the activator solution using a syringe pump (addition over 1.5 h). The resulting yellow solution was stirred overnight at room temperature. After completion of the cyclization (monitored by LCMS), the reaction mixture was acidified by addition of TFA (100 μL). DMF solvent was evaporated under high vacuum and the resulting crude residue was purified by C18 reverse-phase HPLC.

Procedure D

Step 1: Peptide Synthesis

The peptides were synthesized using Fmoc-protected amino acids on a solid-phase Rink Amide MBHA (NovaBiochem, ~0.5 meq/g, 100-200 mesh) or AM (NovaBiochem, ~0.73 meq/g, 100-200 mesh) or 2-aminoethanethiol-2-chlorotrityl resin (AnaSpec, ~0.9 meq/g, 200-400 mesh) with a CEM Liberty Blue automated microwave peptide synthesizer. Peptides were typically synthesized on a 0.1 mmol scale. Typical reaction conditions were as follows: Deprotection Conditions: 20% piperidine (v/v) in DMF (2×2 min at 75° C.); Residue Coupling Conditions: 5 eq (relative to resin) of activated amino acid (2.5 mL of a 0.2 M amino acid stock solution in DMF) was delivered to the resin, followed by 5 eq of DIC activator (1 mL of a 0.5 M solution in DMF), and 5 eq of Oxyma Pure (0.5 mL of a 1 M solution in DMF) and allowed to react for 5 min at 75° C. The resultant product was used directly in the next step.

Step 2: Olefin Metathesis

For a 0.1 mmol scale: The linear peptide was synthesized on solid-support according to Step 1. The peptide was not cleaved from resin. A solution of Benzylidene-bis(tricyclohexylphosphine)-dichlororuthenium (Grubb's generation I catalyst) was prepared by dissolving 16 mg (0.2 equiv) (based on peptide resin of 0.1 mmol) in anhydrous 1,2-dichloroethane (5 mL). The solution was degassed by bubbling nitrogen through the solution for 10 minutes. The degassed solution was then added to the resin-bound peptide in a 10 mL fritted syringe. The reaction was allowed to proceed at 45° C. for two hours and then the catalyst was filtered off. The resin was then re-subjected to the metathesis conditions by adding an additional 5 mL of freshly-prepared catalyst solution (16 mg Grubb's generation I catalyst in 5 mL of degassed anhydrous 1,2-dichloroethane). The reaction was allowed to proceed for 2 hours at 45° C. The resin-bound peptide was then washed with dichloromethane (5×10 mL). The reaction can be monitored for completion by removing a few beads, cleaving the peptide (95% TFA/2.5% H20/2.5% triisopropylsilane) and analyzing by LCMS.

Step 3: Cleavage from Solid-Support

The resin from Step 2 was transferred to either a 50 mL polypropylene centrifuge tube or a 10 mL fritted syringe. The peptides were cleaved from their solid support using trifluoroacetic acid/triisopropylsilane/DL-dithiothreitol/water (92.5/2.5/2.5 (w/v)/2.5) mixture. For 0.1 mmol scale of resin, ~10 mL cleavage solution was used. The suspended resin was rocked in cleavage solution for 3 hours at room temperature. The filtrate was collected in 50 mL polypropylene centrifuge tubes and precipitated with chilled diethyl ether (~50 mL per ~5 mL cleavage filtrate). The precipitated crude peptide was collected by centrifugation. The white pellet was then subsequently suspended in chilled diethyl ether and collected by centrifugation two additional times. The resulting solid was air-dried to afford the crude peptide.

Step 4: Cyclization

For a 0.1 mmol scale: The linear peptide was synthesized, cleaved from solid support, and isolated according to Step 3. The solid crude peptide was dissolved with stirring in 30 mL of a degassed water:acetonitrile (1:1) solution in a 50 mL polypropylene centrifuge tube. Additional acetonitrile was added as needed to ensure complete dissolution of the peptide. To this stirred solution, aqueous ammonium bicarbonate (200 mM, degassed) was added dropwise to bring the pH to ~8. Alkylating reagent 1,3-bis(bromomethyl)benzene (0.1 mmol/1 eq) in acetonitrile (1 mL) was added dropwise to the reaction over ~2 min. After complete addition, the reaction was tested to ensure the pH was maintained at ~8. If the pH was below ~8, additional aqueous ammonium bicarbonate (200 mM, degassed) was added dropwise to the reaction until the pH was ~8. The centrifuge tube was capped and the resulting reaction mixture was stirred at room temperature for 1 h. The reaction was then acidified to pH~1 with trifluoroacetic acid and lyophilized to afford the crude peptide as a powder. The desired product was purified by C18 reverse phase chromatography.

Procedure E:

Step 1: Peptide Synthesis

The peptides were synthesized using Fmoc-protected amino acids on a solid-phase Rink Amide MBHA (NovaBiochem, ~0.5 meq/g, 100-200 mesh) or AM (NovaBiochem, ~0.73 meq/g, 100-200 mesh) or 2-Aminoethanethiol-2-chlorotrityl resin (AnaSpec, ~0.9 meq/g, 200-400 mesh) with a CEM Liberty Blue automated microwave peptide synthesizer. Peptides were typically synthesized on a 0.1 mmol scale. Typical reaction conditions were as follows: Deprotection Conditions: 20% piperidine (v/v) in DMF (2×2 min at 75° C.); Residue Coupling Conditions: 5 eq (relative to resin) of activated amino acid (2.5 mL of a 0.2 M amino acid stock solution in DMF) was delivered to the resin, followed by 5 eq of DIC activator (1 mL of a 0.5 M solution in DMF), and 5 eq of Oxyma Pure (0.5 mL of a 1 M solution in DMF) and allowed to react for 5 min at 75° C. The resultant product was used directly in the next step.

Step 2: Cleavage from Solid-Support

The resin from Step 1 was transferred to either a 50 mL polypropylene centrifuge tube or a 10 mL fritted syringe. The peptides were cleaved from their solid support using trifluoroacetic acid/triisopropylsilane/DL-dithiothreitol/water (92.5/2.5/2.5 (w/v)/2.5) mixture. For 0.1 mmol scale of resin, ~10 mL cleavage solution was used. The suspended resin was rocked in cleavage solution for 3 hours at room temperature. The filtrate was collected in 50 mL polypropylene centrifuge tubes and precipitated with chilled diethyl ether (~50 mL per ~5 mL cleavage filtrate). The precipitated crude peptide was collected by centrifugation. The white pellet was then subsequently suspended in chilled diethyl ether and collected by centrifugation two additional times. The resulting solid was air-dried to afford the crude peptide.

Step 3: Cyclization

For a 0.1 mmol scale: The linear peptide was synthesized, cleaved from solid support, and isolated according to Step 2. The solid crude peptide was dissolved with stirring in 30 mL of a degassed water:acetonitrile (1:1) solution in a 50 mL polypropylene centrifuge tube. Additional acetonitrile was added as needed to ensure complete dissolution of the peptide. To this stirred solution, aqueous ammonium bicarbonate (200 mM, degassed) was added dropwise to bring the pH to ~8. Alkylating reagent 1,3-bis(bromomethyl)benzene (0.1 mmol/1 eq) in acetonitrile (1 mL) was added dropwise to the reaction over ~2 min. After complete addition, the reaction was tested to ensure the pH was maintained at ~8. If the pH was below ~8, additional aqueous ammonium bicarbonate (200 mM, degassed) was added dropwise to the reaction until the pH was ~8. The centrifuge tube was capped and the resulting reaction mixture was stirred at room temperature for 1 h. The reaction was then acidified to pH~1 with trifluoroacetic acid and lyophilized to afford the crude peptide as a powder. The desired product was purified by C18 reverse phase chromatography.

Procedure E1:

Step 1: Peptide Synthesis

The peptides were synthesized using Fmoc-protected amino acids on a solid-phase Rink Amide MBHA (NovaBiochem, ~0.5 meq/g, 100-200 mesh) or AM (NovaBiochem, ~0.73 meq/g, 100-200 mesh) or 2-Aminoethanethiol-2-chlorotrityl resin (AnaSpec, ~0.9 meq/g, 200-400 mesh) with a CEM Liberty Blue automated microwave peptide synthesizer. Peptides were typically synthesized on a 0.1 mmol scale. Typical reaction conditions were as follows: Deprotection Conditions: 20% piperidine (v/v) in DMF (2×2 min at 75° C.); Residue Coupling Conditions: 5 eq (relative to resin) of activated amino acid (2.5 mL of a 0.2 M amino acid stock solution in DMF) was delivered to the resin, followed by 5 eq of DIC activator (1 mL of a 0.5 M solution in DMF), and 5 eq of Oxyma Pure (0.5 mL of a 1 M solution in DMF) and allowed to react for 5 min at 75° C. The resultant product was used directly in the next step.

Step 2: Deprotection and Derivatization

The peptide from Step 1 was not cleaved from the resin. To deprotect the DDe protecting groups, the resin was treated with 15 ml of a solution of 2% of hydrazine. The solution was drained and the resin washed with DCM (3×5 mL). The deprotection step was repeated, after which the resin was washed with DCM (5×5 mL), DMF (5×5 mL). Side chain derivatization was performed by manual coupling. Typical reaction conditions were as follows: Deprotection Conditions: 20% piperidine (v/v) in DMF (2×15 min); Residue Coupling Conditions: 5 eq (relative to resin) of amino acid (0.1M in DMF) was delivered to the resin, followed by 5 eq of DIC and 5 eq of HOAt (0.1M solution in DMF) and allowed to react for 60 min at 25° C. The resultant product was used directly in the next step.

Step 3: Cleavage from Solid-Support

The resin from Step 1 was transferred to either a 50 mL polypropylene centrifuge tube or a 10 mL fritted syringe. The peptides were cleaved from their solid support using trifluoroacetic acid/triisopropylsilane/DL-dithiothreitol/water (92.5/2.5/2.5 (w/v)/2.5) mixture. For 0.1 mmol scale of resin, ~10 mL cleavage solution was used. The suspended resin was rocked in cleavage solution for 3 hours at room temperature. The filtrate was collected in 50 mL polypropylene centrifuge tubes and precipitated with chilled diethyl ether (~50 mL per ~5 mL cleavage filtrate). The precipitated crude peptide was collected by centrifugation. The white pellet was then subsequently suspended in chilled diethyl ether and collected by centrifugation two additional times. The resulting solid was air-dried to afford the crude peptide.

Step 4: Cyclization

For a 0.1 mmol scale: The linear peptide was synthesized, cleaved from solid support, and isolated according to Step 2. The solid crude peptide was dissolved with stirring in 30 mL of a degassed water:acetonitrile (1:1) solution in a 50 mL polypropylene centrifuge tube. Additional acetonitrile was added as needed to ensure complete dissolution of the peptide. To this stirred solution, aqueous ammonium bicarbonate (200 mM, degassed) was added dropwise to bring the pH to ~8. Alkylating reagent 1,3-bis(bromomethyl)benzene (0.1 mmol/1 eq) in acetonitrile (1 mL) was added dropwise to the reaction over ~2 min. After complete addition, the reaction was tested to ensure the pH was maintained at ~8. If the pH was below ~8, additional aqueous ammonium bicarbonate (200 mM, degassed) was added dropwise to the reaction until the pH was ~8. The centrifuge tube was capped and the resulting reaction mixture was stirred at room temperature for 1 h. The reaction was then acidified to pH~1 with trifluoroacetic acid and lyophilized to afford the crude peptide as a powder. The desired product was purified by C18 reverse phase chromatography.

Procedure F:

Step 1: Peptide Synthesis

The peptides were synthesized using Fmoc-protected amino acids on a solid-phase Rink Amide MBHA (NovaBiochem, ~0.5 meq/g, 100-200 mesh) or AM (NovaBiochem, ~0.73 meq/g, 100-200 mesh) or 2-Aminoethanethiol-2-chlorotrityl resin (AnaSpec, ~0.9 meq/g, 200-400 mesh) with a CEM Liberty Blue automated microwave peptide synthesizer. Peptides were typically synthesized on a 0.1 mmol scale. Typical reaction conditions were as follows: Deprotection Conditions: 20% piperidine (v/v) in DMF (2×2 min at 75° C.); Residue Coupling Conditions: 5 eq (relative to resin) of activated amino acid (2.5 mL of a 0.2 M amino acid stock solution in DMF) was delivered to the resin, followed by 5 eq of DIC activator (1 mL of a 0.5 M solution in DMF), and 5 eq of Oxyma Pure (0.5 mL of a 1 M solution in DMF) and allowed to react for 5 min at 75° C. The resultant product was used directly in the next step.

Step 2: Cleavage from Solid-Support

The resin from Step 1 was transferred to either a 50 mL polypropylene centrifuge tube or a 10 mL fritted syringe. The peptides were cleaved from their solid support using trifluoroacetic acid/triisopropylsilane/DL-dithiothreitol/water (92.5/2.5/2.5 (w/v)/2.5) mixture. For 0.1 mmol scale of resin, ~10 mL cleavage solution was used. The suspended resin was rocked in cleavage solution for 3 hours at room temperature. The filtrate was collected in 50 mL polypropylene centrifuge tubes and precipitated with chilled diethyl ether (~50 mL per ~5 mL cleavage filtrate). The precipitated crude peptide was collected by centrifugation. The white pellet was then subsequently suspended in chilled diethyl ether and collected by centrifugation two additional times. The resulting solid was air-dried to afford the crude peptide.

Step 3: Cyclization

To a 250 mL round-bottomed flask fitted with a stir bar, was added PyAOP (210 mg, 0.4 mmol; (7-Azabenzotriazol-1-yloxy)tripyrro-lidinophosphonium hexafluorophosphate), HOAt (14 mg, 0.1 mmol; 1-Hydroxy-7-azabenzotriazole) and DIPEA (90 µL, 0.5 mmol) in DMF (80 mL). The precipitated solid crude peptide from Step 3 was dissolved in DMF (25 mL) and added dropwise to the activator solution using a syringe pump (addition over 1.5 h). The resulting yellow solution was stirred overnight at room temperature. After completion of the cyclization (monitored by LCMS), the reaction mixture was acidified by addition of TFA (100 µL). DMF solvent was evaporated under high vacuum and the resulting crude residue was purified by C18 reverse-phase HPLC.

Procedure K:

Step 1: Peptide Synthesis

The peptides were synthesized using Fmoc-protected amino acids on a solid-phase Rink Amide MBHA (NovaBiochem, ~0.5 meq/g, 100-200 mesh) or AM (NovaBiochem, ~0.73 meq/g, 100-200 mesh) or 2-Aminoethanethiol-2-chlorotrityl resin (AnaSpec, ~0.9 meq/g, 200-400 mesh) with a CEM Liberty Blue automated microwave peptide synthesizer. Peptides were typically synthesized on a 0.1 mmol scale. Typical reaction conditions were as follows: Deprotection Conditions: 20% piperidine (v/v) in DMF (2×2 min at 75° C.); Residue Coupling Conditions: 5 eq (relative to resin) of activated amino acid (2.5 mL of a 0.2 M amino acid stock solution in DMF) was delivered to the resin, followed by 5 eq of DIC activator (1 mL of a 0.5 M solution in DMF), and 5 eq of Oxyma Pure (0.5 mL of a 1 M solution in DMF) and allowed to react for 5 min at 75° C. The resultant product was used directly in the next step.

Step 2: Deprotection and Cyclization

The peptide from Step 1 was not cleaved from the resin. The resin-bound peptide was transferred to a 15 mL polypropylene centrifuge tube. To deprotect the alloc/allyl protecting groups, the resin was treated with a solution of tetrakis(triphenylphosphine) palladium (0) (55 mg, 0.05 mmol) and phenylsilane (125 µL, 1.0 mmol) in dry DCM (degassed by bubbling N₂ gas for 5 min). The reaction vessel was rocked at rt for 2 h (released the pressure every 15 min). The solution was drained and the resin washed with DCM (3×5 mL). The deprotection step was repeated, after which the resin was washed with DCM (5×5 mL), DMF (5×5 mL), 1 M diethyldithiocarbamic acid sodium salt in DMF (2×5 mL), DMF (5×5 mL), and DCM (2×5 mL).

A solution of PyAOP (105 mg, 0.2 mmol; (7-Azabenzotriazol-1-yloxy)tripyrrolidino-phosphonium hexafluorophosphate), HOAt (14 mg, 0.1 mmol; 1-Hydroxy-7-azabenzotriazole) and DIPEA (90 µL, 0.5 mmol) in DMF (5 mL) was then added to the resin and the mixture shaken for 3 h at rt. The solution was drained and the resin washed with DMF (3×5 mL) and DCM (3×5 mL). The cyclization step was repeated for 12 h, after which the resin was washed with DMF (5×5 mL) and DCM (5×5 mL) and dried. The resultant product was used directly in the next step.

Step 3: Cleavage from Solid-Support

The resin from Step 2 was transferred to either a 50 mL polypropylene centrifuge tube or a 10 mL fritted syringe. The peptides were cleaved from their solid support using trifluoroacetic acid/triisopropylsilane/DL-dithiothreitol/water (92.5/2.5/2.5 (w/v)/2.5) mixture. For 0.1 mmol scale of resin, ~10 mL cleavage solution was used. The suspended resin was rocked in cleavage solution for 3 hours at room temperature. The filtrate was collected in 50 mL polypropylene centrifuge tubes and precipitated with chilled diethyl ether (~50 mL per ~5 mL cleavage filtrate). The precipitated crude peptide was collected by centrifugation. The white pellet was then subsequently suspended in chilled diethyl ether and collected by centrifugation two additional times. The desired product was purified directly from the crude reaction mixture by C18 reverse phase chromatography.

Table 6 shows the synthetic procedure that was used to synthesize the compounds disclosed herein.

TABLE 6

| Compound | Synthetic Procedure |
|---|---|
| 001 | E |
| 002 | E |
| 003 | E1 |
| 004 | E |
| 005 | E |
| 006 | E |
| 007 | E |
| 008 | E |
| 009 | E |
| 010 | E |
| 011 | E |
| 012 | E |
| 013 | F |
| 014 | E |
| 015 | E |
| 016 | E |
| 017 | E |
| 018 | E |
| 019 | E |
| 020 | E |
| 021 | E |
| 022 | E |
| 023 | E |
| 024 | E |
| 025 | E |
| 026 | E |
| 027 | E |
| 028 | E |
| 029 | E |
| 030 | E |
| 031 | E |
| 032 | E |
| 033 | E |
| 034 | E |

TABLE 6-continued

| Compound | Synthetic Procedure |
|---|---|
| 035 | E |
| 036 | E |
| 037 | E |
| 038 | E |
| 039 | E |
| 040 | E |
| 041 | E |
| 042 | E |
| 043 | E |
| 044 | E |
| 045 | E |
| 046 | E |
| 047 | E |
| 048 | E |
| 049 | A |
| 050 | E |
| 051 | E |
| 052 | E |
| 053 | E |
| 054 | E |
| 055 | E |
| 056 | E |
| 057 | E |
| 058 | E |
| 059 | E |
| 060 | E |
| 061 | E |
| 062 | E |
| 063 | E |
| 064 | K |
| 065 | E |
| 066 | E |
| 067 | E |
| 068 | E |
| 069 | E |
| 070 | E |
| 071 | E |
| 072 | E |
| 073 | E |
| 074 | E |
| 075 | E |
| 076 | E |
| 077 | E |
| 078 | E |
| 079 | E |
| 080 | E |
| 081 | E |
| 082 | E1 |
| 083 | E |
| 084 | E |
| 085 | E |
| 086 | E |
| 087 | E |
| 088 | E |
| 089 | E |
| 090 | E |
| 091 | E |
| 092 | E |
| 093 | E |
| 094 | E |
| 095 | E |
| 096 | E |
| 097 | E |
| 98 | E |
| 99 | E |
| 100 | E |
| 101 | A |
| 102 | A |
| 103 | B |
| 104 | B |
| 105 | B |
| 106 | A |
| 107 | A |
| 108 | A |
| 109 | A |
| 110 | A |
| 111 | A |
| 112 | A |
| 114 | A |
| 115 | A |
| 116 | A1 |
| 117 | A1 |
| 118 | A |
| 119 | A |
| 120 | A |
| 121 | B |

LC/MS analysis: $(M)^+$: Compound 002, expected: 1950.288, found: 1948.912 $(M+1)^{1+}$; Compound 006, expected: 1810.105, found: 1808.817 $(M+1)^{1+}$; Compound 011, expected: 1578.87, found: 1577.7 $(M+1)^{1+}$; Compound 016, expected: 1571.77, found: 1570.64 $(M+1)^{1+}$; Compound 022, expected: 1410.8, found: 1409.69 $(M+1)^{1+}$; Compound 031, expected: 1578.87, found: 1577.7 $(M+1)^{1+}$; Compound 036, expected: 1636.95, found: 1635.75 $(M+1)^{1+}$; Compound 043, expected: 1643.924, found: 1642.731 $(M+1)^{1+}$; Compound 047, expected: 1634.96, found: 1633.77 $(M+1)^{1+}$; Compound 051, expected: 1638.98, found: 1637.73 $(M+1)^{1+}$; Compound 054, expected: 1831.124, found: 1829.838 $(M+1)^{1+}$; Compound 060, expected: 1618.958, found: 1617.772 $(M+1)^{1+}$; Compound 064, expected: 1507.75, found: 1506.8 $(M+1)^{1+}$; Compound 070, expected: 1603.88 found: 1602.7 $(M+1)^{1+}$; Compound 079, expected: 1657.99 found: 1656.75 $(M+1)^{1+}$; Compound 090, expected: 1892.19 found: 1890.83 $(M+1)^{1+}$; Compound 092, expected: 1988.23 found: 1986.83 $(M+1)^{1+}$; Compound 097, expected: 1690.96 found: 1689.71 $(M+1)^{1+}$; Compound 101, expected: 1555.902 found: 1554.74 $(M+1)^{1+}$; Compound 105, expected: 1283.452 found: 1282.506 $(M+1)^{1+}$; Compound 108, expected: 1616.94 found: 1615.76 $(M+1)^{1+}$; Compound 114, expected: 1634.957 found: 1633.767 $(M+1)^{1+}$; and Compound 114, expected: 1616.98 found: 1615.76 $(M+1)^{1+}$.

Example 2. Identification of Polypeptides that Bind Specifically to Human PCSK9 and Inhibit Interaction Between Human PCSK9 and Human LDLR A set of cyclic polypeptides were identified to inhibit the interaction between human PCSK9 and human LDLR. Each polypeptide has an N-terminal amino acid or moiety and a C-terminal amino acid or moiety that is linked by a covalent bond to the other.

A time-resolved fluorescence resonance energy (TR-FRET) assay was used to measure inhibition of the PCSK9-LDLR protein-protein interaction. Briefly, 20 nM avitag-biotinylated human PCSK9 was incubated with 20 nM his-tagged human LDLR EGFa domain in the presence of 5 nM LANCE Ulight Streptavidin (Perkin Elmer) and 5 nM europium-Anti-6xHis (Perkin Elmer) for 2 hours covered at room temperature in buffer containing 50 mM HEPES, 150 mM NaCl, 5 mM CaCl2, 0.01% BSA and 0.01% Surfactant P20. Compounds were tested in dose-response and concentrations giving half-maximal inhibition calculated using a 4-parameter fit equation.

Table 7 shows $IC_{50}$ values obtained by the assay for a group of select compounds. In Table 7, "A" represents 1 nM≤$IC_{50}$≤100 nM; "B" represents 100 nM<$IC_{50}$≤1000 nM; "C" represents 1000 nM<$IC_{50}$<12,100 nM; and "D" represents 21,000 nM<$IC_{50}$<50,000 nM.

TABLE 7

| Compound | IC$_{50}$ |
|---|---|
| 001 | C |
| 002 | A |
| 003 | A |
| 004 | C |
| 005 | C |
| 006 | C |
| 007 | C |
| 008 | B |
| 010 | B |
| 013 | B |
| 014 | A |
| 015 | A |
| 016 | A |
| 017 | B |
| 018 | A |
| 019 | D |
| 020 | D |
| 021 | B |
| 022 | B |
| 023 | A |
| 043 | B |
| 044 | B |
| 046 | B |
| 047 | B |
| 048 | B |
| 049 | C |
| 050 | B |
| 052 | B |
| 055 | C |
| 062 | B |
| 063 | B |
| 071 | B |
| 072 | B |
| 074 | B |
| 075 | B |
| 076 | B |
| 077 | B |
| 078 | B |
| 079 | C |
| 084 | B |
| 086 | B |
| 091 | B |
| 092 | B |

TABLE 7-continued

| Compound | IC$_{50}$ |
|---|---|
| 093 | B |
| 097 | A |
| 098 | D |
| 104 | C |
| 107 | A |
| 108 | B |
| 110 | A |
| 114 | B |
| 115 | B |
| 117 | B |

Example 3. Alexa FRET

The PCSK9 Alexa FRET Standard assay measured the interaction between PCSK9 and an AlexaFluor647 (AF) tagged cyclic peptide, Reagent A ($K_D$=83 nM). A solution containing 1 nM biotinylated PCSK9+2.5 nM Lance Streptavidin Europium (Strep-Eu) was made in 50 mM HEPES pH 7.4, 0.15 M NaCl, 5 mM CaCl2, 0.01% BSA, and 0.01% Surfactant P20. A separate solution containing 40 nM of the AlexaFluor tagged cyclic peptide was made in the same buffer system. An Echo was used to transfer 0.750 ul of compound to an assay plate followed by the addition of 15 ul of PCSK9+Stept-Eu and 15 ul of AF peptide. The final assay volume was 30.750 ul containing 0.5 nM PCSK9, 1.25 nM Strep-Eu, and 20 nM AF cyclic peptide. The reaction was incubated at room temperature for at least two hours prior to fluorescence measurements using an Envision Multilabel Reader. IC$_{50}$ values were determined by fitting data to a sigmoidal dose-response curve using nonlinear regression. Ki was then calculated from the IC$_{50}$ and the $K_D$ of AF cyclic peptide. Counts (B-counts) of the europium-labeled PCSK9 were followed to observe if compounds were adversely PCSK9. A fall off of the B-counts likely indicated a false positive of inhibition. Data from this procedure was reported as "A='numerical value' (nanomolar)"

Reagent A was prepared in accordance with the following method:

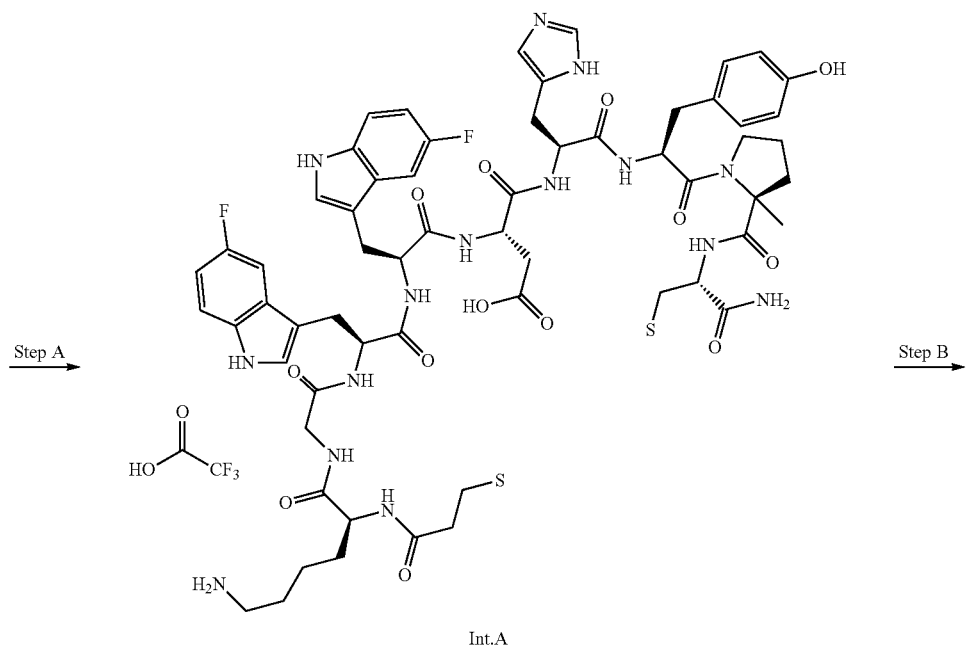

Int.A

-continued
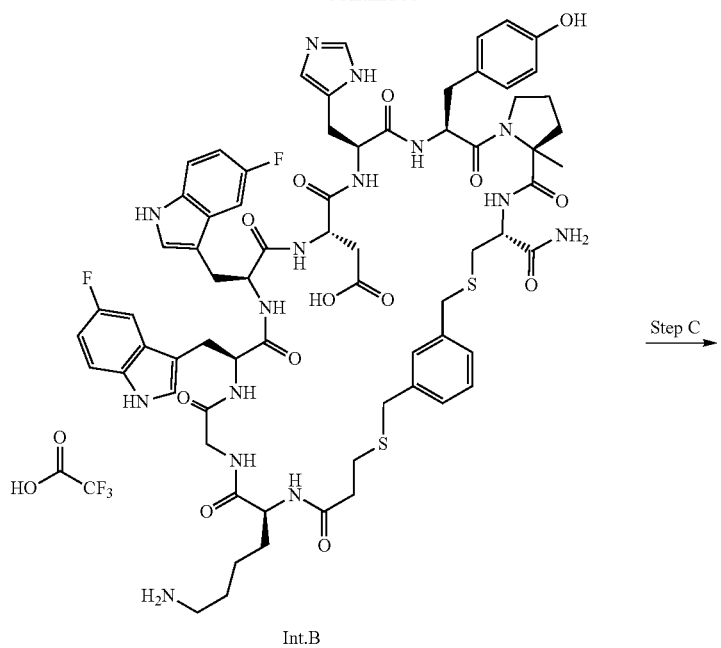
Int.B
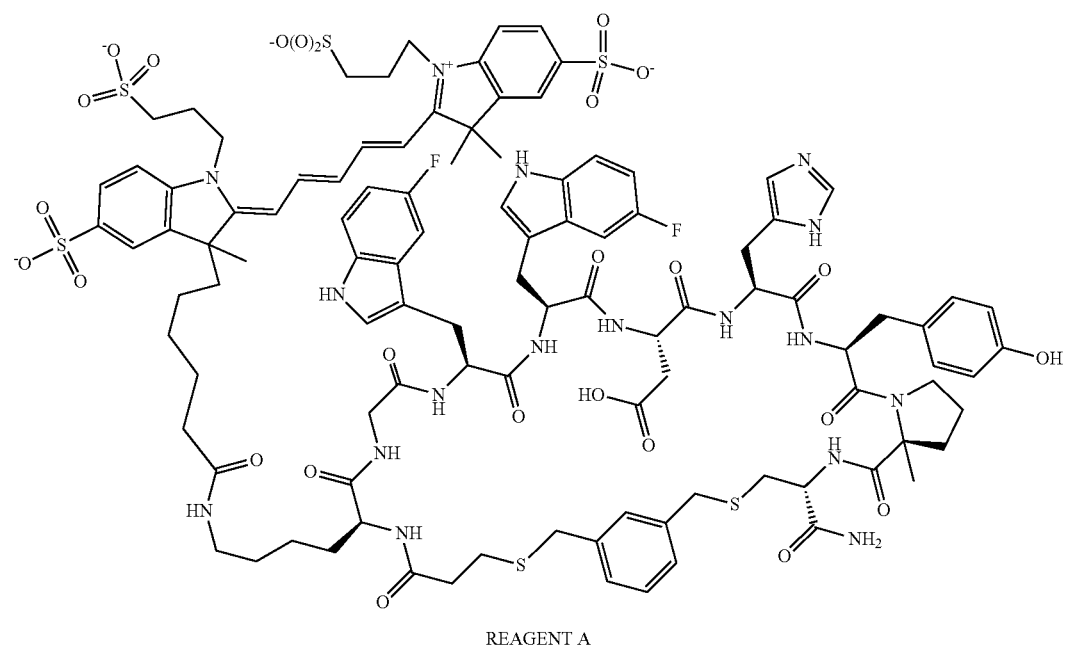
REAGENT A

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol g$^{-1}$. The assembly was performed using single-couplings using 4eq of Fmoc protected amino acid 0.2M in DMF, 4eq of 0.5M HATU in DMF, 4eq of 2M DIPEA (double coupling for Tyr). Fmoc deprotection cycles were performed using 20% (V/V) piperidine in DMF.

The sequence of Fmoc protected amino acids and building blocks used were:
1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (((9H-fluoren-9-yl)methoxy)carbonyl)-L-tyrosine
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)glycine
9. N$^2$-(((9H-fluoren-9-yl)methoxy)carbonyl)-N$^6$-(tert-butoxycarbonyl)-L-lysine
10. 3-(tritylthio)propanoic acid At the end of the assembly, the resin was washed with DMF, MeOH, DCM, Et$_2$O. The peptide was cleaved from solid support using 50 ml of TFA solution (v/v) (91% TFA, 5% H$_2$O, 4% TIPS) for approximately 1.5 hours, at room temperature. The resin was filtered, washed with TFA and solution concentrated to dryness and lyophilized. Lyophilization afforded Intermediate Compound Int. A (399 mg), which was used as crude in the next step. LCMS analysis was calculated for C61H75F2N15O13S2: 1328.48, found: 1328.2 (M+1)$^+$ Step B—Synthesis of Intermediate Compound Int-B Crude Int-A (0.22 mmol) was redissolved in 24 ml of DMF. 6 ml of 1M aqueous solution of sodium bicarbonate was added to raise the pH to 7. Then 0.26 mmol of 1,3-bis(bromomethyl)benzene (0.1M in DMF) was added dropwise. The reaction was left under stirring at room temperature for 20 minutes, quenched with TFA (pH to 3-4) and then concentrated in vacuo to provide crude Int-B, which was purified by RP-HPLC (Waters XBridge, C18, 50×150 mm, 5 □m, 130A; 25% to 40% ACN/water+0.1% TFA modifier over 20 min). Collected fractions were lyophilized to afford 35 mg of Intermediate Compound Int-B. LCMS analysis was calculated. for C71H85F2N15O13S2: 1458.67; found: 1458.8 (M+1)$^+$.

Step C—Synthesis of Compound Reagent A:

Intermediate Compound Int-B (15 mg) was dissolved in 0.2 ml of dry DMSO. Then 15 mg of ALEXAFLUOR 647NHS Ester (A37566, Life technology) dissolved in 1.5 ml of dry DMSO was added. 20 uL of dry DIPEA was added. The reaction was left under stirring at room temperature for 12 hours under Nitrogen atmosphere in the dark. Quenched with TFA (pH to 3-4) and purified by RP-HPLC (Dr Maish, Reprosil Gold C18, 250×20 mm, 120 Å, 10 μm; 20% to 35% of 0.1% TFA in ACN/0.1% TFA in H$_2$O, over 20 min, then 35% to 40% over 5 min at 20 mL/min flow rate). Collected fractions were lyophilized to afford 16.1 mg of Compound Reagent A. LCMS analysis was calculated for C105H122F2N17O26S6$^{3-}$: 2268.58; 1135.8 (M+2)$^{2+}$.

Table 8 shows IC$_{50}$ values obtained by the assay for a group of select compounds. In Table 8, "A" represents 1 nM<IC$_{50}$≤100 nM; "B" represents 100 nM<IC$_{50}$≤1000 nM; "C" represents 1000 nM<IC$_{50}$<12,100 nM; and "D" represents 21,000 nM<IC$_{50}$<50,000 nM.

TABLE 8

| Compound | IC$_{50}$ |
|---|---|
| 002 | A |
| 014 | A |
| 015 | A |
| 016 | A |
| 017 | A |
| 018 | A |
| 019 | C |
| 020 | C |
| 021 | A |
| 022 | A |
| 023 | A |
| 025 | A |
| 026 | A |
| 029 | B |
| 031 | A |
| 032 | A |
| 033 | A |
| 034 | A |
| 035 | B |
| 036 | A |
| 038 | A |
| 039 | B |
| 040 | A |
| 041 | D |
| 042 | A |
| 052 | B |
| 071 | A |
| 086 | B |
| 091 | A |
| 097 | A |
| 098 | B |
| 104 | B |
| 107 | A |
| 110 | A |

Example 4. Alexa Plus FRET

The PCSK9 Alexa FRET Plus assay measured the interaction between PCSK9 and an AlexaFluor647 (AF) tagged cyclic peptide, Reagent B (K$_D$=35 nM). A solution containing 1 nM biotinylated PCSK9+2.5 nM Lance Streptavidin Europium (Strep-Eu) was made in 50 mM HEPES pH 7.4, 0.15 M NaCl, 5 mM CaCl2, 0.01% BSA, and 0.01% Surfactant P20. A separate solution containing 1920 nM of the AlexaFluor tagged cyclic peptide was made in the same buffer system. An Echo was used to transfer 0.075 ul of compound plus 0.675 ul of DMSO to each well of an assay plate followed by the addition of 15 ul of PCSK9+Stept-Eu and 15 ul of AF peptide. The final assay volume was 30.750 ul containing 0.5 nM PCSK9, 1.25 nM Strep-Eu, and 960 nM AF cyclic peptide. The reaction was incubated at room temperature for at least two hours prior to fluorescence measurements using an Envision Multilabel Reader. IC$_{50}$ values were determined by fitting data to a sigmoidal dose-response curve using nonlinear regression. Ki was then calculated from the IC$_{50}$ and the K$_D$ of AF cyclic peptide. Counts (B-counts) of the europium-labeled PCSK9 were followed to observe if compounds were adversely affecting PCSK9. A fall off of the B-counts likely indicated a false positive of inhibition. Data from this procedure was reported as "P='numerical value' (nanomolar)"

Reagent B was prepared by the following procedure.

Step A →
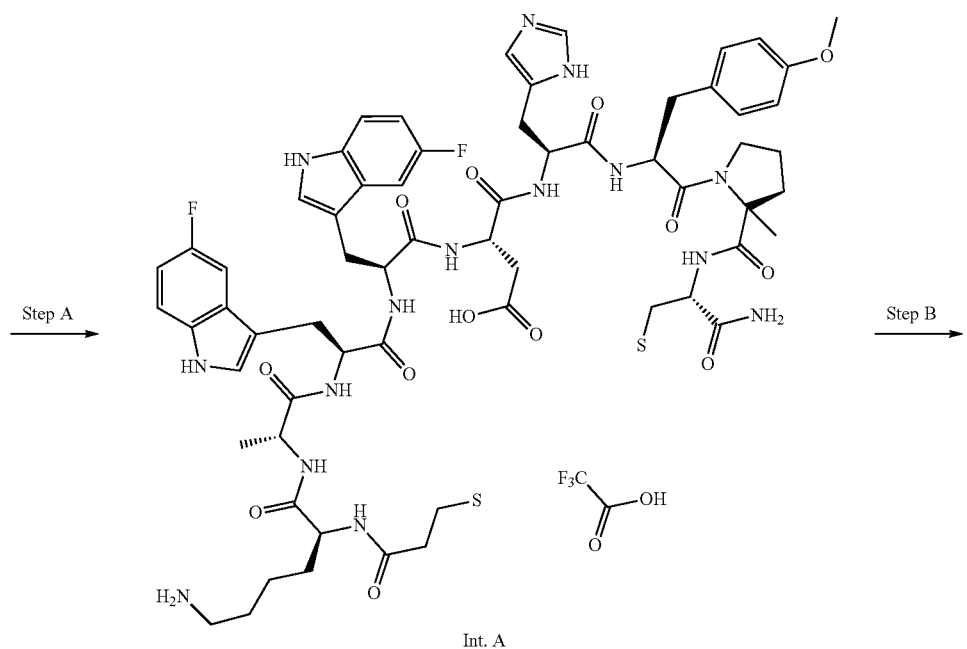
Int. A
Step B →
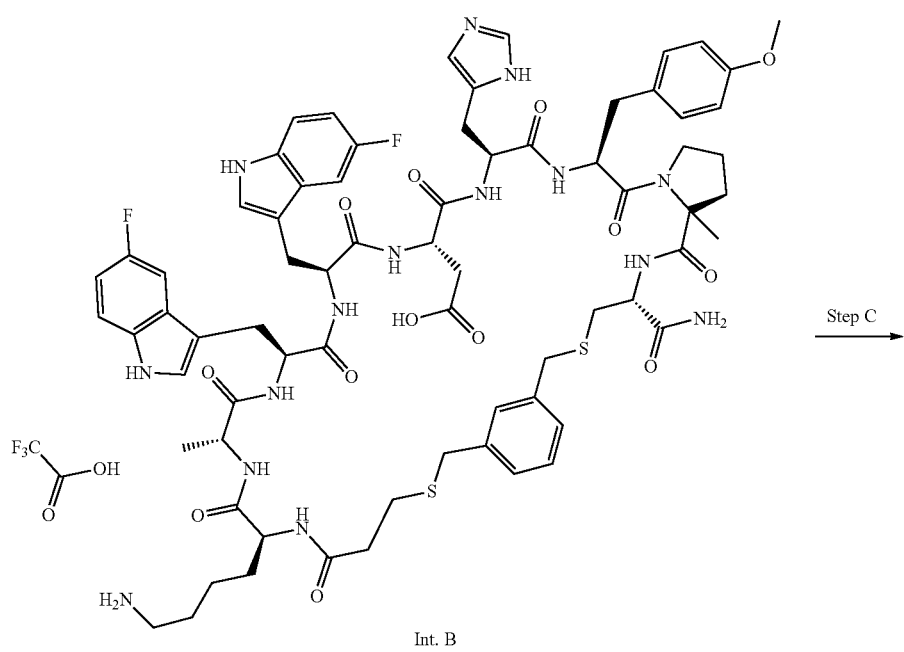
Int. B
Step C →

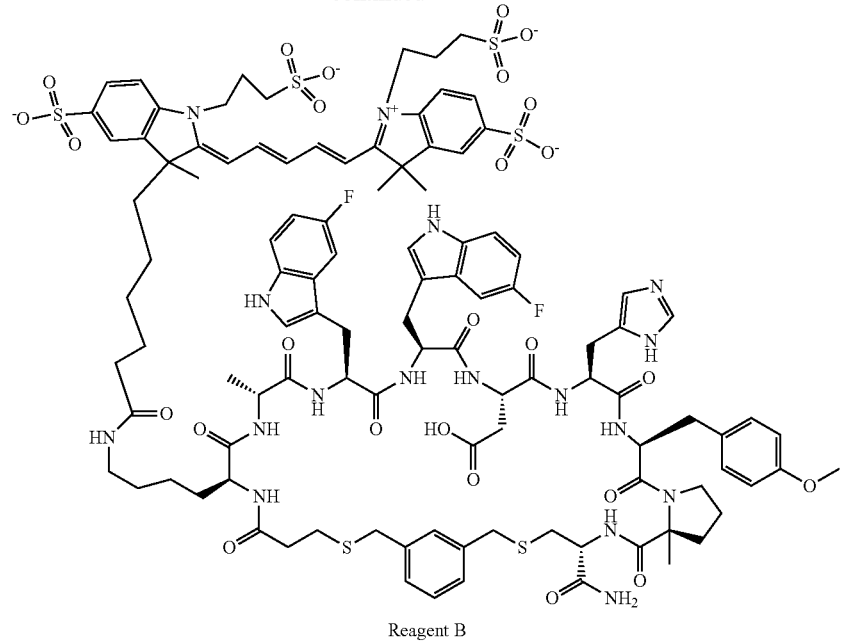

Reagent B

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol g$^{-1}$. The assembly was performed using single-couplings using 4eq of Fmoc protected amino acid 0.2M in DMF, 4eq of 1M Oxyme in DMF, 4eq of 0.5M N,N-diisopropylcarbodiimide (DIC) (double coupling for Y01). Fmoc deprotection cycles were performed using 20% (V/V) piperidine in DMF.

The sequence of Fmoc protected amino acids and building blocks used were:
1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (S)-2-((((9H-fluoren-9-yl)methoxy)carbonyl)amino)-3-(4-methoxyphenyl)propanoic acid
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)-D-alanine
9. N$^2$-(((9H-fluoren-9-yl)methoxy)carbonyl)-N$^6$-(tert-butoxycarbonyl)-L-lysine
10. 3-(tritylthio)propanoic acid At the end of the assembly, the resin was washed with DMF, MeOH, DCM, Et$_2$O. The peptide was cleaved from solid support using 50 ml of TFA solution (v/v) (91% TFA, 5% H$_2$O, 4% TIPS) for approximately 1.5 hours, at room temperature. The resin was filtered, washed with TFA and solution concentrated to dryness and lyophilized. Lyophilization afforded Intermediate Compound Int. A (300 mg), which was used as crude in the next step. LCMS analysis was calculated for C63H79F2N15O13S2: 1356.53, found: 1356.9 (M+1)$^+$.

Step B—Synthesis of Intermediate Compound Int-B

Crude Int-A (0.22 mmol) was redissolved in 24 ml of DMF. 6 ml of 1M aqueous solution of sodium bicarbonate was added to raise the pH to 7. Then 0.26 mmol of 1,3-bis(bromomethyl)benzene (0.1M in DMF) was added dropwise. The reaction was left under stirring at room temperature for 20 minutes, quenched with TFA (pH to 3-4) and then concentrated in vacuo to provide crude Int-B, which was purified by RP-HPLC (Waters XBridge, C18, 50×150 mm, 5 □m, 130 Å; 25% to 40% ACN/water+0.1% TFA modifier over 20 min). Collected fractions were lyophilized to afford 35 mg of Intermediate Compound Int-B. LCMS analysis was calculated. for C71H85F2N15O13S2: 1458.67; found: 1458.8 (M+1)+.

Step C—Synthesis of Compound Reagent B

Intermediate Compound Int-B (15 mg) was dissolved in 0.2 ml of dry DMSO. Then 15 mg of ALEXAFLUOR 647NHS Ester (A37566, Life technology) dissolved in 1.5 ml of dry DMSO was added. 20 uL of dry DIPEA was added. The reaction was left under stirring at room temperature for 12 hours under Nitrogen atmosphere in the dark. Quenched with TFA (pH to 3-4) and purified by RP-HPLC (Dr Maish, Reprosil Gold C18, 250×20 mm, 120 Å, 10 μm; 20% to 35% of 0.1% TFA in ACN/0.1% TFA in H$_2$O, over 20 min, then 35% to 40% over 5 min at 20 mL/min flow rate). Collected fractions were lyophilized to afford 16.1 mg of Compound Reagent B. LCMS analysis for C107H126F2N17O26S6$^{3-}$: 2296.64; found: 1150.6 (M+2)$^{2+}$. Activity data obtained by one or both of the above-described procedures was reported for selected example compounds of the invention in the following format:

Example No.: A (standard TR Fret)='numerical value'; P (Alexa Fret plus standard TR Fret)='numerical value'I, note that all values reported are nanomolar.

Table 9 shows $IC_{50}$ values obtained by the assay for a group of select compounds. In Table 9, "A" represents 1 nM<$IC_{50}$≤100 nM; "B" represents 100 nM<$IC_{50}$≤500 nM; and "C" represents 500 nM<$IC_{50}$≤5000 nM.

TABLE 9

| Compound | $IC_{50}$ |
|---|---|
| 014 | A |
| 015 | A |
| 016 | A |
| 031 | A |
| 032 | A |
| 034 | A |
| 035 | B |
| 036 | A |
| 039 | A |
| 040 | A |
| 041 | C |
| 042 | A |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

What is claimed is:
1. A cyclic peptide having the structure of Formula (I):

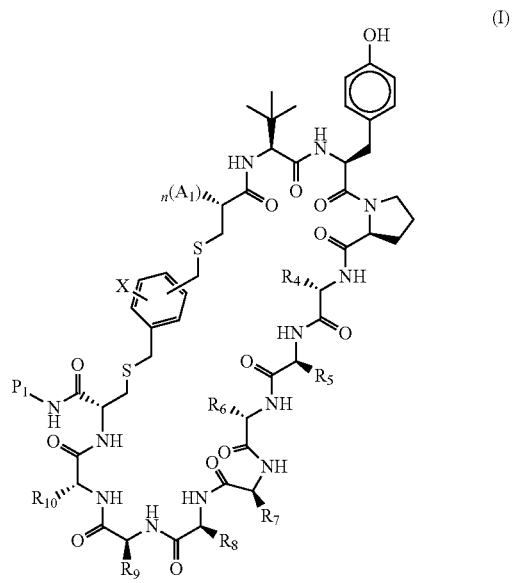

or a pharmaceutically acceptable salt thereof;
wherein:
$A_1$ is an acyl or sulfonyl protected amino acid side chain of

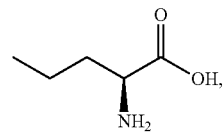

or is an acyl protected amine;
$R_4$ is selected from the group consisting of the amino acid side chains of THR,

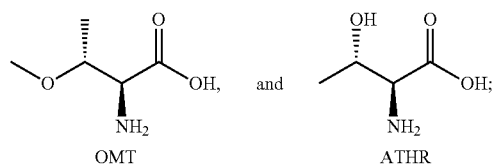

$R_5$ is the amino acid side chain of

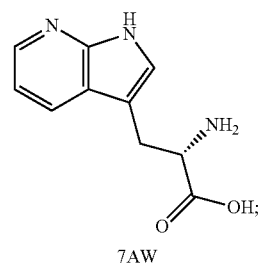 [SMILES: N[C@@H](Cc1c[nH]c2ncccc12)C(=O)O]

$R_6$ is selected from the group consisting of the amino acid side chains of

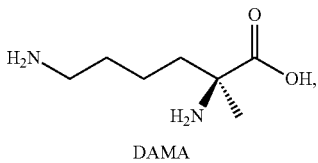
DAMA

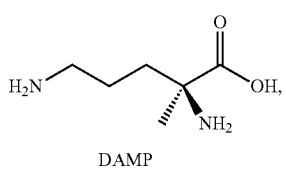
DAMP

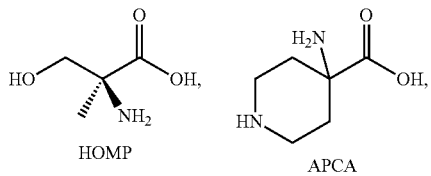
HOMP    APCA

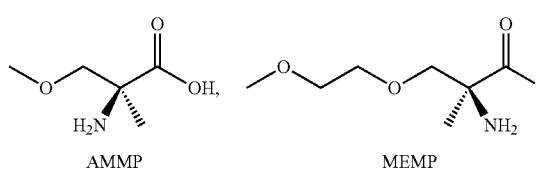
AMMP    MEMP

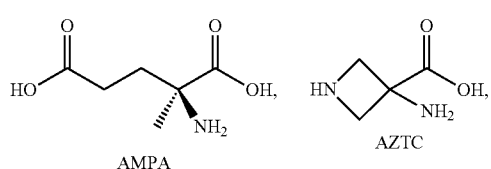
AMPA    AZTC

GLU, and

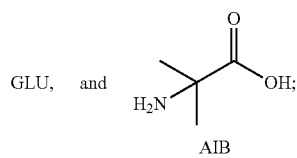
AIB $R_7$ is selected from the group consisting of the amino acid side chains of GLU and ALA;

$R_8$ is selected from the group consisting of the amino acid side chains of TYR and

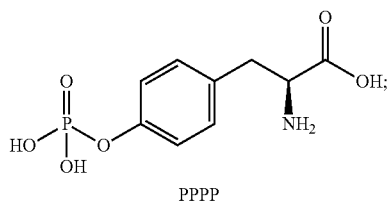
PPPP $R_9$ is

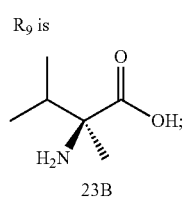
23B $R_{10}$ is selected from the group consisting of the amino acid side chains of THR,

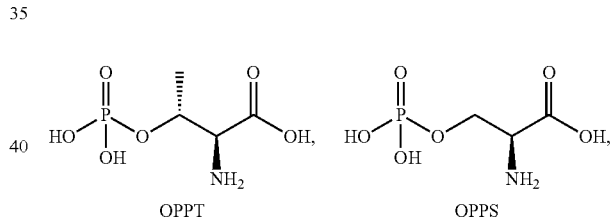
OPPT    OPPS

SER, and LYS;

$P_1$ is H, methyl, an acetyl group, or

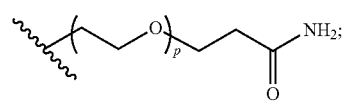

X is H or F;

n is 0 or 1;

p is 2, 3, or 4;

wherein each amino acid residue is optionally an N-methylated amino acid; and wherein each amino acid residue can be in the R or S configuration.

2. The cyclic peptide of claim 1, wherein the cyclic peptide is selected from:
014
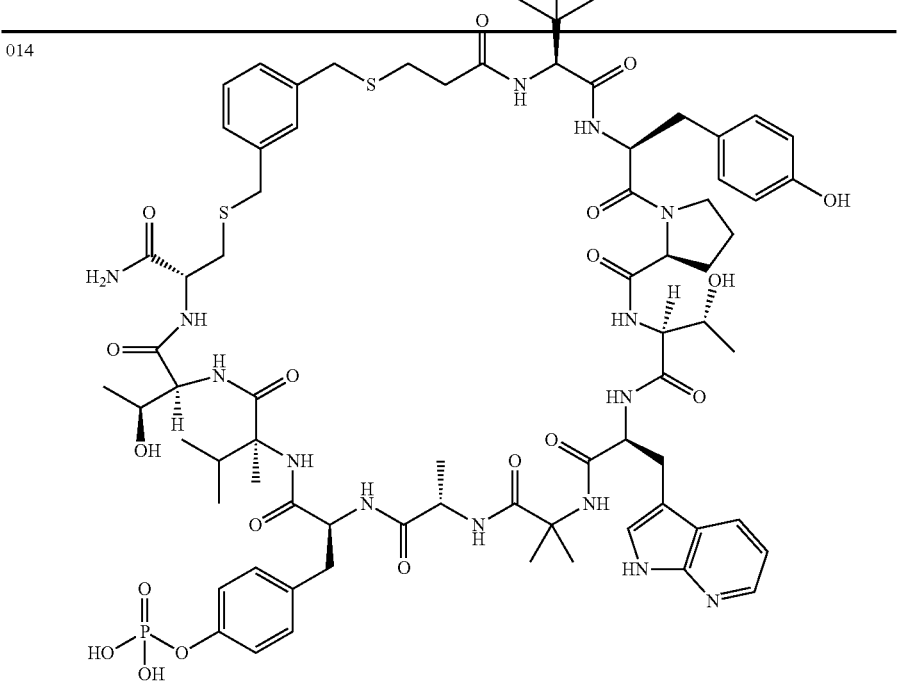
015
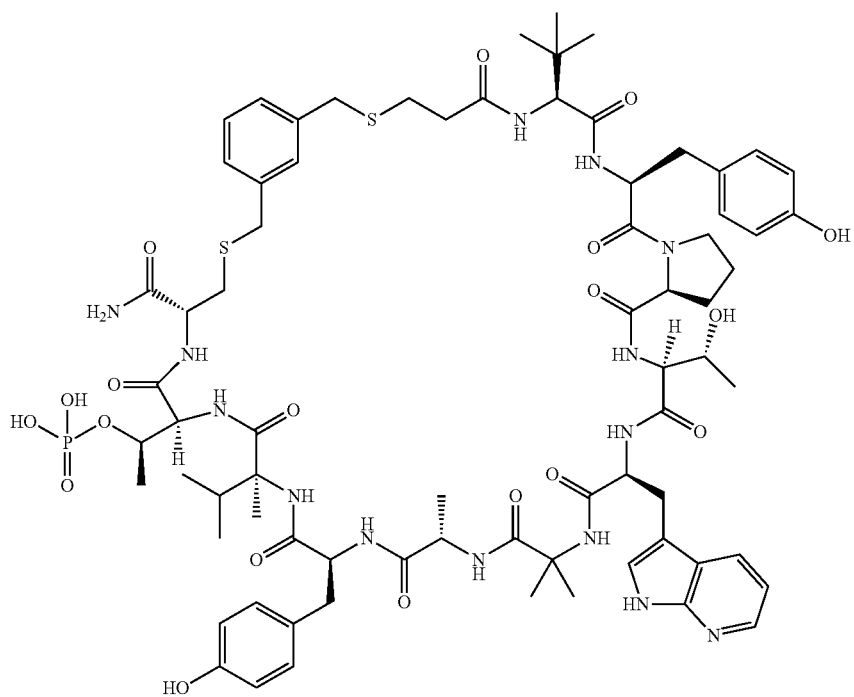 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)OP(=O)(O)O)NC1=O]

016
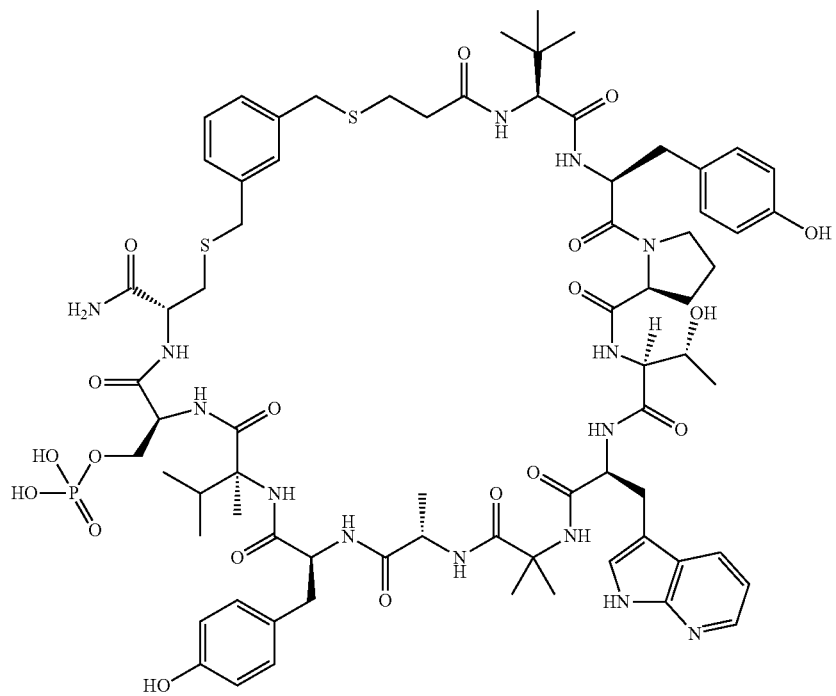 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H](COP(=O)(O)O)NC1=O]
017
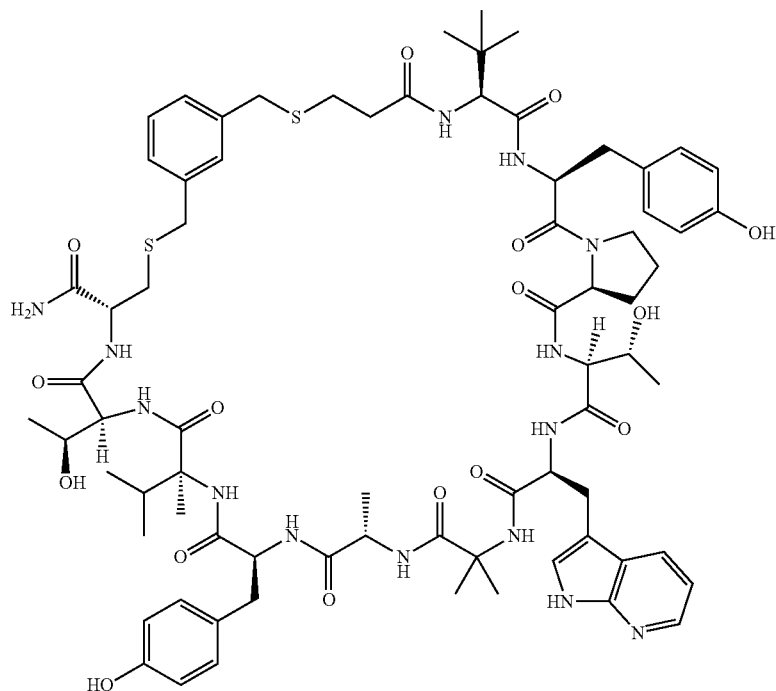 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@H](C)O)NC1=O]

018
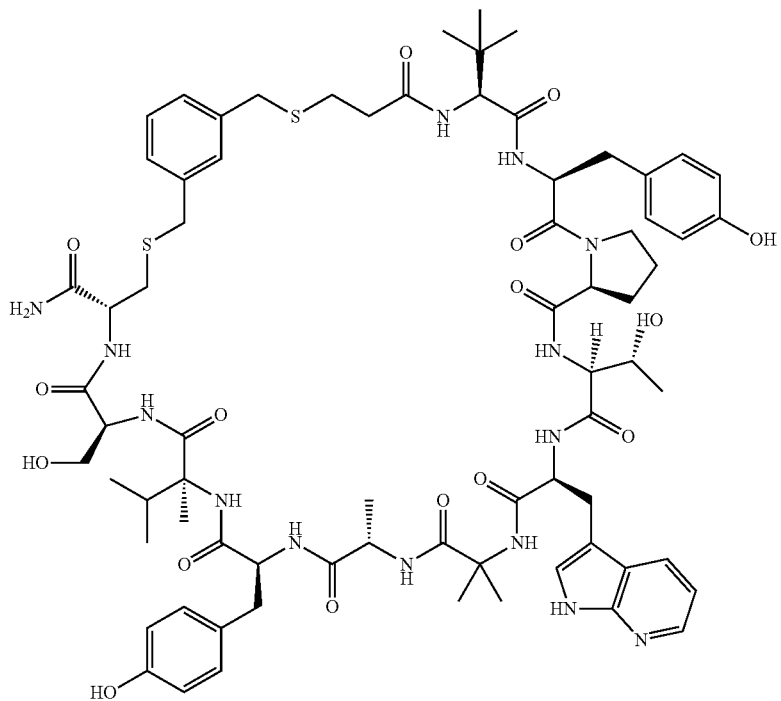 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CO)NC1=O]
019
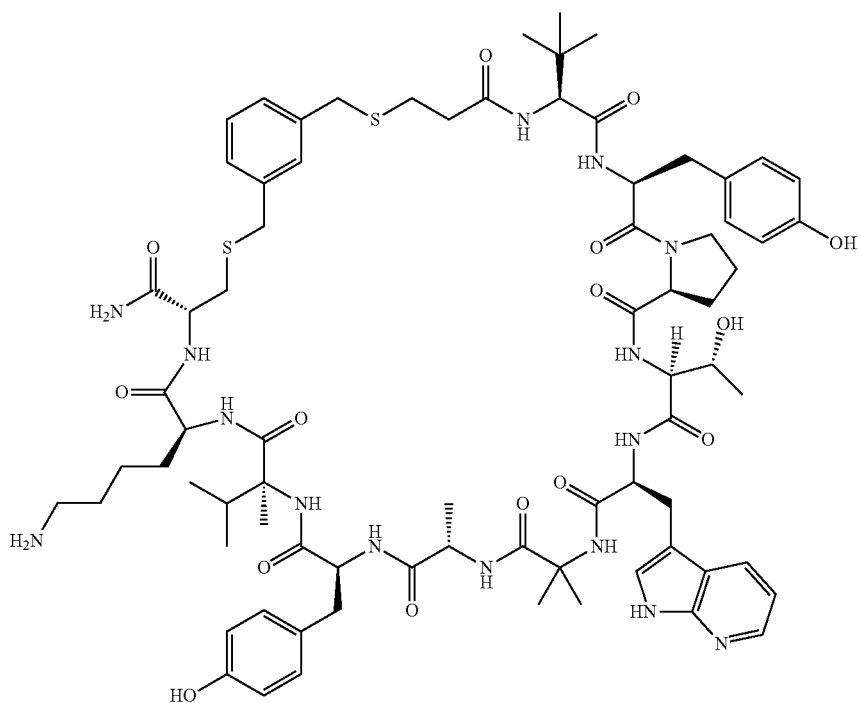 [SMILES: CC(C)[C@]1(C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CCCCN)NC1=O]

020
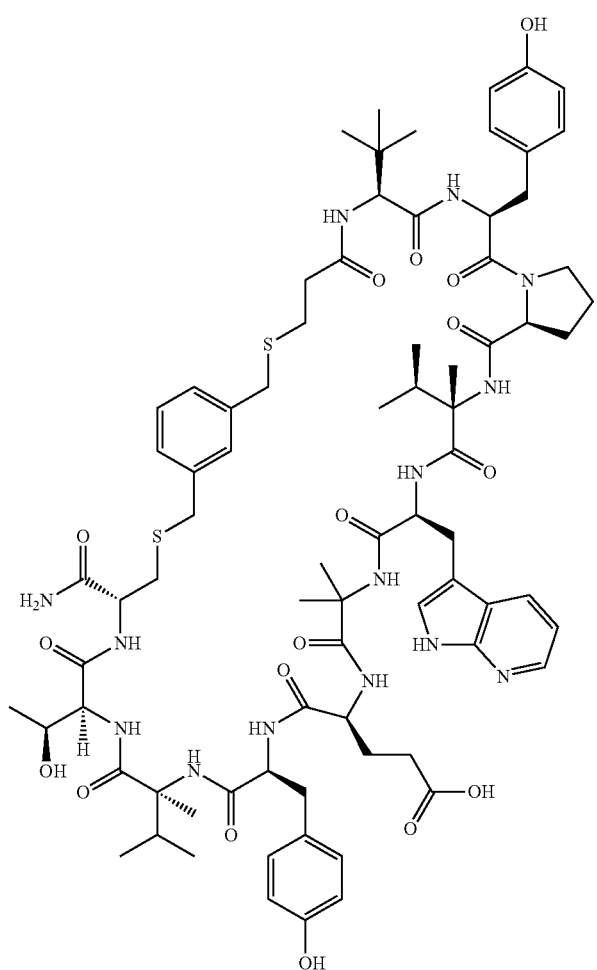

023
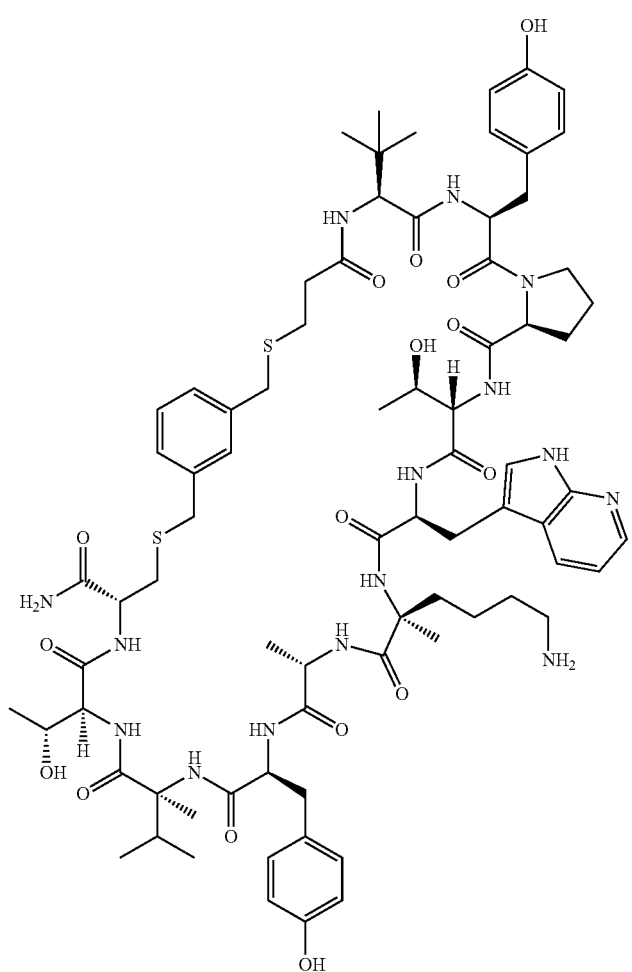 [SMILES: CC(C)[C@]1(C)NC(=O)[C@H](Cc2ccc(O)cc2)NC(=O)[C@H](C)NC(=O)[C@](C)(CCCCN)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]

024
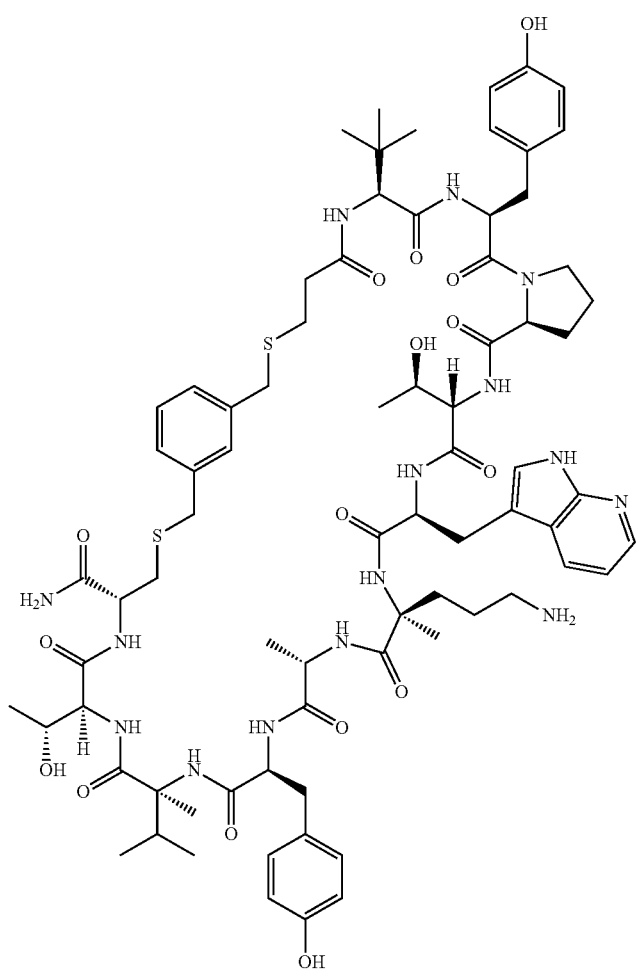 [SMILES: CC(C)[C@]1(C)NC(=O)[C@H](Cc2ccc(O)cc2)NC(=O)[C@H](C)NC(=O)[C@](C)(CCCN)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]

025
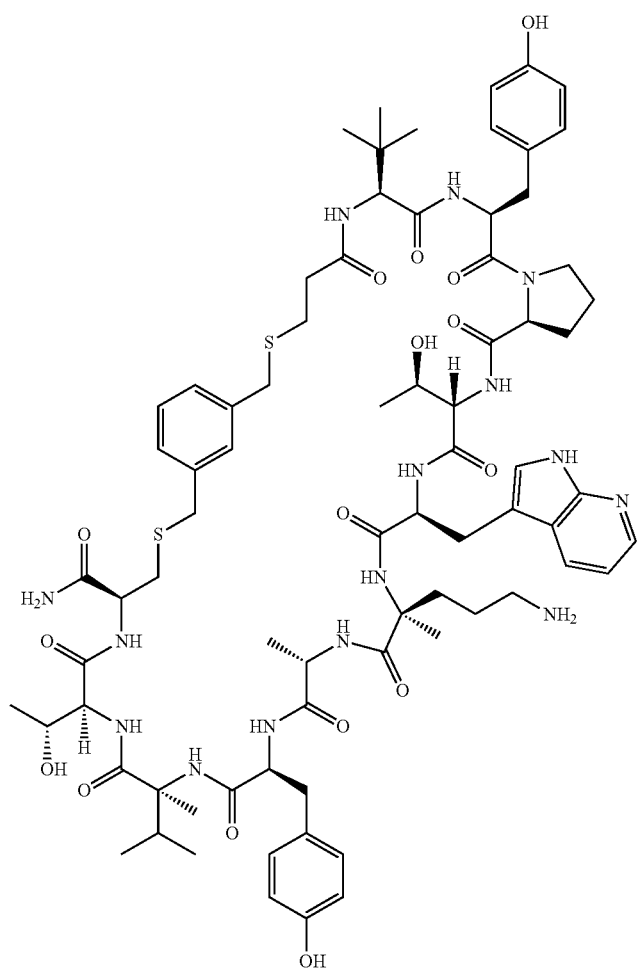 [SMILES: CC(C)[C@]1(C)NC(=O)[C@H](Cc2ccc(O)cc2)NC(=O)[C@H](C)NC(=O)[C@](C)(CCCN)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@H](C(N)=O)NC(=O)[C@H]([C@@H](C)O)NC1=O]

026
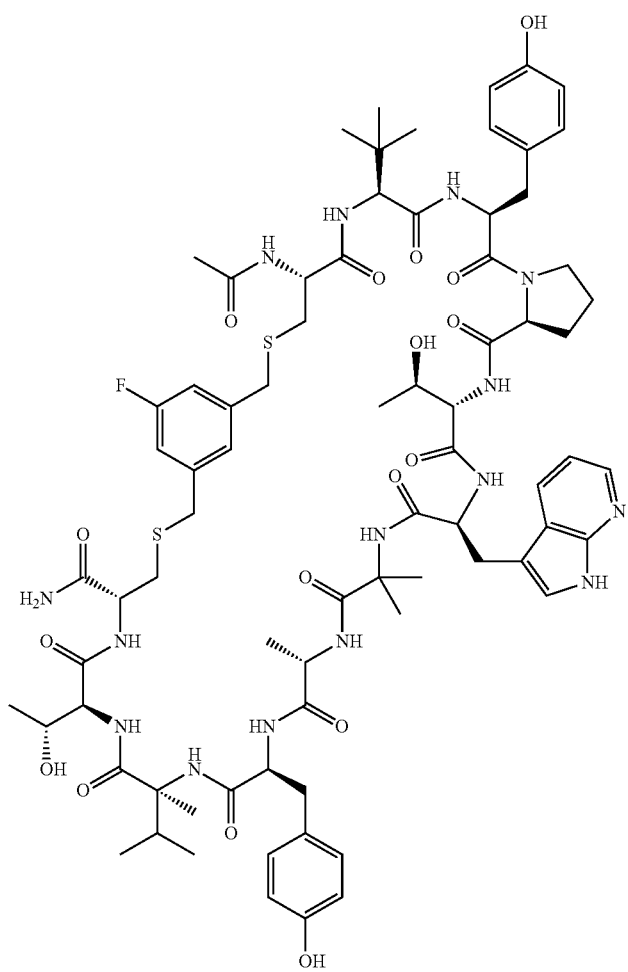 [SMILES: CC(=O)N[C@H]1CSCc2cc(F)cc(c2)CSC[C@@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]

027
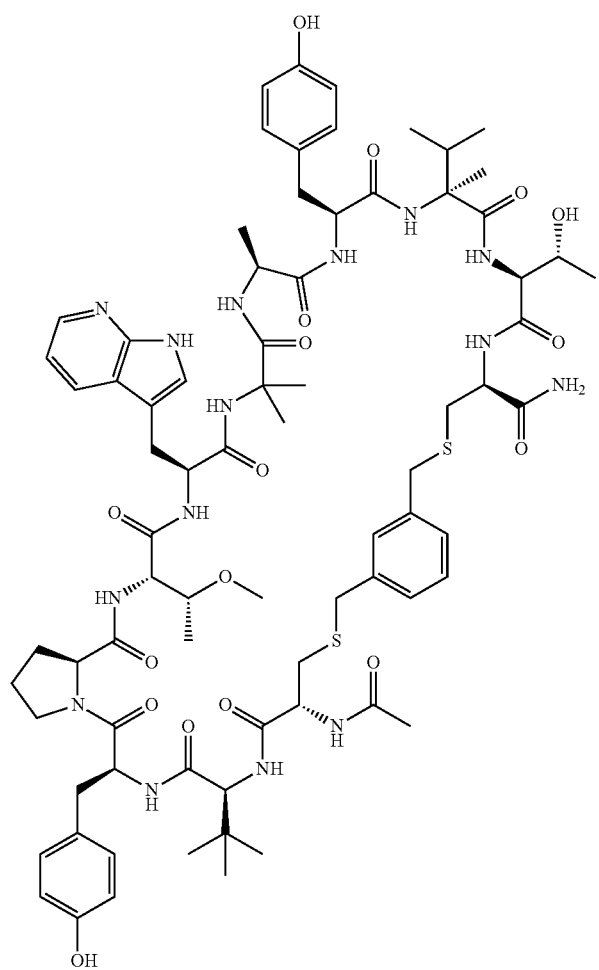 [SMILES: CO[C@H](C)[C@@H]1NC(=O)[C@@H]2CCCN2C(=O)[C@H](Cc2ccc(O)cc2)NC(=O)[C@H](C(C)(C)C)NC(=O)[C@@H](NC(C)=O)CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC1=O]

028
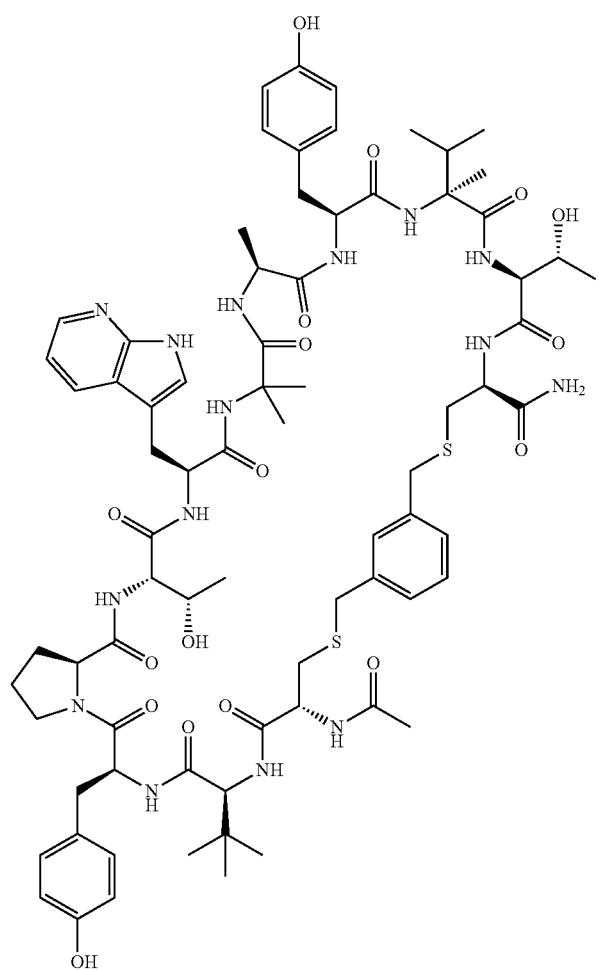 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@H](C)O)NC(=O)[C@@H]2CCCN2C(=O)[C@H](Cc2ccc(O)cc2)NC(=O)[C@H](C(C)(C)C)NC1=O]

029
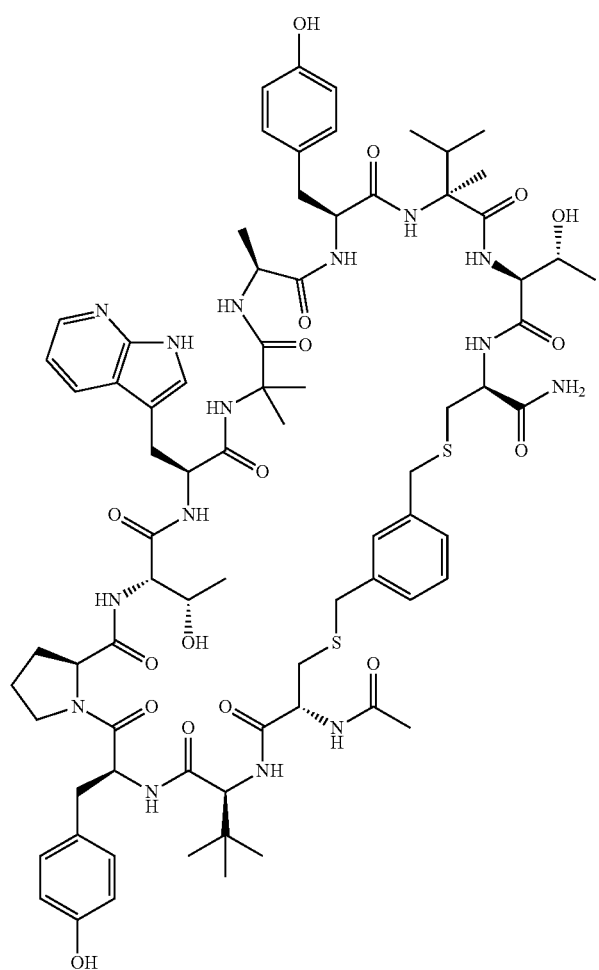 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@H](C)O)NC(=O)[C@@H]2CCCN2C(=O)[C@H](Cc2ccc(O)cc2)NC(=O)[C@H](C(C)(C)C)NC1=O]

030
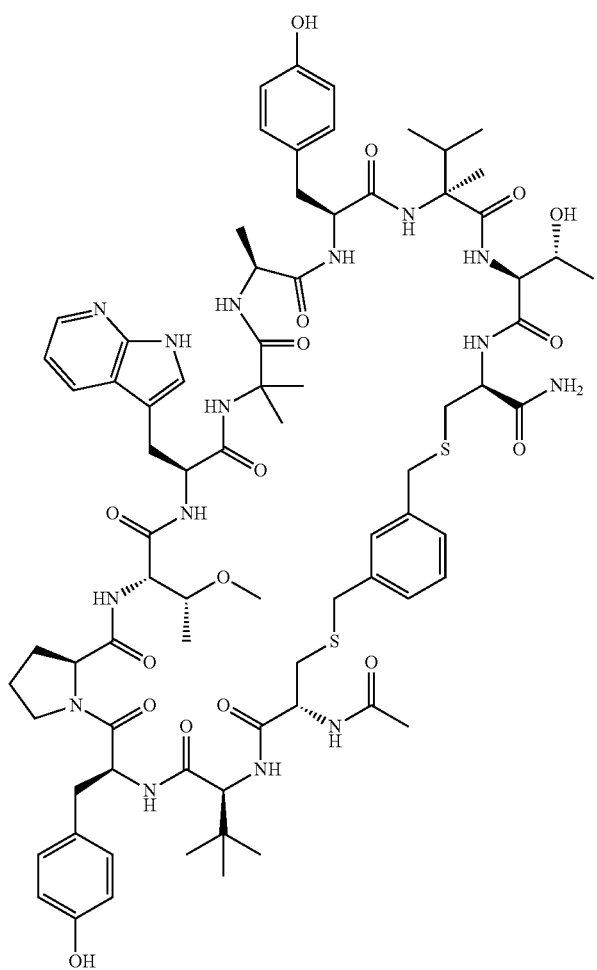 [SMILES: CO[C@H](C)[C@@H]1NC(=O)[C@@H]2CCCN2C(=O)[C@H](Cc2ccc(O)cc2)NC(=O)[C@H](C(C)(C)C)NC(=O)[C@@H](NC(C)=O)CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC1=O]

031
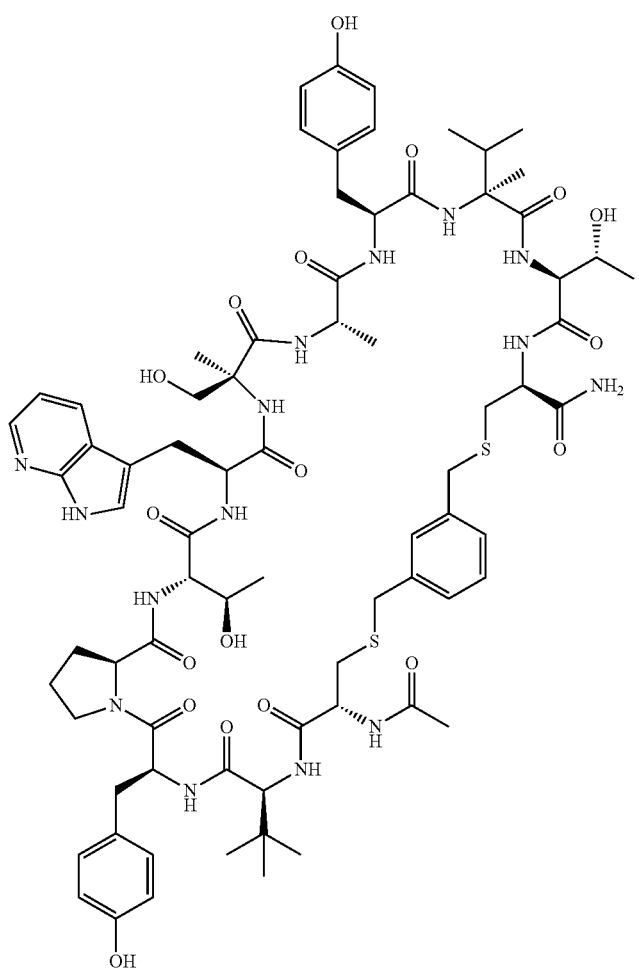 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)[C@](C)(CO)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]

033
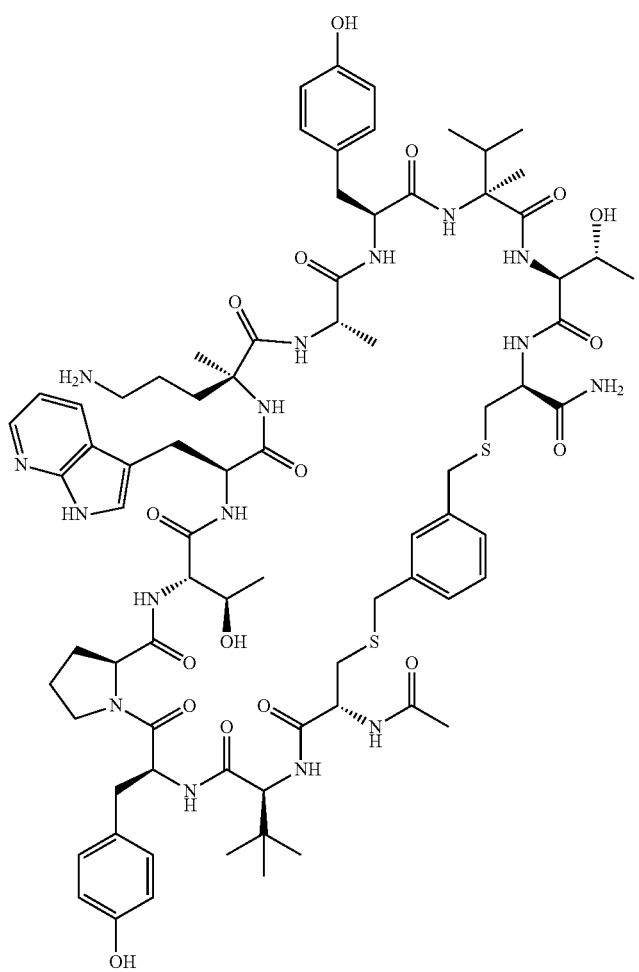 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)[C@](C)(CCCN)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]

034
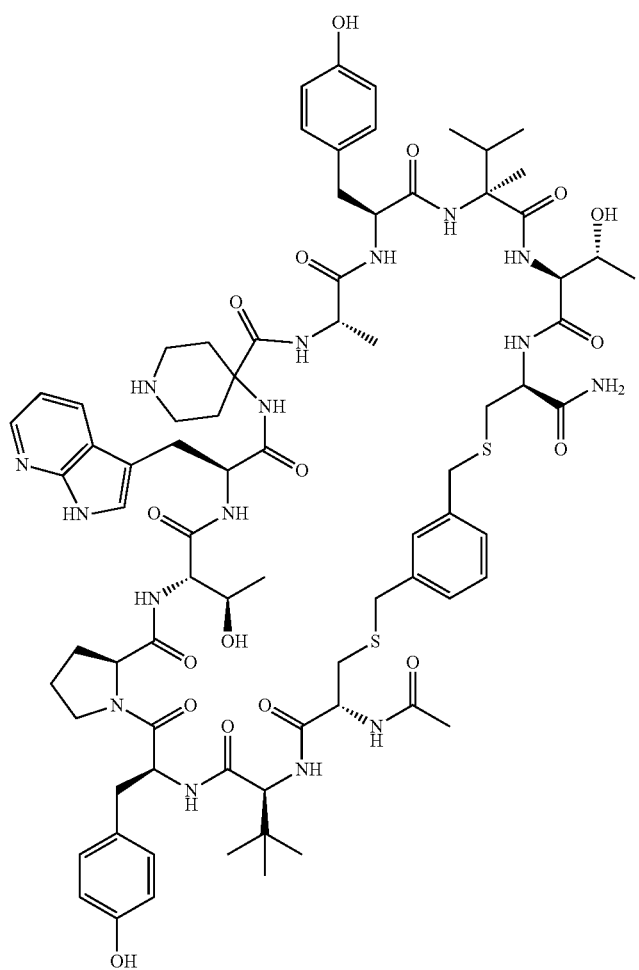 [SMILES: CC(=O)N[C@H]1CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC(=O)C2(CCNCC2)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC1=O]

035
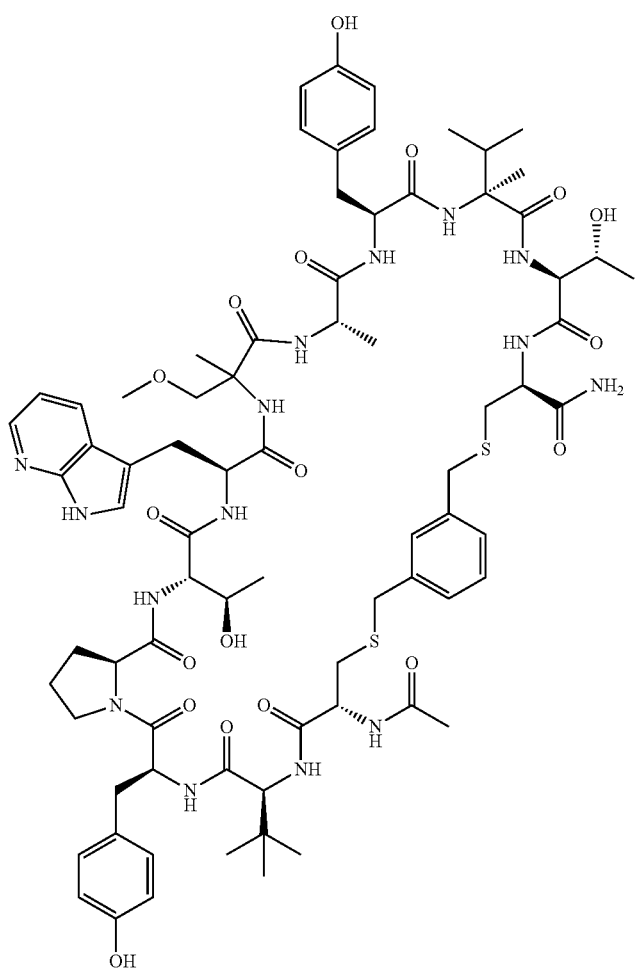 [SMILES: COCC1(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)[C@@H](NC(C)=O)CSCc2cccc(c2)CSC[C@H](C(N)=O)NC(=O)[C@H]([C@@H](C)O)NC(=O)[C@](C)(C(C)C)NC(=O)[C@H](Cc2ccc(O)cc2)NC(=O)[C@H](C)NC1=O]

036
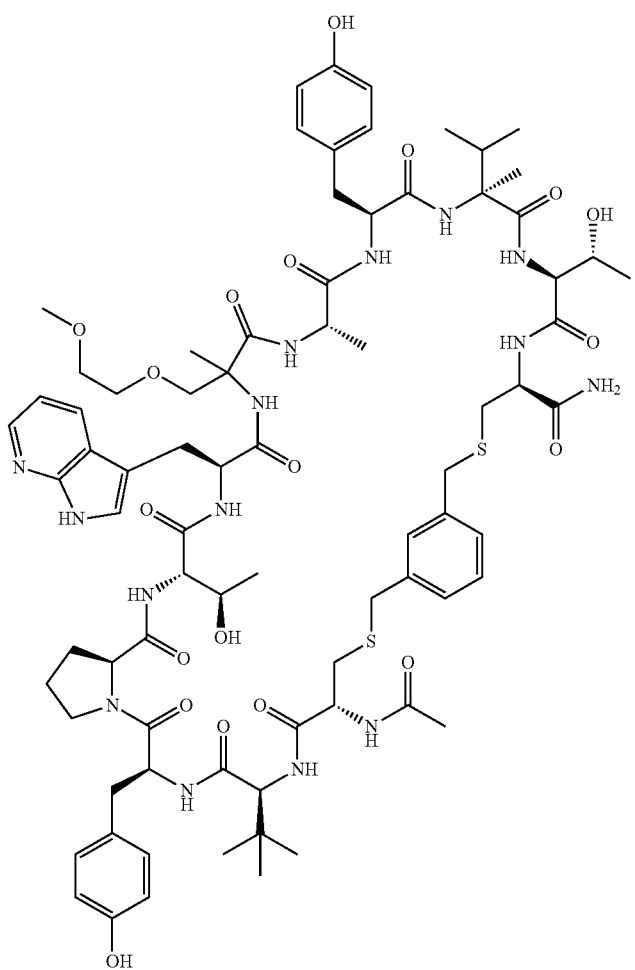

037
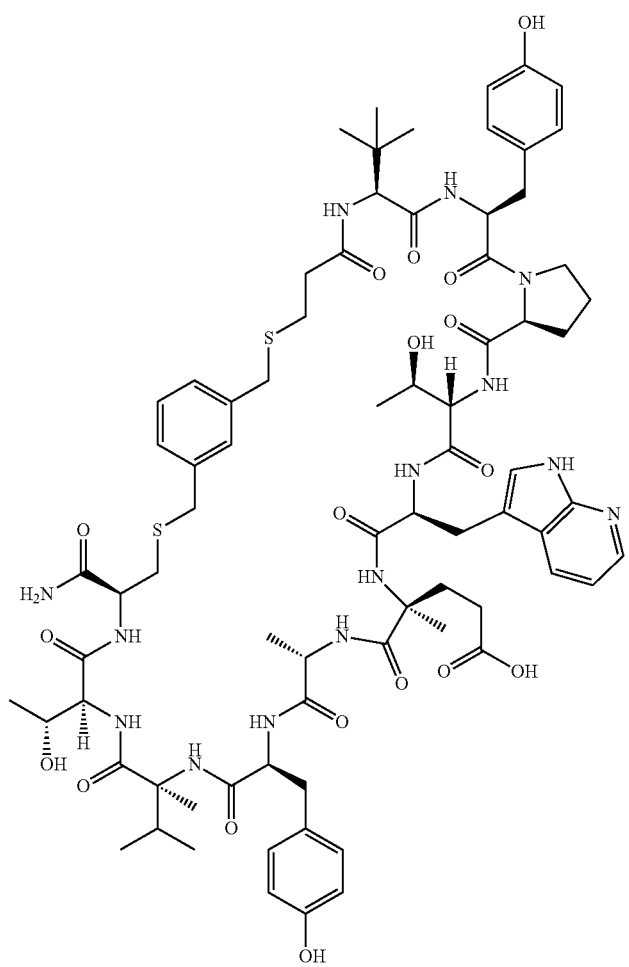

038
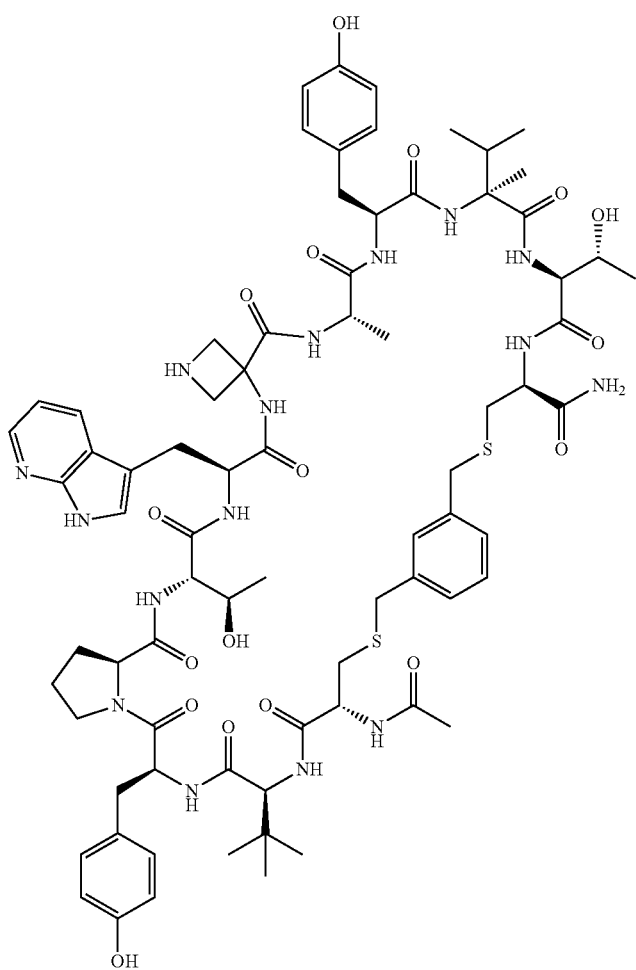

039
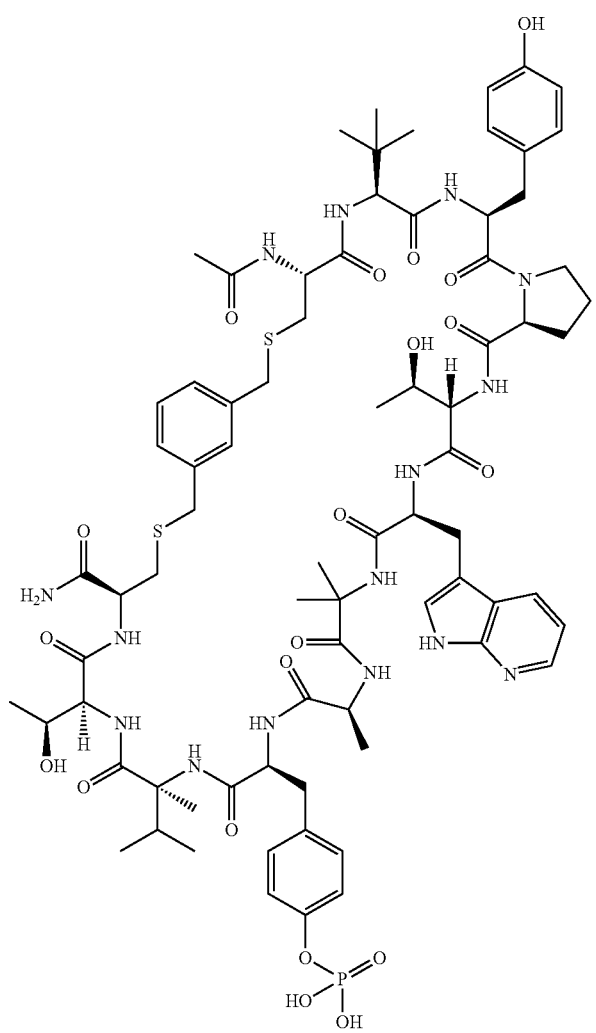

3. The cyclic peptide of claim 1, wherein the cyclic peptide is selected from:
014
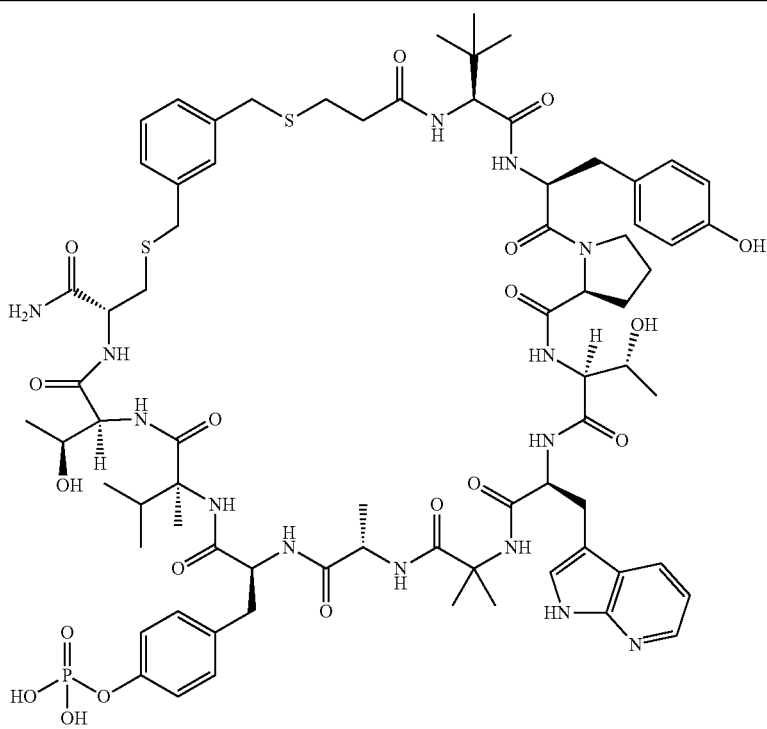
015
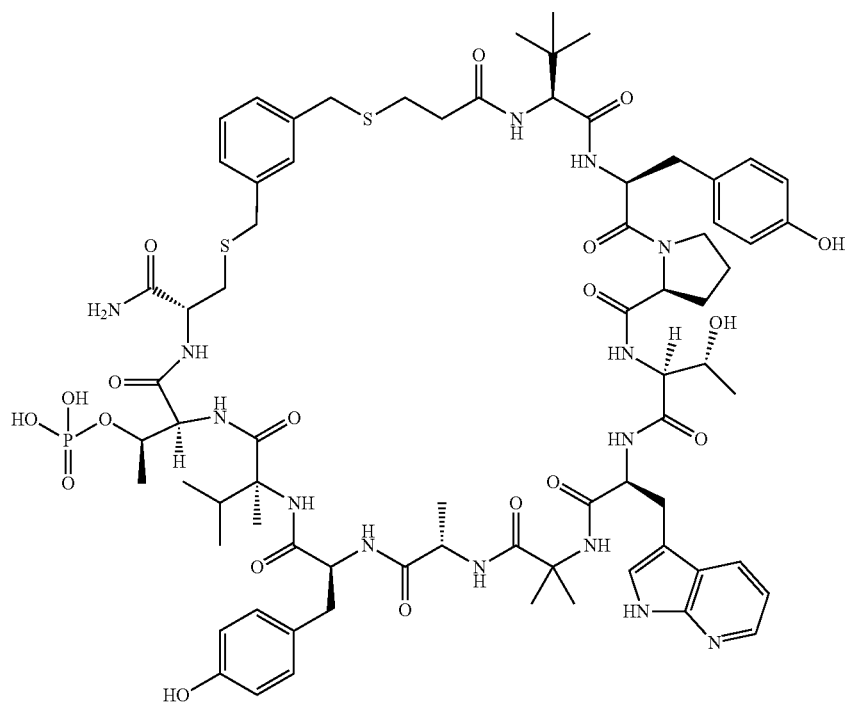

016
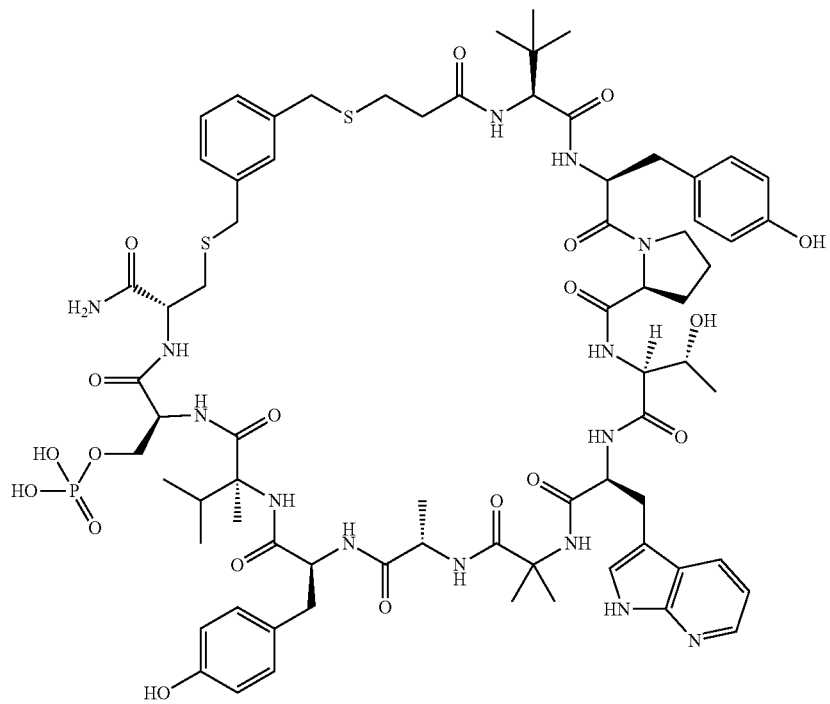
017
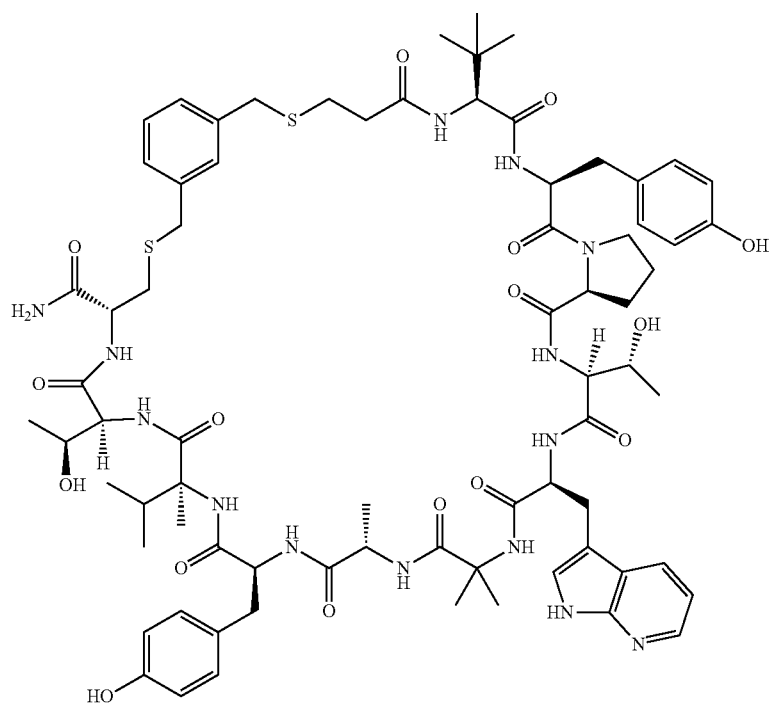

018
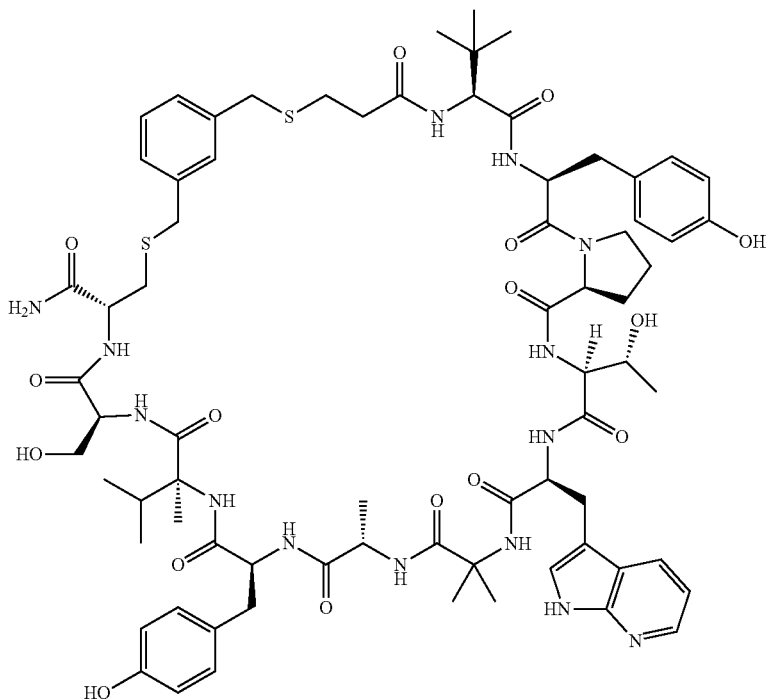
023
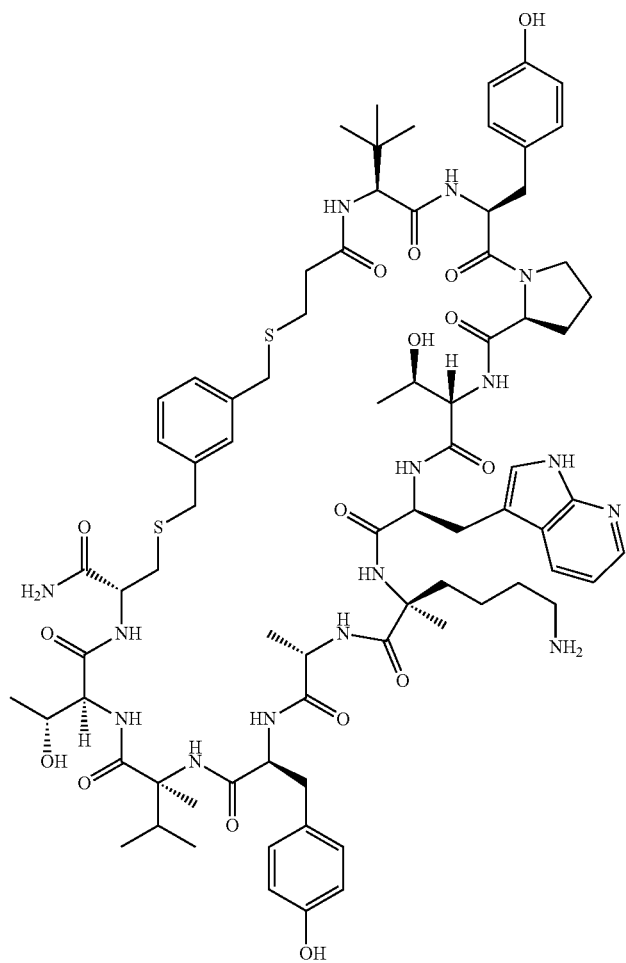

033
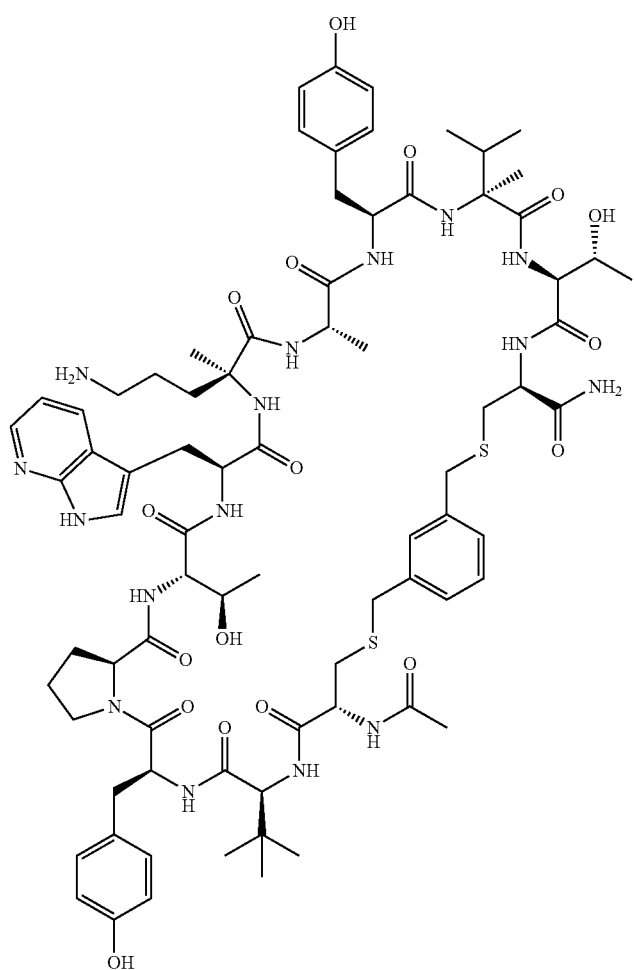

034
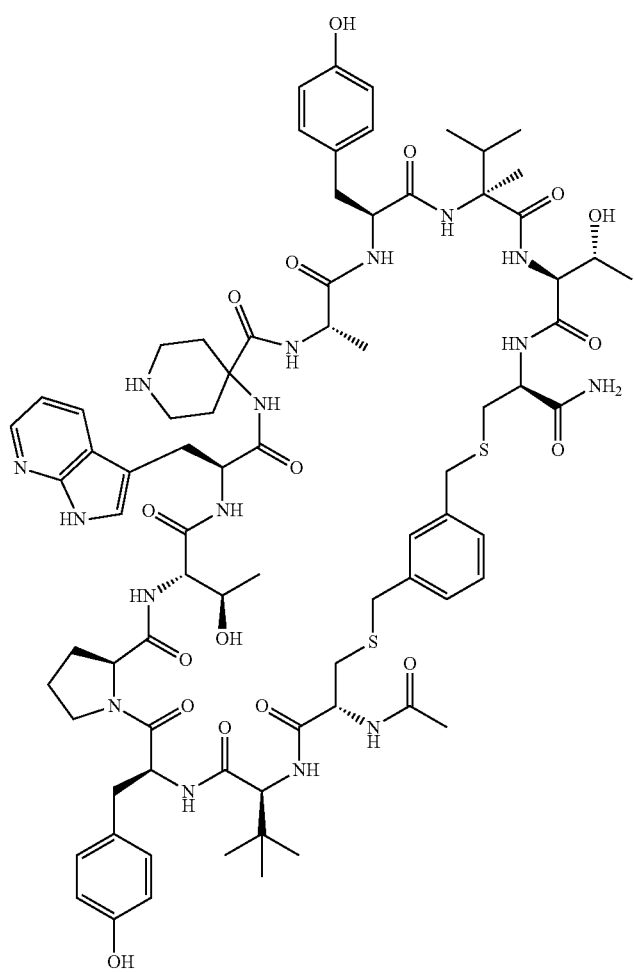

035
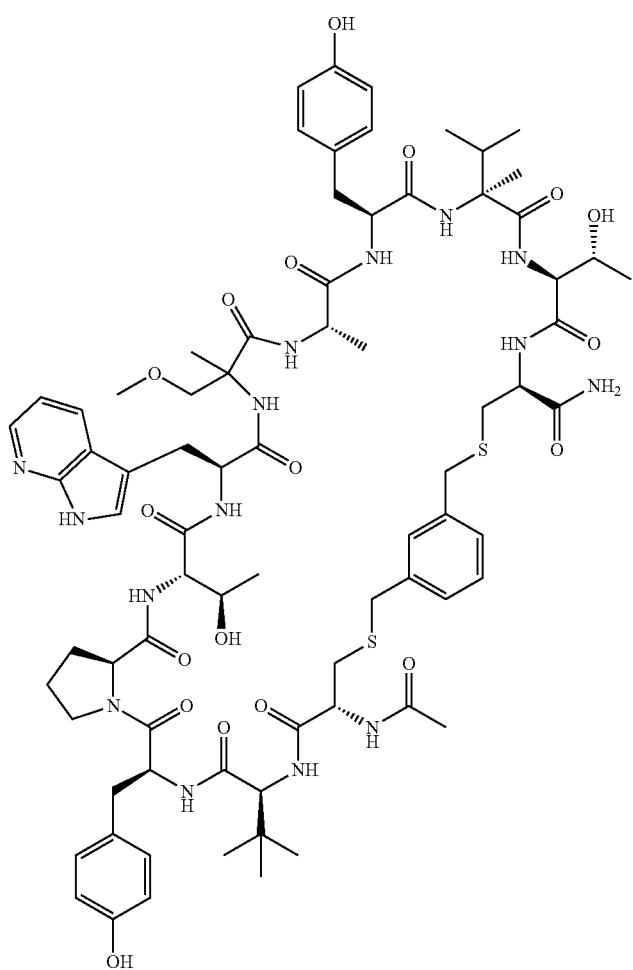

036
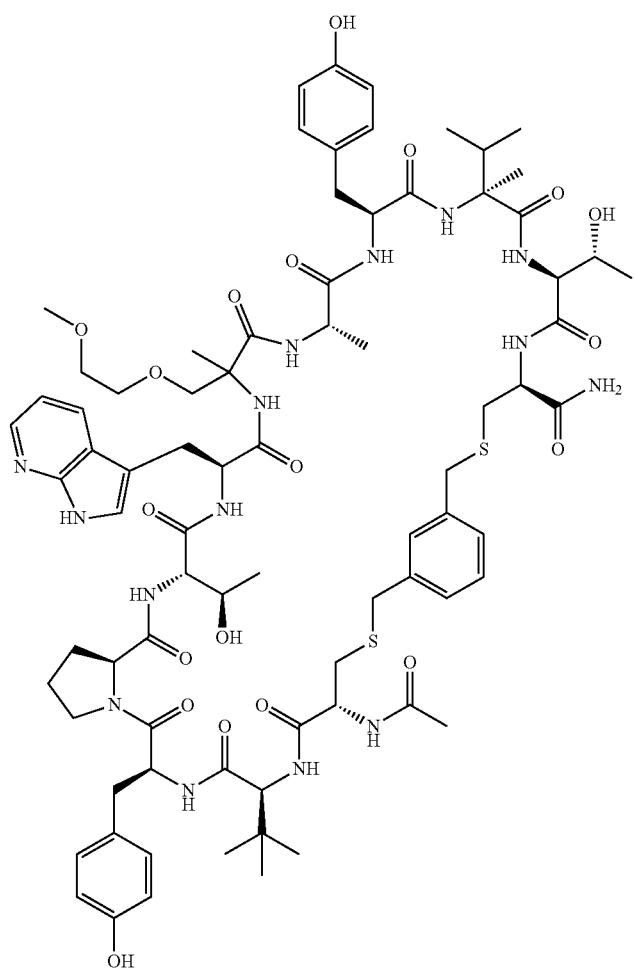

037
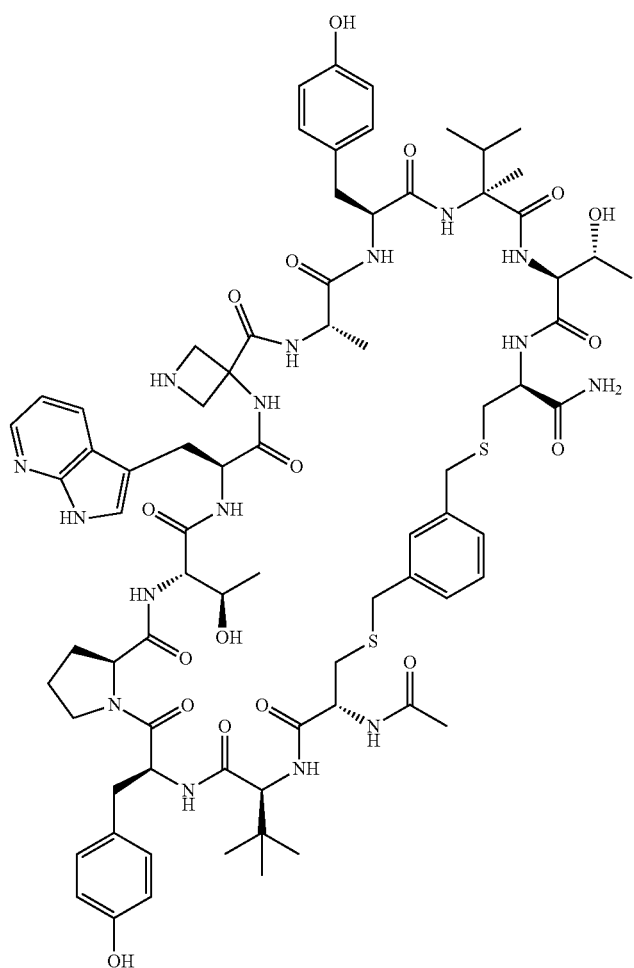

4. A cyclic peptide having the structure of Formula (II):

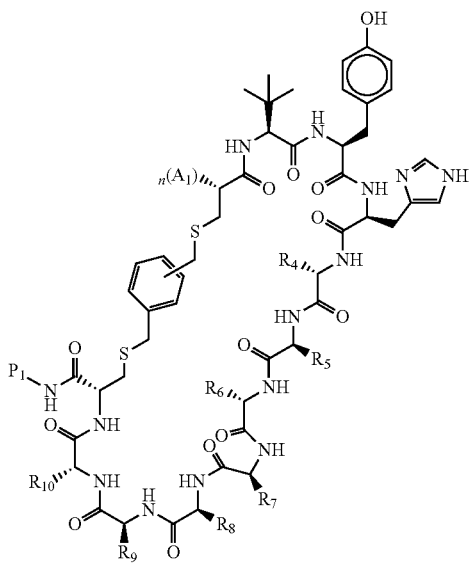

(II)

or a pharmaceutically acceptable salt thereof;
wherein:
$A_1$ is an acyl or sulfonyl protected amino acid selected from the group consisting of the amino acid side chains of

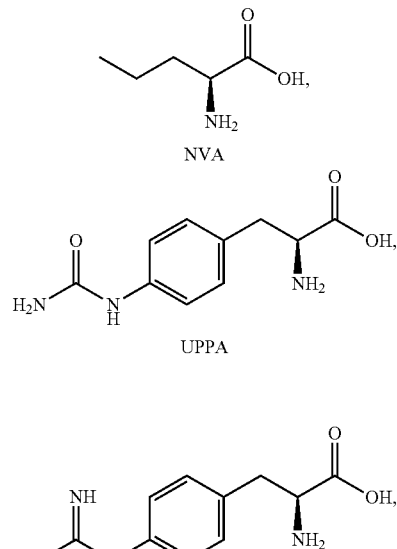

NVA

UPPA

GUF

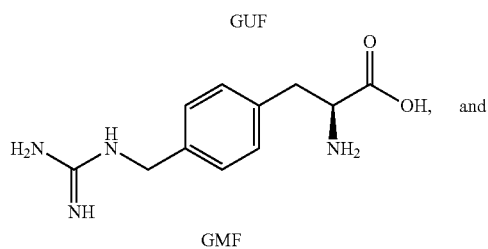

GMF

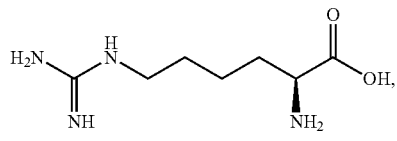

HARG or is an acyl protected amine;
$R_4$ is the amino acid side chain of THR;
$R_5$ is selected from the group consisting of the amino acid side chains of

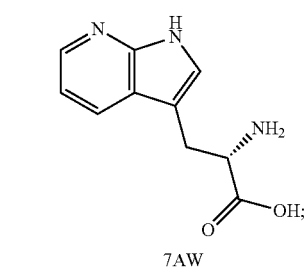

7AW

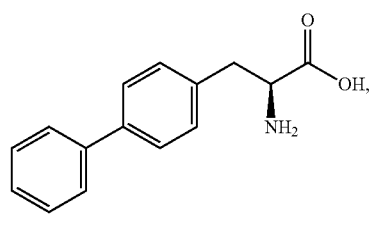

BPA

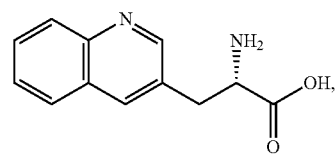

3QA

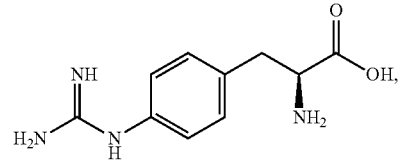

GUF

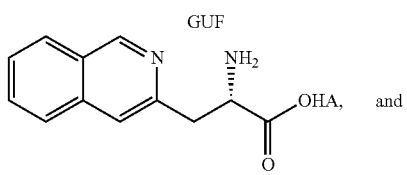

NA3

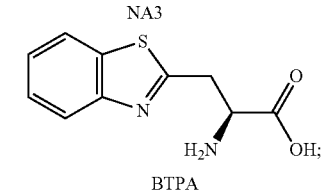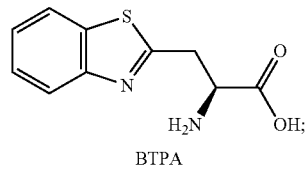

BTPA

221

$R_6$ is selected from the group consisting of the amino acid side chains of

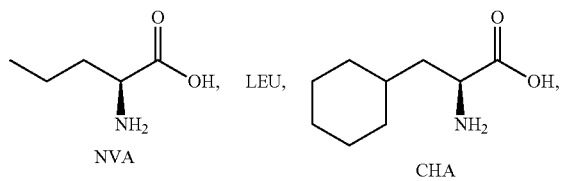

GLU, ALA,

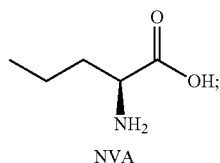

$R_7$ is selected from the group consisting of the amino acid side chains of GLU and

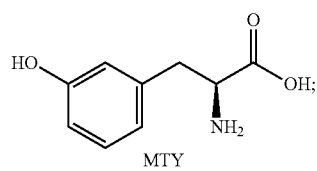

$R_8$ is selected from the group consisting of the amino acid side chains of TYR and

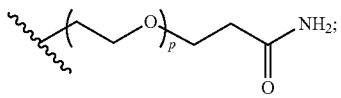

222

$R_9$ is selected from the group consisting of the amino acid side chains of

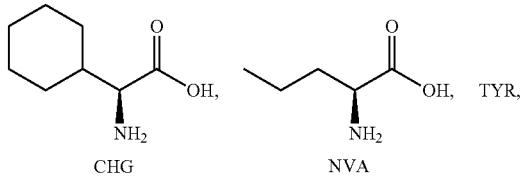

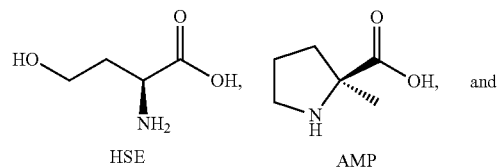

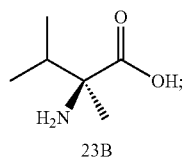

$R_{10}$ is selected from the group consisting of the amino acid side chains of THR,

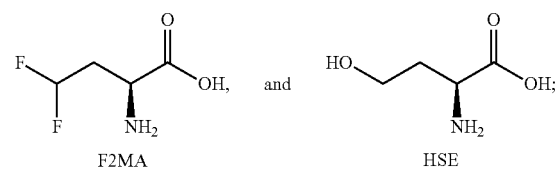

$P_1$ is H, methyl, an acetyl group, or n is 0 or 1;
p is 2, 3, 4, 5, or 6;
wherein each amino acid residue is optionally an N-methylated amino acid; and
wherein each amino acid residue can be in the R or S configuration.

5. The cyclic peptide of claim 4, wherein the cyclic peptide is selected from:
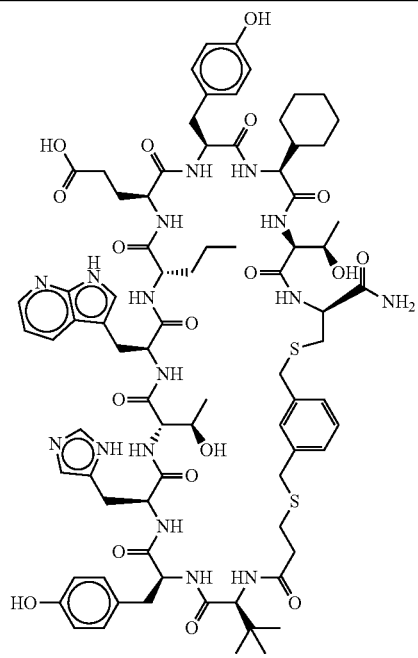
043
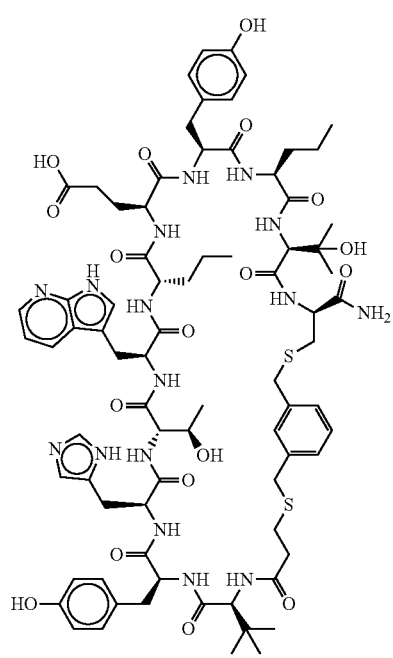
044

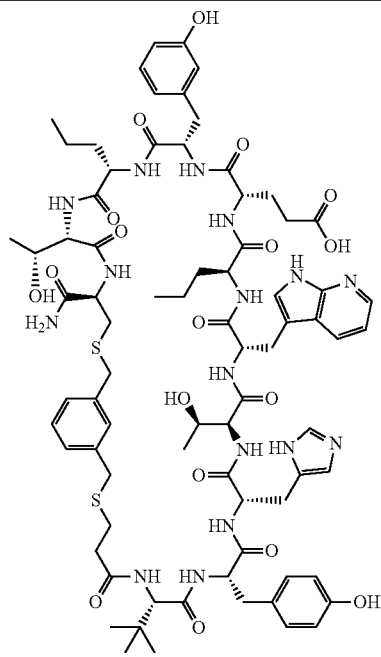
070
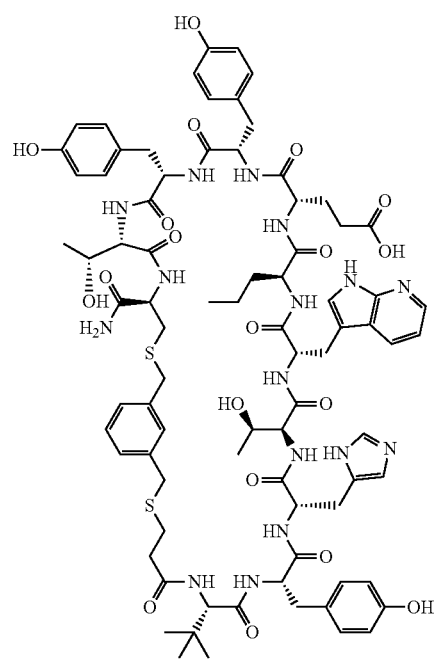 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](Cc2ccc(O)cc2)NC(=O)[C@H](Cc2ccc(O)cc2)NC(=O)[C@H](CCC(=O)O)NC1=O]
071

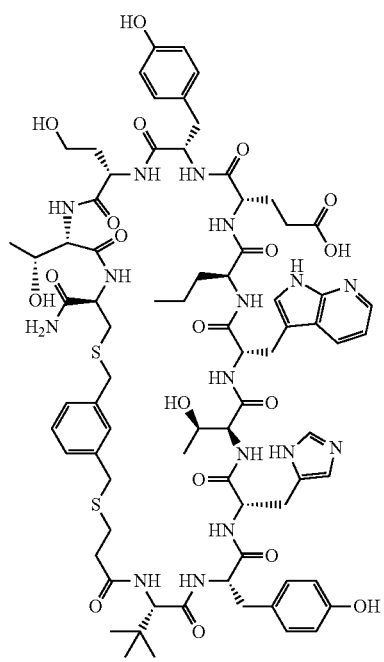 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCO)NC(=O)[C@H](Cc2ccc(O)cc2)NC(=O)[C@H](CCC(=O)O)NC1=O]
072
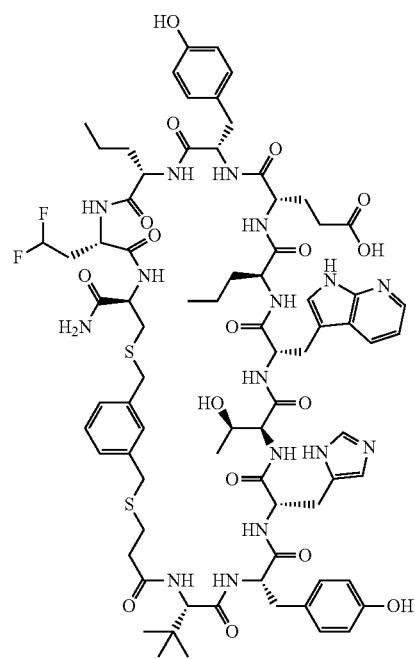 [SMILES: CCC[C@@H]1NC(=O)[C@H](Cc2ccc(O)cc2)NC(=O)[C@H](CCC(=O)O)NC(=O)[C@H](CCC)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CC(F)F)NC1=O]
073

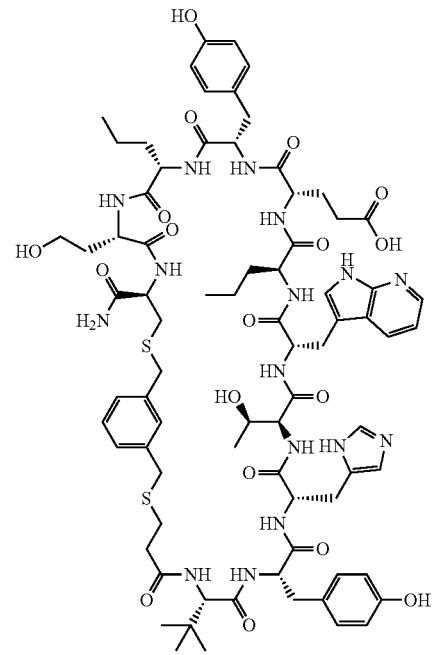 [SMILES: CCC[C@@H]1NC(=O)[C@H](Cc2ccc(O)cc2)NC(=O)[C@H](CCC(=O)O)NC(=O)[C@H](CCC)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CCO)NC1=O]
074
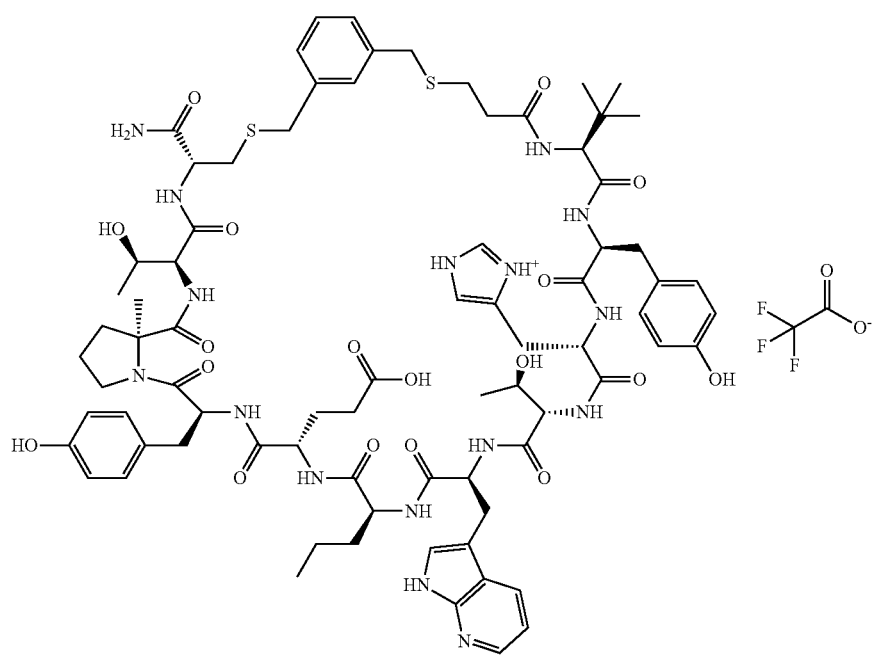 [SMILES: CCC[C@@H]1NC(=O)[C@H](Cc2c[nH]c3ncccc23)NC(=O)[C@H]([C@@H](C)O)NC(=O)[C@H](Cc2c[nH]c[nH+]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@]2(C)CCCN2C(=O)[C@H](Cc2ccc(O)cc2)NC(=O)[C@H](CCC(=O)O)NC1=O ; O=C([O-])C(F)(F)F]
075

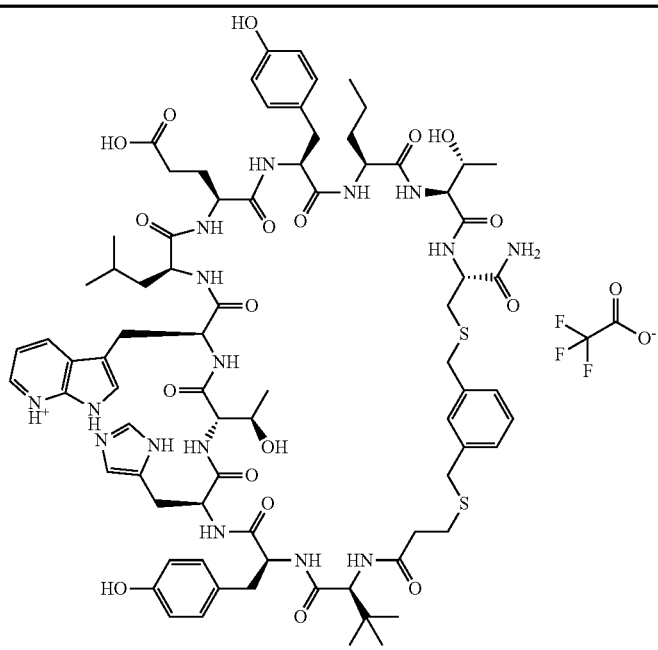
078
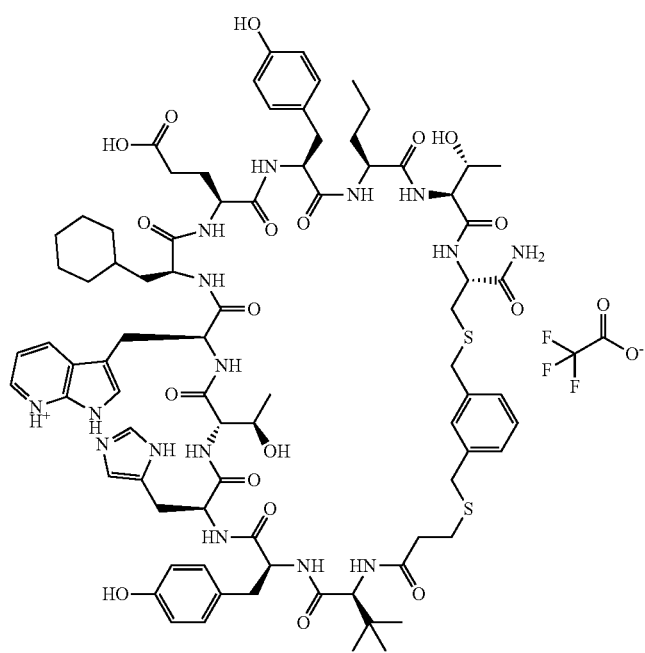 [SMILES: CCC[C@@H]1NC(=O)[C@H](Cc2ccc(O)cc2)NC(=O)[C@H](CCC(=O)O)NC(=O)[C@H](CC2CCCCC2)NC(=O)[C@H](Cc2c[nH]c3[nH+]cccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O ; O=C([O-])C(F)(F)F]
079

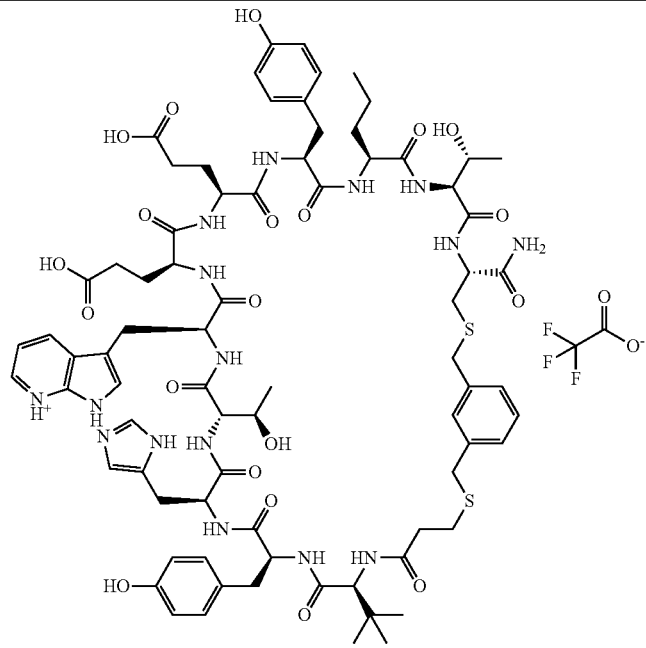
080
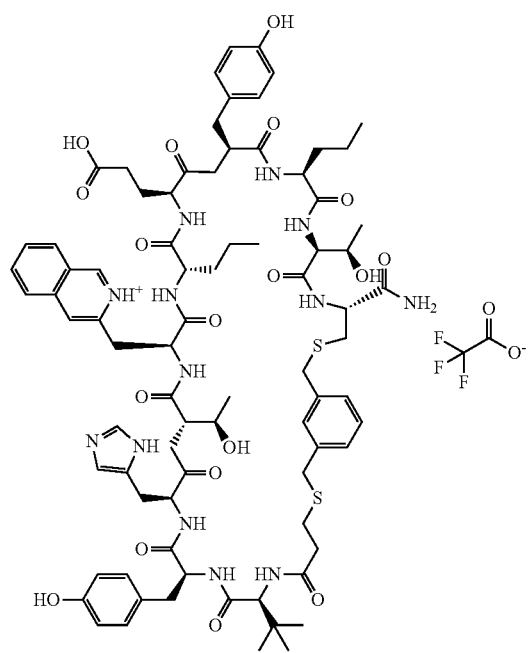 [SMILES: CCC[C@@H]1NC(=O)[C@H](Cc2ccc(O)cc2)CC(=O)[C@H](CCC(=O)O)NC(=O)[C@H](CCC)NC(=O)[C@H](Cc2cc3ccccc3c[nH+]2)NC(=O)[C@H]([C@@H](C)O)CC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O ; O=C([O-])C(F)(F)F]
081

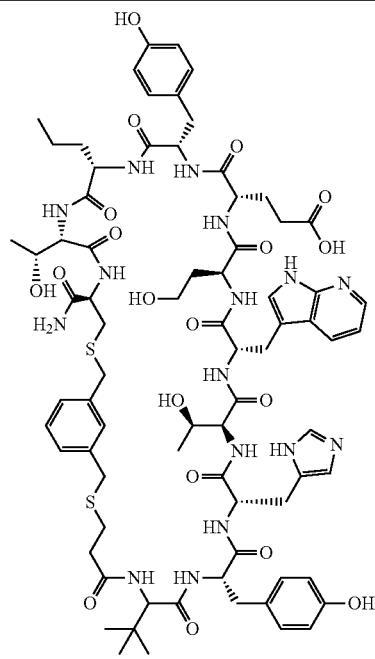
083
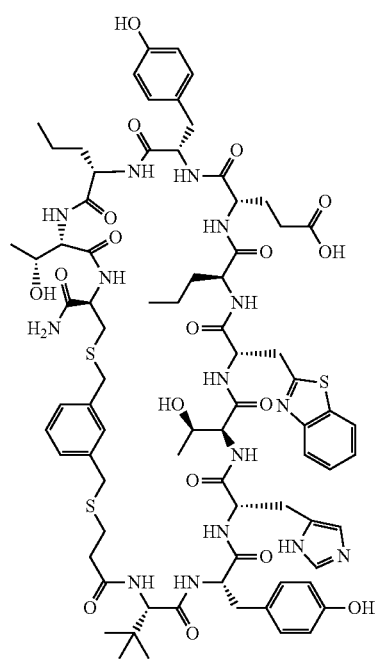 [SMILES: CCC[C@@H]1NC(=O)[C@H](Cc2nc3ccccc3s2)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
084

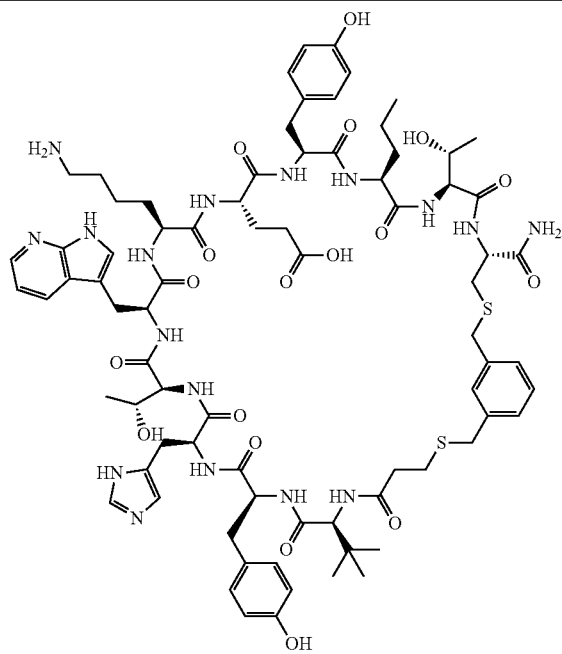
085
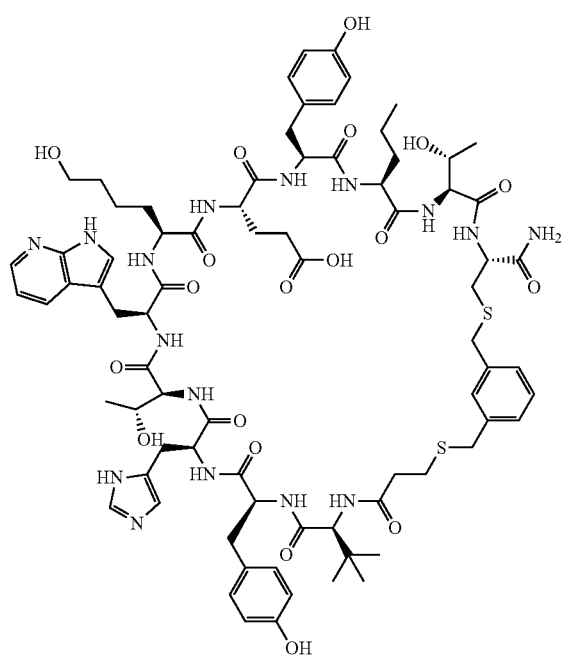 [SMILES: CCC[C@@H]1NC(=O)[C@H](Cc2ccc(O)cc2)NC(=O)[C@H](CCC(=O)O)NC(=O)[C@H](CCCCN)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]
088

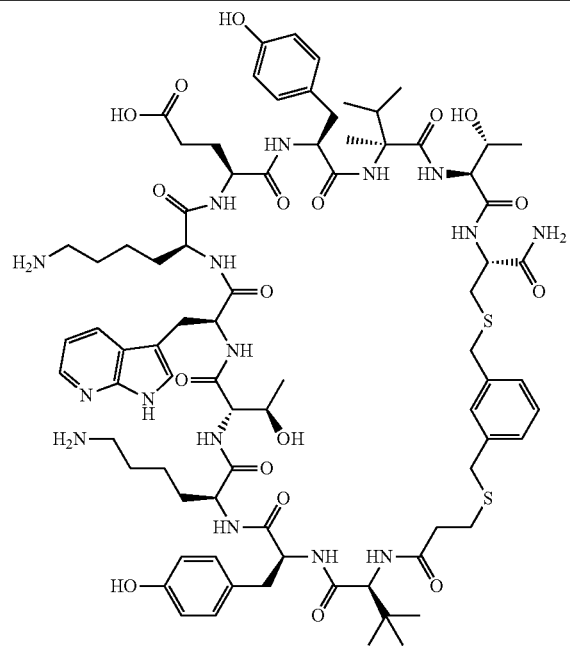
089
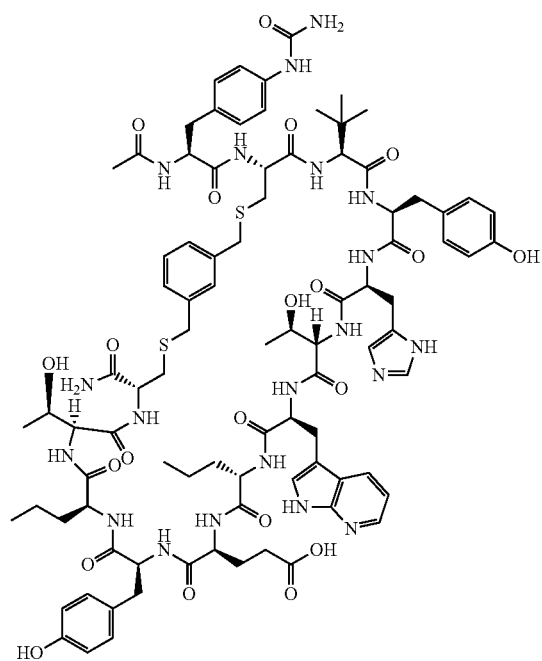 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)[C@@H](NC(=O)[C@H](Cc2ccc(NC(N)=O)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
096

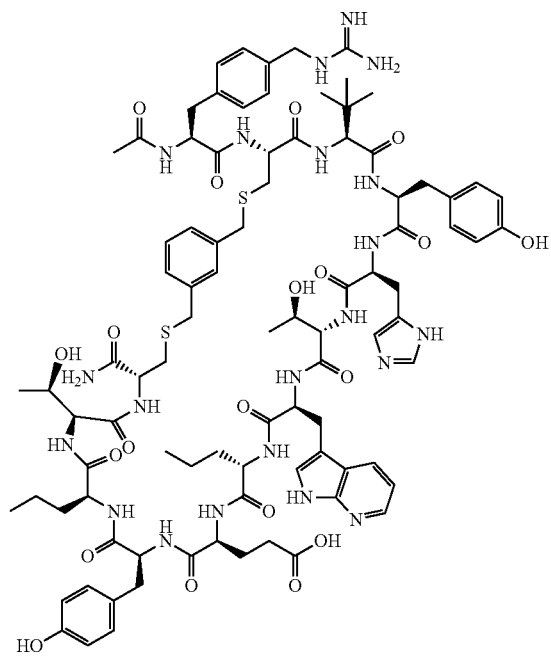 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)[C@@H](NC(=O)[C@H](Cc2ccc(CNC(=N)N)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
098
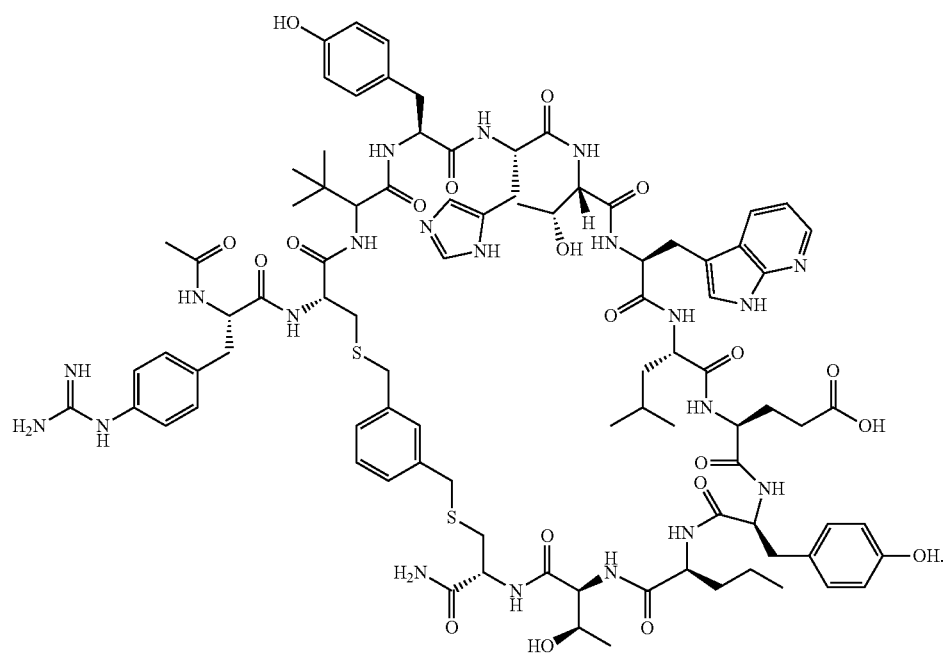 [SMILES: CCC[C@@H]1NC(=O)[C@H](Cc2ccc(O)cc2)NC(=O)[C@H](CCC(=O)O)NC(=O)[C@H](CC(C)C)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)C(C(C)(C)C)NC(=O)[C@@H](NC(=O)[C@H](Cc2ccc(NC(=N)N)cc2)NC(C)=O)CSCc2cccc(c2)CSC[C@@H](C(N)=O)NC(=O)[C@H]([C@@H](C)O)NC1=O]
099

6. The cyclic peptide of claim 4, wherein the cyclic peptide is selected from:
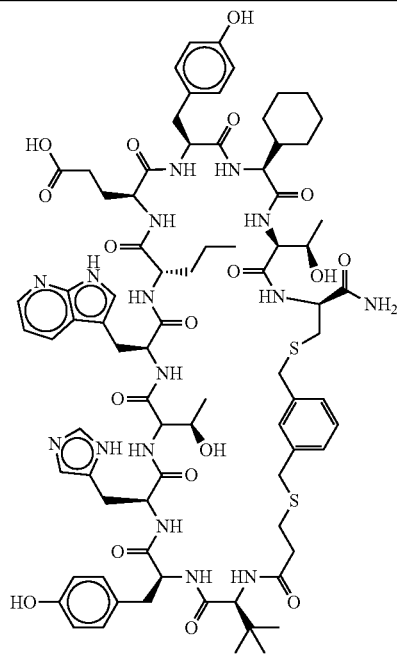
043
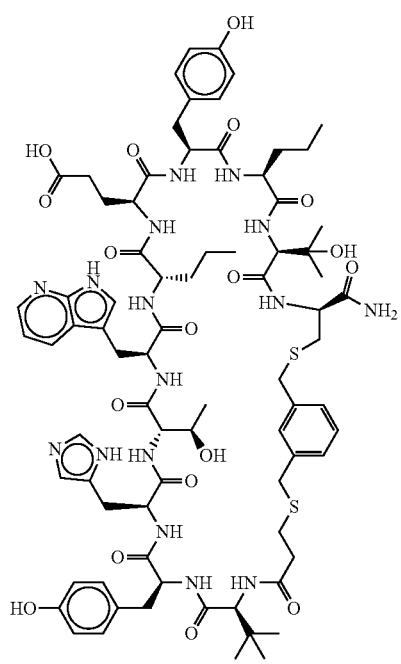
044

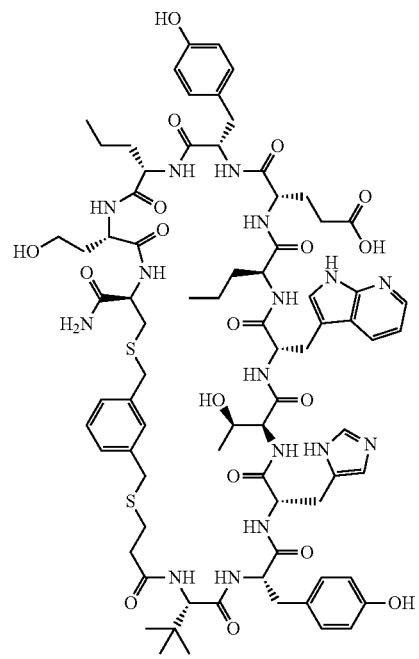 [SMILES: CCC[C@@H]1NC(=O)[C@H](Cc2ccc(O)cc2)NC(=O)[C@H](CCC(=O)O)NC(=O)[C@H](CCC)NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H](CCO)NC1=O]
074
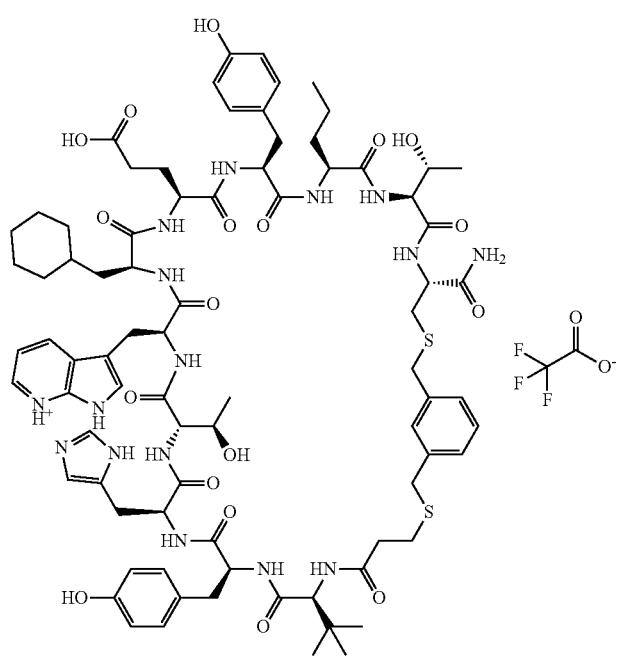 [SMILES: CCC[C@@H]1NC(=O)[C@H](Cc2ccc(O)cc2)NC(=O)[C@H](CCC(=O)O)NC(=O)[C@H](CC2CCCCC2)NC(=O)[C@H](Cc2c[nH]c3[nH+]cccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O ; O=C([O-])C(F)(F)F]
079

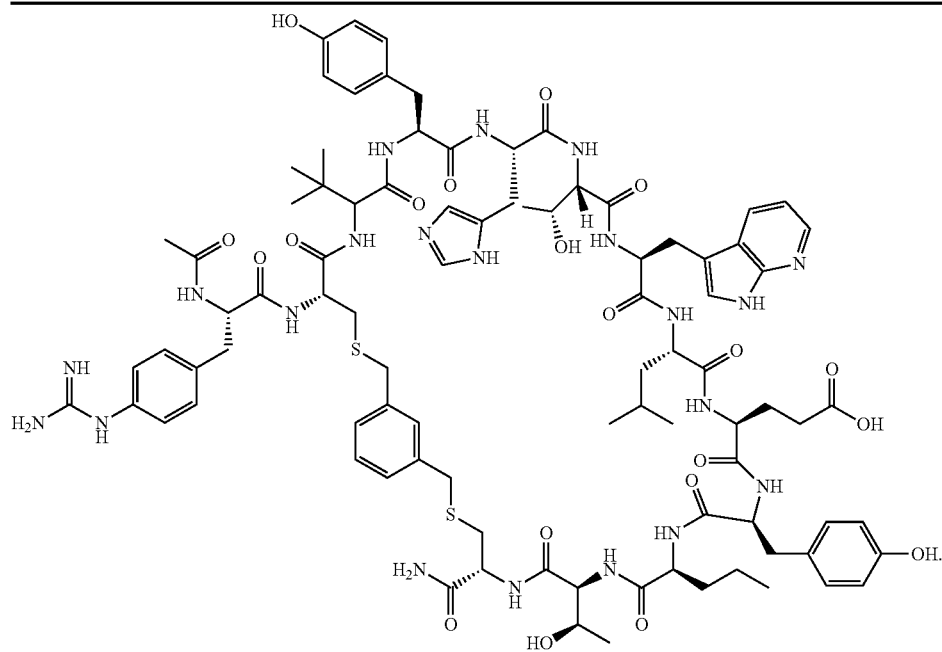

099

7. A cyclic peptide having the structure of Formula (III):

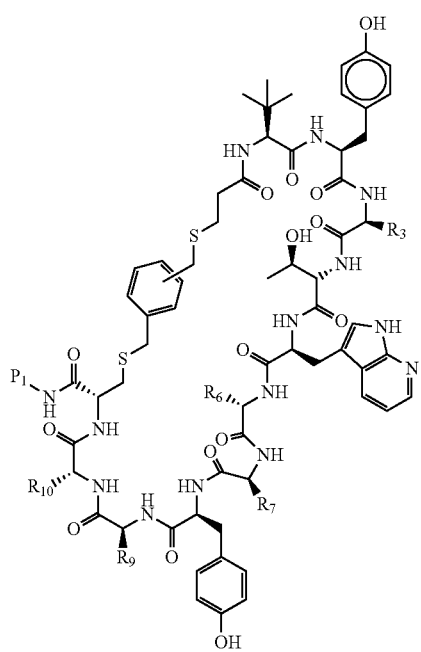

(III)

or a pharmaceutically acceptable salt thereof;
wherein:
R₃ is selected from the group consisting of the amino acid side chains of PRO and HIS;
R₆ is selected from the group consisting of the amino acid side chains of

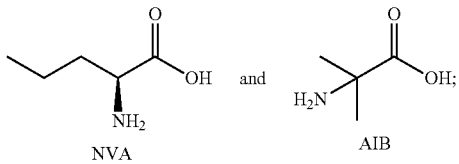

R₇ is selected from the group consisting of the amino acid side chains of ALA and GLU or is covalently bound to R₃ by a linking moiety;
R₉ is selected from the group consisting of the amino acid side chains of

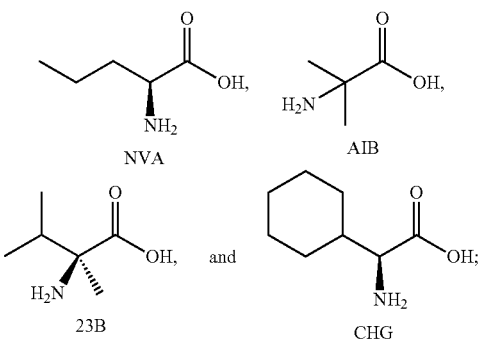

R₁₀ is the amino acid side chain of THR;
wherein each amino acid residue is optionally an N-methylated amino acid;
wherein each amino acid residue can be in the R or S configuration; and
provided either R₃ and R₇, or R₆ and R₁₀ are covalently bound by a linking moiety selected from the group consisting of 249
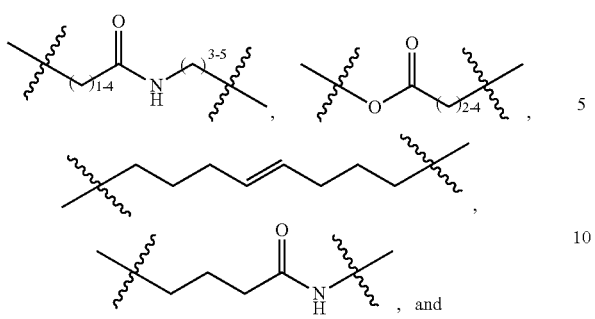
250
-continued
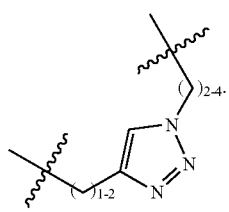
8. The cyclic peptide of claim 7, wherein the cyclic peptide is selected from:
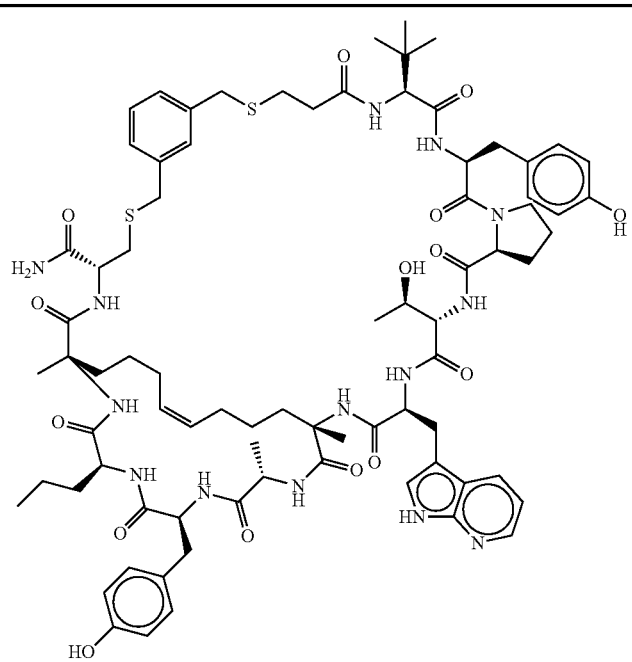
101
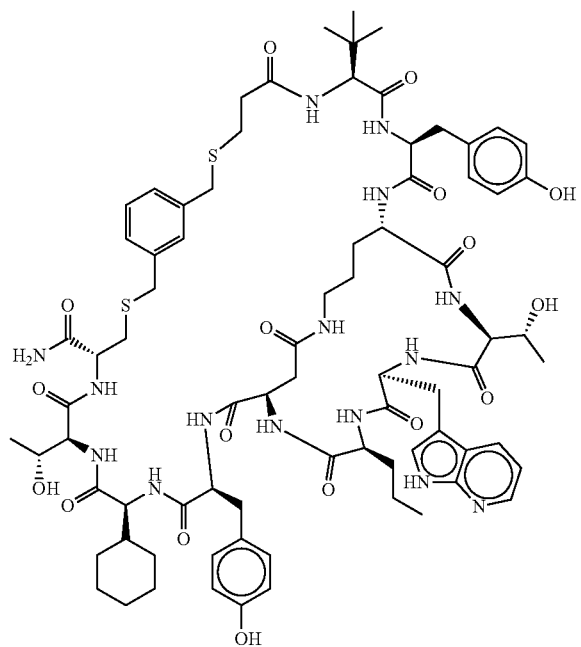
106

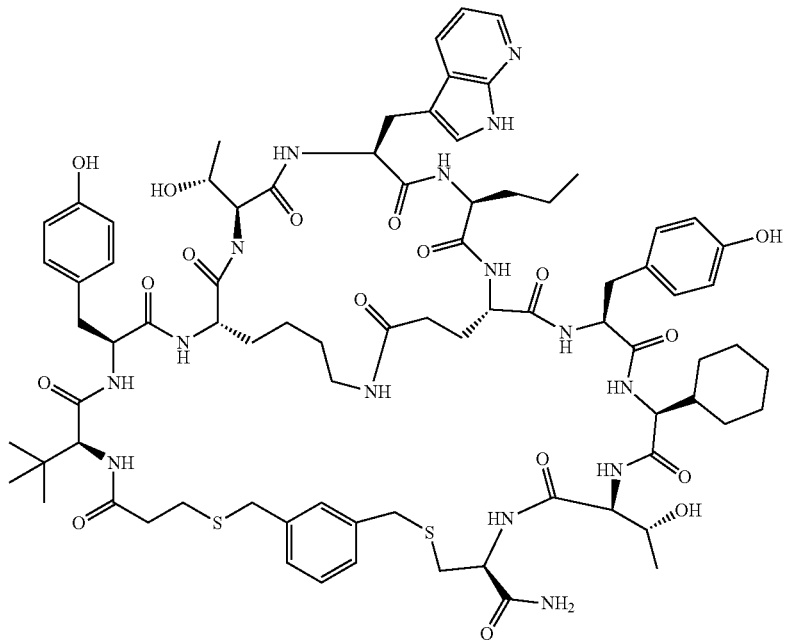 [SMILES: CCC[C@@H]1NC(=O)[C@H](Cc2c[nH]c3ncccc23)NC(=O)[C@H]([C@@H](C)O)NC(=O)[C@@H]2CCCCNC(=O)CC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@@H](C(N)=O)CSCc1cccc(c1)CSCCC(=O)N[C@@H](C(C)(C)C)C(=O)N[C@@H](Cc1ccc(O)cc1)C(=O)N2]
107
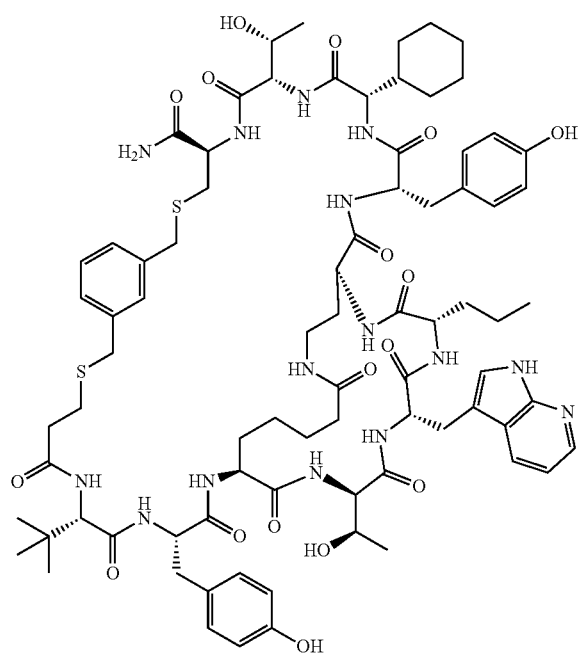 [SMILES: CCC[C@@H]1NC(=O)[C@H](Cc2c[nH]c3ncccc23)NC(=O)[C@@H]([C@@H](C)O)NC(=O)[C@@H]2CCCCC(=O)NCC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@H](C(N)=O)CSCc1cccc(c1)CSCCC(=O)N[C@@H](C(C)(C)C)C(=O)N[C@@H](Cc1ccc(O)cc1)C(=O)N2]
108

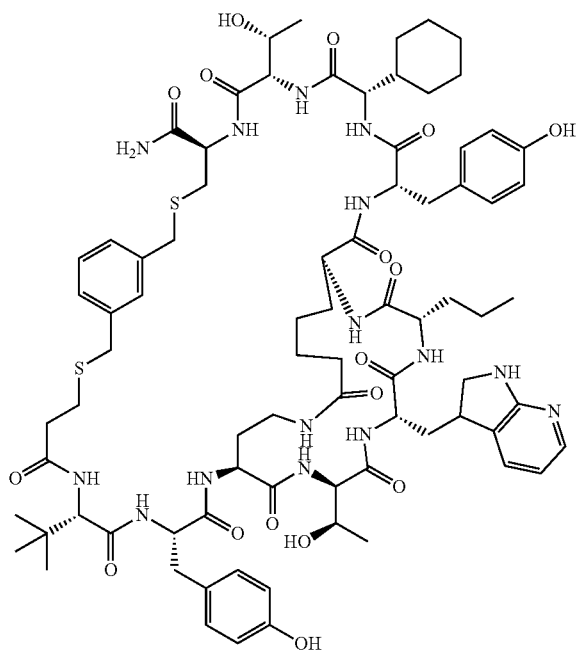 [SMILES: CCC[C@@H]1NC(=O)[C@H](CC2CNc3ncccc32)NC(=O)[C@@H]([C@@H](C)O)NC(=O)[C@@H]2CCNC(=O)CCCC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@H](C(N)=O)CSCc1cccc(c1)CSCCC(=O)N[C@@H](C(C)(C)C)C(=O)N[C@@H](Cc1ccc(O)cc1)C(=O)N2]
109
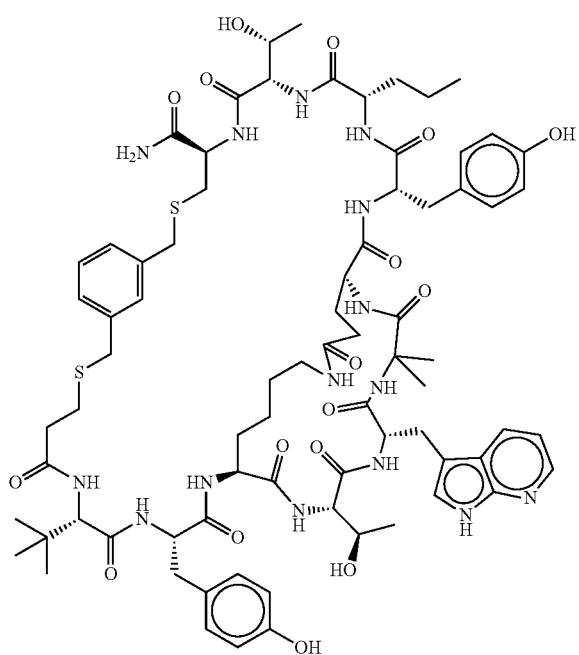
110

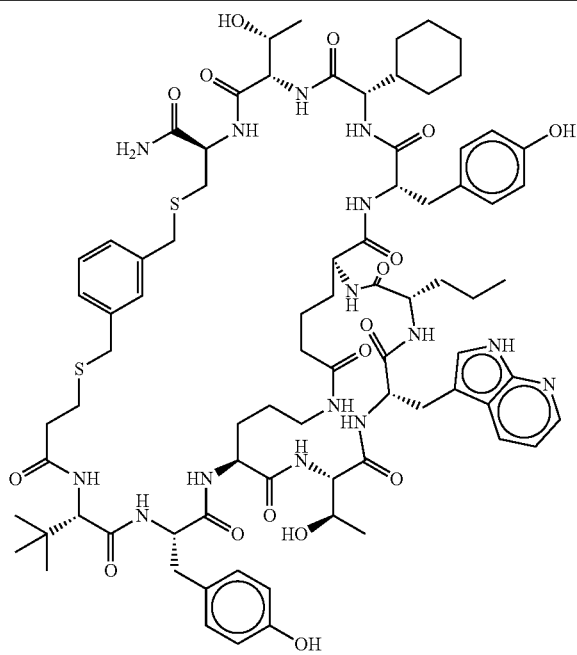
111
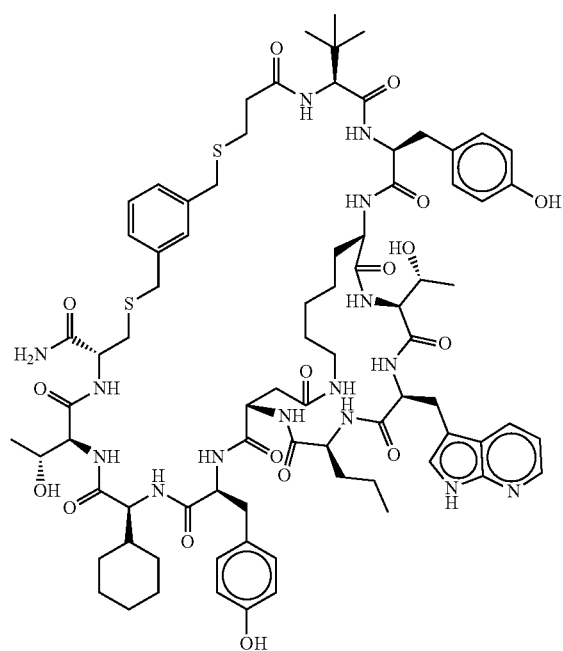
112

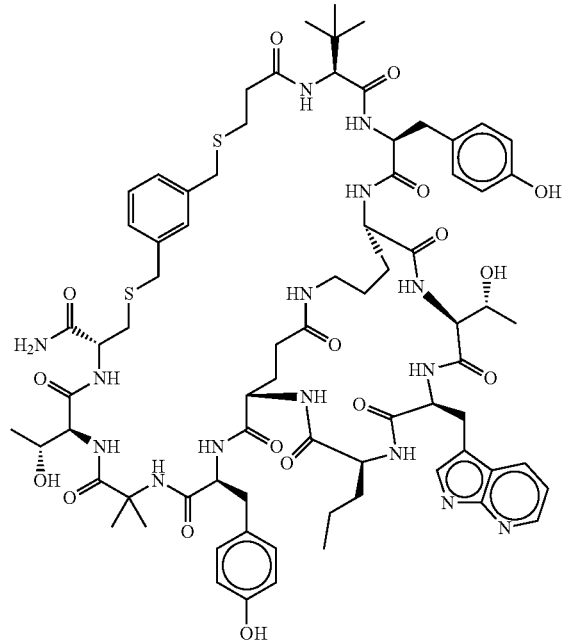
114
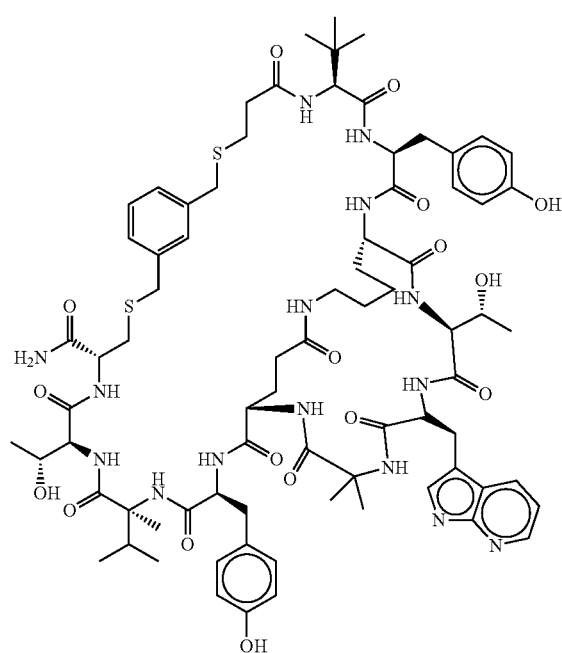
115

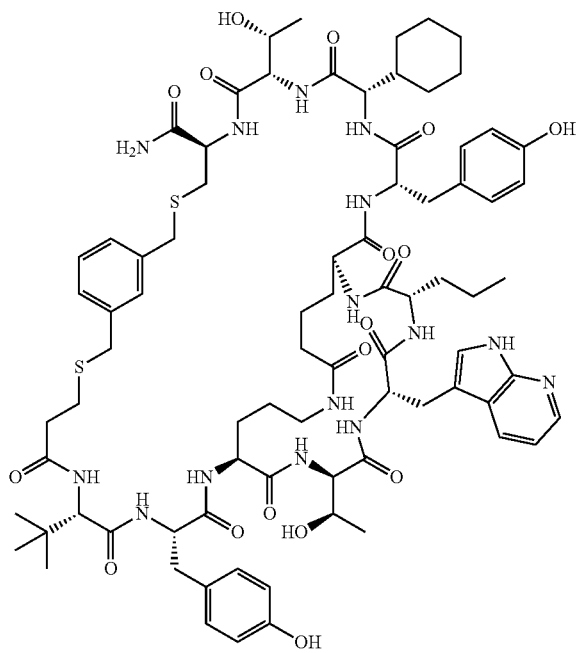 [SMILES: CCC[C@@H]1NC(=O)[C@H](Cc2c[nH]c3ncccc23)NC(=O)[C@@H]([C@@H](C)O)NC(=O)[C@@H]2CCCNC(=O)CCC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@H](C(N)=O)CSCc1cccc(c1)CSCCC(=O)N[C@@H](C(C)(C)C)C(=O)N[C@@H](Cc1ccc(O)cc1)C(=O)N2]
118
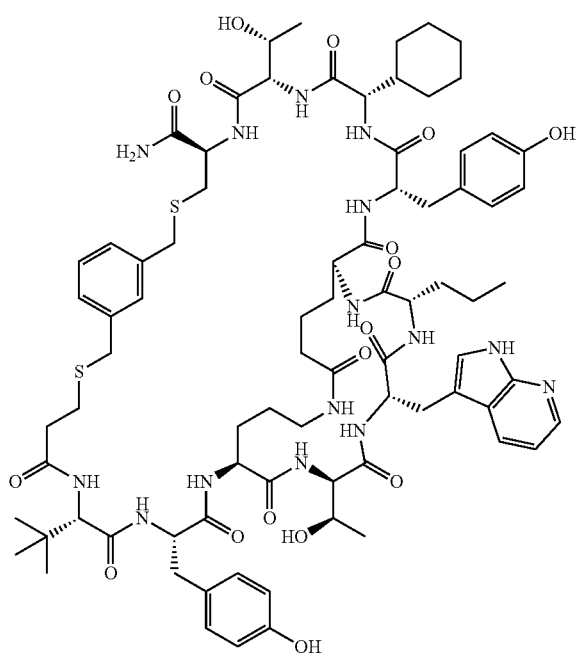 [SMILES: CCC[C@@H]1NC(=O)[C@H](Cc2c[nH]c3ncccc23)NC(=O)[C@@H]([C@@H](C)O)NC(=O)[C@@H]2CCCNC(=O)CCC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@H](C(N)=O)CSCc1cccc(c1)CSCCC(=O)N[C@@H](C(C)(C)C)C(=O)N[C@@H](Cc1ccc(O)cc1)C(=O)N2]
119

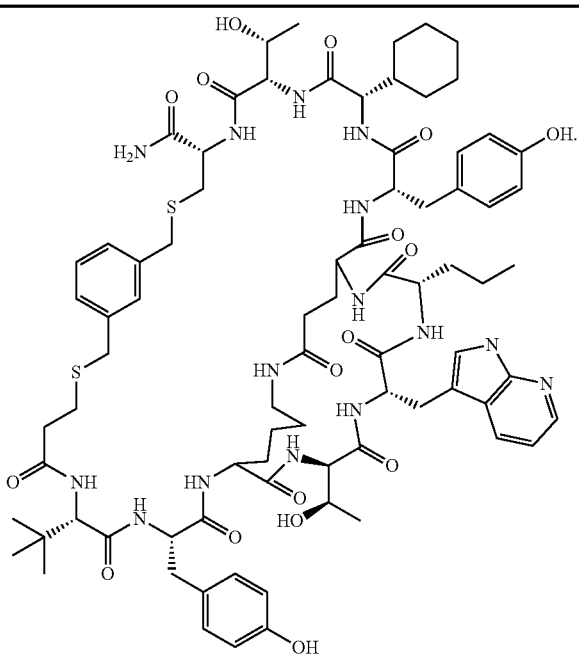
120
9. The cyclic peptide of claim 8, wherein the cyclic peptide is selected from:
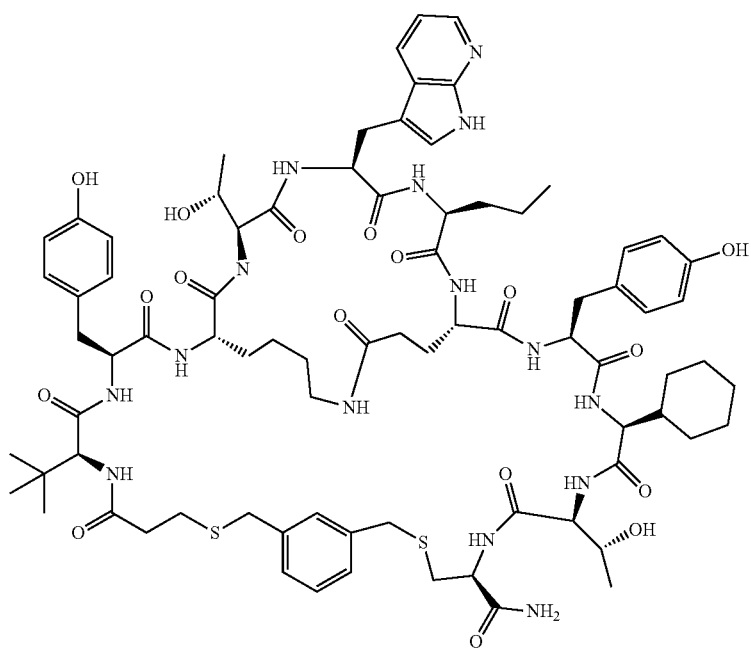 [SMILES: CCC[C@@H]1NC(=O)[C@H](Cc2c[nH]c3ncccc23)NC(=O)[C@H]([C@@H](C)O)NC(=O)[C@@H]2CCCCNC(=O)CC[C@H](NC1=O)C(=O)N[C@@H](Cc1ccc(O)cc1)C(=O)N[C@@H](C1CCCCC1)C(=O)N[C@@H]([C@@H](C)O)C(=O)N[C@@H](C(N)=O)CSCc1cccc(c1)CSCCC(=O)N[C@@H](C(C)(C)C)C(=O)N[C@@H](Cc1ccc(O)cc1)C(=O)N2]
107

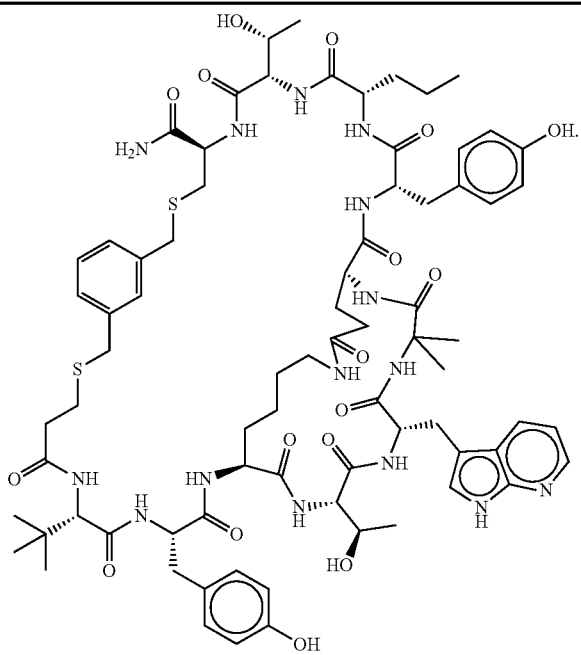
10. A cyclic peptide selected from:
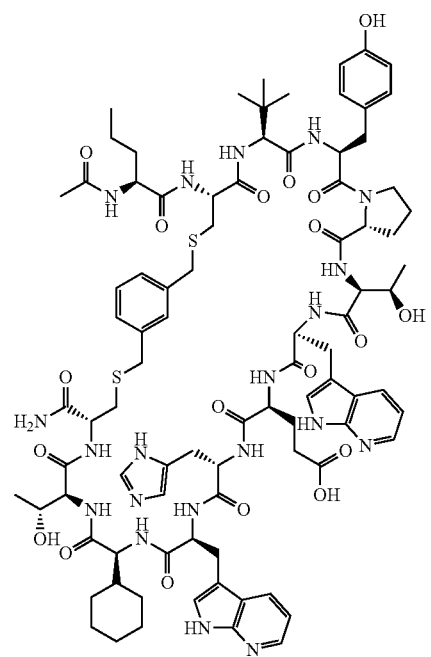 [SMILES: CCC[C@H](NC(C)=O)C(=O)N[C@H]1CSCc2cccc(c2)CSC[C@@H](C(N)=O)NC(=O)[C@H]([C@@H](C)O)NC(=O)[C@H](C2CCCCC2)NC(=O)[C@H](Cc2c[nH]c3ncccc23)NC(=O)[C@H](Cc2cnc[nH]2)NC(=O)[C@H](CCC(=O)O)NC(=O)[C@H](Cc2c[nH]c3ncccc23)NC(=O)[C@H]([C@@H](C)O)NC(=O)[C@H]2CCCN2C(=O)[C@H](Cc2ccc(O)cc2)NC(=O)[C@H](C(C)(C)C)NC1=O]

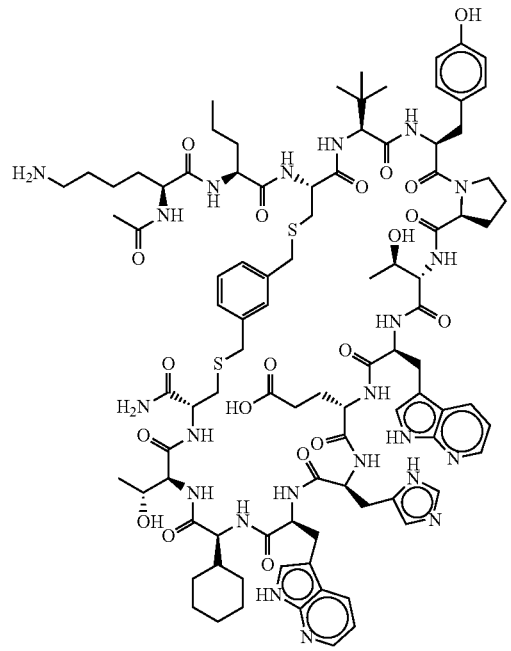
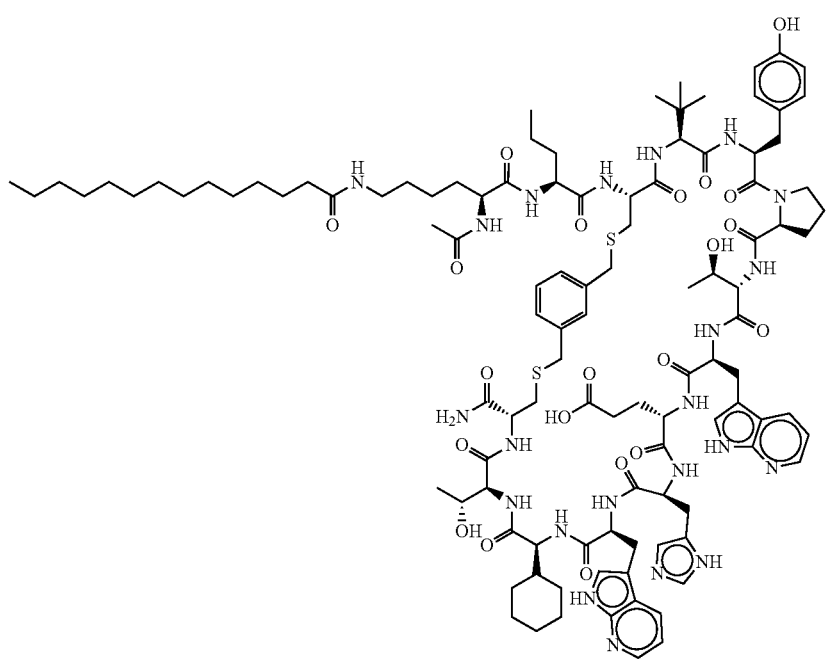

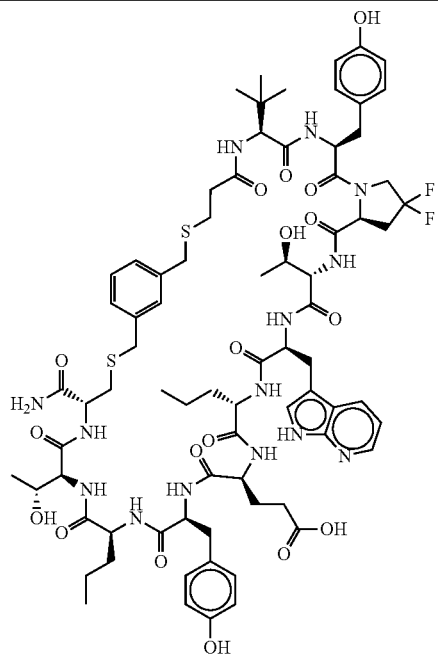
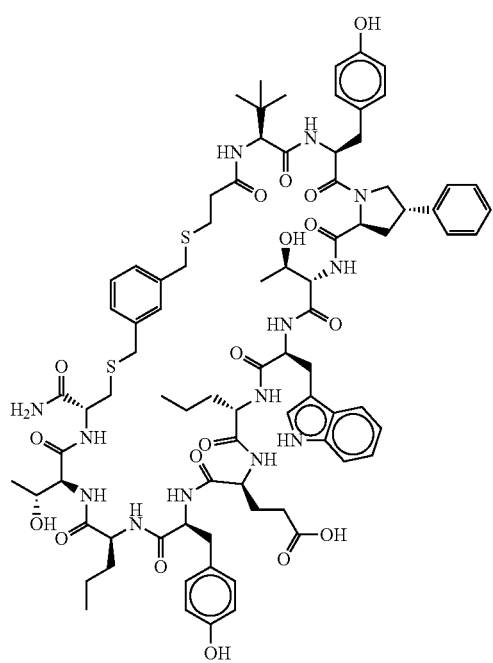

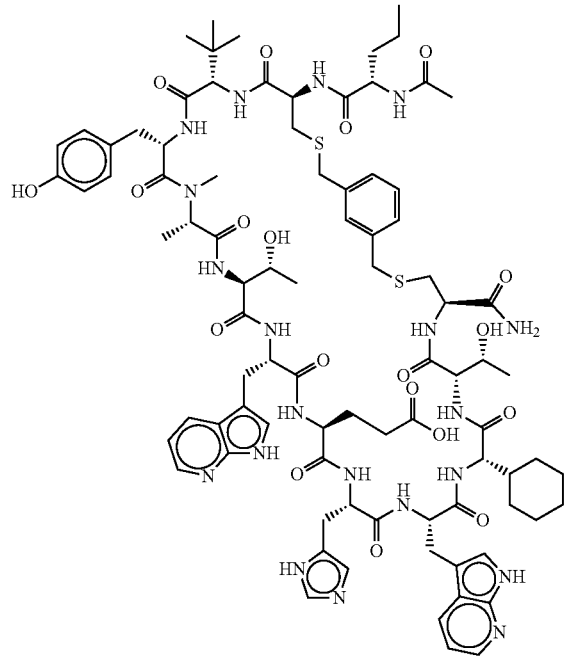
006
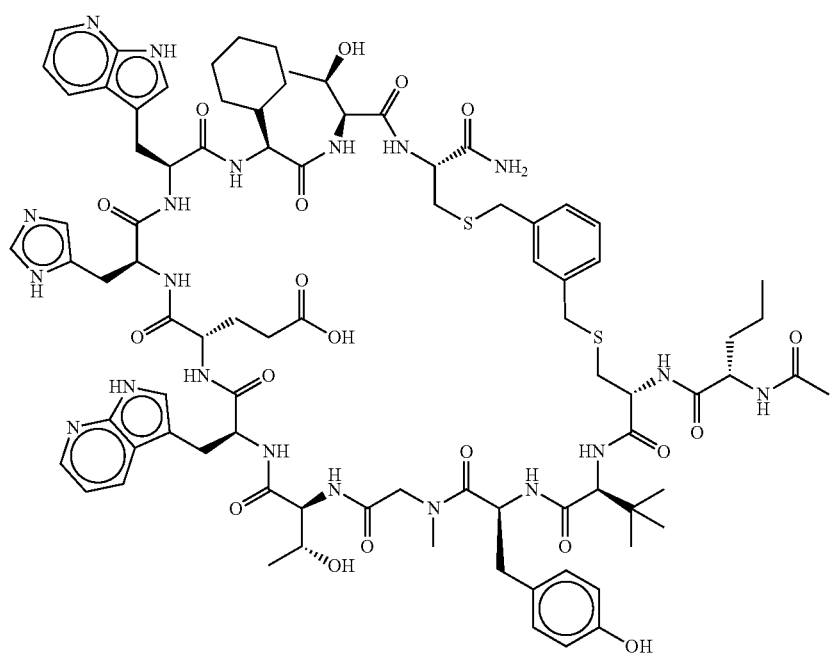
007

-continued
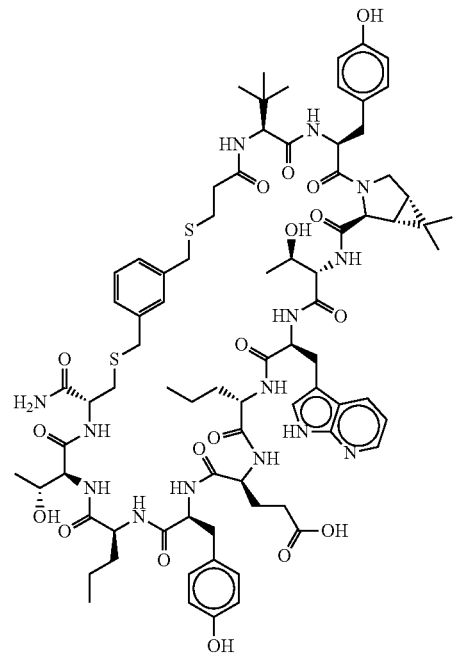
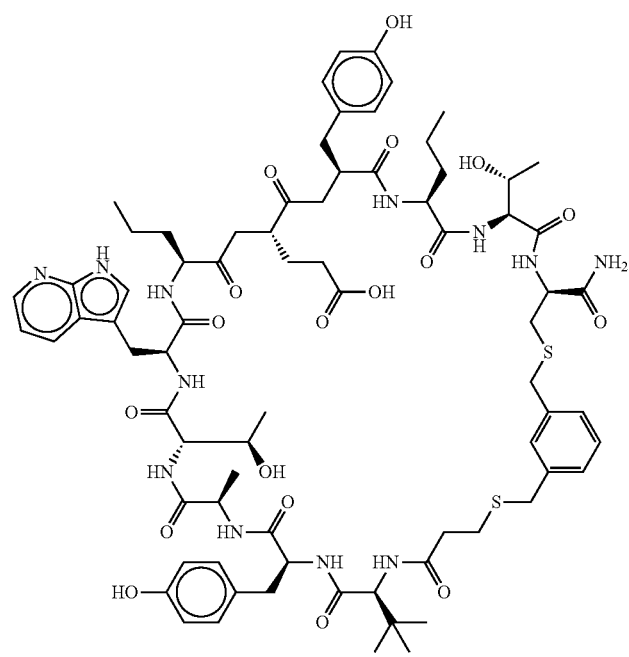

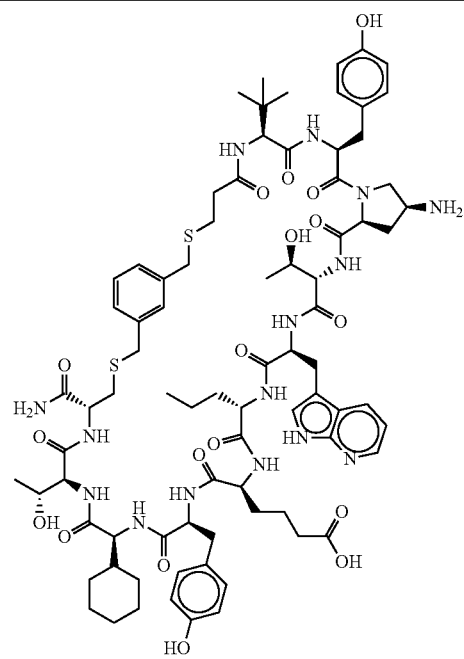
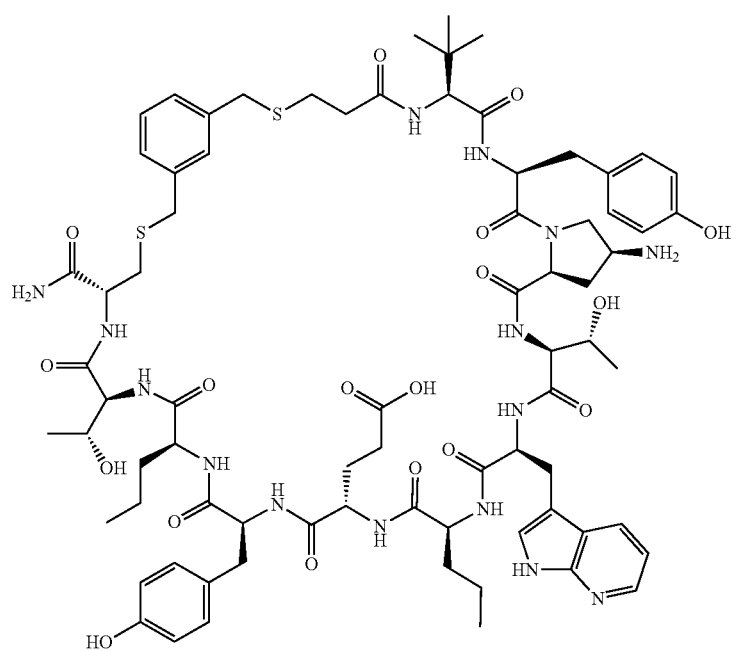 [SMILES: CCC[C@@H]1NC(=O)[C@H](Cc2c[nH]c3ncccc23)NC(=O)[C@H]([C@@H](C)O)NC(=O)[C@@H]2C[C@H](N)CN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]

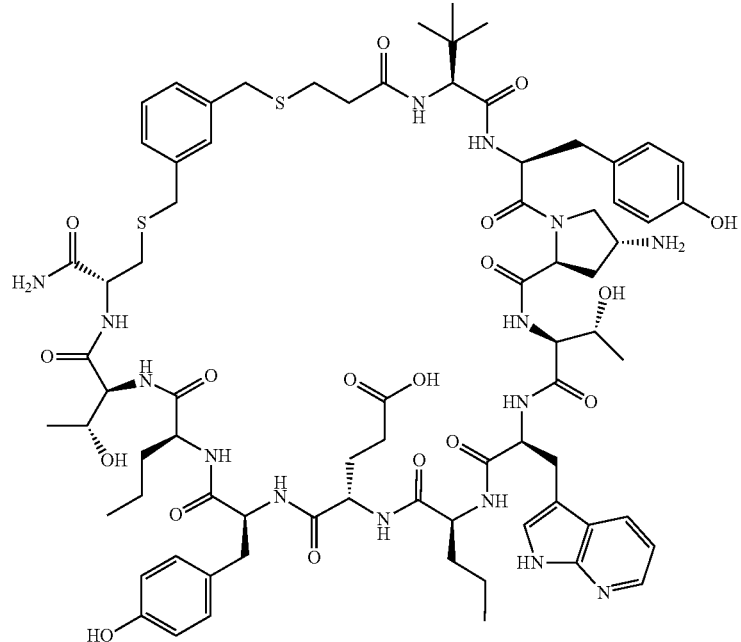 [SMILES: CCC[C@@H]1NC(=O)[C@H](Cc2c[nH]c3ncccc23)NC(=O)[C@H]([C@@H](C)O)NC(=O)[C@@H]2C[C@@H](N)CN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
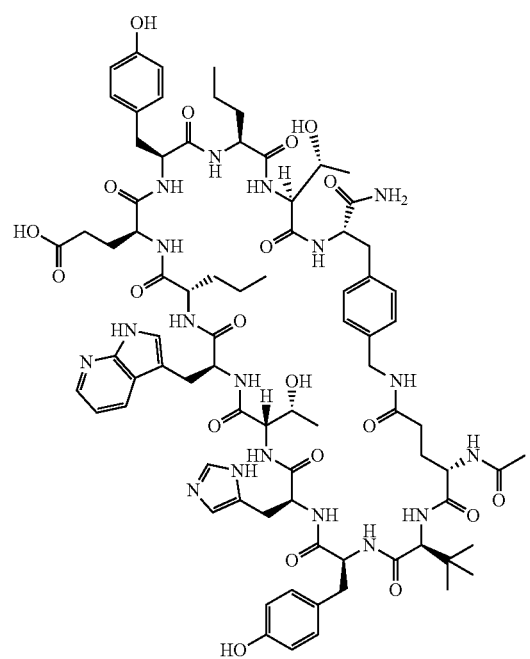 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)[C@@H](NC(C)=O)CCC(=O)NCc2ccc(cc2)C[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]

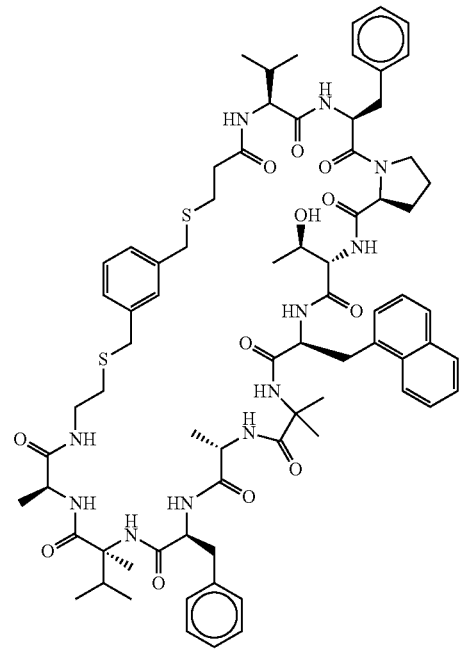
021
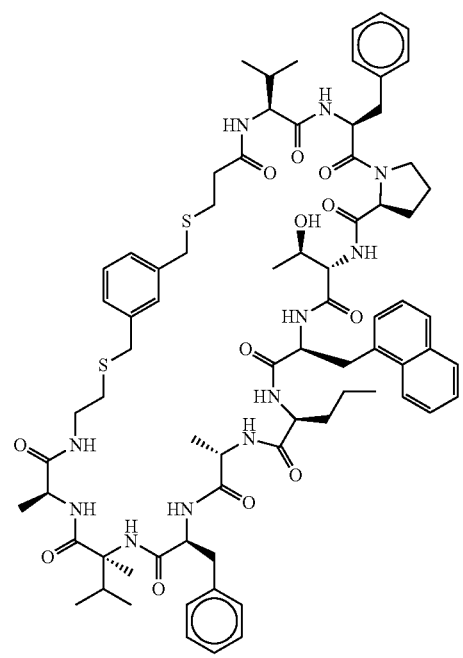
022

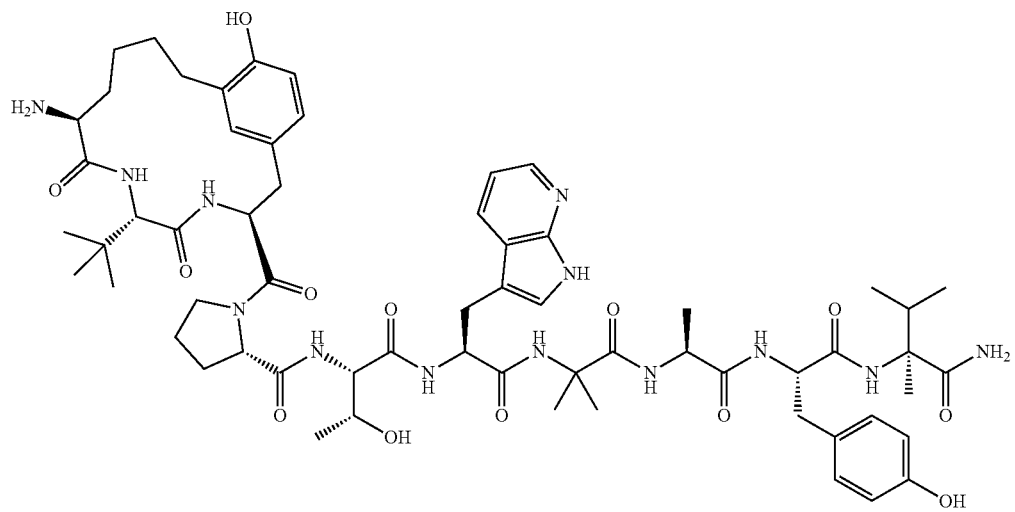 [SMILES: CC(C)[C@](C)(NC(=O)[C@H](Cc1ccc(O)cc1)NC(=O)[C@H](C)NC(=O)C(C)(C)NC(=O)[C@H](Cc1c[nH]c2ncccc12)NC(=O)[C@@H](NC(=O)[C@@H]1CCCN1C(=O)[C@@H]1Cc2ccc(O)c(c2)CCCC[C@H](N)C(=O)N[C@@H](C(C)(C)C)C(=O)N1)[C@@H](C)O)C(N)=O]
032
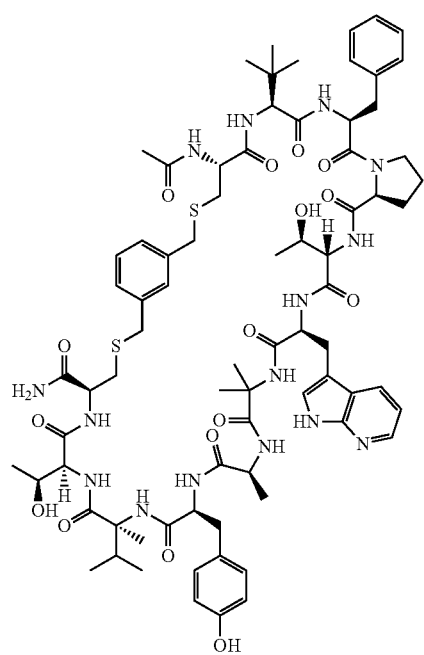 [SMILES: CC(=O)N[C@H]1CSCc2cccc(c2)CSC[C@H](C(N)=O)NC(=O)[C@H]([C@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccccc2)NC(=O)[C@H](C(C)(C)C)NC1=O]
040

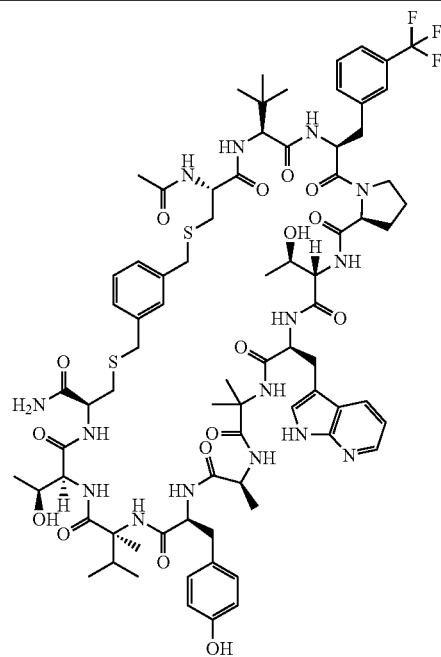
041
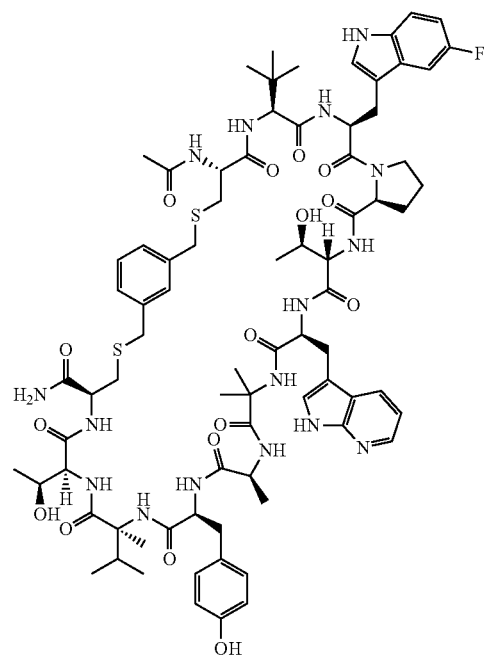 [SMILES: CC(=O)N[C@H]1CSCc2cccc(c2)CSC[C@H](C(N)=O)NC(=O)[C@H]([C@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2c[nH]c3ccc(F)cc23)NC(=O)[C@H](C(C)(C)C)NC1=O]
042

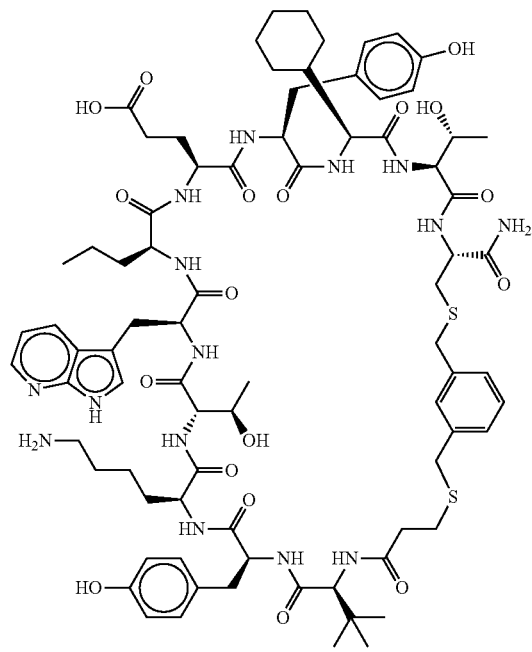
046
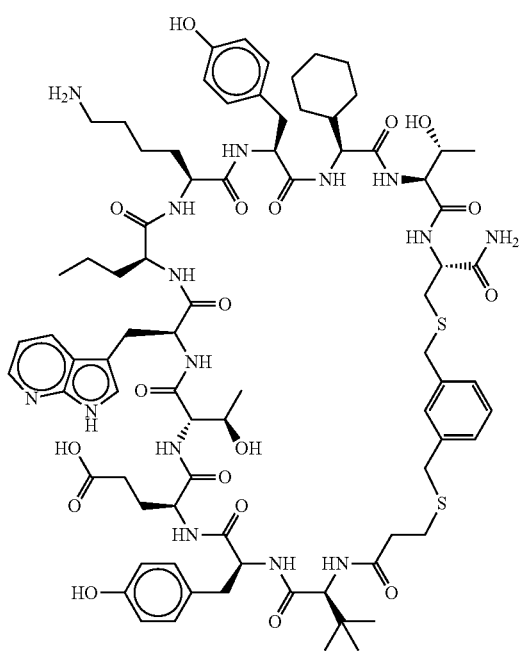
047

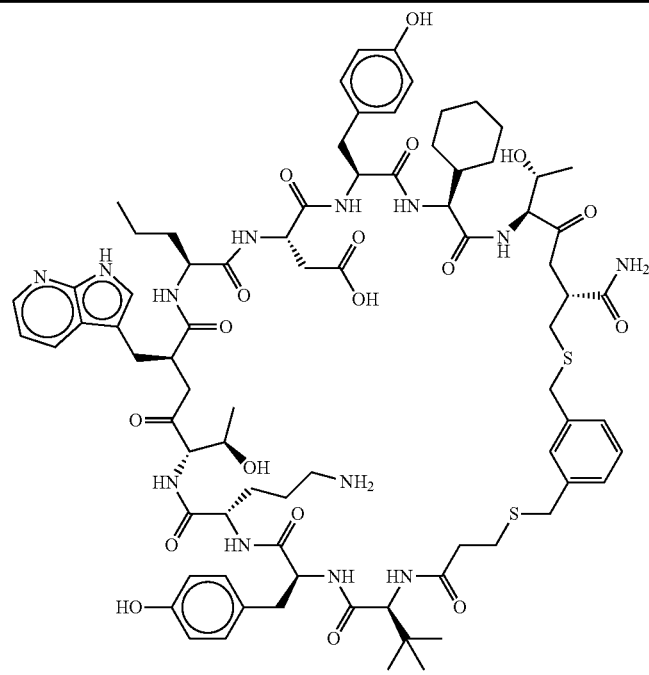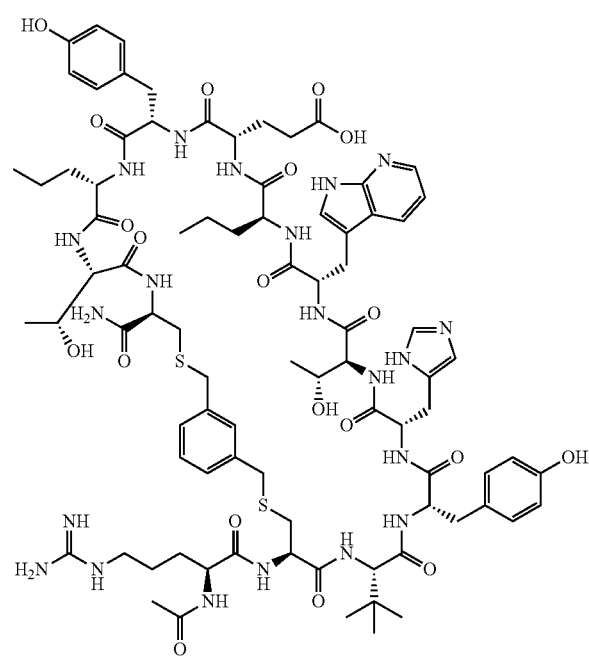 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](C(C)(C)C)NC(=O)[C@@H](NC(=O)[C@H](CCCNC(=N)N)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]

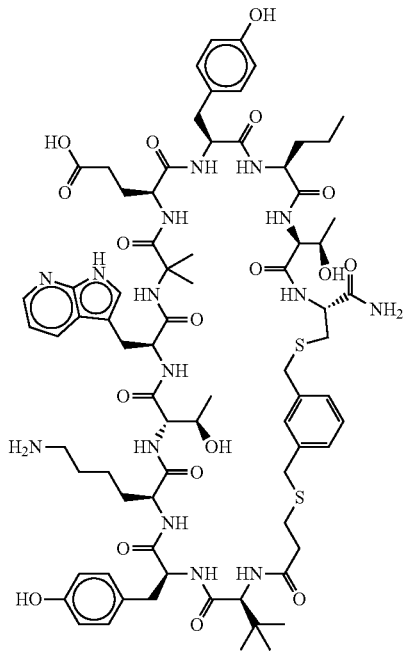
053
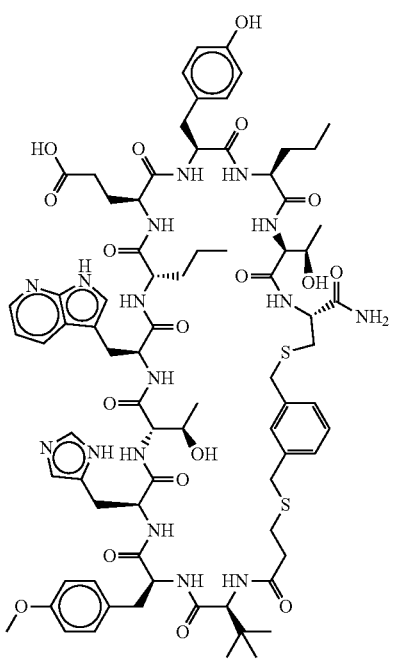
056

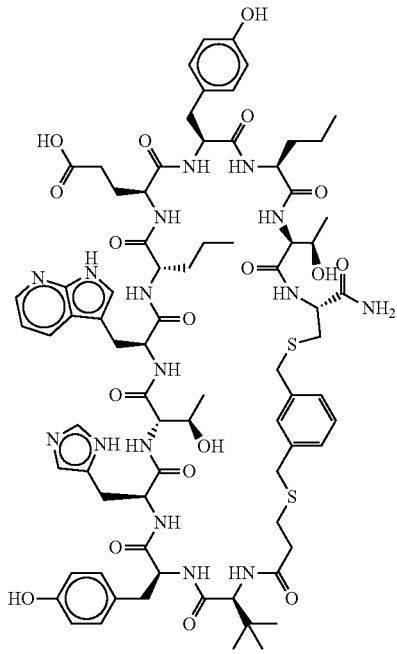
057
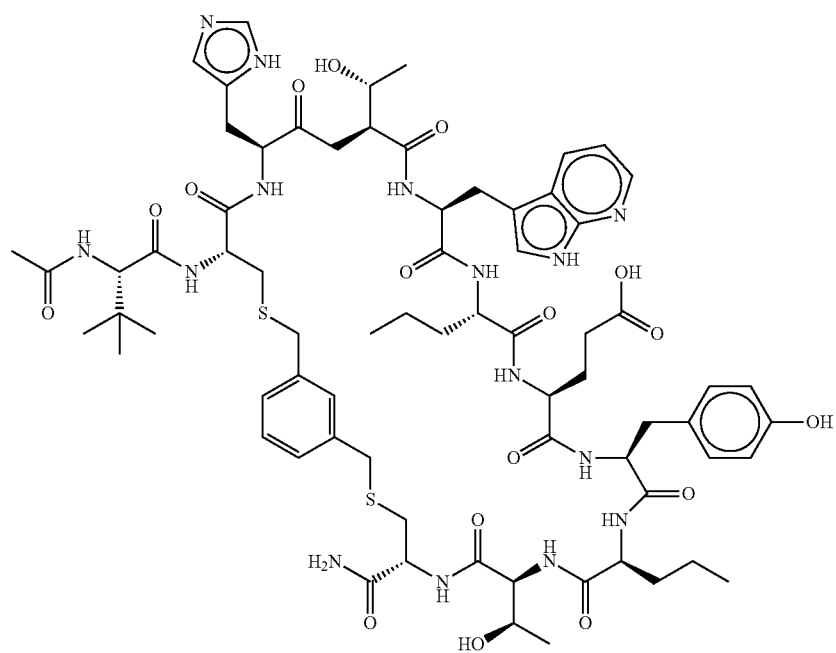
058

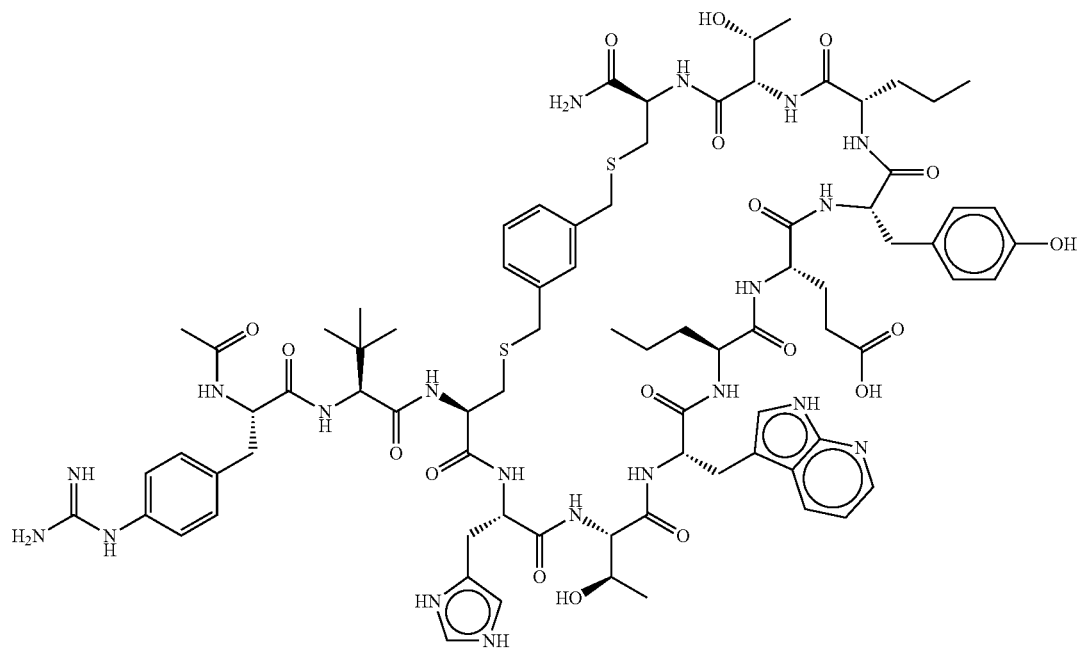
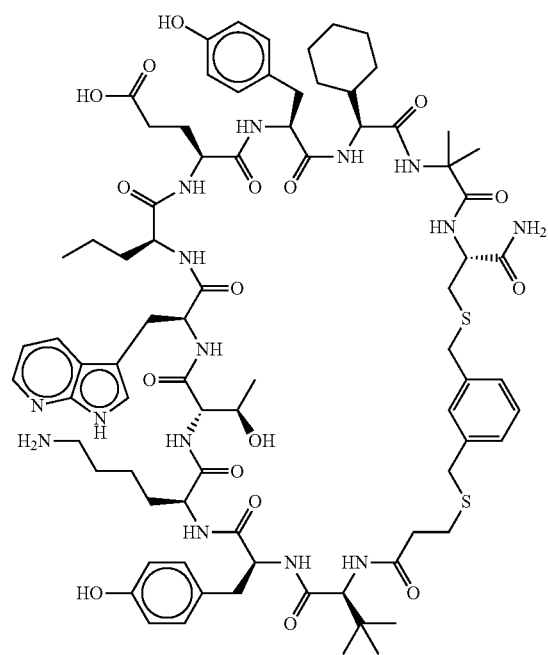

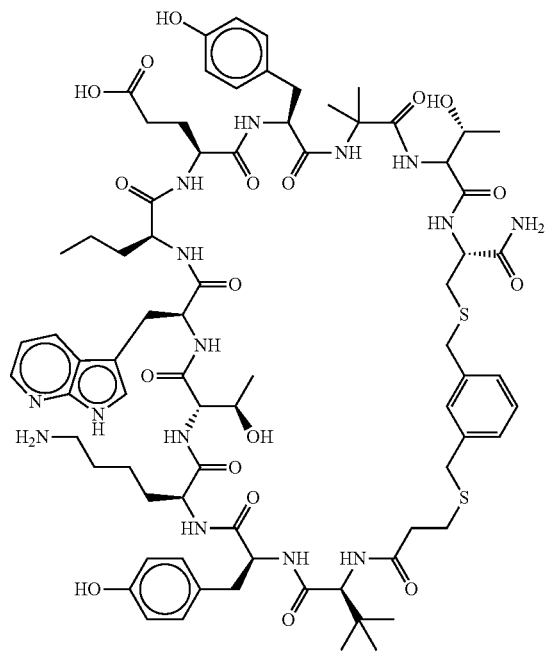
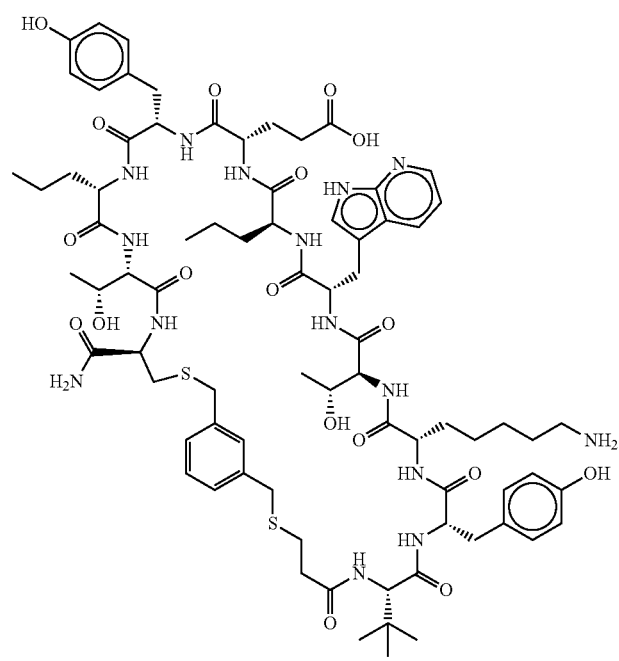

-continued
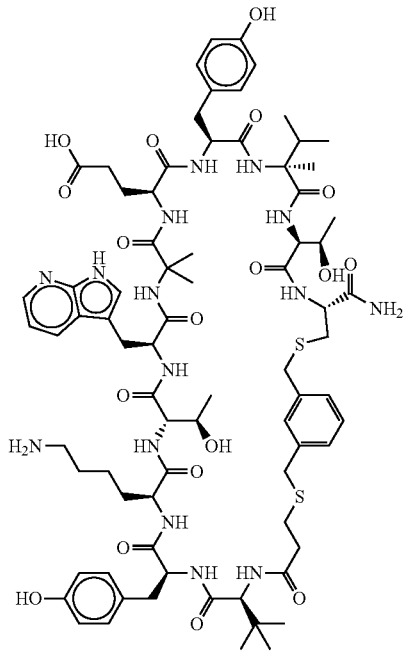
063
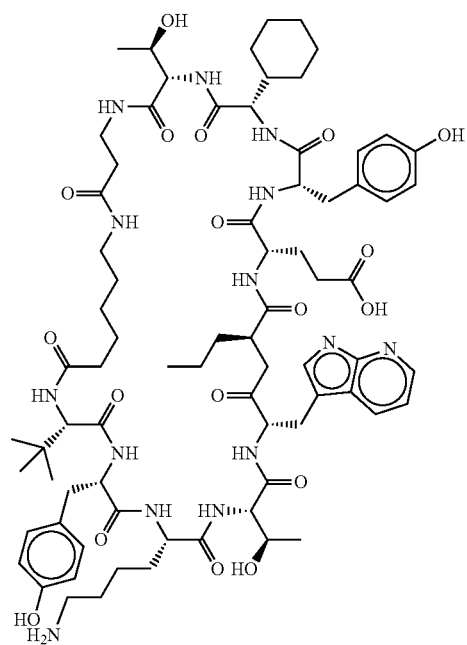
064

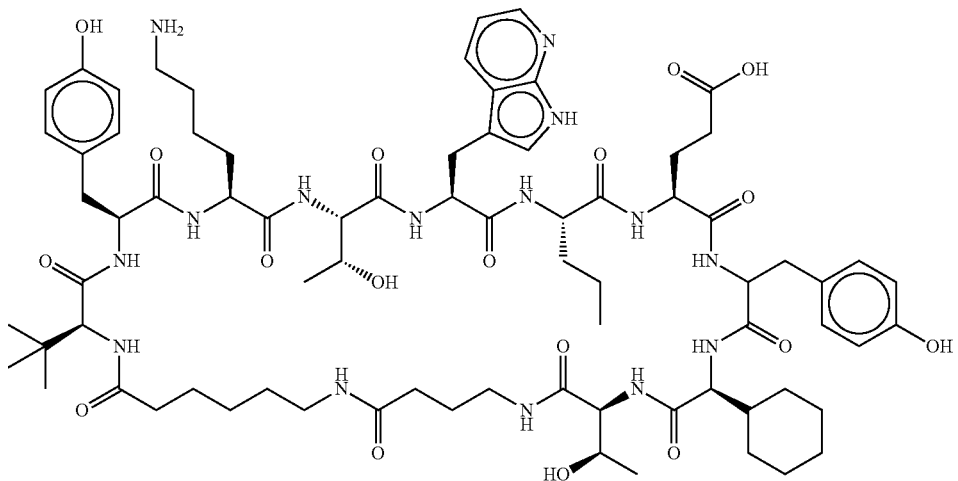
065
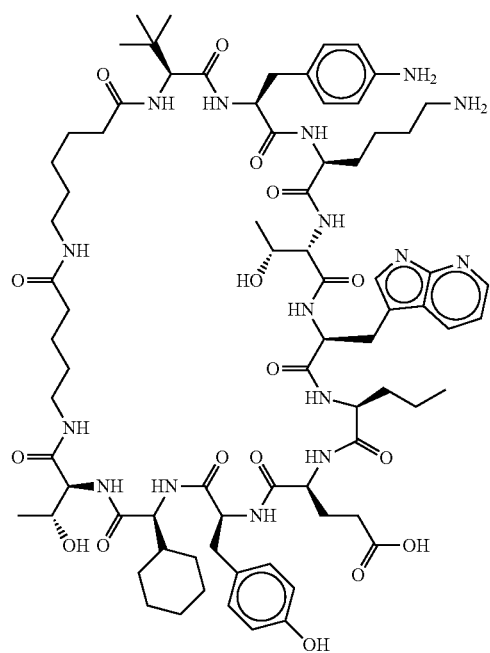
066

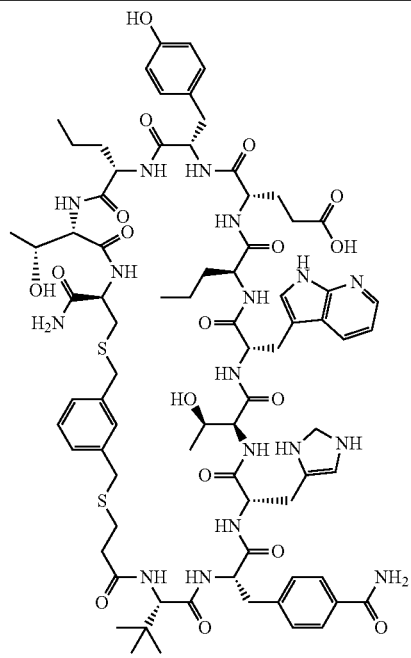
067
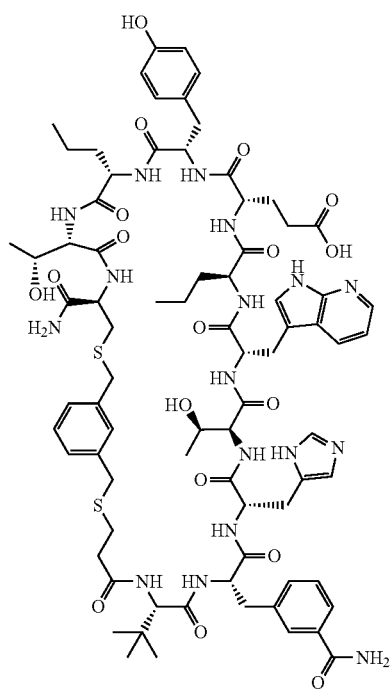 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2cccc(C(N)=O)c2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
068

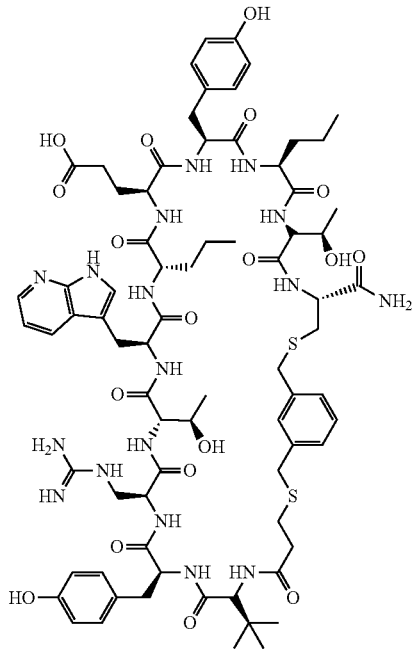
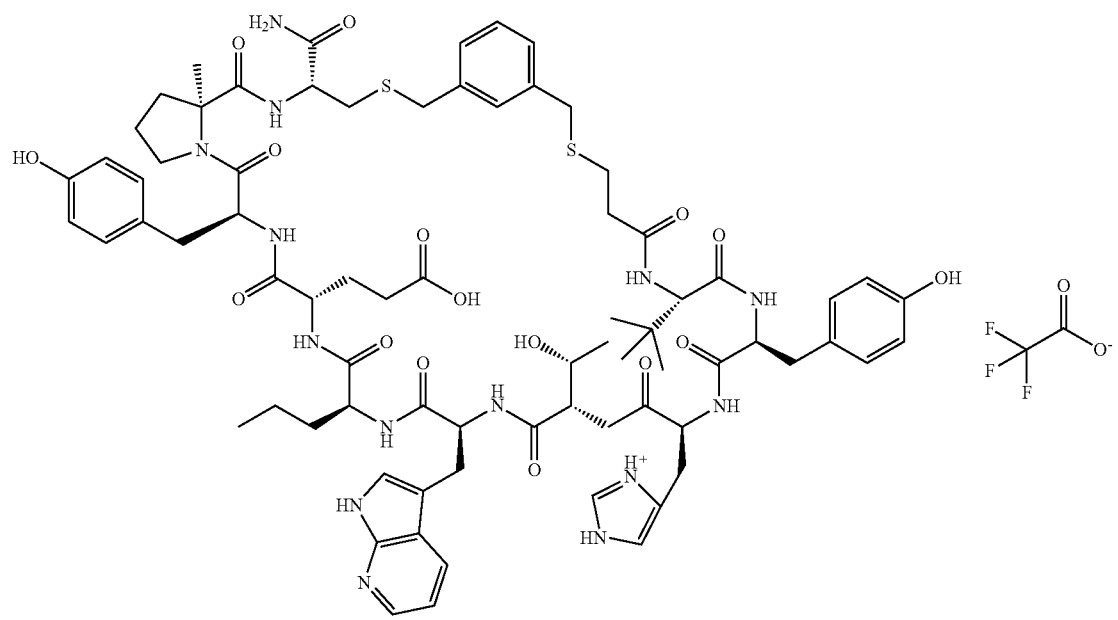 [SMILES: CCC[C@@H]1NC(=O)[C@H](Cc2c[nH]c3ncccc23)NC(=O)[C@H]([C@@H](C)O)CC(=O)[C@H](Cc2c[nH]cn2)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@]2(C)CCCN2C(=O)[C@H](Cc2ccc(O)cc2)NC(=O)[C@H](CCC(=O)O)NC1=O ; O=C([O-])C(F)(F)F]

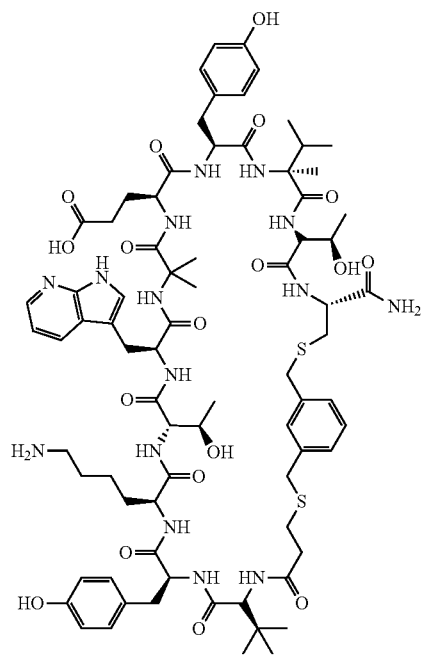
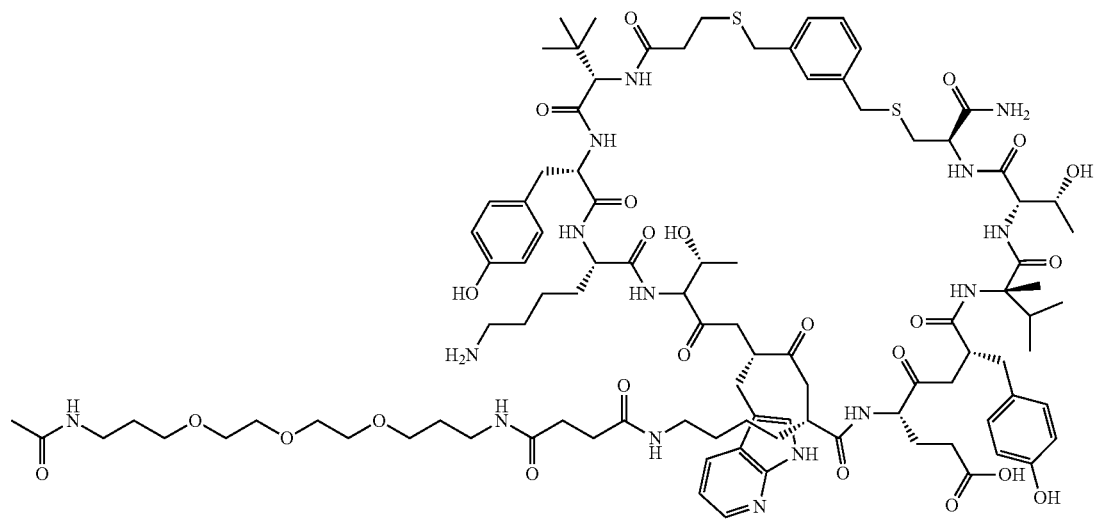 [SMILES: CC(=O)NCCCOCCOCCOCCCNC(=O)CCC(=O)NCCCC[C@@H]1CC(=O)[C@H](Cc2c[nH]c3ncccc23)CC(=O)C([C@@H](C)O)NC(=O)[C@H](CCCCN)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@](C)(C(C)C)NC(=O)[C@H](Cc2ccc(O)cc2)CC(=O)[C@H](CCC(=O)O)NC1=O]

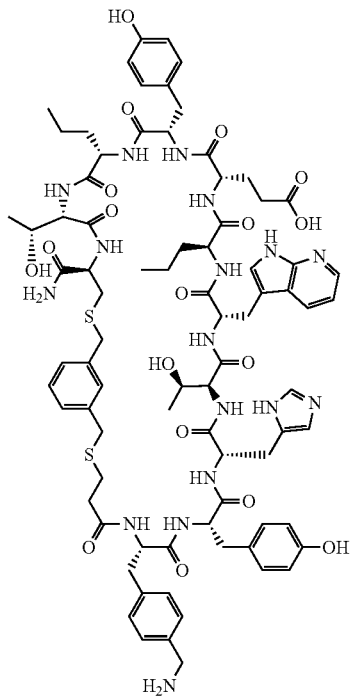 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(O)cc2)NC(=O)[C@H](Cc2ccc(CN)cc2)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
086
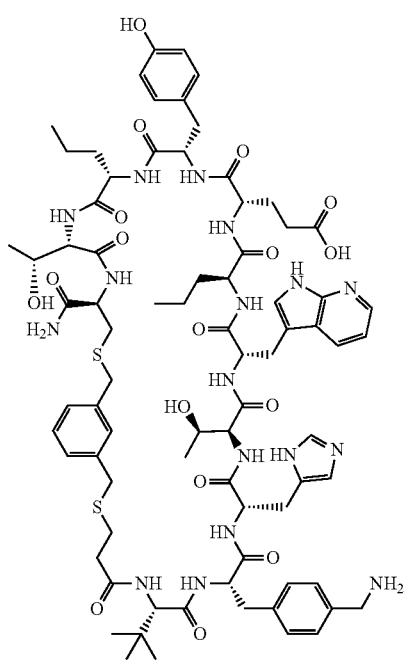 [SMILES: CCC[C@@H]1NC(=O)[C@H](Cc2c[nH]c3ncccc23)NC(=O)[C@H]([C@@H](C)O)NC(=O)[C@H](Cc2cnc[nH]2)NC(=O)[C@H](Cc2ccc(CN)cc2)NC(=O)[C@H](C(C)(C)C)NC(=O)CCSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
087

090
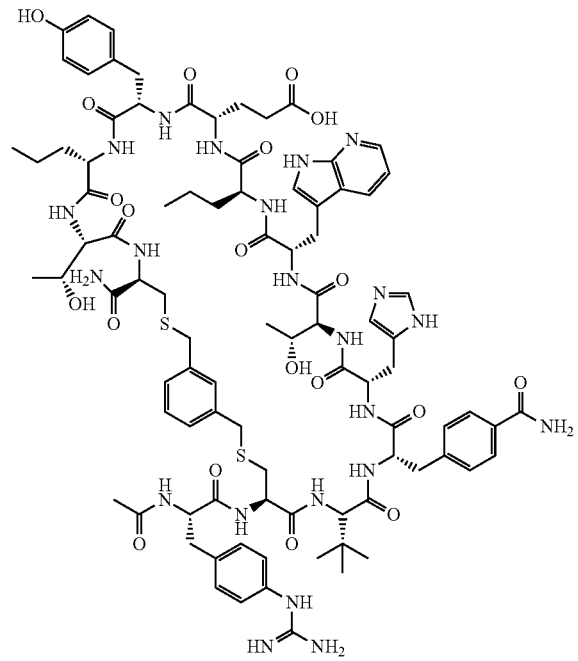
091
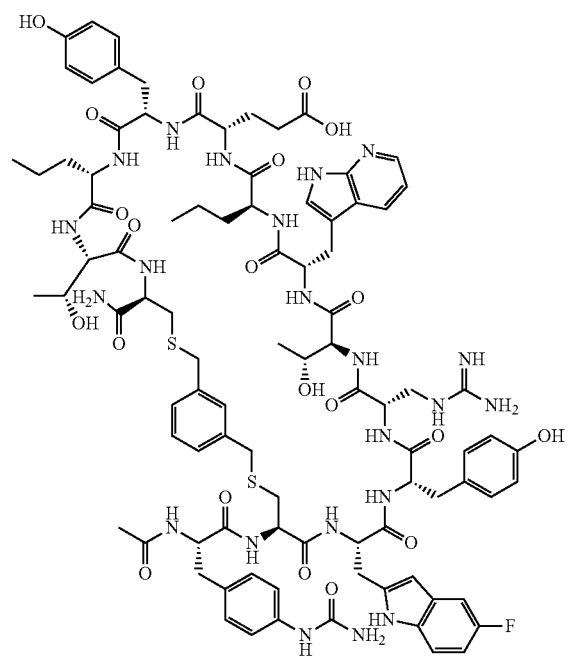 [SMILES: CCC[C@@H]1NC(=O)[C@H](Cc2c[nH]c3ncccc23)NC(=O)[C@H]([C@@H](C)O)NC(=O)[C@H](CNC(=N)N)NC(=O)[C@H](Cc2ccc(O)cc2)NC(=O)[C@H](Cc2cc3cc(F)ccc3[nH]2)NC(=O)[C@@H](NC(=O)[C@H](Cc2ccc(NC(N)=O)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]

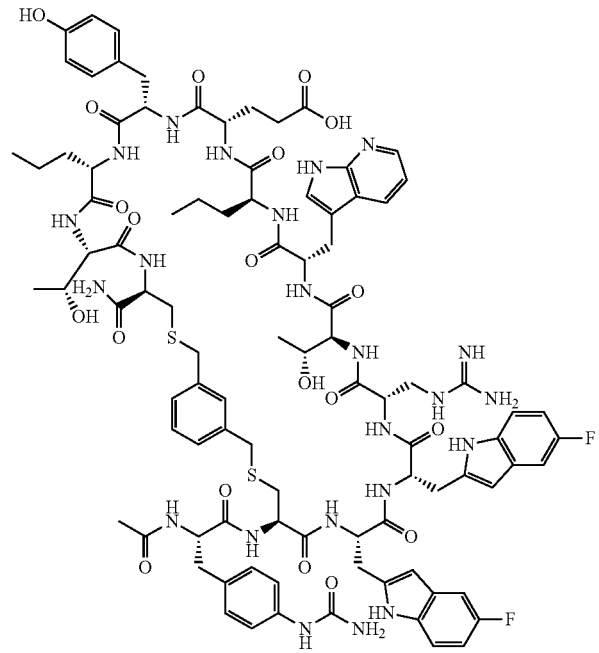 [SMILES: CCC[C@@H]1NC(=O)[C@H](Cc2c[nH]c3ncccc23)NC(=O)[C@H]([C@@H](C)O)NC(=O)[C@H](CNC(=N)N)NC(=O)[C@H](Cc2cc3cc(F)ccc3[nH]2)NC(=O)[C@H](Cc2cc3cc(F)ccc3[nH]2)NC(=O)[C@@H](NC(=O)[C@H](Cc2ccc(NC(N)=O)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
092
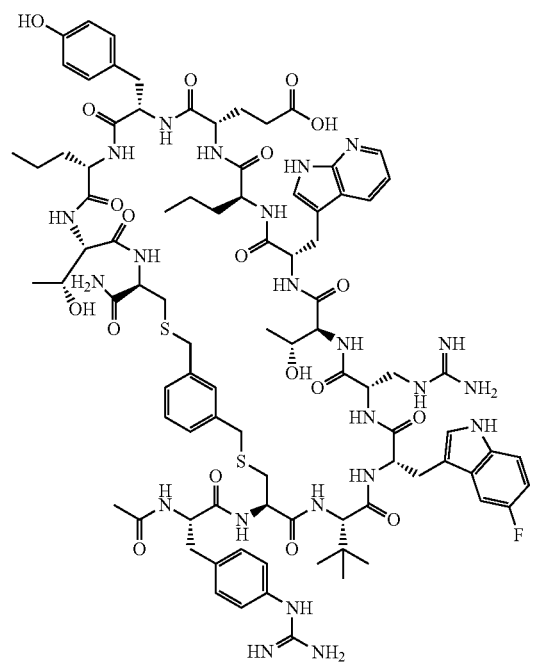 [SMILES: CCC[C@@H]1NC(=O)[C@H](Cc2c[nH]c3ncccc23)NC(=O)[C@H]([C@@H](C)O)NC(=O)[C@H](CNC(=N)N)NC(=O)[C@H](Cc2c[nH]c3ccc(F)cc23)NC(=O)[C@H](C(C)(C)C)NC(=O)[C@@H](NC(=O)[C@H](Cc2ccc(NC(=N)N)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]
093

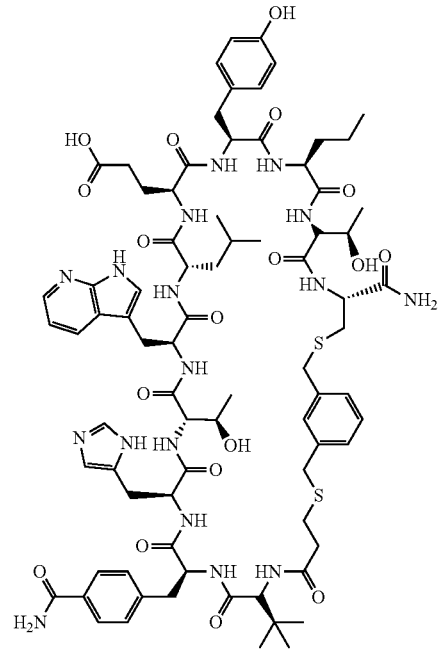
094
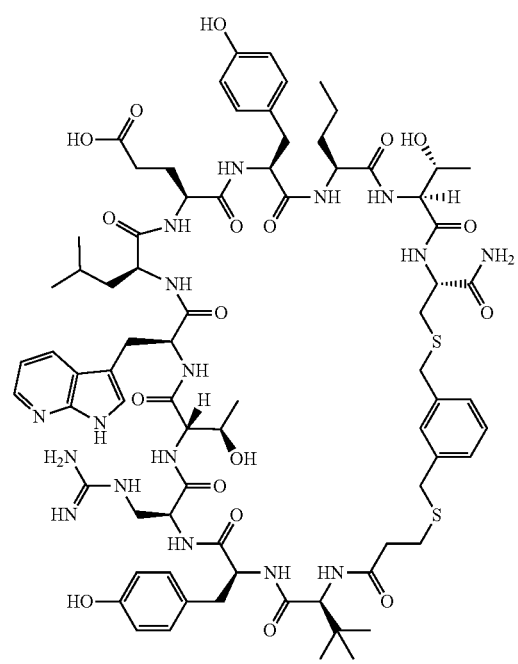 [SMILES: CCC[C@@H]1NC(=O)[C@H](Cc2ccc(O)cc2)NC(=O)[C@H](CCC(=O)O)NC(=O)[C@H](CC(C)C)NC(=O)[C@H](Cc2c[nH]c3ncccc23)NC(=O)[C@H]([C@@H](C)O)NC(=O)[C@H](CNC(=N)N)NC(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@@H](C)O)NC1=O]
095

-continued
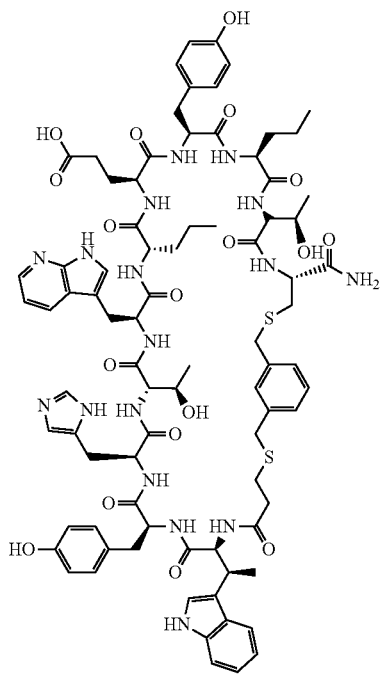
097
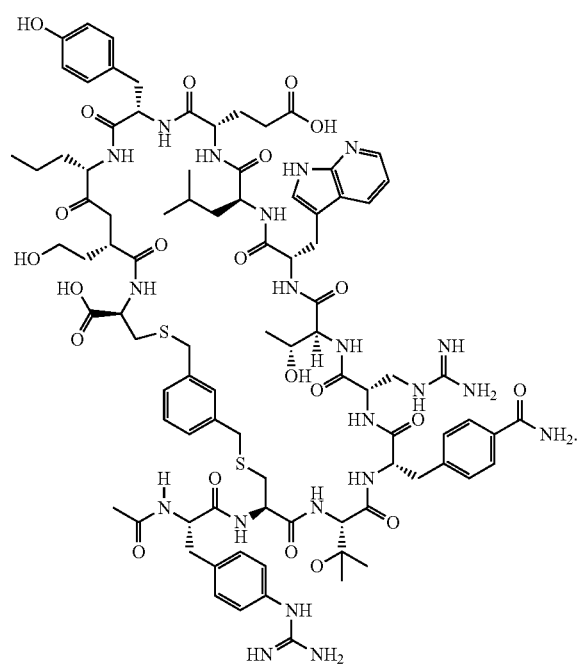 [SMILES: CCC[C@@H]1NC(=O)[C@H](Cc2ccc(O)cc2)NC(=O)[C@H](CCC(=O)O)NC(=O)[C@H](CC(C)C)NC(=O)[C@H](Cc2c[nH]c3ncccc23)NC(=O)[C@H]([C@@H](C)O)NC(=O)[C@H](CNC(=N)N)NC(=O)[C@H](Cc2ccc(C(N)=O)cc2)NC(=O)[C@H](C(C)(C)O)NC(=O)[C@@H](NC(=O)[C@H](Cc2ccc(NC(=N)N)cc2)NC(C)=O)CSCc2cccc(c2)CSC[C@@H](C(=O)O)NC(=O)[C@H](CCO)CC1=O]
100

11. The cyclic peptide of claim 10, wherein the cyclic peptide is selected from:
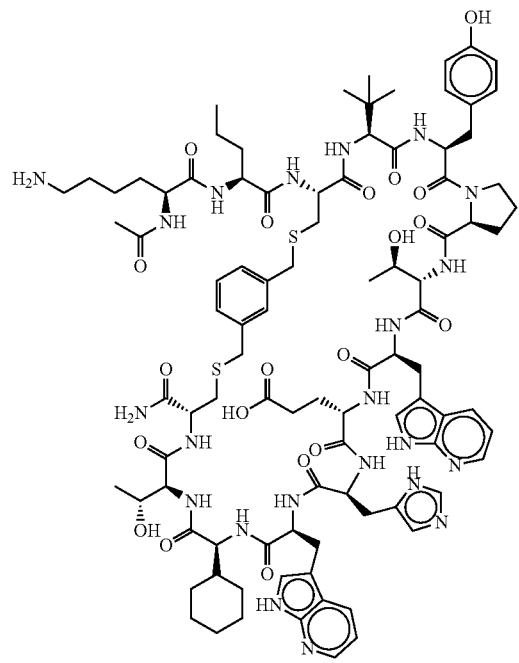
002
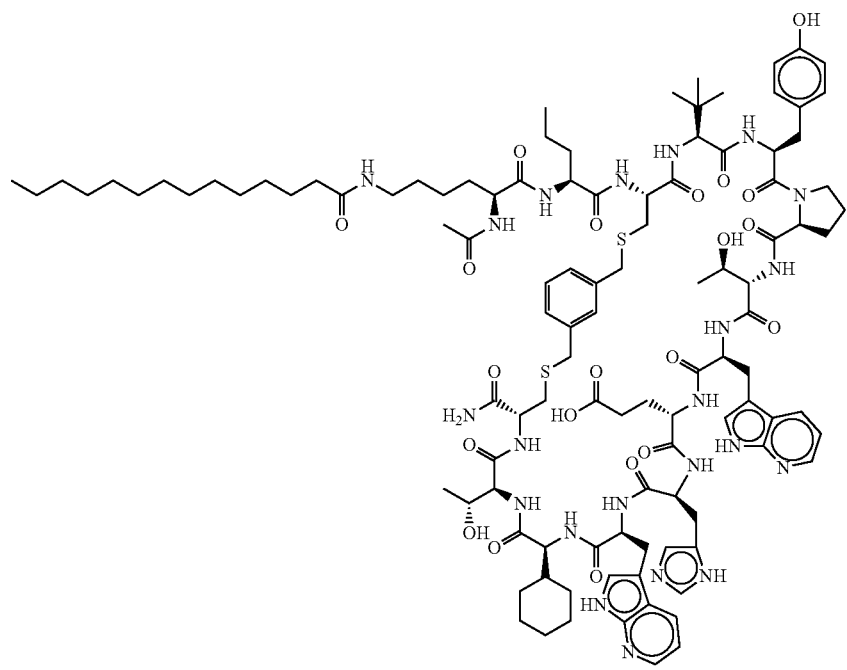
003

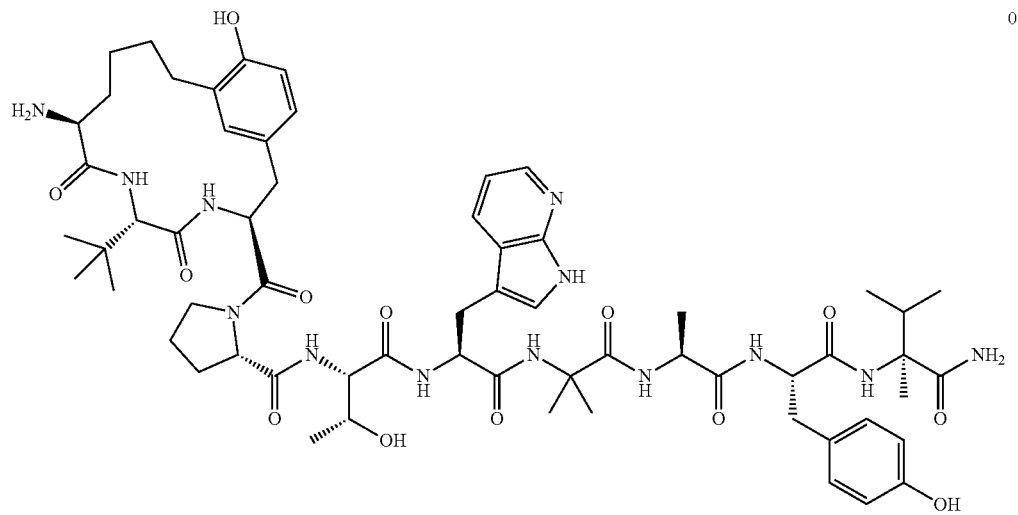
032
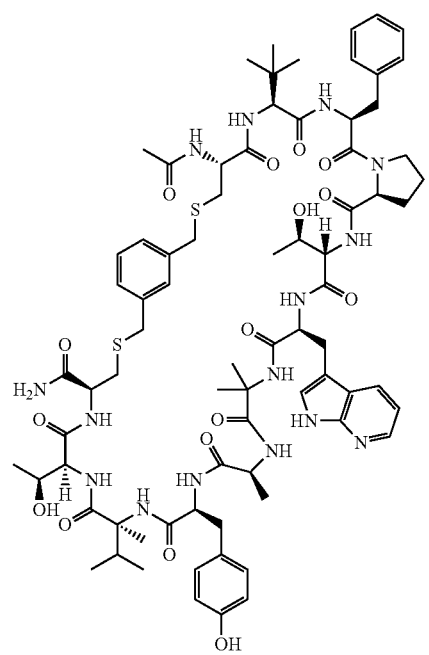 [SMILES: CC(=O)N[C@H]1CSCc2cccc(c2)CSC[C@H](C(N)=O)NC(=O)[C@H]([C@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccccc2)NC(=O)[C@H](C(C)(C)C)NC1=O]
040

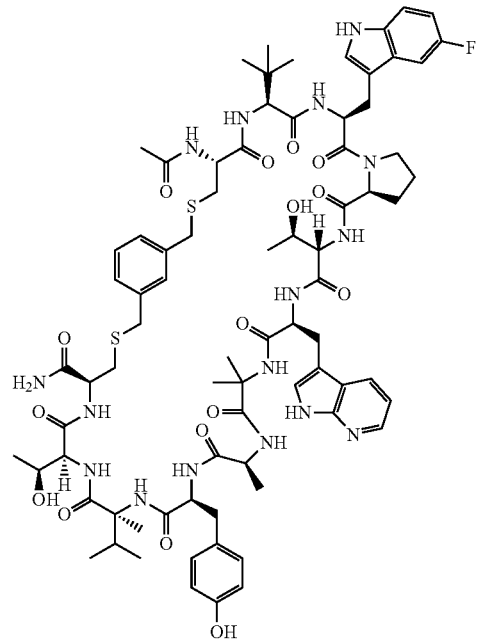 [SMILES: CC(=O)N[C@H]1CSCc2cccc(c2)CSC[C@H](C(N)=O)NC(=O)[C@H]([C@H](C)O)NC(=O)[C@](C)(C(C)C)NC(=O)[C@H](Cc2ccc(O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2c[nH]c3ccc(F)cc23)NC(=O)[C@H](C(C)(C)C)NC1=O]
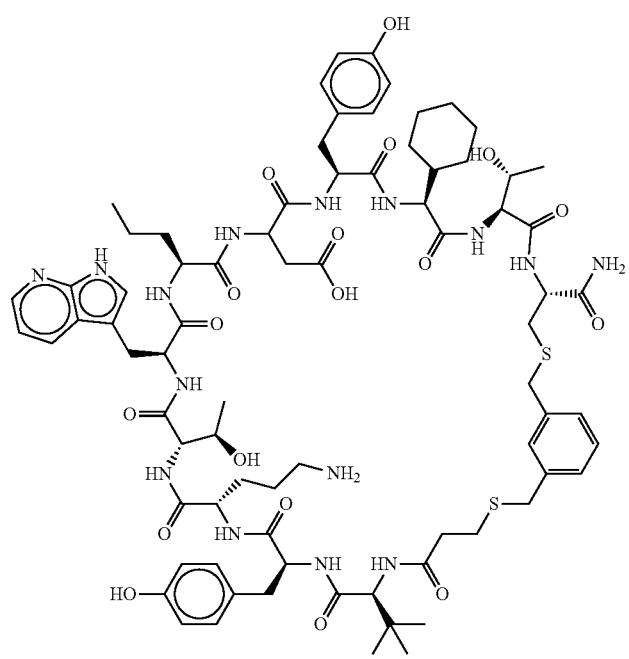

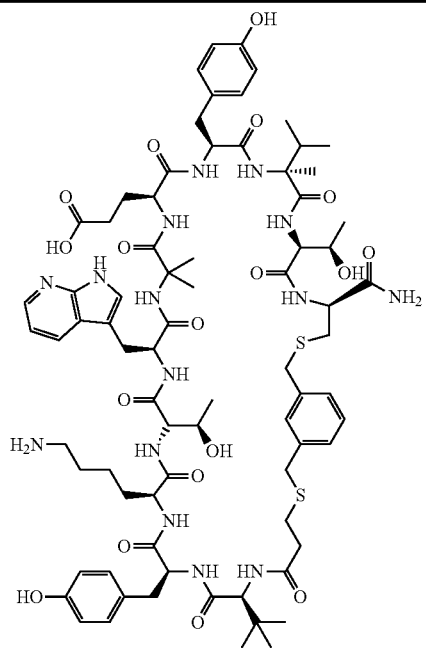

077

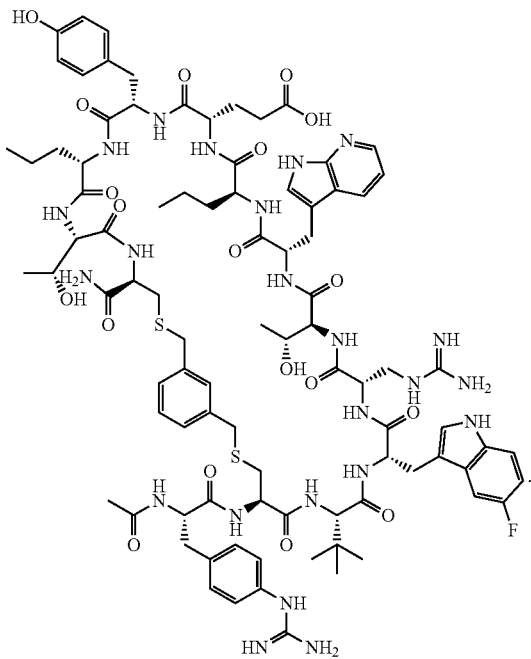 [SMILES: CCC[C@@H]1NC(=O)[C@H](Cc2c[nH]c3ncccc23)NC(=O)[C@H]([C@@H](C)O)NC(=O)[C@H](CNC(=N)N)NC(=O)[C@H](Cc2c[nH]c3ccc(F)cc23)NC(=O)[C@H](C(C)(C)C)NC(=O)[C@@H](NC(=O)[C@H](Cc2ccc(NC(=N)N)cc2)NC(C)=O)CSCc2cccc(c2)CSC[C@@H](C(N)=O)NC(=O)[C@H]([C@@H](C)O)NC(=O)[C@H](CCC)NC(=O)[C@H](Cc2ccc(O)cc2)NC(=O)[C@H](CCC(=O)O)NC1=O]

093

12. A pharmaceutical composition comprising the cyclic peptide of claim 1 and a pharmaceutically acceptable carrier.

13. A method of reducing low density lipoprotein (LDL) cholesterol level in a subject in need thereof comprising administering to the subject a therapeutically effective amount of the cyclic peptide of claim 1.

14. The method of claim 13, wherein the subject has hypercholesterolemia.

15. The method of claim 14, wherein the cyclic peptide inhibits the interaction between human PCSK9 and epidermal growth factor-like repeat A (EGF-A) domain of human low density lipoprotein (LDLR).

16. A method of treating hypercholesterolemia in a subject in need thereof comprising administering to the subject a therapeutically effective amount of the cyclic peptide of claim 1.

17. The method of claim 16, wherein the subject further suffers from a disease that shows comorbidity with hypercholesterolemia.

18. The method of claim 17, wherein the disease that shows comorbidity with hypercholesterolemia is selected from the group consisting of nephrotic syndrome, kidney failure, coronary artery disease, atherosclerosis, stroke, peripheral vascular disease, diabetes, and high blood pressure.

19. A method of inhibiting PCSK9 activity in a subject in need thereof comprising administering to the subject a therapeutically effective amount of the cyclic peptide of claim 1.

20. A method of inhibiting PCSK9 activity in a cell comprising contacting the cell with the cyclic peptide of claim 1.

21. A method of inhibiting the interaction between PCSK9 and the EGF-A domain of LDLR in a subject in need thereof comprising administering to the subject a therapeutically effective amount of the cyclic peptide of claim 1.

22. The method of claim 13, wherein the administration is selected from the group consisting of oral, intravenous, intramuscular, intraperitoneal, subcutaneous, transdermal, and intravitreal.

23. The cyclic peptide of claim 1, wherein the cyclic peptide is

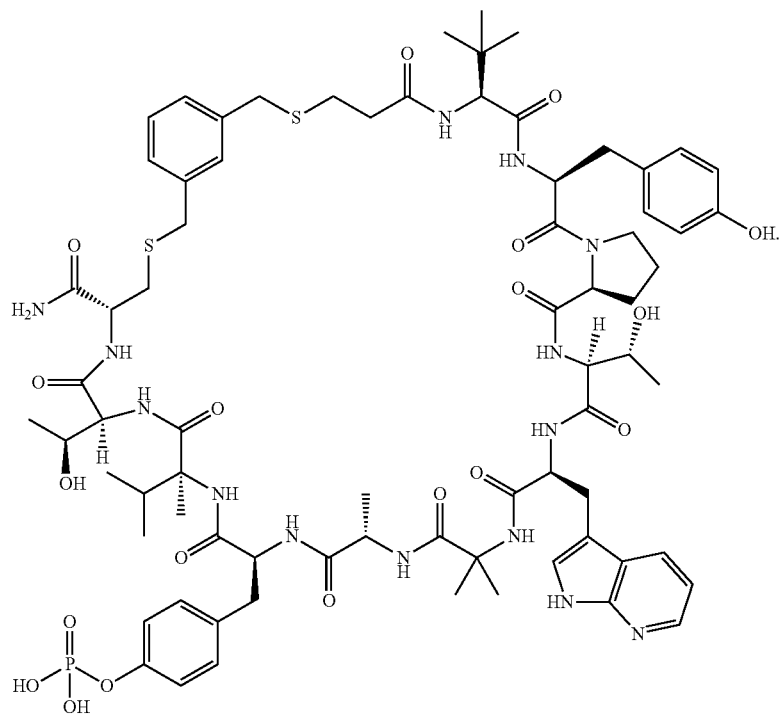 [SMILES: CC(C)[C@]1(C)NC(=O)[C@H](Cc2ccc(OP(=O)(O)O)cc2)NC(=O)[C@H](C)NC(=O)C(C)(C)NC(=O)[C@H](Cc2c[nH]c3ncccc23)NC(=O)[C@H]([C@@H](C)O)NC(=O)[C@@H]2CCCN2C(=O)[C@H](Cc2ccc(O)cc2)NC(=O)[C@H](C(C)(C)C)NC(=O)CCSCc2cccc(c2)CSC[C@@H](C(N)=O)NC(=O)[C@H]([C@H](C)O)NC1=O]

* * * * *